US006537780B2

(12) United States Patent
Beasley et al.

(10) Patent No.: US 6,537,780 B2
(45) Date of Patent: Mar. 25, 2003

(54) ISOLATED NUCLEIC ACID MOLECULES ENCODING TRANSFERASE ENZYMES

(75) Inventors: Ellen M. Beasley, Darnestown, MD (US); Karen A. Ketchum, Germantown, MD (US); Valentina Di Francesco, Rockville, MD (US)

(73) Assignee: Applera Corporation, Norwalk, CT (US)

(*) Notice: Subject to any disclaimer, the term of this patent is extended or adjusted under 35 U.S.C. 154(b) by 0 days.

(21) Appl. No.: 09/818,512

(22) Filed: Mar. 28, 2001

(65) Prior Publication Data

US 2002/0142416 A1 Oct. 3, 2002

(51) Int. Cl.[7] .......................... C12N 15/52; C12N 5/10; C12N 15/63

(52) U.S. Cl. .................... 435/69.1; 536/23.1; 536/23.2; 435/71.1; 435/71.2; 435/471; 435/320.1; 435/325; 435/252.3; 435/254.11; 435/183; 435/193

(58) Field of Search ............................... 536/23.1, 23.2; 435/69.1, 71.1, 71.2, 471, 320.1, 325, 252.3, 254.11, 183, 193

(56) References Cited

U.S. PATENT DOCUMENTS 6,071,732 A * 6/2000 Moore ........................ 435/193

* cited by examiner

*Primary Examiner*—Prema Mertz
(74) *Attorney, Agent, or Firm*—Celera Genomics; Justin D. Karjala

(57) ABSTRACT

The present invention provides amino acid sequences of peptides that are encoded by genes within the human genome, the enzyme peptides of the present invention. The present invention specifically provides isolated peptide and nucleic acid molecules, methods of identifying orthologs and paralogs of the enzyme peptides, and methods of identifying modulators of the enzyme peptides.

23 Claims, 60 Drawing Sheets

```
   1 GGCGGCTTCG GTTGCGGGTC GGAACGGCGC TGCTCTGCGG GGCCGGTCCA
  51 GGCTGGCAGC TGCCGGCGCT TGGCGGTGAG GGCGGGCTCC CGAGTGGCCC
 101 CCCACCGAAG GCGGCGCGGC GGCTCCTCAC TCATCCCAGA TGTTGGTTAT
 151 CTTTCTGAAG TAGACTGTCC ATGGCCTGAA CATTTTCCGA AAATCATTTT
 201 GAGCAAAATA TCTGTTTAAT AACAAGATAA CCACATCAAG ATGGTTGGAA
 251 AGCTGAAGCA GAACTTACTA TTGGCATGTC TGGTGATTAG TTCTGTGACT
 301 GTGTTTTACC TGGGCCAGCA TGCCATGGAA TGCCATCACC GGATAGAGGA
 351 ACGTAGCCAG CCAGTCAAAT TGGAGAGCAC AAGGACCACT GTGAGAACTG
 401 GCCTGGACCT CAAAGCCAAC AAAACCTTTG CCTATCACAA AGATATGCCT
 451 TTAATATTTA TTGGAGGTGT GCCTCGGAGT GGAACCACAC TCATGAGGGC
 501 CATGCTGGAC GCACATCCTG ACATTCGCTG TGGAGAGGAA ACCAGGGTCA
 551 TTCCCCGAAT CCTGGCCCTG AAGCAGATGT GGTCACGGTC AAGTAAAGAG
 601 AAGATCCGCC TGGATGAGGC TGGTGTTACT GATGAAGTGC TGGATTCTGC
 651 CATGCAAGCC TTCTTACTAG AAATTATCGT TAAGCATGGG GAGCCAGCCC
 701 CTTATTTATG TAATAAAGAT CCTTTTGCCC TGAAATCTTT AACTTACCTT
 751 TCTAGGTTAT TCCCCAATGC CAAATTTCTC CTGATGGTCC GAGATGGCCG
 801 GGCATCAGTA CATTCAATGA TTTCTCGAAA AGTTACTATA GCTGGATTTG
 851 ATCTGAACAG CTATAGGGAC TGTTTGACAA AGTGGAATCG TGCTATAGAG
 901 ACCATGTATA ACCAGTGTAT GGAGGTTGGT TATAAAAAGT GCATGTTGGT
 951 TCACTATGAA CAACTTGTCT TACATCCTGA ACGGTGGATG AGAACACTCT
1001 TAAAGTTCCT CCAGATTCCA TGGAACCACT CAGTATTGCA CCATGAAGAG
1051 ATGATTGGGA AAGCTGGGGG AGTGTCTCTG TCAAAAGTGG AGAGATCTAC
1101 AGACCAAGTA ATCAAGCCAG TCAATGTAGG AGCTCTATCA AAATGGGTTG
1151 GGAAGATACC GCCAGATGTT TTACAAGACA TGGCAGTGAT TGCTCCTATG
1201 CTTGCCAAGC TTGGATATGA CCCATATGCC AACCCACCTA ACTACGGAAA
1251 ACCTGATCCC AAAATTATTG AAAACACTCG AAGGGTCTAT AAGGGAGAAT
1301 TCCAACTACC TGACTTTCTT AAAGAAAAAC CACAGGTACT GTGTCTGCTT
1351 TTTCCTCCTG ATGTATACTA GATTGGCTCT TGCATTGAAG TAATATTTTT
1401 AAAGAGATAA TGAAATTAAA AAGACAGAAA CAAGAAAACC AAAAAGAAAA
1451 GAAGAAAAGG GATAGTGATA TGTGCTGGGG AAGAAAGATC AGCGTCTGGG
1501 ACTTGTTGAT TTTAACAATA ATTTAACACA GTCTTAATTT CAGAGAGCTC
1551 AGTGTCTCCC AAAACCAGGG AAATACTTTA TTGATAACCA AATTCTGATT
1601 GCTTGAGGTC CTGCACAAGC CGCCCAGTGG GTAAAGCTGC TCCAGCGTTC
1651 CAGTGCCTAA TTTGAAATAA AAATGTTCAG CGACCCTCTC TGTTCCTAAA
1701 AAAAAAAAAA AAAAAAAAAA AAAAAAAAAA AAAAAAAAAA AAAAAAAAAA
1751 AAAAAAAAAA AAAAAAAAAA AAAAAAAAAA A  (SEQ ID NO:1)
```

FEATURES:

| | |
|---|---|
| 5'UTR: | 1-240 |
| Start Codon: | 241 |
| Stop Codon: | 1369 |
| 3'UTR: | 1372 |

Homologous proteins:

Top 10 BLAST Hits

| | Score | E |
|---|---|---|
| CRA\|18000005141584 /altid=gi\|4507665 /def=ref\|NP_003587.1\| tyro... | 751 | 0.0 |
| CRA\|18000005141583 /altid=gi\|7305591 /def=ref\|NP_038865.1\| prot... | 733 | 0.0 |
| CRA\|18000005169402 /altid=gi\|6678421 /def=ref\|NP_033445.1\| prot... | 490 | e-137 |
| CRA\|108000024653385 /altid=gi\|12742755 /def=ref\|XP_009893.2\| ty... | 488 | e-137 |
| CRA\|18000005144262 /altid=gi\|4507667 /def=ref\|NP_003586.1\| tyro... | 488 | e-137 |
| CRA\|154000124060759 /altid=gi\|12052772 /def=emb\|CAB66558.1\| (AL... | 483 | e-135 |
| CRA\|1000682354906 /altid=gi\|6581081 /def=gb\|AAF18448.1\|AF204241... | 440 | e-122 |
| CRA\|335001114786726 /altid=gi\|12230780 /def=sp\|Q9VYB7\|TPST_DROM... | 438 | e-121 |
| CRA\|18000005169403 /altid=gi\|6686030 /def=sp\|O77081\|TPSA_CAEEL ... | 398 | e-109 |
| CRA\|1000682342388 /altid=gi\|6434389 /def=emb\|CAB60888.1\| (AL132... | 367 | e-100 |

FIGURE 1A

BLAST dbEST hits:

| | Score | E |
|---|---|---|
| gi\|12890586 /dataset=dbest /taxon=960... | 1354 | 0.0 |
| gi\|12789130 /dataset=dbest /taxon=960... | 1342 | 0.0 |
| gi\|12614898 /dataset=dbest /taxon=96... | 1265 | 0.0 |
| gi\|12786641 /dataset=dbest /taxon=960... | 1162 | 0.0 |
| gi\|12905259 /dataset=dbest /taxon=960... | 979 | 0.0 |
| gi\|2158586 /dataset=dbest /taxon=9606 ... | 884 | 0.0 |

EXPRESSION INFORMATION FOR MODULATORY USE:

library source:

From BLAST dbEST hits:

gi|12890586 placenta
gi|12789130 neuroblastoma cells
gi|12614898 liver
gi|12786641 brain
gi|12905259 T cells from T cell leukemia
gi|2158586 total fetus From tissue screening panels:

hippocampus

FIGURE 1B

```
  1 MVGKLKQNLL LACLVISSVT VFYLGQHAME CHHRIEERSQ PVKLESTRTT
 51 VRTGLDLKAN KTFAYHKDMP LIFIGGVPRS GTTLMRAMLD AHPDIRCGEE
101 TRVIPRILAL KQMWSRSSKE KIRLDEAGVT DEVLDSAMQA FLLEIIVKHG
151 EPAPYLCNKD PFALKSLTYL SRLFPNAKFL LMVRDGRASV HSMISRKVTI
201 AGFDLNSYRD CLTKWNRAIE TMYNQCMEVG YKKCMLVHYE QLVLHPERWM
251 RTLLKFLQIP WNHSVLHHEE MIGKAGGVSL SKVERSTDQV IKPVNVGALS
301 KWVGKIPPDV LQDMAVIAPM LAKLGYDPYA NPPNYGKPDP KIIENTRRVY
351 KGEFQLPDFL KEKPQVLCLL FPPDVY  (SEQ ID NO:2)
```

FEATURES:

Functional domains and key regions:

[1] PDOC00001 PS00001 ASN_GLYCOSYLATION
N-glycosylation site

Number of matches: 2

```
1     60-63 NKTF
2   262-265 NHSV
```

[2] PDOC00004 PS00004 CAMP_PHOSPHO_SITE
cAMP- and cGMP-dependent protein kinase phosphorylation site

```
    196-199 RKVT
```

[3] PDOC00005 PS00005 PKC_PHOSPHO_SITE
Protein kinase C phosphorylation site

Number of matches: 6

```
1     46-48 STR
2     50-52 TVR
3   117-119 SSK
4   195-197 SRK
5   207-209 SYR
6   346-348 TRR
```

[4] PDOC00006 PS00006 CK2_PHOSPHO_SITE
Casein kinase II phosphorylation site

Number of matches: 4

```
1     53-56 TGLD
2   117-120 SSKE
3   207-210 SYRD
4   281-284 SKVE
```

[5] PDOC00007 PS00007 TYR_PHOSPHO_SITE
Tyrosine kinase phosphorylation site

Number of matches: 2

```
1   148-155 KHGEPAPY
2   217-223 RAIETMY
```

[6] PDOC00008 PS00008 MYRISTYL
N-myristoylation site

Number of matches: 2

```
1     76-81 GVPRSG
2   277-282 GVSLSK
```

Membrane spanning structure and domains:

FIGURE 2A

| Helix | Begin | End | Score | Certainty |
| --- | --- | --- | --- | --- |
| 1 | 7 | 27 | 1.701 | Certain |

FIGURE 2B

BLAST Alignment to Top Hit:

```
>CRA|18000005141584 /altid=gi|4507665 /def=ref|NP_003587.1|
            tyrosylprotein sulfotransferase 1 [Homo sapiens]
            /org=Homo sapiens /taxon=9606 /dataset=nraa /length=370
          Length = 370

 Score =  751 bits (1917), Expect = 0.0
 Identities = 365/365 (100%), Positives = 365/365 (100%)
 Frame = +1

Query: 241  MVGKLKQNLLLACLVISSVTVFYLGQHAMECHHRIEERSQPVKLESTRTTVRTGLDLKAN 420
             MVGKLKQNLLLACLVISSVTVFYLGQHAMECHHRIEERSQPVKLESTRTTVRTGLDLKAN
Sbjct: 1    MVGKLKQNLLLACLVISSVTVFYLGQHAMECHHRIEERSQPVKLESTRTTVRTGLDLKAN 60

Query: 421  KTFAYHKDMPLIFIGGVPRSGTTLMRAMLDAHPDIRCGEETRVIPRILALKQMWSRSSKE 600
             KTFAYHKDMPLIFIGGVPRSGTTLMRAMLDAHPDIRCGEETRVIPRILALKQMWSRSSKE
Sbjct: 61   KTFAYHKDMPLIFIGGVPRSGTTLMRAMLDAHPDIRCGEETRVIPRILALKQMWSRSSKE 120

Query: 601  KIRLDEAGVTDEVLDSAMQAFLLEIIVKHGEPAPYLCNKDPFALKSLTYLSRLFPNAKFL 780
             KIRLDEAGVTDEVLDSAMQAFLLEIIVKHGEPAPYLCNKDPFALKSLTYLSRLFPNAKFL
Sbjct: 121  KIRLDEAGVTDEVLDSAMQAFLLEIIVKHGEPAPYLCNKDPFALKSLTYLSRLFPNAKFL 180

Query: 781  LMVRDGRASVHSMISRKVTIAGFDLNSYRDCLTKWNRAIETMYNQCMEVGYKKCMLVHYE 960
             LMVRDGRASVHSMISRKVTIAGFDLNSYRDCLTKWNRAIETMYNQCMEVGYKKCMLVHYE
Sbjct: 181  LMVRDGRASVHSMISRKVTIAGFDLNSYRDCLTKWNRAIETMYNQCMEVGYKKCMLVHYE 240

Query: 961  QLVLHPERWMRTLLKFLQIPWNHSVLHHEEMIGKAGGVSLSKVERSTDQVIKPVNVGALS 1140
             QLVLHPERWMRTLLKFLQIPWNHSVLHHEEMIGKAGGVSLSKVERSTDQVIKPVNVGALS
Sbjct: 241  QLVLHPERWMRTLLKFLQIPWNHSVLHHEEMIGKAGGVSLSKVERSTDQVIKPVNVGALS 300

Query: 1141 KWVGKIPPDVLQDMAVIAPMLAKLGYDPYANPPNYGKPDPKIIENTRRVYKGEFQLPDFL 1320
             KWVGKIPPDVLQDMAVIAPMLAKLGYDPYANPPNYGKPDPKIIENTRRVYKGEFQLPDFL
Sbjct: 301  KWVGKIPPDVLQDMAVIAPMLAKLGYDPYANPPNYGKPDPKIIENTRRVYKGEFQLPDFL 360

Query: 1321 KEKPQ 1335
             KEKPQ
Sbjct: 361  KEKPQ 365  (SEQ ID NO:4)
```

FIGURE 2C

```
   1 NNNNNNNNNN NNNNNNNNNN NNNNNNNNNN NNNNNNNNNN NNNNNNNNNN
  51 NNNNNNNNNN NNNNNNNNNN NNNNNNNNNN NNNNNNNNNN NNNNNNNNNN
 101 NNNNNNNNNN NNNNNNNNNN NNNNNNNNNN NNNNNNNNNN NNNNNNNNNN
 151 NNNNNNNNNN NNNNNNNNNN NNNNNNNNNN NNNNNNNNNN NNNNNNNNNN
 201 AGATTCTGCT CGGTAGCAGG CTGGACACAC AGGCAGGGTT TCTATGTTGT
 251 AGTTCTTTTC CAGGAAACCT CAGTCTTTGC TCTTAAAGCC TTTACCTGTT
 301 AGATGAGGCC TTCCTGTATT ATGGAGGGTA ATCCACTTTA CTAGAAATCT
 351 GTTGATTTAA GTGTTAATCA CATCTAAAAT ATACCTTCAC AGACATATCT
 401 AGATTGGTGT TTGATCAAAC AACTGGACAC CAAAGTCTAG CCAAGTTGAC
 451 ACATAAAATT AACTGTCACA CTTGCCTTCT GAGGATTCAG GGTAAATTAT
 501 TTTGGTGTAC ATGTAGTCTG GTTGCTGTCT GTTTCCCACT GTATACCCTT
 551 GCTCTAGCTA AACTAGCAGC TCCAGCTGTT TCATATACAT GCTTCTGCTT
 601 TTGCACATCC ATGTCTTTGG TCATAGTGTA CCTGCAGCAT GGAGTGCTTC
 651 CTGTGTCCAG ATCTTACCTG TCCTTCTGAG GATTAGATCA CAGATACTTA
 701 TACATACAAT TTTGTTTGCA GCCTATACAC TAGCTTTCCT AAACTTCTTC
 751 CTGTCACCTA ATTATGCTGT GTTCTGTCTT GCCATTGTGC TTTTGCACAC
 801 AAGTTCCTTT GGTTTAGAAT ATCCCTCCCT CTGTCTTTTC TTTCTTAAAG
 851 AGACAGGGTC TCAGTGTGGG CTGGTCTCGA ACTCCTGAGC TCAAATGATC
 901 CTCCCATCTC GGTCTCCCAA AGAGCTGTGA TTACAGGCGT AAGCTGCTGC
 951 ACCTGGTCCT TCCTTCCTAC TTTCTGTAAA ACTTTTACAG CTTCCTCAGG
1001 TCAATTACAT GCTCCTTTTC ATTATGCTCC CATTGTCCCT TTGCGTATTT
1051 CCACGGAGGC ACTCATCACA TTTTATTGTT ATTGTTTACA TATCTGTCTG
1101 TCAAAAGGCT TTGTTTTCCA ACAGCAGAAG TTACTATACT GTTTTCCTTT
1151 TCAAAGTTGG TCCTCAGTCG AGCCTATCTG GTCTGTAGTA CCTAAATAAA
1201 TTGTGGGATA ATAAACTGAA TCTCTGTTAA AGATTTGGAA GTTGTTTCAT
1251 ATTTCTTCTA TAATTTCTCA TTGTTAGAAT GTGGAGATAA TGACTGCTTG
1301 GAGATAAAGC AAGTCTGAAT AGCAGAGATC AGCCTTGGGT TGGACTCCAG
1351 ACATTCTTGG GCTTATTAAA TATTTGGTTG ACTCACTGAT AGAAATAGTT
1401 TTATTTATTT TCCATTCTTT ACCAGGTACA TAGCTTCAAA ATTACTTCAT
1451 TAACAAAAGC TGTTTCTGAT TATAAACATT GATTTATTTT TACTCAAATT
1501 TGTATATACT GTATATACTG AGTAAAACAA ATTTTACTCA TTTGTTTTTG
1551 TTTTGTTTTG TTTTGTTTTG TTTTTTTGAG ACAGAGTCTT GCTTTGTTGC
1601 CTAGGCTGGA GTGCAGTGGC ATGATCTCAG CTCACTGCAA GCTCTGCCTC
1651 CTGGATTCAT GCCATTCTCC TGCCTCAGCC TCCCGAGTAG CTGGGACTAC
1701 AGGCACCCGC CACCATGCCC AGCTAATTTT TTTTGTATTT TTTTTTAGTA
1751 GAGATGGGGT TTCACCGTGT TGGCCGGGAT GGTCTCCATC TCCTGACCTC
1801 GTGATCCGCC CGCCTCGGCC TCCCAAAGTG CTGGGATTAC AGGTGTGAGC
1851 CACCGCGCCC GGTCTCAATT TTGTTTTAAG AATATCAAAG AATCCAAGAC
1901 TGTTTCAGCT TCTTTCTACC TAAAATGCAG TGGTGATAAC TGGTGACTGA
1951 TTTGTAAGCA ATCTCAATGT AATGATAAAT AACCTTTTCC TTTCTCTACT
2001 AGATGTTGGT TATCTTTCTG AAGTAGACTG TCCATGGCCT GAACATTTTC
2051 CGAAAATCAT TTTGAGCAAA ATATCTGTTT AATAACAAGA TAACCACATC
2101 AAGATGGTTG GAAAGCTGAA GCAGAACTTA CTATTGGCAT GTCTGGTGAT
2151 TAGTTCTGTG ACTGTGTTTT ACCTGGGCCA GCATGCCATG GAATGCCATC
2201 ACCGGATAGA GGAACGTAGC CAGCCAGTCA AATTGGAGAG CACAAGGACC
2251 ACTGTGAGAA CTGGCCTGGA CCTCAAAGCC AACAAAACCT TTGCCTATCA
2301 CAAAGATATG CCTTTAATAT TTATTGGAGG TGTGCCTCGG AGTGGAACCA
2351 CACTCATGAG GGCCATGCTG GACGCACATC CTGACATTCG CTGTGGAGAG
2401 GAAACCAGGG TCATTCCCCG AATCCTGGCC CTGAAGCAGA TGTGGTCACG
2451 GTCAAGTAAA GAGAAGATCC GCCTGGATGA GGCTGGTGTT ACTGATGAAG
2501 TGCTGGATTC TGCCATGCAA GCCTTCTTAC TAGAAATTAT CGTTAAGCAT
2551 GGGGAGCCAG CCCCTTATTT ATGTAATAAA GATCCTTTTG CCCTGAAATC
2601 TTTAACTTAC CTTTCTAGGT TATTCCCCAA TGCCAAATTT CTCCTGATGG
2651 TCCGAGATGG CCGGGCATCA GTACATTCAA TGATTTCTCG AAAAGTTACT
2701 ATAGCTGGAT TTGATCTGAA CAGCTATAGG GACTGTTTGA CAAAGTGGAA
2751 TCGTGCTATA GAGACCATGT ATAACCAGTG TATGGAGGTT GGTTATAAAA
2801 AGTGCATGTT GGTTCACTAT GAACAACTTG TCTTACATCC TGAACGGTGG
2851 ATGAGAACAC TCTTAAAGTT CCTCCAGATT CCATGGAACC ACTCAGTATT
2901 GCACCATGAA GAGATGATTG GGAAAGCTGG GGGAGTGTCT CTGTCAAAGT
2951 GAGTAGAAGA TACGTTTTTT ATTTTGACTC TATATTTAGC TAATAATGAT
3001 CTATACATAT GTATGTATGT GTTTTATGTA TATATGTGTG TATGTTCCTG
```

FIGURE 3A

```
3051 TGTGTATATA TAGAAACTGA AGACCTTTTC TGGAACAGAT ACAGCTTCAT
3101 TGATGAGGTT TCTTTTTTTA TTAATTCTCT ACTAGTTTAT TACAGATGTT
3151 CACTTATTTA TACTTCATTT TTTCATTTAT ATATCGTGGC CCTCTTTATT
3201 TGTTTGATGG ATACAAACCC ACCTTACAGG CGGTGAAAAG CCTTCTTCAG
3251 GGTCTCAGAC CTTAATGCCA ATCATTCAGT TTTAGTGGCT TCTGATTTCT
3301 AATTTCTAGA TATTGTTGTT AATGAGGATA GTTGGCTTTT GTGTGGATTA
3351 AGGTTAAAAT CAGGAAGTGC ATATATCATG TTAATGAGCA CATAGTGAAT
3401 TATAAGCATT TTGAAATTTT TAGTGGTAGA GAAAAATAAA AGCTTCGTCT
3451 AACCTAATCT CTTCATTTTA TGGACAAGAA GACTGAGTCA CAGTAAGATT
3501 AAAACGATTT GTTCAGATTT AGATGGCAAG GCCAGAATTC GAATCTGTGC
3551 CTTGGTCTCA ATGAGGTCGT GCTTTTCTCC GTGGCATTTT ACTACGTGTT
3601 GTGCTTCCTT TGTCATCTGA AGGATATAAC CTCTCTTATT TTTTACAAAA
3651 GGCTAGAGAA TCTCCAAAAT TTGGAAGCCT AATCCATACA AGAAGTTCCT
3701 TGGATTCAAA ACTTCTCAAA TGATGATTTT TAGCATTTTG CTTCTTTTCT
3751 TATGAAGTGA CAACTAGTAT ACCCTCTAAC CTGTCTTGAT GACTTATATA
3801 CCTGGAATGA GGATATAAAA ATGGAAACTA CTATTAAATT CAGGTAGCAT
3851 CTCTTCATGA AGAAGAGTTG GCTATAACTA AATTTTATTT TTGTTTTTTT
3901 TCTTTTATCA AAGTAATATA TAACACCTGT AAAAAAGAAA TATATAAGGT
3951 GTTATATATA CATATATAAA AAGAAATATA AAAGGTGTTA TATATACTTT
4001 TTATCAAAGT AATATATAAC ACCTGTAAAA AATACTTTCC TTGTGTGCCC
4051 TTCTTACTTT CACCAAGGAA TATCTGCTTA ATTTTTTTTT GCTGTATAGA
4101 ACTTGTATAG TAAATAGATT TCTTATGTAG ATAATCTCAA AGGAACAGCT
4151 GCCTGCCTGT ACCAAGCTTT CAATTATTGA TTATAAGTTA TGACATACCA
4201 TCATTGTAGT GGCTCTAGGT TGTTTTTATT GATTCAAAGA AAATTTCAGC
4251 TCTGGCTACT CTGATTGCAG TTTATTATTA TTTCCAGATA ATAGACTATA
4301 ATTGATTTTT AATCACCTGT ATTAGGTATT TCAGTCTTTG TGCTTGTATG
4351 TTGGCCCGGC ACCGATGCCA CCTACATCTG CTAATATAAA AGGAGGCCAT
4401 TAGACCACCA GCCTCTTCAG TAGGGATTAA AGAGATATGC TTAAGTTAAA
4451 TTTTGGTGCT AATCAGGAAG AGAACATTTT GTGTATATAC TTGCTATGTT
4501 TAAGGTAAAC ATAAAGGCCA AGAAAATTCA TAGAAATTAT ATTATGAATT
4551 AATGAATTTT AGAAAGTAAA GAGATGTTAC TTAGCATTTC AGTATGTGGA
4601 ATGGAGGCCC TGTAAGGCTC TATGTTTTTT CAAAAATTAA CATGTCACAA
4651 TCATGAGTAG AACCTACCAT GCTTATTCCA AGATTTTTGC ATTGGGGTCT
4701 TTCTAGTTTG GGGCTATTAT GGATCAAAGT TGCTAAGAAC GTTCTTGTAC
4751 ATTACTTTTG GTGGATATAG CATTCATTTC TTTTAGGTAT ATACCAATGA
4801 ATAGAATTGC TGGATGACAA GGGGTGTGTG TGTGTGTGTG TGTGTTTGTG
4851 TGTGTGTGTG TGTGTTTAAC AGATACTTTC TAACAGTTTT CCAAAGTGTC
4901 TCTATCATTC ATGTATGGCT GTACTGTAAA TGAACATGTT CTAGTTGCCT
4951 CACATCTTTA CCAACACTTG GTATTTTAGT CTTTTCTGGT AGGCTACAAT
5001 TGTTTTTTAA AACTTAAAAG CAAAATAATA TTTGAACCCC TTTTTGAAAG
5051 AAAATCTTAC CCAGAATTCC AATATAAAAC AAGAGCTGCT TTGGTTGAGG
5101 TGAGTCTAAA CTAGACCATA TTTCCTTCTT TTGTTTTTGA GATGGAGTCT
5151 CTCTGTGTCA TCCAGGCTGG AGTGCAGTGG CATGATCTCT GCTCACTGCA
5201 ACCTCCATCT CCCAGGCTCA GGTGATCCTC CCATCTCAGC CTCCCGAGTA
5251 GCTGGGATTA CAGGCACGCA TCACCATGCC CAGCTAATTT TTTTTTTTTT
5301 TTTTTTGTAT TTTTGGTAGA GCCCCATGTT GGCCAGACTG GTCTCAAACT
5351 CCTGAGTTCA GGCAATCCAT GTACCTCAGC CTCCCAGAGT ACTGGGGTTA
5401 CAGGTGTGAG CCACTATGCC TGGCCAGCCA TACTTCTTTT TTAAAGATTG
5451 AATCCCTACT CTCAAAAACT GCTTTTTGGG GAATAAGGCA GAAAATACAA
5501 AATTATTACA TAGTGCCAAG TTGTAAATAT CCCATGTTCA TTATAATAAA
5551 GAATTTATTG CCCACAGTCA GTCATCCTGT GTGCTTTTCG TTTTTTAAAC
5601 ATTTTTATTC TGGGAAATTT TTTTTTTTTT TTTTTTTTCT TCGAGACGGA
5651 GTCTTGCTCT GTCGCCCAGG CTGGAGTGCA GTGGCATGAT CTCGGCTCAC
5701 TGCGAGCTCG GCCTCCCAGG TTCACGCCAT TCTCCTGCCT CAGCCTCCTG
5751 AGTAGGTGGG ACTATAGGTG CCCCCCACCA CGCCCAGCTA ATTTTTTTAT
5801 TTTTATTTTT AGTGGAGACA GGGTTTCGCC ATGTTAGCCA GGATGGTCTC
5851 GATCTCCTGA CCTCGTGATC TGCCTGCCTC GGCCTCCCAA AGTGCTGGGA
5901 TTACAGGCGT GAGCCACCGC GCCTGGCCGA AAATTGTTTA AAGTAAATAT
5951 TTTAATACTT AGTTCAGTAT TACTTAGTAT TACAATACTT AAATATTTAG
6001 GCAGCCTTGA AGGTTTGAAG ATGTCACCAG ATGGCCTAGG GATACTTGTA
6051 GAAGCTGTTG AAAATAGAGA TATCAGGAGA CCTTCACAGT TCTGCCTCTT
```

FIGURE 3B

```
6101 ATCTTGTTAA TTTTTGAGAG TTAACCTTTA CTTTGCTTAG AAATTTCCAG
6151 TTATTTACAG TCAGGGTGGC ATCTCTTGCG TCTCTGGGCT GTTCCAGTTA
6201 CAGAAAAGTC AGAGGCTCCT GCTCAAGTAT CTTGAAAAGA AAGCAGAAGT
6251 AAAGTTTGAG GCTATTTACG TTGCCCTCTT CTCATGGTTT GTGGAATTTT
6301 TTGTGGAATT TTAGTTGTCT CCATCAGGGA ACTTTTGGGA AGTTACAAGA
6351 GCGTACAGTT ACTTCTGTTA TTAAACTCAT TATGATACCA TGAAATTACG
6401 TGGAACAAAT AAAAGTCAAG TTTGCTAGGT CAAAAGAGCA AATCCAGAAA
6451 AGCAGATTAA TGTAACAGTG ACGCTTAGAC AACAAGTACA GGAATCACAA
6501 CTACAATTCA GAGACGAGTT CTTATCTACA CTTAGGGCAG AAAGAGAATA
6551 TAGCAACTAT TAAACACAAA TAAATTAGAA TGAAAAAGAT AATAGTAGTG
6601 ATAAGTACAA GAGAACAAAT AAGAACATGA AAACTGACAC CCTACAGCTT
6651 CTAATAAGTA AAGCAGACAA AAAATCCTCT AAATCAGATC AAAAGCAAAG
6701 AAAGACTGAA TAAATGAGTG AAAATAATGT AAAAAGGTTT TTGGAAATGG
6751 AGACATTTTT GAGGAAGTAG GAAGAATAAT TAGTAATTTA TTAAATTCAT
6801 AACTTTCTTT TTAATATAGA AAGTGAAATT TAGTTTTGTT AAAGAAAAAA
6851 TTATTCAGTG ATACCTGCTA AGGCATGAGG CAGTGTTTAT TTAGCACCAC
6901 TGCAGGAGGT ACAGGGACCA CTGCAGTCGG GTCTTGCAGT GGGGAATAGA
6951 GATTGGACTT AACTCTGAAT ACAGCATGGG CAAGTGAGAA TTTGTAGCCA
7001 GAGAGTAAGG TGAGGGTCAG TGGATGGAAA ATTACTACGA GGAAACATCA
7051 GGGGTCAGGG GCATTCTGGC TAAATTTACC TGATAGGATT CTCACTGAAG
7101 ACAGGCCGGG GTGATCAGAC ATCACCTGGA GGGTGGTGGA GGATGAGAAA
7151 CCCGATCAGA TCCTGAGAGT GATTAGATAT CAAGGGTAGG AGGTTGCTTG
7201 CTAAACTGCC TTAGCAGGGT TACTTTGCTA AAACTGGATT TTATAAAGAA
7251 GTGCACAGAT GGTCCTAGGA GAAGGTTCAG GAGCCTGACT GAAGTTTGGT
7301 CACACAAAGA ATCTTTGTCA GTTTGGAAAC TTAAAATTCT TATGTCTTAT
7351 GGGATTAACA GAAAGATAAC TCAATAGCCA CTTGAAATTC TTCTGAAATT
7401 TAAGGATAAC AAGAATATTT TGAGCAAGTG AAGAGAATGA CAGACCATAT
7451 TCACAAAGAT ATGAGCATTA ATAGCATGGA AAATTAACAG CAGGCAAATT
7501 AGGATCACCT GAGCTCTACT AGCTCAGTCT GAAATATCCC AGAAGAATTT
7551 TATAAATATT ACATGTGGTG TTTTGTTTTT GTTTTTGTTT TCATGAAGCT
7601 ATCAGAGAAC AAGTCTGTTT ATTTGTGAAA ACTTCTCCTT TGTGAAGCAC
7651 TGCCTAAGGA TGCTATTGGG CTATTGGGGT TGGGTCTTTT TTGGTTTTTT
7701 TTTTGGAGAC AGGGTCTTGC TCCATCACCC AGGCTGGAGT ATAGTGGCAA
7751 GATTGTAGCT CACTGCAGCC TTGAACTCCT GGGTTCAAAT GATCTTCCCA
7801 CCTTAGCTTC CTGTTAGTAG CTGGGATTAC AGGTGCATGC CATCATGCCT
7851 GGCTAATTTT TTTTTTTTTT TTTTTTTTTT TTTTTTGGGG GAGACAGGGT
7901 CTCACTATGT GTTACCCAGG CTGGATTCGA ACTCCTGGCC TCAAGCAGTC
7951 TTCCTGCCAT GGCCTCCCAA AGTGCTGGGA TTACCGCTGT GAGCTGCCAT
8001 GCCCAGCCTC CTTTTACAAG CTATATTGAA GAGAGAAGTG ACTGAGACAT
8051 CTTAGCTGGA GAGGAGGAAT TGAATAAACA AGGGATACAA GTGACAGAGT
8101 AAAATGGGCT GTGAAAGGAA ATCAGAGAGC TGATGAAACA TTGCATTTCA
8151 AAGTGTGTCA GGGAAAGATT GAGAAGAAGC AGAACCAGAA CATGAATTAA
8201 TAAGGCAACA TTTGTACTTT TCTTGGAGAA TATAGCAATT GGTAGCAAAA
8251 ATTAGAAGTT GGATATCAGA TCATTTATTA GTTTGATTAG ATTTCTCTAC
8301 AAATAGTAGA GATCCAAAAT AACAAAGATT TCCAAATAAT GACTACTATG
8351 TAGAAGGCAG ACCAGGGCTG CTTTGTCAGC TTTGCAGTCA TCTGGCATTT
8401 AGGCTGCTTC CAGCTTTTGT CTCCATCATC CCCAGGATCC AAGTTGGAGC
8451 GCCAGTCATT TCATCTACAT TCTAAGCAGC ACAGCAGGGG TGGATGTGTG
8501 TAAAACAAAT GGCGTTTAGT ATTTTTTGAG GATATTTCTT AGAAGCTTCC
8551 AGGTAGTACT TCTTGCTTTT CACTGGCCAT AACTGGGGTT CCTTTTACTA
8601 AGAAAAATCA ATTGGATATT GGGATAGGCA GATAGTAGTC TCTGCTACAT
8651 TATTGAGCAC CTACTATGTG CCAGACACTG TGTTAGCTCC TTGAGATAAA
8701 AGGTCTTTGC CTTAAAGGAA CATATGATCT AATAGAAGAC TTAGATTCAT
8751 ATATAATGCA GGGTTAAGAA CTATGGTCAC CACTGCTTCT TCATTGGTGA
8801 ATAATTAAAA ACAAACAAAA AGAGGCCAGG CACCCAGTGG CTCACACCTG
8851 TAATCCCAGC ACTTTGGGAG GCTGGGGTGG GCAGATCACC TGAGGGCAGT
8901 AGTTCAAGAC CAGCCTGACC AACATGGTGA AACCCCATCT CTACTAAAAA
8951 TACAAAAATT AGCCAGGGGT GGTGGCCCAT GCCTGTAAAC CCAGCTACTC
9001 GGGAGGCTGA GGCAGGAGAA TCACTTGAAC CTGGGAGGTG GAGGTTCCAG
9051 TGAGCTGAGG TCGTGCCACT GCACTCCAGC CTGGGTGACA GAGCAAAACT
9101 CTGAACAACA ACAACAACAA CAAAGAACTA TGGAAAACCA AGGAGAGGTG
```

FIGURE 3C

```
9151 CCTAACCCAG TCTGAGGTGT TCAGAGAGGT CATCTTGGGC AATGTGTCAT
9201 GAAACTGAGC CCTAAAGAAG GGTTTCCTCA AGCTTGGTAT GACATTTTAG
9251 TCAGATAATT ATTTGTTGTG GCAGCCATCC AAGATGATCA ACAGATAAAG
9301 GGAAGCGCAT TTAGTTTTGA CTTAGGGAAT ATTGTGCTCC CTGGGTGACC
9351 CATGGTTAAG GCGCTGTAGT TCTTCCTTGA CTGTCCAGAA TGTCTTTCCT
9401 TTTCCTTAGC CAATGAGCCA CCCAAGAAAT GTTACTCCTG GGAGAAGCCT
9451 GTGCCTAACT GTGGTTTACA GAATTCAAAG GGAAGAGGTA GTATGGAGGA
9501 CTCCTTGTGG CTTCACTCCT GGCCCAACCC AGGGCCTCAA AAGGACCTAA
9551 GGAACAACTA CGCCCTGTTA TGCCTGACCT ATGGACCCTA CCCTCTTGAC
9601 CATATAATGG AAGTCAGCTA AGCTTAGTCC CACCTGGACC TAGAACATGG
9651 TGTTTGTTTC CCATAGGTGA ATATATTTTT GAAAAATATA TTTTTGAAAA
9701 ATAAGTAAAA CAAAACCAAA TCAGGAAATA ATCATTGAGA AGTTACAATA
9751 TGAACACCTT AACAAAGATG AGTAACAATG TGGTGTTTTT TGCTAGAGAG
9801 TTCATTTCCA GGCAGGAAGT AGTGTGAAAC AAGGTTTGAG AGAAATGATG
9851 CGGACCAGGC TTTGGAGGGC CTTATATTTT AAGCTAAAGA TATTGAATTT
9901 TAAGCCAGTT GCCTTCAGAC TTCTCTTATT AGTGGAGCAC CCTTTTTTTC
9951 AAGTGAAATC TTGTTCGGAA CCTTGGTAGA TGATGTACTT GGAAGTGAAG
10001 TGGCCCTCCT TTAGGCAGCA TTTAATTTTG GTTGGATTTA ACAAAGAAAA
10051 CTGAAGTGAA GCTCATGGAA TTGCAAAACT ACAATTTTGT TTTTAAAAGA
10101 AAAACATTGA TTGTAATGTG TAAAATTTAC AAAACTGATA CACTTTTAAT
10151 TGGGATTATA TTGGTTTATA AAAACATTTA GTGTTTTTTT TTTTTTTTTT
10201 TGAGACAGAG TCTCGCACTG TCTTCTGGGC TGGAGTGCAA TGGCATGATC
10251 TCGGCTCACT GCAACCTCTG CCTCACGAGT TCAAGTGACT CTTCTGCCTC
10301 AGCTTCCTGA GTAGCTGGGA TTGCAGGTGC GTGCCACCAC ACCCAGCTAA
10351 TTTTTTTTTT GTGTGTGTGT TTTTAATAGA GATGGGGTTT CACCATGTTA
10401 GCCAGGATGG CCTTGATCTC CTGACCTCAT GATCCGCCTG CCTCGGCCTC
10451 CCAAAGTGCT GGGATTATAG GCGTGAGCCA CCGTGCCTGG CTCAAAACAT
10501 TTAGTTTTAA TAGGCATTTT AGGGTATGTC TTAGTCCATT TGGGCTGCTA
10551 TAACAAAATA CCACAAACTG GGTTCTTACA AACACAGAAG TTGATTTCTC
10601 GCAGTTTTGG AGGCTGGGAT GTCCAAGATC AGGCACTGAT GGATTCAGCA
10651 TCTAGTAAGG GCCTGCTGTC TGGTTCATAG ATGGCACCTT GTGTCCTCAC
10701 ATGGTAAAGG AGGTGAAGAA TCTCTCCCTG GCCTCTTTTG TAAGTGCACT
10751 AATAAGGACA CTTCCCAAGT TCCCATCTCC TAATACAGTC ACATTGGTGA
10801 TTAGGTTTTA ACATGAATTT GGGGGGACAC AAACATTCAG TCCATAATGA
10851 GGTATAAAAC TTAGAAGATT CCTGTTTTTT TTAAAAAAAT TCTTTTTTTT
10901 TTTTAAGATT TAAAATGTAA GCCTAGTTCA GAGTATTTTG CCAAGATGAA
10951 GTGTAGGGCA AATTGGATCT TTAAGTAGAG TAACCTATTA CATTGATTAA
11001 CTACTGTCAA AGAAAAGCCA AGCACATCAA GGGAATTATG GTTGGTACCC
11051 ATCCAGATAT TATACATGAA TTCATGGTTC CTCCTTGGTC CTTTTCTGAA
11101 TTACCTGTCT AATGAAGAAT TATTTCATTG TTTTTGAAAA CATCCTTACA
11151 TTTCCTCATT GCTGAAAATC ATGTTTTCAA ACATCAACCA TTCATCACAA
11201 TCACATACAG AACCTTTAAA AGACCTAAAA TTTCTGATTC AGGAGGTCTG
11251 GGATAGGCCC AAGAACTTGC GCTTCTAACA GGTTTCCCGG TGATGCTAAT
11301 GTTCCTGGCC TGATTTCACT TTGAGAACCA CTGCTTAAAA TCATGCTACG
11351 TTTTGTTTGC TTCATTTGTG GACTCAGACT TTCTTGCCCC TACAGCCTGG
11401 GCTGCAGCCA CACTGAAATA ATTGTAGCTA CAATTATTGC CACACCATTT
11451 ATTTAATCAG TTCCTTTGAA TGTGTTGTTT CCTGTGCCTG CAACACCTTT
11501 CTCTCACTTC ATTTCTTCAT CTGACCAACT CATGGTTGTA TTTCAAGATT
11551 TAGTTCAGGT TTCCTTTCCC TAAGGAAGAT CTCTCCAAGG CCCCCCTCTG
11601 TCTGGGATGT ACTTCCTATG CTTTCATGAG ACACTTGGCA AATGGAAAAG
11651 GGTTGATACT TTGAAGCTGG CTAGACTTTG TTTAAAGTCT TTCATTGACA
11701 CTAACTGGTT TTGTAACATT GCATCAAATA CTATCTCTCT CCGTGTCTCC
11751 ATTTTCTTAT CTATAAAACA GGGAAGATGG TGATGATGGT AATGATACCA
11801 TCCAACATCT ACTGAACATT TGTTATGTGC CAGGCAGTAT GCTGAGCTCT
11851 CTGTGTGCCT TATCTCATTT AGTTTTTATA TTTACCCTTT CACACTCACC
11901 CATAGGTGCC TTAAACATCT TAATTTTATA GATGAGGGAC TTGAGGCTCC
11951 CAGAAGTTGA GGAGCTTGTC CTCCGTCCCA CAGTTGGAAG ATGGTAGAGC
12001 CAGGCTGTGG ACTCAGGTCT TTGTCTTCAT CTATACTTTT AGCTCTTGTT
12051 GTATATACTT ACAGCATTTA TGAAGACAAA CTAAAACAGT GTGACAGTGG
12101 CTAAGCACAC GTTTTAGAGT CAGACAGACA TAGGTTCAAA TCCTAGCACT
12151 GTCCTTTATT GATTATGTGA CCTTGAGTGA GTTATTTGGT TTTGTCTAGT
```

FIGURE 3D

```
12201 CTTGGTTATC TCATCTTTCC TTTAGTTTTC TTATCCTGGA AATGGGAATG
12251 ATAATATGTT AGATCCCCCT TATCTGCAGA TGATATGTTC CAAGACCCCA
12301 GTGGATGCCC GAAACCCCAC TGATGGTACC GAGCCCTATA TATACTATGT
12351 TTTTTCCTGT GCATATATAC CTGTGGTTAA TTTATAAATC AAGCACAGTA
12401 AGATTAACAG CAGTAACTAA TTATAAAGTA GAACAATTAT AACAATATGC
12451 CAGTATTACT ACTTTTGAGC TTTATGGCCA TGATTAAGTT AAACAAGAGT
12501 TACTTCAACG TAAGCACTGC GATACTGCTA CAGTCCATCT GATAACAGAG
12551 GGCTACTAAG TGACTAATGG TGGGTAGTGA GTGTACATTG CATGGACGTG
12601 TTGAACAAAG GGATGATTTA CATCCCAGTC TAGACAGAGT GAGACAATGT
12651 TAGATTTCAT CATGCTACTG AGAATGACAT GCAATTTAAA ACTTATGAGT
12701 TGTTTATTTC TGGAGTTTCC CATTTAATGT TTTCAGACCA CAGTTGACTG
12751 CAGAGAACTA CCTGAAACTG TGGATAAAGG CTTACTGAAA TAGTATCCAT
12801 TAAGGATGAT AATAATAACT ATCCATAGGG TTGTCGTGAG GATTTAGTTA
12851 GAATGACTAT AAAGCCCTTA GCCAAGTGCC TGGTATATAA TGAGAGGTTG
12901 AAAATGTTAC CTGTTGTCTT TATTATTATA ATAATAAGGA TGATAATAAT
12951 ACCGATTGCA GATGATGGTA AGTAGTATTT ATAGAGTTGT GAGAATTAAA
13001 TTACTACAAA GCCTTTAGAA TAGCACCTGG CACATAGAAA TTGTTCAAAG
13051 TGGTACTTAT TAGTATGTTA TTTTTATTGT CGAACGCTTA TGCACTGTTC
13101 CCCTCCCTCT CCCCATCCCA AAATAATGAG TGTGAAACAC CTAGGTTAGT
13151 AGCAAGTGCA CCACAGGCTT TTGTTAATGT TCTTACACAT GCTCCTGTAA
13201 GCTTGTTTAG GGCAAAGGTA GTCTTGAAGT CATGAAATGT TTGTCTCAAT
13251 GAAGCAAAGT AAGCACCCGA TTTGAATAGC TCTAGTAGGA AACTAACATG
13301 GCAGGTTGGG AATGCTGGCA TTACAGTAAC AATAATCTCT GAAACTACTT
13351 GGAGGTGACC TTTGATATTT CATTGTCATG TTTTCCCTTT TTCCTTTGTT
13401 TCTTTGTTTA GTTTGCCTGT TGGTAAACTT TATATAAATG GGATCATGGT
13451 CTGTGTTTTT TTCGGTCAGG TTCTTTTTTT TTTTCTCTGG CCTAACATTT
13501 TCTTTTGAGA TTTACCTGTG TTGTGGTATA TAGCTATATC ATCAGTTTTA
13551 ATTGCCAAAA TACTATTCTC TGGTATAATA TAGATTATTT ATACATTTTT
13601 ACTATTGATG AACATTTGGA TTGTTTTTAG TTTGGAGCTA AGGACATTTT
13651 TGAAGGTGTT TCCTTCAAGA GTTTCTCTAA GATATACACT TTGGATTAGA
13701 ATAGCTGGAT TATGAGCAGT ATGCATATTC CACTTGTTTT TCTTTTTTGT
13751 TTTTTGAGAT GGAGTCTCGC TCTGTCGCCC AGGCTAGAGT GCAGTGGTGC
13801 GATCTCGGCT CACTGCAAGC TCCGCCTCCC GGGTTCACGC CATTCTCCTG
13851 CCTCAGCCTC CCAAGTAGCT GGGACTACAG GCGCCTGCCA CCACACCCGG
13901 CTATTTTTTT GTATTTTTTA GTAGAGACAG GGTTTCACTG TGTTAATCAG
13951 GATGGTCTCG ATCTCCTGAC CTCGTGATCT ACCCGCCTCG GCCTCCCAAA
14001 GTGCTGGGAT TACAGGCTTG AGCCACCGCG CCCAGCCTTT TTTTTTTTTT
14051 TTTGAGACGG AGTCTCGCTC TGTCGCCCAG GCTGGAGTGC AGTGGCGCGA
14101 TCTCTGCCCA CTGCAAGCTC ACACCATTCT CCTGCCTCAG TCTCCCAAGT
14151 AGCAGGGACT GCAGGCGCCC ACCACCATGC CCGGCTAATT TTTTGTATTT
14201 TTAGTAGAGA CGGGGTGTTA GCCAGGATGA TCTCGATCTC CTGACCTTGT
14251 GATCCGCCCA CCTCGGCCTC CCAAAGTGCT GGGATTACAG GCGTGAGCCA
14301 CCGTGCCCGG CCAGTAGCTT ATCTTTTAAC TTCCTTTTTA ATATCTTTTT
14351 TGTCAATGAC CTCACTTTAA CAGAATTAAG AAAAATAAGA AAAATCTTTT
14401 GATGAATTTA AGTTTTAAAC TTGTATTTAC CAATCTTTTT CTTTAGAATT
14451 TTTTGTAAAA AAATTCTTCC ATACTCTGAG GTCATAAAAA TAGTTTCCCA
14501 TGTTTTTTCC AAAACTTAAA ACAAATTTCT TTTCATGTTA ATCTGGAATT
14551 TATTAATCAA TATGGAATTT ATTTTCTTGT GTGAGGTGCA GATTCATTTT
14601 CATATTTTTT CTATAAAGAT GACCAGTTTC CCGGAACCAT CTATGGAAAT
14651 ACAGTCAGTA CTTTGGATCC ATGGGTTCCA CATCCATAGA TTCAACTAAC
14701 CTCAGGTCAA AAACATTCAG GGGGGAAAAA TTCCACAGAG TTCCCAAAAT
14751 TACAACTTGA GCTTGCCATG TGCTGAATAC TACATTGAAT CTACGTGAAT
14801 GAAGTGATGT GTGGGCATCG TTAGGTTAGG TATTATAAGT AATCTAGAGA
14851 TGATTTAAAG TATAAGGGAA GATGTATGTA GGTTATATGT AAATACTGTG
14901 CCATTTTATA TGAGAGATTT GGGCATCTGT GGATTTTGGC ATTTGTGGGG
14951 AGTCCAGAAA CCTAGGGGAT TGTCCTAATG ACATGCAGTA CCAGCTAGGT
15001 TAAACATCAG GTTTCCATGT ATGCATTATT CTTTTAGTGA GATCGCTTTC
15051 TTTTTTTTTT TTTTTTTTGA GACAGAGTCT CACTCTGTTG CCCACGCTGG
15101 AGTGCAGTGG CACGATCTCA GCTCACTGCA ACCTCCGCCT CCTGGGTTCA
15151 AGCGATTCTC ATGCCTCAAT TCTCCCGAGT AGCTGGGACT ACAGGCGTGT
15201 GCCACCATGC CTGGCTAATT TTTTGTATTT TTAGTAGAGA CGGGATTTCA
```

FIGURE 3E

```
15251 CCGTGTTAAC CAGGATGGTC TCTCTCTCCT GACCTTGTGA TCCGCCCACC
15301 CTGGCCTCCC AAAGTGCTGG GATTACAGGC ATGAGCCACT GCACCCAGTC
15351 AAGAAATCCT TCTTCACTTA GTCTATCCTA ATGCCATATA CCACTCTATT
15401 TTAATTACTG CAGTTTTAGA AAATGTCTTC GAGTTAGCCA GGCGCGGTGG
15451 CTTATGCCTA TAATCCCAGC ACTTTGGGAG GCTGAGGTGG GCGGATCACT
15501 TGAGGTAAGG AGTTATACCC CAGCCTGGCC AACACGGTGA AACGCCATCA
15551 TTACCAAAAA ATAAAAATTA GCTGGGCATG GTAGCGGGCA CCTTTAGTCC
15601 CAGGGAATGG AGGCAGAAGT TGCAGTGATC CAAGATTGTA CCACTGCACT
15651 CCAGCCTGGT TGACAGAGTG AGACTCTGTT TCAAAAAAAA AAAAAAAAAA
15701 AAAGAAAGAA AGAAAATGGC TTAGAATCTA ATAGGGTAAT CTCCCTGCTT
15751 AGTTCTTCTC TAGGAATGTC TAGGCTGTTT TTAAACCCTT TGGTCCTCCG
15801 TATATATTTT AAAATCAACT TGCCTGATTT CATGAAAAAT CAGACTAAAT
15851 TTACATTGAA CCTGTAGGTA ATTTGGGGGA GGATTGCCAT TCTTAAAATA
15901 TTAAGCCATT CTATCCATAA TACAGTGGGC CTCTCCTTTT ATTTAGGTCG
15951 TCTACAATAT CCTTTGATGG TATTGTATTT TATAATGTTC TTCATAAAAG
16001 TATTGTACTT TATTTGATAA GTTTATTATT CAGTACCTTC TTTTCATTGG
16051 TAATGTAAAT ATGTGTATTG TTTTTATTTA TTTAAGTTAT TCATTTATTC
16101 TTTTGGGATG GAGTCTCACT GTGTTGCCCA GGGTAGAGTG CAGTGGTGCG
16151 ATCTCAGCTC ACTGCAACCT CCGCCTCCCG GATTCAGGAG ATTCTCCTGC
16201 CTCAGCCTCC CGAGTCGCTG GGATTGCAAG TGTGAGCCAC CAAGCCTGGC
16251 TAATTTTTGT ATTTTTAGTA GAGACAGGGT TTTGCCATGT TTTCCAGGCT
16301 GGTCTCAAAC TACTGAACTC AGGTGATGCA CTCGCCTCAG CCTCCCAAAG
16351 CGTTGGGATT ATAGGCACAA GCCACCATGC CCAGCCAGAT ATGTGTATTG
16401 TTTTTAAATG TTCTTTTAGT TGCTGGTGTA TATAATTGTA AATGACTTTT
16451 GTATATCTAT ATCCCGCAGC TTTCCTAATG TTTTGTGGTT TTGCCTAGGC
16501 TAGGACTTCT AATAGTAGTA AGCAACCTTA TTTTAAAACA GTTGTTGTTG
16551 CCAGGCGTGG TGGCTCACGC CTGTAATCCC AGCACTTTGG GAGGCCAAGG
16601 CGGGTGGATC ACGAGGTCAG GAGATCGAGA CCATCCTGGC TAACATGGTG
16651 AAACCCCGTC TCTACTAAAA ATACAAAAAA TTAGCCGGGC GTGGTGGCGG
16701 GCGCCTGTAG TCCCAGCTAC TCGGGAGGCT GAGGCAGGAG AATGGAGTGA
16751 ACCCAGGAGG CGGAGCTTGC AGTGAGCGGA GATCATGCCA TGCACTCCAG
16801 CCTGGGTGAC AGAGCGAGAC AACGTCTCAA AAAAAAAAAA AAAAAAAAGT
16851 TGTTTTTAAG TGGGGACAGT TTGTTCCCTA GGGGACATTT GGCAATGTCT
16901 GGAGACTTTT TGGTCATCAC AGTTGGGGAA GTGGAGGTGA TACTGCTGGC
16951 CTCAAATAGA AAGAGGCCAG GGTGTTGCTA AACATCCTGC AATTATAGGA
17001 CAGCTACTAC AACAAAGAAT TTATTCAGCC CCAAATGTCA GCTGTGCCAA
17051 GGTTGAGAAA CTGTATTTTA AAGGGAATGC CTTAAACAAT ATTTTATTAT
17101 TATGCAGAAT TCCAAACACA AAAATAAATT GGTAAACAGA ATTCCCAATA
17151 CCAACAGTTA ACTATTGTAG GCCAGTATTT AACTCCTTTC CTTCCCCCAA
17201 CTTCTGCTGA ATTATTTTAA AACAAATACA AGATATCACA TCATTCCATC
17251 TGTAAATACT TCTCTGTGTG TCACTAAAGT AGAGGTTCCC AAATTATGGT
17301 TTCAGAATAC CCAAAAAATC CTTCAGACCC TCCCAGAAGA TCTCCAAGGC
17351 TAAAACTATT TTCACAATGG TACTAAGATG TTATTTGAAT TTTCATTCTG
17401 TTGACATTTG TGCTGATAGT GCAAAAGAGT TGAAAATTGT GGATGCCTTA
17451 GCACAAATCA AGGCTCTGGC ACCAAACTGT ACTTAGTGGT CATTGTACTT
17501 TTAGTACTGT CAAATTCTCT TCTGCTTAAA AAAAAAACCA ACTAGATTTA
17551 AGTAAGAATG TGATTCATGA AGCAGTACAG TTTTTTTTAG TCTTCTACCT
17601 AATGGTTTTA GTGATCATTG ATGAATCATT GCCCAGACCT ACTATTTTAT
17651 TAAGTCTGGC CAAATGGTGG TAGTCTAATT TAAAATTTCC TTCTGTATTC
17701 ATTAATGATA TTTTTCTATA AAGAAGACTG TGCTTATACC AACTGTTTAG
17751 TTACTCCTAA ATATCCTTTG TGTAGGAAAT GGAGGAAAAT GATTTATTTA
17801 TTTTTTCCCA GAACAGAGTT CACTCTAAAG GGAATATGTT TAATGAATTT
17851 TGTTGTATTT ATTTTAATGT ACATTATTGG TATATGCTGT TAGTTTTCTT
17901 TCTCTTTGTT GATATCTTTT ATCAAGTTAA AGAATTTCTC TTCTATTTCT
17951 AGTTCACTAA GAGTTTTCAA AGTTAATGGA TATTGTATTC ATTTTCCATT
18001 GCTGTGTAGT AAGTTACCCC AGAATTTAGT GGCTGAAAAC AACAAACATA
18051 AAAGTTTCTG TGTGTCAGGA ATATGGACAC AGCATAGCTG GATCTTCTGC
18101 TTCAGAGTCC CTCACAAGGC TGCATCAGGG CTCGACTGGG GAAGGAATGA
18151 TTTCCTAGTT CATGTGGTAT TTGGCAAGAT TCAGTTCCTT CTCTGTCTTA
18201 GGTGGAGGGC CTTAGTTTCT TGCTGTGTGT TTCTGTATAT GGCTACTTAA
18251 CATGGCAGCA GGCAAACAAG AAGAGCCAGA GAAAGTAAAG AAGATGGAAG
```

FIGURE 3F

```
18301 TTACATCTTT TCCAGCCTTA TCTCAGAAGT GACATCCTAT CACTTTTGCC
18351 ATATTCATGA GAATCAAATT CCTAGGCCCA GCTAAAATCA AGTAGACGGG
18401 ATTACACGAA GGTAGGAATA TCAGGAGTTG GGAACCATCA GGTGCTATTT
18451 TAGAAGCAGC CTTCCAGCCT GCCCTGTGGC CCCCAATGAC TCATGTCTCT
18501 TGCATATGGC CCTCTTAATT TGCCCCTTCC TCCAGGTCTC CAAAAGTCTC
18551 ATTCTGTTAC AGCATCAGCT CAAAGTCCAG AATCTTGTCA TCTAAATCAG
18601 GTCCAGTTGT GAGTGAGGCT TATGGGTGAA GTTTCTTTTT TTTCTTGAGA
18651 CAGCATCTCA CTCTGTTGCC TAGGCTGGAG TGCAGTGGCG CAGTCATGGC
18701 TCACTGCAGT CTCAACCTCC TGGGTTCAAG TGATCCTCCT GCCCCAGCCT
18751 CCTGAGTAGC TGGGATTACA GTTGTGTGCC ACCACACCTG GCTAATTTTT
18801 TTATTTTTAG TGGAGATAGG GTTTCGCTAT GTTGCCCAGG CTGGTTTCAA
18851 ACTCCTGGGC TCAGCCCCCC AAAGTGCTAG GATTACAGGT GTGAGCCACT
18901 GCACCTGGCC AAAGTTTTTA AAATACAGTT CCTTGTGTAC AGTTCCATTC
18951 AGTCTGTAGA AATGTGACAT TAAAGATACA AGTTATCCTC CCTTCCCTAT
19001 ATCCAGTATA CAAGGGTGGA ACAGGCATGG GATAATAGAC ATTCCTGTTT
19051 AAAGGAGGGA AAATAGGAGG CACAGAAGTG TTACTAGTCC ATATCAATTC
19101 TGAAATCCAG CCAGGATGTT AGAAGTTCCT TGATTCCACC TCTGAGTTAT
19151 TCTTCCTTTT TCATGAAAGG TAGCATGTGT TAGCAGCTGT GTAGTTTTTT
19201 ATTAGTCTGC TTCCTGCCAG TAGAATTTTG GGAGTCTAGT GACCTCTTTT
19251 CGTGTTATAC TATTTCTGGG TTTTTTTGGT CCAGCCTGGC AGTGTTGCTG
19301 CTGATATAAT TTTCTCAAAA ACTTTGTCAG TCCTTTGTGA AACTCACTGG
19351 TGTTCATTCC ATTGGGTAAT AGTCACACCC ACGAATCTAA GGTACACCCT
19401 TCTTTACTTT GTGATCTTTC TCAGATGGCT GAGGGACAAT GTTCTTAAGT
19451 TTCCTAGAGC CCCTGTTGTT GAGTCGCGAG GACCTATTAG GCACACCCTT
19501 AATTTCTTTA AAGAGCCCTT TGTATGACAG AATTACTGGG AACCATTTTC
19551 CAAGTAGCCC ACCACAAAGG TTGTATTTTG TCAAATTGAA GGAGTCATCT
19601 GACTTTCCTT AATCATAAGC TACAAATATA ATAAGCTACA TTAATAGATT
19651 TTCTAATATT TATTTAACTT TGAATTTCTG GAAAAAACCC AACTTGGTAA
19701 TGATTTATCA TCTGAGCTTT GTTTTTGGCT TTGGTATGCT AATTTTTGGC
19751 TTAGGATTTT TATATCTATT TCATGAGTGA CACTGACCTG TAATTTTCCC
19801 TTTTCTTACT CTCTATGTCT GTTTTTTTTT AATATAGTTA TGCTTCCCTT
19851 ACAAATTACT TTTGATTGTC TTTTCCCTCA ATTTTGGATC ACATTTTCCT
19901 GATGCTCTCA TTTGAGTAAT TTTGGAGTTA TATTTTGTGT TTCTAAGTCC
19951 TGTTAAAATC CTTGGAAGAA TGCTGATTTT ATTTTTGTTT TGGTAGACTG
20001 TCAGGCTGGT TAGGTTCTAA ACCACAAGTT TTCTCACCTG TGAATAGTAT
20051 TTCCAGTATC AGTTCAAAGA CTGTGCTATG CTACTTTGGG TCTTTCCTAT
20101 CCACAGACCA TTTATTAGTT AGTTTGGAGC TTTGGCAACA GTTTATATTT
20151 TAATTTATTC TCAGAGCCTT TGCTGTGCTT CCCTGAATCT CTCTTATGTG
20201 TGAGCTAGAA GTTGTGCTGG TTCATGTGCA AAATTACGGG AAACCCTTTC
20251 TCTGGCTCAT CTTTTCCTGG ATTCCCCACA TCTCTCTGGC TCACAGAGGC
20301 TCCTTTCATT GTTATTCTAG TCAGACGTTT GGATTTCTTT CAGAGCTTTA
20351 GCTGCCTGCG ATGCGTTTCT GTATGGCTGG TGCCACCCTT AGGGTGAAGA
20401 GCTCAGAAAA AGTGTTAAAA ATAATGAGAA TGATTCTTAC GCTCCTTAGA
20451 CCACTGTGGT CTTTCCCAAT TATTTTTGCC TGAAATGAGG GGTTTTGCCC
20501 AGAGTTTTTG CTGCTCACAT TTGTGCATAG TGTGGACTTA TGGTTCTAAT
20551 TTTATTCTAA GGATCTTTAT ATTTCTCAGG GTTTTTTGTT TTGTTTTTTG
20601 AAAAAGTCTT AGTTTCTTAG CAGGTTATTT TTGGTTTATT TAATTCTGGG
20651 TTGGCAATAA TTTTCTCTTA GTGTTTTGAA GATATTATTC CACCATCCAC
20701 TAGTTGCAGT GGTTGCTGTT GAAAAACCTG CTGTCAATAA TTGTCAGGCC
20751 TTTGTTATAT GTCATTTCTC TGACCACTTT AAGCTCTTTA TCTTTTGTGT
20801 ATTTTGTTTT TATTACTGTA TTTTGTGAGT AGGTGTGGAT TCCTTTTTTT
20851 GTTTAGCTTG GTAAATGCTC TTCTTGTAAA TATAATTTTA GTTTCTTTAG
20901 ACAACATAGG GCTATTTAAA TTGTTTCTTA AGTGAGCTTT GGTAGTTTGT
20951 CTTTCAAGGA ATTTGTTCAT TTCCTCTAAG TTGTTGAATT TATGGGCATA
21001 AAGTTGTTCA TAATCCTTAT TATCATTTTC AATCCATAGA ATCTGTAGTG
21051 ATCTGTAGAA CCTTGCATTC CTGAAATCAG TAATTTTTAC TTGGAACGTG
21101 TTGAGCTCTT TGGATCAGTG AGTTTTATAG TTTATATAAA ATTTGGAAAA
21151 TTGTGTACTT TTTTTTTCCA AATTTTTTTT CTCTTCTTTC TCCTTTCCTT
21201 CAGGACTCCA ATTACACATA TATGAGACTG TTGGAAATGT TTCCATAGTT
21251 CACTGATTTT TTTCAATTTT ATTTTCAAAA ATAGGCTTTG TTTTTTATAG
21301 CAGTTCTGGA TTCATGGCAA ACTTGAACAG AAAGTGTAGA GAGTTCCCAT
```

FIGURE 3G

```
21351 ATATGACTTA TCCACACACA TGCACTGCCT ACCCCAATAT CAGTATCCTA
21401 CTGGTATATT TATTACAATC GATGAATTTA TATTGACACA TTATTATAAC
21451 CCAAAGTCCA TAGTTTACAT TAACGTTCAC TCTTGGCATT GTATATTCTG
21501 TGGGTTTTGA CAAATGTATA CTACCATATA TCTACCATTT TAGTATCATA
21551 CAGAATATTT TAACTGTCCT AAAAATCCTC CGTGTTCCCC CTATTTATCC
21601 TTTCCTTTTT CAGCCCCTTG GCAACCACTG ATTTTTTATT CTAGCCATAG
21651 TTTTGCCTTT TCCAGAATGT CATGGAGTTG GAATCATACA GTATGTATTC
21701 TTTTCAGATT GGGCTCTTTC ACTTAGTAAT ATGCTCTTTA CTCCATGTCG
21751 TCTCATGTCT TGATAGTTTA TTTCTTTTTA GCACTGCTGT CAATACAGCT
21801 TAAGTATCTC TTATCCGAAA TGCTTGGACT AGAAGTGTTT CCAATTTTGG
21851 ATTATTTTGG ATTTTGAAAT ATTTGCATAT ACCTGATTAG ATCTACTTGA
21901 GAATGGGATA TAAGTCTAAA TATGAAATTC ATTTATGTTT CATATTACAC
21951 CTTATGCACA TAGCCCAAGG TGATTTTATA CAATATTTTG AATAATTTTG
22001 TTAATGAAAC AAAGTCTGTG TTAAGTATGT GTGGAATTTC CCACTTGTGG
22051 AGTCAATGTG AATGTCACAA AATTTCGTAT TTTGGAGCAT TTCAGATTTT
22101 TAGATTAGGG ATGCTCAACG TGTACTTGAA TGACTGTACT CCATAATAAC
22151 TGTGGAATAA TCTGTGGAAT AACTGTTTTA ATGCATTTGG TAATTCTAAC
22201 ATCTGTGTTA TTTAAAAATG AGTATTTTTC TCATTACGAG TTGTGTTTCC
22251 CTGTTTATTT GCATGCCTGA TAATATTTGG ATGCCAGATG TTGTAAATTT
22301 TACTTTTTTG GTTGCTGGAT ATTTTTTGTT TGTTTTATTT TTGTTTGCTG
22351 GATATTTTTG TAGTTCTGCA AATATTCTTG AGCTTTGTTC TGGGATGCAG
22401 TTAACTTACT TGACCAGTTT GATCTTTGGG GTTTTTGCTT TTATGATTTG
22451 TTAGGTGAGT CTGAAGAAAT ACTTAGTCTG TGCCTGATTA TTCCCTATTA
22501 CTGAGTCAAG ACCTGGCTGA GTACTCTACT AATATCCAAT AAATTATGAG
22551 TTTGTCCACT CTGGGTGGTA AGAGCAAGCA CTATTCCTTG TTCTATGTGA
22601 GTTCTGGGCA CAGTTCCCTG TAAATTCGTT CTTTCCATTT AGCACATCTC
22651 CAGAATTCTC TCTGTATACA GCTCTCTCCT CTTTGATTCT CTGGCCTGAA
22701 AACTCCAACC AGGACTTTCA GCTCCATTTC TCAACTTAGA GTCTGCTGGG
22751 CTCTGCCTGG GACCCCCTTC TTATACCACA GTCTGGATAT TTTCTCAAGG
22801 CAGTAAGCTG GGGCAATTAT GGGGATCACT TTTTTCCCCA TTTCTCGGGA
22851 AACAGTCTTC TTCATTGCCC CTAATATCCA GTGTTTTGAA AATTGTTGTG
22901 CAACGTATAT TGTCTTTTTT TTTTTTTTTT TTGGTTCTTT CGGGTTGGAT
22951 TACTTTGAAG CCTTTCATTT ATAGATATTT CAATATGGTC CTTTGAAAGA
23001 TAAGCACTCT TTACTTTTTT CTGAAACCTT TTATATTATC TGAACTCATC
23051 ACGTGTGGGC AGCACTGTGT TGCTGTGTTC ATGAAACATT TATAAGTTAT
23101 GTACTAGTTT GCTTTATTTC CCAGTATATC AGTTTTGTTC AGTAACAATC
23151 ATTTGATAGA TTAGTGCTCA CCTTTAAATT TTTTAAAATT TTGGGCAGCT
23201 GATGGCTATG TGTGTTATCT CCTATTTCTT TATGTTATCC TGGATTCAGA
23251 GCCATAGAAT ACTACCTAGA TTCTTTAGGA AAGTCTTTGT GTGCCTGACA
23301 TTCTGTTTAT CATTTTCATA TATTTAAAAA AATATATTTA ATACATGTAT
23351 TTTTCCATAA AATATATGTT GTCATATTGG GTTCAGATCT TGGCTTTACC
23401 ACTTACTGAC TGTGGGACCT TGAATCAGAT ACCTAACCTT TGTATGCCTC
23451 ATTTTCTTCA TGTGTAAAAT GGTGATAGTA ATGGCATTTA CGTCATAGGG
23501 TTGTTAATAA GGTTTAAATG CATTAATAAT ATGTAAAGAG CTTAGGATAG
23551 TATCTGGCAT CTAAGTGCTA TAAATGTGTG TTAGCTCTTA TTATTTTTAC
23601 CACAACTACC ACCACCACTG CATATATTAC TGCTAGTGTC CATGCCAGGA
23651 GAACCATGTC TGTTCCCTAG GTGGCATATG GGTGTGTGTA TGTAAAGATG
23701 AGGTGACTGT GTGGTCTTGT GCTGCTCTCT CTGAGCCCTC CTTGGCCTCT
23751 GGAGTAATAG TATTGCTGTC CACCTGGTCA ATGTGTCCTG CTGATAAGTG
23801 CTGTTGCAGT CTGTGGTCAG CAAATGGTCC AGTGGTTCTC CTTGCTTCAC
23851 TGGCCTCACC TTGGCTCATG CTGACTCTGA GGTTTGGGTG TCATATTCTT
23901 TAAGCCCTGG ACCTGGGCAG TAAGACAAAT AGCCCTTAGT TACTGAATCT
23951 CTTTGCCTCC CCTGGGGCAA AACCCTGTCC TTCAGTGATT TTGCTAGCAG
24001 AATCCCCACC TCCCTTCCTC TTCTTTCATT GGGCATACAG AAAATTTGGG
24051 ATGCCTTTTA TGCCTTGTGG GAGCCAGAGA ACTCTGGATA ACTAAATCCA
24101 TGCCCTCCTT CCTCCTAACC CTTCTATGTT GATGATTCCG CCCCCACATT
24151 TTCATTAAGG GTCATCTTGT GTAGCAGTCT CCTCCCAGAA CCCCAAATGG
24201 GAGATGGATC AAAGATGCCT GTTTTTTTAG CTTTTTCTTC CATCTGCCTA
24251 GCATGTCTTT TCCCTTTTGG AACTCTATCC TGGAGAGAGG AGATGAGAAC
24301 AGACTTGTGT CACTGCTGCT TCCTTCCCAC TGTTCTCTTC TCCTGTCATG
24351 AAGACACCAG AAGTCTAGGC CGGGTAGACT TTCCATTTCC TCTTCCACTT
```

FIGURE 3H

```
24401 TCCTTTGGGC ATGATGGCAG GTGTGATACT GGGAAGGGGG AATCTGCTTG
24451 CTGATAAGGA AATGTGTGTT GGGAGATATT TTAAAAAATA TAATCCTTGG
24501 CTGGGTGCGG TGGCTCATGC CTGTAATCCC AGCACTTTGG GAGGCCGAGG
24551 TGGGCAGATC ACCTGAGGTC AGGAGTTCAA GACCAGCCTG GCCAACATGG
24601 TGAAACCCCA TCTCTGCTAA AAATACAAAA AAATTAGCCA GGTGTGGTGG
24651 CATGTGCCTG TAGTCCCAGC TACTGGGGAG GCTGAGGTAC TAGAATCGCT
24701 TGAACCTGAG TGGTGGAGGT TGCAGTGAGC CCAGATCGTG CCACTGCACT
24751 CCAGCCTGGG TGACAGAGTG AGACTCCATC TCCATAAAAA AATAAAAAAT
24801 AAAAAAATAA AAAAATAAAA TAAAATATTA TCCTTGTTAA ACAGGTTAAA
24851 GGGAAAAAGA ATATTTTAGG GTAAAGGTGG GGGTGCCAGT TTAGATGGGA
24901 ATTAGGGAAG GTTTCTCTGA GGACATAACA CTTGAACAAT TTCAAGGCTG
24951 TTTTGTAGTA TTGACAAAAT TTAATACTAG GATCAAGATT GCTTGTGCAC
25001 AAAGCCAAAA GATGGGCTCT CTTATGCCCT CTTCTTCCCA TACTGCAGTT
25051 AGTACATTCT GTTTTCTGCA GTGGTAACTC TTTCTGGCCT AATTGCTCAG
25101 TTTCTCGTAC TAGTCTCTGT AACACATTTA TTCTGCTTAT CACTATAGAG
25151 TCCTAGTATG TAGAGGCTGA CAAAAACCTG AGGCAATATT TCTTCAAGCA
25201 AGCTACCGGT TTCAGAACCA TCTGGAACAC TTAAAATTGC TCCTCTCGAA
25251 CCCACTCCAG TGTCATAATT ACTAACAGTT TCATTTGGAA TCTGATACTG
25301 TTGAATTTAT CATATTACTT GAGGACGAGC AGTTTGTTAT TGTTATCTTT
25351 TTAGCCACAC AGCATTGTAA ATTCTAAGTA AATGCTTGAT AAATTGATTT
25401 ATTAGGAAGC TAGGAGAGAG GCATTTCAAG TGGTTTAAAA AGTTTTGCTA
25451 TTTGGGGGTG ACATCAGCAA AAGCGGCACA GTAAAGAAGT GTAAAATTTT
25501 ACCCTTCCAT AAGAGCGACA GAAGAACTGG CAACACCTGT CAGAATCAAC
25551 TTTTTCAGAA CTCTAGAAAT TAACCAAAGA CTTGAAAAAA AGTGTGAAGA
25601 GTGCTCATTC ACAAAAAATG GCTGAATCTT AGTAAGAATA GTGAGCTTAC
25651 CCAAGCCCCA TTCCCTGTTC CATGTGTCAG CTGGGGCTGA AATAACAGCC
25701 TGTGTTTCTG TACTGGAGGG AGCAGAACAG ACCTCATTGT AAGTATTTGT
25751 TTTGCCTTCT TAGGTGGATC CCTGGATGAA TGACTTCAAA ACCTTGTCTC
25801 TATTTCTCCT GACTCAGAAC TGCCCTACTT CTGAGATCGG GGAGGACAGT
25851 AGTTATCAAG AAACATTTAC AGACAAATAA TTTAGTCATT GCTTCCTGAA
25901 TCAAGAAATA ACAATGGGGG CAAACAGTAG ACTAACTAAA GAGCCTAGGA
25951 GCAGAGATTG GGAATGAGAT GTCTATGAGA GCTTTGAAAA GCTTCACATA
26001 TTCCCAAGAA TGTAGAAGGC CACATGCTTG GCAAGGACTG TATGCATGCC
26051 CAGGGAAGAC TTCTACCTCT CGCTGATCTT GAGGCTCTGT GAAAGCAGGA
26101 AGTGAAGCCT AAGGCAGAGT TAGAAGCTAC CTGGCTAAGT AGTGAAGGTG
26151 TATCCCAAAC CTACCCAGAG CCCTTCTGCA AAGACAGACA GGTTTTTTGG
26201 TTCCAAGCAT TTAAGGCAGT CTGTTCAGTT GTTAGCTGGC CATTAAGCTA
26251 ACAGAATAGA GACTCCAGTG ACTGCACATA ACAAGGAATA CAGATTTTAC
26301 AGAATTAGTT TTGATAAGTC TTGAAACAAA CAACTACAAC AATAAGCAGC
26351 AACAAAAAAT TCTGGAGAGG GGAGAGAATC TGATTCCCAG AGTTGCCACA
26401 TTATAAGATT TAAAATGTCT AGTGTTTAAC AAAAAAGTGT AAGATATGAA
26451 ACACAACAAG AAAAAAAGCC ATGAATAGAA ATTGTCCCTG AGGAAGCCCA
26501 GACGTTAGAA TTTCTAGACA AACACTTTAT ATTAGCTATT TAAAATAATT
26551 CTTCAAGAGC TAAAGAAAAC CATATCTTAA ACAAAACAAA ACAAAACAAA
26601 AAACCCAAAA ACCTAACTGA AAGTTTGAGA ACAGTGTCTC ACCAATTGAG
26651 AATATCAACA AAAAGATAGA AATTATGAAC TAAACCAGAT AGACAAGCAT
26701 GGTAACTGAA ATGAAAAATT TGCTTCTAGG GCCCATCAGG AGATTTGAAC
26751 AGGAAGAAGA AAGAAATTTG AAGGTAGTTC TATTGACTTT ATCTAATTTG
26801 AAGAACAGAA AAGGAAAAAA GTAATTAGGA AATATAAATA GAGCCTAAAG
26851 AGACCTGTGG GATACCATCA AGTGTACCAA CATACACATG ACAGGAATCT
26901 CAGAAGGAGA GGAGAGATGG TGGGGCAGAA GGATATTTGA AGAAATAATG
26951 GGCCAGGTGC AGTGGCTCAT GCCTGTAATC CCAGAACTTT GGGAGACCAA
27001 AACAGGCAGG TCTCTTGAGC CCAAGAGTTT GAGACCAGCC TGCGCAACAG
27051 CGTGAAACCC TGTCTCTACA AAAAATACAA AAATTAACCA TACGTGATGA
27101 CATGTGCCTG TAGTCCCAGC TACTCAGGAG GCTGAGGTTG GAGGATCACT
27151 TAAGCCCAGG AGGCCATGGC TGCAGTGAGC TGTGATTGCA CTACTGCACT
27201 GCAGACTGGA CGACAGTGTG GAACCCTGTC TCAAAAAAAA AAAAAGAAAA
27251 AAGAAAAAAA GGGAAAGGGA AGTGAAATAG TGGCTAAAAC CCCAAATTTG
27301 ATGGAAAAGC ATGCATTTAT GCATACAAGA AGCTCAGTAA ACTCCAAGCA
27351 GGATAAAACC AGAGATTCAC AGCTAGACAC ATCATAATCA AACTGTTGAA
27401 AGCCAAAGAT AGAATCTTTA AAGCGGCAAG AGAAAAGCAG CTCATCATGT
```

FIGURE 3I

27451 ACAGGGTAAC CTCAGTAAGA TGAACAGCAG ACTTCTCACC AGAAACTATG
27501 GTGCCCAGAA GGCAATGGGT TGATGTACTC ACATCCCTGA AAGGAAAAAG
27551 CCCAACAAAA ACTACCATAT CTGGCAAAAC TCCCCTTGAG AAATGAAAGA
27601 GAAAGAAGAT ATTCCTCATA AACCAAAACT GTGAGAATTG TAGCTAGCAG
27651 ACCTGCCTAC AACAAATGCT AAGGGGAATT CTTCCAGCTG AAATCAAGAT
27701 GCACTAGATG GTAACTCAAA TCTGCATGAA AGAATAAAGA ACATGGGTCA
27751 AGTTAACTAC ATCGGTTAAC TTAGCACTGG CCCAAGCTGG TTCCCAGAAA
27801 AAGGAGACCG TCCAATAATC AACTGCCAGA GGACAGGAAG GATGAAACCA
27851 TATTTTTCTC TCCTCTTCAC TTTCAGGAGC CCTGCACACT TCCCATATTT
27901 CAGTATATAA TTTTTGAGTA AATTAGCAAG GTGAGATCTT TTCACCAGTC
27951 TAATTCTACT AAAAAAAAAA AAAAGTAGGC TTAGTATTAT TAGTCCATAG
28001 GGAATGCAGT TTAAAACCAC AGTGAGATAC CCCTCTATAT TCACCAGAAT
28051 GGTTAATATT AAATGAATGG ACATTACAGA GTAATGGCAA GGATAATGTT
28101 GGTAGGAGTT AAACTAGTAT AACCATTTGG GGAAACTATA TATTATGGCT
28151 ACTTAGCAAA ACATGCCTAG CTTATAACCC TACAAATCCA CTCCTACATA
28201 TATTCACAAC ATAAAGAAGT TATACACTTT AAAAATTACA CTAAAAGACT
28251 TACAGAAGAA TATTTATAGC AGCACTATTC ATAGTAATAG CTGAAAGCTA
28301 GAAATGGATC CAAGTACCTA TCAACAGGGG GATGTATAAA TAAAATACAT
28351 TATATTCATG CAATTAGATA TTACTCAGCA ATAAAAAGAA GCAAACCAGT
28401 GATACATACA ACATGGTTGA AGCTCAGAAA TATACTAAGT GTACACAGCC
28451 AGCTGCAAAT AAGTATATAC TGTAGGTTTC CATTTATATG AAGTTCAAAA
28501 GTAGCTAAAA CCAATCTTTT GTGATAGTAG TTAGAATAGT GGTTATTCTG
28551 GGGGGCTGAC TGGGAGGCAA CACAAAAGAG ACTGTTGAGG GGCTAGAAAT
28601 GATCACTGTC CTATCTAGGT GGTGGTTACA TGGCTGTATA TATAAAATTT
28651 TGAGTTACAC ACTTCAGACA GTGTTGCTGT TAAGATCTGT GTATACTCCA
28701 TATTATGAAA GATAATTTTT AGGATCTTAA AAAAAATCTT GATTGCTCTG
28751 TCAGTGTTAT TGAAATCAAG GATGTATAAT ATTATCAAGT TCAATCATCC
28801 TAAAAGGAAA TTCAATTATA GTTTCATTTT TGTAACTGTT AAAAGCATTA
28851 AGATATAAAC ATGTTAAACA ATTCTCCTTT GAGACATAAA CATAAAAACA
28901 GGTCTACTGA TGAGTCTGTT GATTACCCTA TTGCATTTTA GCCAATGTTT
28951 AAATATTTGG TCATGTATGT TATTCTTGAA GTGCAGAATG TGCTTAGGGT
29001 AATTATTAGC AACATTTAAC CAAATTGGTT CTGTTATTTC ACGCTGGAGG
29051 ACCAGAGCAG GATGAGTCAG TAAGGGGACT TTTGAGAAAT GAAATGTCAG
29101 TGTTTTTGCA ACCATTTGTA GGCCATAAAA AAAAAAAATC AGATTTGTTC
29151 TTACAAAGAA TGCAGGACTG GCCAAACACC AAGATGTTGC TACACAGAGA
29201 GAATAAAACA ACCAGAGACA AAACCACAGC AGAACTGCTT TCATCCCCAA
29251 ATTGCAGAAT AAGTACTGAG ATATGACCGA GAAACAGGGG AGAGAAAGGG
29301 TAAACAGTGG AGGAAAGAGA TTTTTTTGAC CTTATGCTAA CTATTAATCT
29351 GAAGCTAGAA ATGCTGATTT TATCTGAAAA ATTAGAGCTT TCCACAGTTA
29401 TTCATTTATT CAACAAATAT TTGTTAAACT TCCATTATGT ACCTAGAATC
29451 ATCCTGGGCG CATAAGATGG AGCAGCAGAC AAAACAAAAA TTCCTGCCCT
29501 TATGGAACAT ATATTGGGGG AGGGGGTGTG GCAGAAATGC ATACACATAT
29551 TGTACATGTA GCAATGAGGT TAGATTAGAT GGCTACTTTT TCTCTTTCTT
29601 TCCTTCTTTC CTTCCTTTCC TTCCTTTCCT TCCTTCCTTT CGTCCTTTTT
29651 TTTTGACAGG GTTTCCATCT ATCACCCAGG CTGGAGTGCA GTGGTACAGT
29701 CTTGGCTCAC TGCAACCTCC TCCTCTCGGG CTGAAGTGAT TCTCCTACCT
29751 CAGCCTCCCA AGTAGCTGGG ATTACAGGCA TGTGCCACCA CGCCCAGCTA
29801 ATTTTTACAT TTTTAGTAGA GATGAGGTTT TGCCATGTTG CCCAGGCTGG
29851 TCTTGAACTC CTGACCTCAA GTGATCCACC CACCTCAGCC TCTCAAAGTG
29901 CTGGGATTAC AGGTGTGAGC CACTGCACCC GGCCAAGGTG GCTACTTTTT
29951 AAAGTATGCC ATAGTTTAGC CTTCAACTAT ATATGCCTTA TGGAACCTCC
30001 AGTTTAATGC TGCTGTTGAT ACCCCTCTTA GATTTTCTAA TGAGACCTTC
30051 CTCAGCACTT TAATAATGAA ATCTACTATA TGACTCAAGG TTGATGTGTC
30101 TTACTCAGTG GCAAAGAACA GAATAAGAAA TAGATCCAAA CATATCGGAA
30151 TTTAAGACAG TGGAATGATA TCTTACAGAA AGGAGTCAGG GTATTGGGTC
30201 CTAAAATCAA CACAGATCAA AGCTGAAATT AATAAAATAG AGAAAAATAG
30251 AATAGGATAA ATAAAAACCA AAATCAATTC TTTGGGATGG TCAGTAGAAA
30301 TGTAAACCCT TTGCAATATT GATGAAAATA AAAGTGAATA TGTATCATAA
30351 AGGATGAGGA AAGAGAAATA ATCACAACTG TAAACGATTT TTTTTTTTTT
30401 TGAGACAGAA TCTTACTCTG TTGCCCAGGC TGGAGTGCCT GGCTCACTGC
30451 AACCTCTGCC TCTCAGGTTC AATTGATTCT CCTGCCTTAG CCTCCTGAGT

FIGURE 3J

```
30501 AGCTGGGATT ACAGGCACGC GCCACCACGC CTAGCTAATT TTTGTATTTT
30551 TAGTAGAGAC AGGATTTCAC CATGTTGGCC AGGCTGAACT CCTGACTTCA
30601 GGTGATCCGC CTGCCTTGGC CTCCCAAAGT GCTGAGGTTA CAGGGGCGTG
30651 AGCCACCACG CCCGGCCTAT AAAAGACATT TTTAAAAAAT GATAGGAGAA
30701 TACAAGAAAG TACATTTGTA ATACATTTGA AAGTCTAGAA ACAGTGGCTG
30751 ATTTTTGAAG ATAGATGGAG AGCTTCAGTA GGTTGATTAG CACCAAAGAG
30801 ATTAAACGGT GATTAAGAGA TATCATTTAA AAAGGAAGAG ATGATACACA
30851 ACTGAATTAT TTCTAATCAG TGGAGAACAG ATGAGTCCGA TGCTATTTAA
30901 GCTATTTTAG TAGATGGAAA ACTCCCCATT CATTTTCCAA AGCTATGATT
30951 TAATGTCAGA ACCCAATAGA AATTACATAA AAGAAAACTT TAGATTAGTT
31001 TTCTTATGCA TGCAGATGCT AAAACCATAA ATAAAATACC AGTAAATAGA
31051 ATTCAGCAGT GTAGCAAAAA CTGATCAGCT ATTATGACCA AATAGTTTTT
31101 ATTTCAGCAA CAAAAGAATA GTTCACTACT AGAAAAATCT GTCAACAGAA
31151 TGTACTACAT CAATAAATTA AAGGAGAAAA CCATATGATC ATATCATTCA
31201 GTGCTGAAAA GGCTCTGGGT ACAATTCAGT TGTCATTCAT AATAAAAGCT
31251 CTTAAGAAGG AACAGGAAAA ACACTACCTA GATATAGTAA AGACTGCACT
31301 CAACATGTTT TTACTAAGCA TCCATTATAT GCCCAGTAAT ATTCCAGCAG
31351 TTAACAGACA AAACATTTAG AGCCATCTCA TTTTTTAAAA AAGAAGGAGT
31401 TGAATGTTTA GTTTGTCAGA TGGTAATAAG CGCTTTGAAA TAAGAAATAA
31451 AGCAGGGAAT AGGAGGTTGC CAAGAGCTGA GATGTAGGAA TTGTCAGGGA
31501 AGGACTCATT GGTAAGGTGA TATTTGAGTA GAGAACTGTA GGAGAGCAAG
31551 TCAACAAAGC AGGCAAAAAT TCCAGCCATC ATGTATCCTA CGGTCTCATG
31601 GTGGGGGAGG GGGCAATACA AAAAACATGA TAAAAACATA TAGCATATTA
31651 GAAGGTTATA GTGGAAAAAA GGAAAAACAG AGGAAAGTAA AGGGGACCAG
31701 GGCCCAGAGG ATTTTGAAGG TCAGATTATA AAGTTAGTAG TCTCATTGAG
31751 AAGGTGATAT CTGAGCAAAG TCTCAAAGGA GGTGAGGGAG TTAGCCAAGT
31801 AGATATTACA GGAAGGAGTG CTCCAGGCAG AGAGAAGAGT CACAGTAAAG
31851 TAGCTATCAA GAGACCACGC CTGGCCTAGT CAAGGACCTA CAAAGATGTC
31901 AATAGGACTG GAGTAGAGTG AACAAGGGAG TGTGTGAAGG TCAGGTTATT
31951 TTATGTGGGA CCTTGTAGAC CACTGGAAGG ACTATTTTAA AAATTACCTT
32001 AATGAATTTT TATAAGGCAA ACACTCTTAT AACTATTACC CATGTTAAGA
32051 AATAGAACCA TATCAGTCAG TCCAGAAGCT TTTTCATGTA CCCTATCCCA
32101 AACTAAGTCC CCTCCTCTTC TCCCAAACTA TCCACTATTT TGGCACCTTT
32151 AGAAATCACT TACTCTGCTT CTTTATACTT TTATTACCCA AATGTGCATT
32201 TAGACATTGT AGCTTATTCT TACTCATTAA AAATAATTTG ACAAGTCTTC
32251 TCTTTTAATC GACAGATTTC CAAGTGATCC ATTCCTTTCT TTACCATACA
32301 CTATTTTTTG AAGAACCCAA GCTATTTAGC CTGTAAAGTT ATTCACAATC
32351 TGAATTTTGC TGATTGGAAA ATTGTGCAGT TTTGCAATCG AACTGCTGAT
32401 TATCCAGCAT GTTCTTCTGA ATTCTCTACT TCCTGTAAAT TGATCGCTGA
32451 GCCCAGAGGC TTAATCACAC TCAAGGTCTT ATTTGGTGAG GCTATATACA
32501 TTATGTGTGG TTGTCATTTT TCTTGTGATT TTAGCAGCCA TTGATCCTCA
32551 GTGCCTAGAT TCATCAATTT GTTGACTATT GTAAAGTGCT GATATTCTAA
32601 TTCTGATCTC TTTTCTACAT CTTACTTGGA ACAATTTTAT GAAGAGACAT
32651 ATCCTTGCCT CTATATTTTT TGGTTGCCCA GGGTTACAGC TTTTCATATA
32701 CAAAAAGCAT AATAAATACT TGATTCTTTT GCTTTTTTGG GGCCAGTTTT
32751 CAAGATAATG GTTTGGTTCC TTTTCATCTT CCCAAGAGAC CAATTTTATA
32801 TGTTTCTATC TGTTGCAATT AGCATTTTTA TTGAGTTCAA ATTGTTCCTT
32851 CTCTGGCCAC TAGATGCTTC TACACATTAC CTCCTGAGTA CTTTTGCTGT
32901 GACCTCAGTT GTGTCTGATA GCTTCCTTGC TACCTGGTAT GATAACATCT
32951 GGTGTGACAA GATAGTACAT GCTCAGCTGA GCTTAGTGAT CAGCTGGGAC
33001 TACAGGTGCC CGCCGCCACG CCCGGCTAAT TTTTGTATTT TTAGTAGAGA
33051 CGGGGTTTCA CCCTGTTAGC CAGGATCATC TTGATCTCCT GATCTCGTGA
33101 TCTGCCCGCC TCAGCTTCCC AAAGTGCTGG GATTACAGGC GTGAGCCACC
33151 GTGCCTGGCT TGTTTATTTT ATATCAGTGC AAGTTGGTAC CCTTTGACCT
33201 ACATCTCCCC ATTTCCTCCC ATTTCTGCCC CTGGTAACCA CCATCCTACT
33251 CTGCTTTGAT GTGTTTTACT TTTTTAGATT CTGCATATAA GTGAGATCAT
33301 ACAGTATTTG TCTTTCTGTG TCTAATTTAT TTCACTTAGC ATAATGTCCT
33351 CCAGGTTTAT CCATGTTGTT ACAAATGGCA GTGTCTCCTT TTTAAAGGCT
33401 GCATAATATT TCATTGTGAG TATATATTAA TCCATATATA TGTATATATC
33451 CATATCCATA TCGTATATGT ATCACCATTT CTTTAGCCAT TCATCCCTAC
33501 ATTTTAGGAT TTTTTTTTTT CATTTTAGGA CATTTTCAAA GGATTGTAAA
```

FIGURE 3K

```
33551 AATTCTAAAA AGAGAATACG CAACAGATTA TTCTTTGGAT TATAGAGCCT
33601 AAACTATTTG CTGTCTAGTC TTTTACAGAA AAAATTTGCT GACATACACT
33651 CTAGTAGATT CTTCAGAAAG TGTCTGTGGG AACAATATTC TCTGAGTTTG
33701 TAACTTTGAT AACAGCTGCT CTGTGCCTTT TATACTTTTA CAAGTCATTT
33751 TTCCTGGATG TAAGATTCTT GGCTTATTTT TCTTCCATAT GTATATTAAA
33801 TAGATTGTTC AATTTCTTCT GGGGGAAAAA AGTATTGATA TTCTACAAGA
33851 AAAGAAAATT AGAAGCCAGT ATTTCTGGTG AATATAGATG CAAAAATCCT
33901 CAACAAAATA TTAGGAAACA AAATTCATCA GCACATTTAT AAGGATCATT
33951 CACCATAATC AAATGGGACT TATATTTGGG ATACAAAGGT GATTCAAAAT
34001 AATGCAAATT AATAAATGCG ATATACCACA TTTACAGAAT GAAGGACAAA
34051 AATCGTATGA TCACCTCAAT AGATGCAGAA AAGGCATTTG ACAAAATTCA
34101 GCATCTTTTC ATGATAAAAA CTCTCAACCA AATTAGATAC AGAAGGAAGG
34151 TATGTCAACA CAATAAAGAC TATCATAAGC CCACAGCTGA CATCATCCTC
34201 AGTGGTGAAA AGTTGAAAGC TTTTCCTGCA AGATCAGGAA CAAGACAGAA
34251 TACCCACTCT CACCCCAATT CTTTTTTTTT TTTTTTTTCT GAGACATGGT
34301 TTCACTCTGT TGCCCAGGTT GGAAGGCAGT AGTGCAATCA CAGCTCACTG
34351 CACCTCCTCC TCCGGGCTCA AGCAATCCTT CCACCTCAGC CTCCCAAGTA
34401 GCTGGGACTA CAGGCACATA CCCTCATGCC TGGCTAATTT TTGTATATTT
34451 TATAGAGTTG GGGTTTTGCC ATGTTGCCCA GGCTAGTCTT AAACTCCTAG
34501 GCTCAAGCAG TCCACTCACC TTGCCCTCCT AAAGTGCTGG GATTACGGGT
34551 GTGAGCCACT GTGCTTGGCC TTACTCTCAC CACTTCTGTT CAGTACAGTA
34601 CTGGAGTCCT AGCCAGAGCA ATTAAGCAAG AGACAGAAAT AAAAGGCATC
34651 CACATCAGAA AGGAAGAAAC TAAATTGTCT CTATTTGCTG ATGACATGAT
34701 CTTACATATA GAAAGTCCTA AAGACTCCAC CAAAAATTGT TAGAACTAGT
34751 TAATGAATTC AGTAAAATTT CAAGATACAA AGTCAACATT CAAAAATCAG
34801 TAGTGTTTCT ATACACTAAC AATGAACTGT CCAAAAAAGA AATGATGAAA
34851 ACAATCTCAT TCACAATAGC TACCAAAAAA AAGACTTATG AATAAATTTA
34901 AAATTTAATC AAGGAGGTGA AAGACTTGTA CACTAAGAAC TATAAAACAC
34951 TGATGAAAGA AACTGAACAC ACTAATAAAT GGAAACATAT CCTGTATTCG
35001 TGGATTGGAA TATTGTTTAA ATGGCCACAC TACCTAAAAT GATCTATAGA
35051 TTTCAATACA ATCCCTATCA AAATTTCAAT GACATTTTCA CAGAAATAGA
35101 AAAAGCACTT GTAAAATTTA TGTAGAACTA CAAAAAGCCC CAAATAGTCA
35151 AAGCAATCTT GATAGAAAAG AACAAAGCTG GATGCATCAC AGTATTTGAC
35201 TTCAAAATAT ACTGTAAAGC TATAGTAATC AGAATAGCAT GGTACTGGCA
35251 TAAAAACAGA CATATAAACG AATGGAACTG AATAGAGAGC CCCCAGAAAT
35301 AAACCCACAT ATTTATGGTC AGTTGATCTT AAGGGTGCCA AGAATACACA
35351 ATAGGGAAAA GACAGTCTCT TAAATAATGT TGGGAAAACT GGATATCCAC
35401 ATGAGAAGAA TGAAGTTAGA CTCTTACCTC ACATCATATA CAACAACCAA
35451 CTCAAAATGG ATCAAAGTTT TATCTTGGAA AAAAAAAATT TTTTTTTTCT
35501 TTTGAGACAG GGTCTCACTC TGTCACCCAG GCTGGAGTGC AGTGGTGTGA
35551 TCTTGGCTCA CTGCAACCTC CGCCTTCTGG GTTCAAGCGA TTCTCTCACC
35601 TGAGCCTTCC TAGTAGCTGG GACTGCAGGC ATGTGCCACC ATGCCCAACT
35651 AATTTTTGTT GTTGTTTTCT TTTTTCTTTC TTTTCTTTTT TTTTTCTTTG
35701 GTAGAGACGG GGTTTCACCA TGTTGGCCAG GCTGGTCTTG AACTCCTGAC
35751 CTTAAGCAGA CCCACCTTCC AGCTGGGCGC GGTGGCTGAC GCCTGTAATC
35801 CCAGCACTTT GGGAGGCCGA GGCGGGTGGA TCACAAGGTC AGGAGATCGA
35851 GACCATCCTG GCTAACACGG TGAAACCCCA TTTCTACTAA AAATACAAAA
35901 AATTAGTCAG GTGTGGTGGT GGGTGCCTGT AATCCCAGCT ACTCAGGCTG
35951 AGGCAGGAGA ATGGCGTGAA CCCGGGAGGT GGAGCTTGAA GTGAGCGTTG
36001 AGATCGCGTC ACTGCACTCC AGCCTGGGCG ACAGAGTGAG ACTCCGTCTG
36051 AAAAAAAAAA AAAGATCCAC TCGGCCTCTC AAAGTGCTGG GATTACAGGC
36101 ATGAGCCACC TGTACCTGGC CTCAAAATGG ATTAAAGGTT TAAATGTAAA
36151 ACCTGAAACT GTATAACTAT CAGAAGAAGA CATAAGGGAA AAGCTCTGTG
36201 ACATTGGTCT GGGCAATGAA TTTTTGGATT TGACCTCAAA AGCACTGGCA
36251 ACAAAAACAA AAATGGTCAT ATGGGATTAT GTCAAACAAA AAAGCTCTGC
36301 ACAGTAAAGG AAACTATCAA CAGAGTGAAG AGACAACCTA TAGAATGGGT
36351 TGATATATTT GCAAACCATA TATCTGATAT GGAGTTAATA TCCAAAATAT
36401 ATAAGGAACT CAATTCGGCA AGAAAACAAA TCTAAAAAAA TGGGCAAAGA
36451 ACCTGATAGA CATTTATCAA AAGAAGACAT ACAAATGGCC AACAGTTATA
36501 TGAAAAAAAT GCTTAGCATC GCTAATCATC AGAGAAATGC AAATTAAAAC
36551 TACAGTGTAC CTCATACCTG TTAGAATGGC TATTATAAAA AAGATAGGCC
```

FIGURE 3L

```
36601 AGGTGCAGTG GCTCACACCT GTAATCCCTG CACTTTGGGA GGCCGAGGTG
36651 GGTGGATCAC GAGGTCAGGA GGTCGAGACC ATGCTGGCTA ACACGGTGAA
36701 ACCCCATCTC TACTAAAAAT ACAAAAAATT AGCCAGGTGT GGTGGCGGGT
36751 GCCTGTAGTC CCAGCTACTT GGGAGGCTGA GGCAGGAGAA TGGCGTGAAC
36801 CCGGGAGGCA GAGCTTGCAG TAAGCCAAGA TTGAGCCACT GCACTCCAGC
36851 CTGGGTGACA GAGCGAGACT CCGTCTCAAA GAAAAAATAA AAAAAAATAA
36901 AAAAAGATAA CAAGTGTTGG CAAAGATGTG GAGAAAAGGG AGACCTATAC
36951 ACTGTTGGTG AGACTGTAAC TTGGTACAGC CGTTATGGAA AACAACATGG
37001 AGGTTCCTCA AAAAATTGAA AATAGAGCTA CCATATGATC CAGCAATCCC
37051 ACTACCAGGT ATGTACCCAA AGGAATTGAA ATCAGAATGT GGTAGATATA
37101 CCTGCACTCA CATGTTCATT ACAGCACTAT TCACAATAGC CAAGATATCA
37151 ACCCAAGCAT CCATTCACAG ATGAATGGAT AAAAAGAAAA TGCGGCATAC
37201 ATACACAATG GAATACTATT TAGCCTTTAA AAGGAGGAAA TCTTGTCATT
37251 TGCAACATCG TTAATAAACC TGTAGAACAT TATTGTAAAT GAAATAAGCC
37301 AGGCATGGAA AGACAAATAC TTGGGATCTT ATTTCTATGT AGAACCTAAA
37351 AAAGTCAAAT TCATAGAAGC AAGAGTAGAA TGGTGGTTAN NNNNNNNNNN
37401 NNNNNNNNNN NNNNNNNNNN NNNNNNNNNN NNNNNNNNNN NNNNNNNNNN
37451 NNNNNNNNNN NNNNNNNNNN NNNNNNNNNN NNNNNNNNNN NNNNNNNNNN
37501 NNNNNNNNNN NNNNNNNNNN NNNNNNNNNN NNNNNNNNNN NNNNNNNNNN
37551 NNNNNNNNNN NNNNNNNNNN NNNNNNNNNN NNNNNNNNNN NNNNNNNNNN
37601 NNNNNNNNNN NNATATTTTA AAACATGTTA TATATTCAGT TTTCATCAGT
37651 TTAAAAAACT TAATTTAAAA AAAAAAAGTT TTGATGTTGA AAAGTCTGAT
37701 CTAATTTTCT TCTCCTATAG GTAATTTGGA TACCTATACT TTGCCTAGAT
37751 ACTCAAATAT TTTTTCTTTA AAGTGCAATA ATTTTAATAT GTTTTGTTGG
37801 TCATCATATA GCAGATATTC TCAGATATAC CATGTGTTCT GTCAATATAT
37851 AGATTAAAAA AACTTTTTAA AAATAATGTT TTCTTAAATT TTGGTTTTTA
37901 GTATTTGCTG TGTTCCCTTT GATTCTCTTC TTCAAAGACT CCTATTTTTC
37951 ATTAAAGACT TTTTTTGCCT GTTAATATTT TTCACTTTCT TTTGAATTGT
38001 TTTATTTCTT CTTAAATTTT AAAAACATTT CATATATATA TATATATGTA
38051 TTTTTTTGAG GCAGAGCCTC ACTTTGTCTC CCAGGCTGGA GTGCAGTGGT
38101 GTGATCTCGG CTCATTGCAA CCTCTGCCTC CTGGGTTCAA GTGATTCTCC
38151 TGCGTCAGCC TCTCAAGTAG CTGCGAGTAC AGGCATGTGC CATCATGCCT
38201 GGCTAATATC TTCTATTTTC AATTAGTTTA AATTGGAAAG CTTTTAAATC
38251 TTTGAAGGCA TTCTATTTCA CTTATAATTT CTTTTAAGAT TCTCTTGTAT
38301 TTATTAACTC TTGTCTTCCT TCTAGTTTAG TTTATTTTTG TAATGATTTT
38351 TCCTTCCATT TCTAAATTCC TGAGCTCTAT CACCTTATTT CTAATATGAT
38401 TTATGTATCA TTTTCTCAGT GTCTTTTAGC TTGTTTTAAA ATAGTAAGTT
38451 ACAATTTTAA TGTTTTGTGG GCATGTCTTT TTTTCTCTAT AGGAATGTTC
38501 TTCTTCTTCT CTGTTTTCTT TTAACAACTC TTTATGGTAT TTGACCAAAT
38551 ACTTTTTTGT CACTCATTTT TACTGAAAAA CAGTTTTCTC AAGCTTTTGG
38601 GAGGAGGAAT AGTTCAAGCT GTCTTTATTA ATTTCATAGC TCTCCATCTC
38651 CTGTTTTTTG GTTTTGTTCT GGTAAAGCGT TAAATAATAT GGTGGCTTGC
38701 TTTCTGAGAC TTCCTGACTC CATAGCCTCC CCTCGCTTGT ATCGGGGCCT
38751 TCTCTTTCCT TTGTCTCTGT CACCATTGTA ATTAGCCCAA TTCTGATTCT
38801 CCTCCCAGAA GTTTCTAATT GCGATGTCCT GTCCTGGAAA GGAGCTTTGG
38851 CTGGTTGGTT TCAAGTTCAT GTTTCCCATC TTTCTCTGGC CCCTTTGAGA
38901 ACCTACCAGT GGCCCTTATA GTCACTTTTT GGTTTGATGA AACCCTTCCC
38951 AATTTCAACT GGTGTTCTCA AATAGATCTG CTCTGATTTT TAGAGTTTGG
39001 TTTATGGCTG CTGTGGTGTT TCCCATTCTC AGTTTTCAGA TGCGTTGTTG
39051 CTTCTTTTTC TTTCACCACA TTAACATTCA TTCCATGAGG GGATTGTGGT
39101 TACTGTTGGT TGTCTCCACG AACTTGTATT TTGGAGTTTG TGAGCTACTT
39151 TGTCATCTAG TTTTGTTGTC CATGGTGTTT TAGTTTTGTT ATTGGATTAC
39201 TTTGCATGTT TTTAGGGAAT GATTTGGTGA GATGAAAACT ATTCAGAATA
39251 GTTTTTTCTA TTTGGATGAT CTCATCAAAT CATCCCCTAA ATCTATACAA
39301 ATCAGGAAAT CTATTCAAAT AGGAAAAACT ATTCTGTGAT TACTCAGATT
39351 CCCTCTCATT TCCAGTGCCT AGTCACTCTG AGTGACTAGG GAGTCATTGC
39401 AGGATTTTGA GCAATGGAGT GACATGACCT GACTGGTGTT TTAAAGGCTC
39451 TGTCTGGTGA TAGACTGAGA ATAGACCATA GAAATGTAGA GGAAGAAGTA
39501 GGGGGACCTA TTAGAAGAAT GTTGCAGAAA TAGGCTGGGT GGATCACTTG
39551 AGGTCAGGAG TTTGAGACCA GCCTGGCCAA CATGGCGAAA CCCTGTCTCT
39601 ACTAAAAATA CAAAAATTAG CTGGGTGTGG TAGTGGGTGC CTGTAATCCC
```

FIGURE 3M

```
39651 AGCTACTCAG GAGGCTGAGG CTGGAGAATT GCTTGAGCCC ATGAGGTGGA
39701 CGTTGCAGTG TGCTGAGATT GTGCCACTGC ACTCCAGCCT GGGCAACAAG
39751 AATGTGACTC CATCTCAAAA AAAAAAAAAA AAAAAAAAAA AAAAATTGCA
39801 GAAATCCAGG TGAGAGATGT TTGCTTGGAC TTGGGGAGCA GCAGTGGAGT
39851 TAATGAGAAG TGGCCAGATT TGCATATATT TTGAGGTATA GTTGATAAGA
39901 TTTCCTGATG GATTTGATGT GAAGTATGAG AGAATGTAGT TGAAAAATAA
39951 CTCTGGTTTT GTCCTGAGCA ACTGTAAGAA TGGAGTTGCT TTTAACTGAG
40001 ATTAGAAGGC TGAGGCTGCC GTGCGGGTAA GGTAGACTTT AGGGGTGACA
40051 TAAAGAGCTC AGTTTGGACT ATGTTGAGCT TGAGATAGTT ATTAGACTTC
40101 TGAGTGAAGA TACTCTTCGT GATTCTGCGA GTCCCATGAC AGCATGAGGT
40151 AAAAAAAGAA AGACATTGGG CCGGGCGCAG TGGCTCACGC CTGTAATCCC
40201 AGCACTTTGG GAGGTCGAGG TGGGCGGATC ACGAGGTCAG GAGATTGAGA
40251 CCATCCTAGC TAACACGGTG AAACCCCATT TCTACTAAAT ATACAAAAAA
40301 GTAGCTGGGC TTGGTGGCGG GCGCCTGTAG TCCCAGCTAC TGGGAGGCTG
40351 AGGCAGGAGA ATGGCGTGAA CCTGGGAGGC GGAGCTTGCA GGGAGCCGAG
40401 ATCGCACCAC TGCACTCCAG CCCACTGCAC TCCAGCCTGG GTGGCAGAAC
40451 GAGATTCCGT CTCAAAAAAA AAAAAAGTTT ATCATAGAAA ATTGGAAAAT
40501 ATGGATAAGT TAGGTAAGAA AATAAAAATC ATGCTGCATT GTAAACATTC
40551 TGATATGATT CTAAACATAC ATATAACATG CATTTAGAAC ACATCGCTTT
40601 TTTCTTTCCA ACTTTTAGGT TCAGGGAGTA CATGCACAGG TTTGCTACCG
40651 GTAAATTGTC TGTCACGGGG GTTTGGTGTA CAGATTGTTT CATCACCCAG
40701 GTAATAAGCA TAGTACTCTA TGGGTAGTTT TTCGATCCTC ACCTTCCTCC
40751 CACCCTCGAC CCTTAAGTAG GCCCAAGCGT CTGTTGTTCC CCTTTGTATC
40801 TATGTGTGCT CAGTGCTTAG CTAGCACTTA TAAGTGAGAA CATGCAGTAT
40851 TTGGTTTTCT GTTCATGTAT TAATTCGCTT AGGATAATGG CCTCCAACTC
40901 CATCCATGTT GCTGCAAAGG ACACTATTTC ATTTTTTTAT AGCTGTGTAG
40951 TATTCCATGG TGTATATCTA CCACATTTTC ATCATCCAGT CCACTGTTGT
41001 GGGCATTTAG GTTGGTTCCA TGTCTTAGCT ATTGTGAACA GTGTTGCGAT
41051 GAACATACAG TTACATGTGT CTTTATAGTA GAACGATTTA TATTCCTGTG
41101 GGTATATATC CAGTAAGGGG GTTACTGGGT CTAATGGTAG TTCTGAGTTC
41151 TTTGAGAAAT CTTCGAACTG CTGTCCACAG TGGCTAAACT AATTTACATT
41201 CCCACCAGCA GATATAAGCA TACTCTTTTC TTTGTTTTGT TTTGTTTTAA
41251 AACTAAAGCT TATTCTGGCC AATTTACTCT ACTATTTTCT AATAACAGCT
41301 CATAGATCAG AAACGGTCTT TGTTTTAAAC TTTCCTATCC ATATGAAACA
41351 CAATGATGTT GGGGTAAGAG GGGCCTTTTC TCTAAATGAA AATACAATAC
41401 TTATTCTGTA CAATTCTAGA GGGCCCAGAG ATGTGGAAAT AATGTATTTG
41451 TAAGAATTAT ATTAAACAAT CTTTATTTGA TAAATAGTAC CTTACAATCC
41501 TAATGCTATC TATCAAGCTT CAGTAAGAGC AATTTCAGCA TCAAGTAATG
41551 AACAGTAGCT AAACTGACAA GAGATCAATC AAAAGGGCTT TAAATGGAGC
41601 AGCACCAGCT GATGTGCTGC TAAGGCTCTG GGCATTCAGG ACTCTCCTAT
41651 GGGGAAAACG GAATCAAACC AGCAGGTGCT CTGGACCTAA GCCTTCACAT
41701 CGTGACCTGC CTCCCTCCTG GGGGTGTGGT GGCCCACAGT CCCCCTGGCA
41751 TTTCTCGGCC CTTGTGGGCT GCAGACGGAA ATCCTGGCAC CAAAGGACAG
41801 CTTGGGAAAG GCTGAAACTT GACCTCACAG TCAACTGGCT TCTGCCTATT
41851 GTGGTCATTT TCTTTCCAGA GCACCTAGAG CACTCGCACA GTGGACGTGG
41901 AAGCCACCCA GCATTCTTGG GCTGTTTTCT CATAGAAGAG GACCTTCCTC
41951 TAAGCATTGG AAGCGTCTTT CTCCAATTCC TGGGCCAGAT CTTGGGCCAT
42001 CTTCTTGTAG GTCATGGGTC TGACACACAT GGTTCAAGTT TTCGTGGCTA
42051 TTGTGAATGG GATTGTGTTT TTGATTTAGC TCTCAGCTCG GATATTGTTG
42101 GTGTATGGAA ATGCTATTTT TGTACAATGA TTTTGTATCC TGAAACTTTA
42151 CTGAAGTTGT TTATCAGATC TAGAAGCTTT TGGGCAGAGA CTGTGGGGTT
42201 TTCTAGGTAT AAAGTCATAT CGTCTGCAAA TATGGAAGAT AGTTGACTTC
42251 CACTCTTCCT GGATGCCTTT ATTTTTCTTA CTACTCTATC TAGGACTTCC
42301 AGTACTGTGT TGAGTAGGAG TGGTGAGAGA GGGCATCCTG GTCTTATTCT
42351 GGTTCTCAAT GGGAATACTT CCAGTATGGT ATGCTTCCAG CAGCACATCA
42401 ACTGGTGCTG CTCCCTTTAA AGCACTTTTG ATTGATCTCT TGTTAGTTTA
42451 GCTATTGTTC ATTACTTGAT GCTGAAATTG CTCTTATTGA AGTTTGATAG
42501 ATAGCATTAG AATTGTAAGG TACTATTTAT CAAATAAAGA TTGTTTAATA
42551 TAATTCTTAC AAATACATAA TTTCCACATC TGTGGGCCCT CCAGAACATT
42601 TCAGCATGTT CTGGATGTTG GCTGTGGGTT TGTCATAGAT ATCACTTATT
42651 GTTTTGAGGT ATGTTCCTTC GATGCCTAGC TTGTTGAGAG TTTTTAACAT
```

FIGURE 3N

```
42701 GAAGGGATGC TGAATTTTAT TGAAAGCATT TTCTGTGTCT ATCGAGATGA
42751 TCATGTAGTT TTTGTCTTTA GTTCTGTTTA TGTGATGAAT CACATTTATT
42801 GGTTTGTGTA TGTTGAACCC ACCTTGCATC CCAGGGATAA AGCCTACTTG
42851 ATTGTGGTGG ATTAGCTTTT GATGTGCTTC TAGTCTCTGT TTCCTAGTAT
42901 TTTTGTTGAG GATTTTTGCA TCTGTGTTCA TCAGGGATAT TGGCCTGAAG
42951 TTTTCTTTTT TTGTTGTATC TCTGATAGGT TTTGGTGTCA GAATGATGCT
43001 GACCTCATAG AATAAGTTGG CAAGGAGTCC CTCTTCCTGA ATTTTTGGGA
43051 ATAGTTTCAG TAGGTTTGGT ACAAGGTCTT CTTTATACAT CTGATAGAGT
43101 TTGGTTATGA ATCCCTCCTG TCTAGGGCTT TTTCTGGTTG GTAGGTTTTT
43151 TAGTACTAAT TCAATTTAGG AACTCATTAT TGGTCTGTAG AACACATTTT
43201 CACAAAGTTG AATTTCTATT GTATATACAT TTTAAAATCT TCTTTCACAA
43251 GACATGACCT GAGCATTTTC TAATAGTGAA AGTCTTTGAA AACATGGTTT
43301 TTAATGGTAT TTCATTACAT GTTTTACTGT AATAAACCTA ACCACTTGGA
43351 TTATGTACTC TTTCACTCAT TCCTTTTTGC ATATCTGTTC CATCCCCTAT
43401 GCTTTAATAT GGAGGATTTG GTTTCTTGTA GTAGTTGCTG GGTATCATAA
43451 TTCAGACCTG TGGTTTGGCA GTCAGCCTGG CTGTAGTGTT TAACTGAGTC
43501 TCGTGGAAGA TCCATGCTTA AAATGAATGT CGTGGAGAAT TGTATTCACC
43551 TCAGTCATTC AAGACTTTGG CATAGACCCC ATTCCTTGAG GAGGAGTTGC
43601 CGCCACTGTG ACTGCCACAG ACGGAAGGAA GCCTGGGCAG TTGGGACTGG
43651 GGAGAACTTG CTGAGTCACA GATATCTTGT CTCAGTGTGC ATGGGCCGTG
43701 TGTATTGAAA TGTACCAGTC TGTGAGGCAC TATGTTTTGA GGTCTCAGTA
43751 AGCTAAAGGG GTGTAGAATG GTATCTAGTT CATACCGTAG TATGCTTTAG
43801 ATCTAAGTGT TGGTTAATTC TGTAAGGACT GAAGGAATAG GGGAGATTTA
43851 ATGAGCTCCT TGCAGTCTGC AGGTTATTAT CGAGAAAAGA AAATTAGGCT
43901 CTCAGTTCCA GGCCCATTTC CCTCTAATCA CTGTGTCCTT TTGAACAAAA
43951 GTTGGCAAAC TTTTTCTGTA AAGGGCCAGA TATTTTTAGC TTTGCAGGCC
44001 ATATGATTTC TGTTGTAAGC ATTGAGCTCT TCTGTTATAG AGCAAAAGCA
44051 GCCATAGGCA GTACAGGAAC AAATGGCCAT GGTTATGTTC TAGTAAAACT
44101 TTATTTACAT AACAGGCAGC AGGCCAGATT GGAGCAATAG TTGTCAACTC
44151 CTGCTTTGAA AATGTTTTGG AAACTGTGTC TCCGTCTGTT AGTGGTCATT
44201 ATCCTCAGTC TCTTAGGATC AGAGTTTTTC TTAGATTACA AAACTGGATC
44251 ATACAGACCT GACTTCCAGG TCTGCGTTCT CTCCACTACA CTTTGCTGCC
44301 TCTTAGAAAA ACATAAGCTA AATAACTAGA ACCCATGGAA AGAGGGAAAA
44351 GTGAAGCCCA GAGAGCTGAT GCGGGACTAA GAGGCAACTC TGAGAGTTTC
44401 AATGTGGAAT GTTTGTGTGG CTCCCCAACC AGACCGTGAC CTCCTTGAAG
44451 ATTGGGACTG CATCGTATCT TGTTCTCATT TTCTATTTTA TTTTAATGAT
44501 CTATCCTTTG GGTTGAACGA ATGTGTTTCT TGAACCCGAT AAGTGCAACA
44551 CTGAGTAAAC ACTTGTTTCT TTTCTCCCTT CCATCCTCCC AACTTAGTAG
44601 CTTCAATACA TTCTTAGCTC TCCTCACTTG CTATTCTCTA ACCATACCAC
44651 GTGGCTGGGC ACGGTGGCTC ATGCCTGTAG TCCCAGCACT TTGGGAAGCC
44701 GAGGTGGGCA GATCACCTGA GGTCAGGAGT TCAAGACCAG CCTGGCCAAT
44751 GTGGCAAAAC CCCACTAAAA ATACAAAAAT TAACTGGGTA TGGTGGTGGC
44801 CTGTAATCCC CAGCTACTCA GGAGGCTGAG GCAGGAGAAT CGCTTGAACC
44851 CAGGAGGCAG AGGTTATAGT GTGCTGAGAT TGCGTCACTG CACTCCAGCC
44901 TGGGTGACAG AGCAAGAGTC CGTCTCAAAA AACAAAAACA AAAAAAACCC
44951 CAGGTTATCT CCATGAATGT GAATATTGAT GTGGTCCTTC TGTCAGGAAG
45001 ACATCACCTG AGACCACACA CAGAAAGCCT ATTTTTCCTT AGGATACAGT
45051 CCTACATCAG GGTTGACAAA GTTTTTTTGT AAGGGTTAGA TAGTAAATAT
45101 TTTAGATTTT GCAAGCCATA TGGTCTCTTC CTCAGCTACT CAACTCTGCC
45151 GTTGTACTAC AAGAGCAGCC ATAGACAATC TATACATGAA TGAGTGTGGC
45201 TGTGTTCCAG TAAACTTTAC TTATGGATAT TGATACTCAG ATTTCACATG
45251 ATTTTCATGT GTAATGAAAT GTGATTATTT TTATTTAAAA CATTAAAAAT
45301 GTAAAAGCCA TTTTTTGCTT GCAGGCCAGA CAAAAACAGG CAGTGTGAGT
45351 CAATTTAATT TAATGTGTGA CTCATAGATG CTAACCCTTG CCTTAGCTGC
45401 TTAGTAACTT GCCCTAGTCA TGTGTTACCC CATGAAAAGA ATGGCCTACT
45451 TCTGTCATAT TGTCTCTAAC CTCTGTCATT TCATTTATGA TGCTATGTAT
45501 TATGTGTACC TTTGTCTCTC TTGCTGGATT CTGAGTATCT TGAGAGGTAG
45551 GCCATGGCCT AGTCAGTCAT CTTTGTATCC TTAATATCAA ACCCACATAG
45601 TGGGTATTTA AGAAGTGACT GTTGAATTTG AATTTTATGC TTGATATATA
45651 TAAAATGTCA TTTCTGCTGA TCTTAAAGAG AAACACTTGA CTGATATGCA
45701 TAGGTTTCCC ATGTTCTTCC CCTTGAGAGG CCATAGTTAA CTGCATTTGC
```

FIGURE 3O

```
45751 TGCTAGCGGC TCTTGTAAAC TCAGTGGTTA TACAGCAAAG CCTTTGCAAA
45801 GTCTTTTATT TTAGAGCTCT TTTTCAGACA AGAAATGATT ATACTTTTTC
45851 TTCAAATCAT TTATTCAATC ATAATGATAA ATATGGCTTT CACTATTCTG
45901 ATGAAGCAGA GCTACCATCA GTGTGAAATA ATAATAGCCG TTGTTTAGTG
45951 AGCATCTACT ACATTCCAGT CAATTCAGAT TTTTTCTCTA GATTTTTGGT
46001 GACCTTCTGA TTACTATTAA TTTACATTTT TTTTTATTGT TCTCTACATG
46051 TCAAACAAAA CAAAGCAACA ATATCAAAAA CCCACATGCT TTTTCTTCAT
46101 ACTGTCTATA TTATTGAATG ACAGACAAAC ATCTGTCCTT CAAGTCAAAT
46151 ATTAATTAAT CATAGACTCC TTTCTCTTCT TCTTCACCCC GCCTTATCTA
46201 ATTGGCCACT GTCTTAGCTT TTTTTTTTTT TTTTTTTTTA AAGATGGAGT
46251 CTTACCCTGT TGCCTAGTCT GGAGTGCAGT GGTGTGATCT CGGTTCACCG
46301 CAACCTCCAT CTCCTGGGTT CAAGCAATTC TCCTGCCTCA GCCTCCCAAG
46351 TAGCTGGGAT TACAGACATG CACCACCACA CCTGGCTAAT TTTTGTATTT
46401 TTAGTAGAGA TGGGATTTCG CCATGTTGGC CAGGATGGTC TCGAACTCCT
46451 GACCTCAAAT AATCCACCCA CTTTGGTCTC CCAGTGTCTT AGCAGTTTTA
46501 AAAATTATCT TTGGAATTTG TCTCATCTCT ATTTCTAATT CATTTAATCT
46551 AATTGAAGCC TTAATCATTT CTTTTCTTCC AACATGTTGA GCATCTGTTC
46601 TGATTTTCCT GACCCCACTT GCCTCATTCT CCAATTATTC TTCCCATAGT
46651 TATCAGCACT GAATGCTAAT AATAATACTT TGTTCATATC AGTTGTTATT
46701 AAAACTCTTC ACTTATTCCT TATTATCTTC AAGGTAAGCC CAGCTTCCCA
46751 GTCATGACAT ACAAGACTCT ATGTGTGACC CCAATACTTA ACACAGATGT
46801 GTTTCAGAAT TCAGAATTTT TTGGATTTTA GAAAAGTAAT ACGGTTTATG
46851 CAATACATAT ATAACATCCT CTGCTCATTC CTGAACACTG ATGGGAGTGA
46901 ATGGCAGGTG CTTTTAATAA TTACGCTGAG GTAAATTATG CTAGGTGTAA
46951 ACTGGACCTG TCCTGGGCAA ACGAGGATGT TCTTTACACA GTTTAAGAAT
47001 GTCAAGCAAA GAACATTAGG GATGAAGCAA TACAGGGAGA ATAGATAGAG
47051 TGAAGGGAGC AGTGGGTTAA GTGGAGTCCT GGAGAAATAT TTGAAAAGGG
47101 AGAAAGGAAT GTGGCTCCTG AGGTAGGAGG GAAACCTGGA GCAGGTAGCC
47151 CCACAGAAGC CCAGGGAAGA GGCATTGTTT TTCTATTATT TTGGAAGCAG
47201 ATCCCCTTTA GGAGACTCCT CATCAGATAA TGATTATTCA CTAAGAGGTT
47251 ATATTCTTAA TTAAAAGGGC CTTTACCTTT TCTTAGAATA CTATGTTTGA
47301 ATAACTTTTT ATGTATTACG ATATAAAAGT CTCTTTTAAG CATTTCTGTT
47351 TTATAGTCAT TTGGCCAAAA TCTAATTCAG ATCCAGCTTA AATCCAAATG
47401 TCATTTGATG CTACATTTTA TCCTGAGGTT GCTAGTTATT TAGTCAAATA
47451 TAGTGAGTAT AATCACTACA GGCTTAGAGT AAATTTCCAT GTCAAGAGGT
47501 AGAACACATT TATTCTGTAA TATTGAATCC TGTAATATTG AAAATCAAAA
47551 ACAGCCCTTT TTTTTCTTCT GTAGAAAATA AGATTTTTAA GGAAGGCAGC
47601 AGGAAAATAG AACAAGTGAA TATTTTACGT TCTTAGTGGT TTATGGTTGG
47651 CAGTTTTCCC CCAACATTTT GTTACGAAAA GTTAAAATGT ACAGAAGAAT
47701 TGAAAGACTT ATACCCACCA GCTAGATTGT GCCATTAACA TGTTGCTGTA
47751 TTTACTTTAT CACTGTCCAT CTCTCTGACC ATCTATTTGT CCCTCTTTCC
47801 ATCCATCAGT CTGTCTTTTT TTTGGTAAGC ATTTCAAGTA AGTTGACTGG
47851 CAATTTTTCT AAGCAGCTGT ATCTTTATTT TGTTACTGTT TTTTTCCTGG
47901 ATGTTGTAAT TACAGTGTCA AGACATTTAA TAATGCACAT GTTTCAGCTA
47951 ACCCTTTTCC CAATTTCTAG AAATCTGAGA TTGCCAATAA TCCCTGTCAA
48001 TCTTAAATTA TTTTTTAATT CTGGTAAATA GTGTCAAACC TGATTAGTGC
48051 CCTCTTTCTC AATTGTTTTG TAATCCAGAC AACTGTTAGT CATTAAAACA
48101 TAATTTATAG TGGTTTTAAA GCATGATTTT CTAAAAAATT TTAAATAAAT
48151 ATTTATTCAT ATTATGTTGT TTTCAGAGTG GAGAGATCTA CAGACCAAGT
48201 AATCAAGCCA GTCAATGTAG GAGCTCTATC AAAATGGGTT GGGAAGATAC
48251 CGCCAGATGT TTTACAAGAC ATGGCAGTGA TTGCTCCTAT GCTTGCCAAG
48301 CTTGGATATG ACCCATATGC CAACCCACCT AACTACGGAA AACCTGATCC
48351 CAAAATTATT GAAAACACTC GAAGGGTAAG TGAGATTTTT TAAAGCAACT
48401 GAGAAAACTA GATTTTGAAT TTGGGATCTG AATACGTTTT TTTCTTATTT
48451 TATTTCTTGC TATTTAATGA TCAGAAAAAT ATATTTTTTT TTTTTTCATT
48501 TATTTTTATT TTATTTTATT TTATTTTTTT TATTATACTC TAAGTTTTAG
48551 GGTACATGTG CACATTGTGC AGGTTAGTTA CATATGTATA CATGTGCCAT
48601 GCTGGTGCGC TGCACCCACT AATGTGTCAT CTAGCATTAG GTATATCTCC
48651 CAATACTATC CCTCCCCCCT CCCCCAACCC CACCACAGTC CCCAGAGTGT
48701 GATATTCCCC TTCCTGTGTC CATGTGATCT CATTGTTCAA TTCCCACCTA
48751 TGAGTGAGAA TATGCGGTGT TTGGTTTTTT GTTCTTGCAA TAGTTTACTG
```

FIGURE 3P

48801 AGAATGATGG TTTCCAGTTT CATCCATGTC CCTACAAAGG ATATGAACTC
48851 ATCATTTTTT ATGGCTGCAT AGTATTCCAT GGTGTATATG TGCCACATTT
48901 TCTTAATCCA GTCTATCATT GTTGGACATT TGGGTTGGTT CCAAGTCTTT
48951 GCTATTGTGA ATAGTGCCGC AATAAACATA CGTGTGCATG TGTCTTTATA
49001 GCAGCATGAT TTATACTCAT TTGGGTATAT ACCCAGTAAT GGGATGGCTG
49051 GGTCAAATGG TATTTCTAGT TCTAGATCCC TGAGGAATCG CCACACTGAC
49101 TTCCACAATG GTTGAACTAG TTTACAGTCC CACCAACAGT GTAAAAGTGT
49151 TCCTATTTCT CCGCATCCTC TCCAGCACCT GTTGTTTCCT GACTTTTTAA
49201 TGATTGCCAT TCTACCTGGT GTGAGATGAT ATCTCATAGT GGTTTTGATT
49251 TGCATTTCTC TGATGGCCAG TGATGATGAG CATTTCTTCA TGGTTTTTTG
49301 GCTGCATAAA TGTCTTCTTT TGAGAAGTGT CTGTTCATGT CCTTCGCCCA
49351 CTTTTTGATG GGGTTGTTTG TTTTTTTCTT GTAAATTTGT TTGAGTTCAT
49401 TGTAGATTCT GGATATTAGC CCTTTGTCAG ATGAGTAGGA TGCGAAAATT
49451 TTCTCCCATG TTGTAGGTTG CCTGTTCACT CTGATGGTAG TTTCTTTTGC
49501 TGTGCAGAAG CTCTTTAGTT TAATTAGATC CCATTTGTCA ATTTTGTCTT
49551 TTGTTGCCAT TGCTTTTGGT GTTTTGGACA TGAAGTCCTT GCCCACGCCT
49601 ATGTCCTGAA TGGTAATGCC TAGGTTTTCT TCTAGGGTTT TTATGGTTTT
49651 AGGTTTAACG TTTAAATCTT TAATCCATCT TGAATTGATT TTTGTATAAG
49701 GTGTAAGGAA GGGATCCAGT TTCAGCTTTC TACATATGGC TAGCCAGTTT
49751 TCCCAGCACC ATTTATTAAA TAGGGAATCC TTTCCCCATT GCTTGTTTTT
49801 CTCAGGTTTG TCAAAGATCA GATAGTTGTA GATATGCGGC ATTATTTCTG
49851 AGGGCTCTGT TCTGTTCCAT TGATCTATAT CTCTGTTTTG GTACCAGTAC
49901 CATGCTGTTT TGGTTACTGT AGCCTTGTAG TATAGTTTGA AGTCAGGTAG
49951 TGTGATGCCT CCAGCTTTGT TCTTTTGGCT TAGGATTGAC TTGGCAATGC
50001 GGGCTCTTTT TTGGTTCCAT ATGAACTTTA AAGTAGTTTT TTCCAATTCT
50051 GTGAAGAAAG TCATTGGTAG CTTGATGGGG ATGGCATTGA ATCTGTAAAT
50101 TACCTTGGGC AGTATGGCCA TTTTCACGAT ATTGATTCTT CCTACCCATG
50151 AGCATGGAAT GTTCTTCCAT TTGTTTGTGT CCTCTTTTAT TTCCTTGAGC
50201 AGTGGTTTGT AGTTCTCCTT GAAGAGGTCC TTCACATCCC TTGTAAGTTG
50251 GATTCCTAGG TATTTTATTC TCTTTGAAGC AATTGTGAAT GGGAGTTCAC
50301 CCATGATTTG GCTCTCTGTT TGTCTGTTGT TGGTGTATAA GAATGCTTGT
50351 GATTTTTGTA CATTGATTTT GTATCCTGAG ACTTTGCTGA AGTTGCTTAT
50401 CAGCTTAAGG AGATTTTGGG CTGAGACGAT GGGGTTTTCT AGATAAACAA
50451 TCATGTCGTC TGCAAACAGG GACAATTTGA CTTCCTCTTT TCCTAATTGA
50501 ATACCCTTTA TTTCCTTCTC CTGCCTGATT GCCCTGGCCA GAACTTCCAA
50551 CACTATGTTG AATAGGAGCA GTGAGAGAGG GCATCCCTGT CTTGTGCCAG
50601 TTTTCAAAGG GAATGCTTCC AGTTTTTGCC CATTCAGTAT GATATTGGCT
50651 GTGGGTTTGT CATAGATAGC TCTTATTATT TTGAGATACG TCCCATCAAT
50701 ACCTAATTTA TTGAGAGTTT TTAGCATGAA GGGTTGTTGA ATTTTGTCAA
50751 AGGCCTTTTC TGCATCTATT GAGATAATCA TGTGGTTTTT GTCTTTGGCT
50801 CTGTTTATAT GCTGGATTAC ATTTATTGAT TTGTGTATAT TGAACCAGCC
50851 TTGCATCCCA GGGATGAAGC CCACCTGATC ATGGTGGATA AGCTTTTTGA
50901 TGTGCTGCTG GATTCAGTTT GCCAGTATTT TATTGAGGAT TTTTGCATCA
50951 ATGTTCATCA AGGATATTGG TCTAAAATTC TCTTTTTTGG TTGTGTCTCT
51001 GCCTGGCTTT GGTATCAGAA TGATGCTGGC CTCATAAAAT GAGTTAGGGA
51051 GGATTCCCTC TTTTTCTATT GATTGGAATA GTTTCAGAAG GAATGGTACC
51101 AGTTCCTCCT TGTACCTCTG GTAGAATTCG GCTGTGAATC CATCTGGTCC
51151 TGGACTCTTT TTGGTTGGTA AACTATTGAT TATTGCCACA ATTTCAGAGC
51201 CTGTTATTGG TCTATTCAGA GATTCAACTT CTTCCTGGTT TAGTCTTGGG
51251 AGAGTGTATG TGTCGAGGAA TGTATCCATT TCTTCTAGAT TTTCTAGTTT
51301 ATTTGCGTAG AGGTGTTTGT AGTATTCTCT GATGGTAGTT TGTATTTCTG
51351 TGGGATCGGT GGTGATATCC CCTTTATCAT TTTTTATTGT GTCTATTTGA
51401 TTCTTCTCTC TTTTTTTCTT TATTAGTCTT GCTAGCGGTC TATCAATTTT
51451 GTTGATCCTT TCAAAAAACC AGCTCCTGGA TTCATTGATT TTTTGAAGGG
51501 TTTTTTGTGT CTCTATTTCC TTCAGTTCTG CTCTGATTTT AGTTATTTCT
51551 TGCCTTCTGC TAGCTTTTGA ATGTGTTTGC TCTTGCTTTT CTAGTTCTTT
51601 TAATTGTGAT GTTAGGGTGT CAATTTTGGA TCTTTCCTGC TTTCTCTTGT
51651 AGGCATTTAG TGCTATAAAT TTCCCTCTAC ACACTGCTTT GAATGCGTCC
51701 CAGAGATTCT GGTATGTGGT GTCTTTGTTC TCGTTGGTTT CAAAGAACAT
51751 CTTTATTTCT GCCTTCATTT CGTTATGTAC CCAGTAGTCA TTCAGGAGCA
51801 GGTTGTTCAG TTTCCATGTA GTTGAGCGGC TTTGAGTGAG ATTCTTAATC

FIGURE 3Q

```
51851 CTGAGTTCTA GTTTGATTGC ACTGTGGTCT GAGAGACAGT TTGTTATAAT
51901 TTCTGTTCTT TTACATTTGC TGAGGAGAGC TTTACTTCCA ACTATGTGGT
51951 CAATTTTGGA ATAGGTGTGG TGTGGTGCTG AAAAAAATGT ATATTCTGTT
52001 GATTTGGGGT GGAGAGTTCT GTAGATGTCT ATTAGGTCTG CTTGGTGCAG
52051 AGCTGAGTTC AATTCCTGGG TATCCTTGTT GACTTTCTGT CTCGTTGATC
52101 TGTCTAATAT TGACAGTGGG GTGTTAAAGT CTTCCATTAT TAATGTGTGG
52151 GAGTCTAAGT CTCTTTGTAG GTCACTGAGG ACTTGCTTTA TGAATCTGGG
52201 TGCTCCTGTA TTGGGTGCAT AAATATTTAG GATAGTTAGC TCCTCTTGTT
52251 GAATTGATCC CTTTACCATT ATGTAATGGC CTTCTTTGTC TCTTTTGATC
52301 TTTGTTGGTT TAAAGTCTGT TTTATCAGAG ACTAGGATTG CAACCCCTGC
52351 CTTTTTTTGT TTTCCATTTG CTTGGTAGAT CTTCCTCCAT CCTTTTATTT
52401 TGAGCCTATG TGTGTCTCTG CACGTGAGAT GGGTTTCCTG AATACAGCAC
52451 ACTGATGGGT CTTGACTCTT TATCCACCTT GCCAGTCTGT GTCTTTTAAT
52501 TGCAGAATTT AGTCCATTTA TATTTAAAGT TAATATTGTT ATGTGTGAAT
52551 TTGATCCTGT CATTATGATG TTAGCTGGTG ATTTTGCTCA TTAGTTGATG
52601 CAGTTTCTTC CTAGTCTCGA TGGTCTTTAC ATTTTGGCAT GATTTTGCAG
52651 CGGCTGGTAC CGGTTGTTCC TTTCCATGTT TAGCGCTTCC TTCAGGAGCT
52701 CTTTTAGGGC AGGCCTGGTG GTGACAAAAT CTCTCAGCAT TTGCTTGTCT
52751 ATAAAGTATT TTATTTCTCC TTCACTTATG AAGCTTAGTT TGGCTGGATA
52801 TGAAATTCTG GGTTGAAAAT TCTTTTCTTT AAGAATGTTG AATATTGGCC
52851 CCCACTCTCT TCTGGCTTGT AGGGTTTCTG CCGAGAGATC CGCTGTTAGT
52901 CTGATGGGCT TTCCTTTGAG GGTAACCCGA CCTTTCTCTC TGGCTGCCCT
52951 TAACATTTTT TCCTTCATTT CAACTTTGGT GAATCTGACA ATTATGTGTC
53001 TTGGAGTTGC TCTTCTCGAG GAGTATCTTT GTGGCGTTCT CTGTATTTCC
53051 TGAATCTGAA CGTTGGCCTG CCTTGCTAGA TTGGGGAAGT TCTCCTGGAT
53101 AATATCCTGC AGAGTGTTTT CCAACTTGGT TCCATTCTCC ACATCACTTT
53151 CAGGTACACC AATCAGACGT AGATTTGGTC TTTTCACATA GTCCCATATT
53201 TCTTGGAGGC TTTGCTCATT TCTTTTTATT CTTTTTTCTC TAAACTTCCC
53251 TTCTCGCTTC ATTTCATTCA TTTCATCTTC CATTGCTGAT ACCCTTTCTT
53301 CCAGTTGATC GCATCGGCTC CTGAGGCTTC TGCATTCTTC ACGTAGTTCT
53351 CGAGCCTTGG TTTTCAGCTC CATCAGCTCC TTTAAGCACT TCTCTGTATT
53401 GGTTATTCTA GTTATACATT CTTCTAAATT TTTTTCAAAG TTTTCAACTT
53451 CTTTGCCTTT GGTTTGAATG TCCTCCCGTA GCTCAGAGTA ATTTGATCGT
53501 CTGAAGCCTT CTTCTCTCAG CTCGTCAAAA TCATTCTCCA TCCAGCTTTG
53551 TTCTGTTGCT GGTGAGGAAC TGCGTTCCTT TGGAGGAGGA GAGGCGCTCT
53601 GCGTTTTAGA GTTTCCAGTT TTTCTGTTCT GTTTTTTCCC CATCTTTGTG
53651 GTTTTATCTA CTTTTGGTCT TTGATGATGG TGATGTACAG ATGGGTTTTC
53701 GGTGTAGATG TCCTTTCTGG TTGTTAGTTT TCCTTCTAAC AGACAGGACC
53751 CTCAGCTGCA GGTCTGTTGG AATACACTGC CGTGTGAGGT GTCAGTGTGC
53801 CCCTGCTGGG GGGTGCCTCC CAGTTAGGCT GCTCGGGGGT CAGGGGTCAG
53851 GGACCCACTT GAGGAGGCAG TCTGCCCGTT CTCAGATCTC CAGCTGCGTG
53901 CTGGGAGAAC CACTGCTCTC TTCAAAGCTG TCAGACAGGG ACACTTAAGT
53951 CTGCAGAGGT TACTGCTGTC TTTTTGTTTG TCTGTGCCCT GCCCCCAGAG
54001 GTGGAGCCTA CAGAGGCAGG CAGGCCTCCT TGAGCTGTGG TGGGCTCCAC
54051 CCAGTTCGAG CTTCCCGGCT GCTTTGTTTA CCTAAGCAAG CCTGGGCAAT
54101 GGCGGGCGCC CCTCCCCCAG CCTCGCTGCC GCCTTGCAGT TTGATCTCAG
54151 ACTGCTGTGC TAGCAATCAG CGAGATTCCG TGGGCGTAGG ACCCTCTGAG
54201 CCAGGTGTGG GATATAGTCT CGTGGTGCGC CGTTTCTTAA GCCGGTCTGA
54251 AAAGCGCAAT ATTTGGGTGG GAGTGACCCG ATTTTCCAGG TGCGTCCGTC
54301 ACCCCTTTCT TTGACTCGGA AAGGGAACTC CCTGACCCCT TGCGCTTCCC
54351 AGGTGAGGCA ATGCCTCGCC CTGCTTCGGC TCGCGCACGG TGCGCACACA
54401 CACTGGCCTG CGCCCACTGT CTGGCACTCC CTAGTGAGAT GAACCCGGTA
54451 CCTCAGATGG AAATGCAGAA ATCACCCGTC TTCTGCGTCG CTCACGCTGG
54501 GAGCTGTAGA CCGGAGCTGT TCCTATTCGG CCATCTTGGC TCCTCCTCCC
54551 CCAGAAAAAT ATTTTGAATT AGAAAAATTT GGGCCTAGTG GCCTGGCACG
54601 CTGGCTCATG CCTGTAATCC CAGCACTTTG GGAGGTCGAG GCGGGTGGAT
54651 CACAAGGTCA GGAGATCGAG ACCATCCTGG CTAACACGGT GAAACCCCTT
54701 CTCTACTAAA TACACAAAAA ATTATCCAGG CGTGGTGGTG GGCGCCTGTA
54751 GTCCCAGCTA CTTGGGAGGC TGTGGCAGGA GAATGGCATG AACCCGGGAG
54801 GCAGAGCTTG CAGTGAGTAG AGATCACGCC ACTGCACTCC AGCCTGGATG
54851 ACAGAGCGAG ACTCCATCTC AAAAAAAAAA AAGAAAAACT TGGGCCCAGC
```

FIGURE 3R

```
54901 ATAGGGCTGA CACCTGTAGT TTCAGCACTT TGGAAGGCCG AGATGCGAGT
54951 GAGCCCAGGA TTTCAAGACT AGCCTGGGCA ACATAGTGAG ACCCCCATCT
55001 CTACAAAGAA TATAAAAATT ATCCAGGCAT GGTGGCACAT GACTCTAGTC
55051 CCAGCTACTT GGGAGGCTGA GGTGGGAGGA TTGATTGAGC CTGAGAGGTC
55101 AAGGCTGCAG TGAGCTGAGA GTATGCCACT GTACTGTAGC CTGGGTGACA
55151 GAGCAAGACC CCGTCTCAAA ATAAGAAAAA AGAATGAAGA AAAATTATAT
55201 TTGTAGAATG CTTTCTTATC AGCAGTCTTC CACTGCATTT TAAGGATAAC
55251 TGGCTCGTTG GGGATAGTTC TTAGGGTATT TTGCTCAGTT TCTAGGAATG
55301 ATACTCACTG TTGGGAGATT TATTCTCAGC CAATTACTGC AGATCTGCAT
55351 AAACACCATA ATTATTAGTG ACCTTACTTC TGATTTCTTT CTTTCTGTAA
55401 ATCTAATAGC CACTTTACTT TTAAACCTTT GTTTAGATGA GGCATAATTT
55451 TTGGATACCT AAAAGCTAAA CATTGGTTAC ACTAGAAAAA TTATTAAACA
55501 CTAGCCTTCT GATTAAGAGA AAGTTGCTAT TAAAGTGACA TTACAGTTTT
55551 TATTTTAATA AGTTATGCTC ACGTCTTTAC AATATATTAT TTCAGAAAGT
55601 GCTGAAAATT CAGAGCTAGA TTATATAGCC TACCAGTTGA GTCTATTTCA
55651 AATCAGATCT TATACATTCT TTTCTTTATT GCAGTAAGAT ATATTTAACA
55701 TAAAATTTAC CACTCTGACA CTTTTTAAAG TGCACAATTC AGTGGCATTA
55751 AATACATTCA CATTGTTGTG CAACTGTCAC CACCGTCCAT CTCCAGAACA
55801 TTTTTTGTCT TCCCAAACTG AAATTCTGTA CCCATACTCT TCATTGCCTG
55851 GTCCCTGTCA ACTGCAGTTT TTTGTGTCAC TTGTATATAT TCTTTTTTGA
55901 AACTACATTT CAAATAAGAC AACCATGCTA GCATAAGTTC ACTGATAGGC
55951 TATTTGATTC CAAGGTGAAA ATTCCTTGGC TTTGTCTGAA TTCTCTTGTT
56001 TATATCAGTG TCCTTCCCTC CCTACAACCA TATAACCGTA TCATGTTTTT
56051 ATTCTGTCTT TTGATAACTT TAATTGACAA ATTTATGCCA CATTTATTTC
56101 ATGAGATTAA TTTCTATGTG AATTCCTTTC TCTTAGGTAT TACTTTTATT
56151 TCCCCTTTTC AATTCATTAT TAGCAGCTAT ATGGGAAGAG CTGCCTTCTT
56201 GTAAACCATC ACATATGAGG GCAAATTAAA AAAAACAATA ATCGCTATCC
56251 TCTTTACACT TTTTATATAT ATATAAATAT TTCCATTATA AAAATATAAG
56301 CTCATTATAT GAAACTTACA AAATTCAAAG GATAAGAGAA TAAAAATCAC
56351 CTGTAATGTT CCCACCTAGA CACATACACA TATTATTCTT TTTTATTTTC
56401 TTATTTATTT ACACATATTA TTCTTAATAT TTTGATGTAT TTTCTCTCCT
56451 CTGCATTATG TTAAACAAAG GTAAGATTAC GTATATCATC TTACCTTTAT
56501 ATACACAGTT TTGTATCCAG TCCTTTTAAT ATTCACGAGC ATTTTCCCAT
56551 TGTGTGCATG CTTTTTAAAC ATAATTTTTA TAGTTATAAA CCTTCATAGA
56601 AGCCACCTTA AATTCTTTCT GAAGCACAGT AGTAAATGAA TGAATAAATC
56651 AACAAACAAA ATACATTTCC CTGGTAGATG TTCTACAATT GATTTTACCA
56701 TTTTGTTGTT TACCGTTTTC TCTTTGACAA ATTGTGCTGC AGTGAACATC
56751 TTTGCAGATA CTCAATTTTA GGATTTTTTT TTTAAGGTAG GATCAATAAA
56801 AATAGAACTA AACCAGGGTA AAGTATCTGA GATTTTTAAA AGGTGTTTGA
56851 TATCTATTGA TACTAAAAAA CCTTTGGGCT GGCCACAGTG GCTCACGCCT
56901 GTAATGCCAG CATTTTGGGA GGCTGAGGTG GGTGGATCAC TTGAGCTCAG
56951 GAGTTCAAGA CCAGCCTGGA CAACGTGGCA AAACCCCATC TCTACAAAAA
57001 ATACAAAAGT TAGCCAGGTG TGGTGGCACA TGCCTCTGGT TTCAGCTGCT
57051 TGGGAGGCTG AGGTGAGAGG ATTGCTTGAG CCCAGAATTT TGAGGTTACA
57101 GTGAGCTGAG ATTGTGCCAC TGCACTCCAG CCTGGGTGAT GGAGCGAGAT
57151 CCTGTCTCAA GAAAACAAAA ACAAAAAACA AACAAACAAA AAACCTTTGA
57201 ACTGCCAGCA TAATTGAGGT AATTTATTTT AGATTTTTGT TGGTTTTAAT
57251 AGATTTCATT GATTAATGTA ATTGAACATT TTCCAGTTAT TAGCTATATG
57301 TATATATTCT TTTATGAACT AAGTTTTTAC TTTATTTATT TGAGACAGAG
57351 TCTTGCTCTG TTGGCACAAT CTTGGCTTAC TGCAACCTGT GTCTCCTGGG
57401 TTCAAGTGAT GATTCTCTTG CCTCAGGTGG GATTATAGGC ACATGCTACC
57451 ACGCCTGGCT AATTTTTTTT AATTTTTTAT TTTTAGTAAA GTTAGGGTTT
57501 CGTTGTGTTG GCCTGGCTGA TCTCAAACTC CTGACCTCAA GTGATCTACC
57551 TGCCTTGGCC TCCCAAAGTG CTAGGATTAC ATGAGCCACT CTTTAAAGTT
57601 TTATATGTAT TAAAGTTTTG TGAGCTCTTT GTAATTGGTA ATTCATAGCT
57651 ATCTCCTTTG CACAATAGTG AAAGGGTTTT TTATTACCAA GATACATGTA
57701 CAATGCTATT TTGAGGGTTC TTAGGCAGTA GACATTATAG TTTTCCTACA
57751 TGCAAATTGG CTTGGCTAGA TTATCCTTTG CTTTCTTGAG TGGTGGGTTG
57801 GGAAGAATGC TATGGTTTGA ATCCATGTGA CTAAAGAATC TATTTCATAC
57851 ACACTTGTGG TTTTTGAAAG GATTTCAAAA TACCCACTGA AATAAAAAAA
57901 CACCCACCCT TTCCCCCCCC CCCCCCCGTC TCTGCCTATC TTTAAAGTGA
```

FIGURE 3S

```
57951 CAGATAATTT TGAGGAAGAA AAGATGAAGT GTGAACTATA GTGGTGTTTT
58001 TGGGCCTTTT GTGGTAATGC ATACAAACTG ACAGTCTTGT CTTGTGAGGG
58051 TAGGTTTCAT AAGACCTTTT TGCAAACTAA ATCCTGTGTA TCTTCAAAGC
58101 TTTTTTGCCT GTAATAAGTC AGATGCTAAT GTATCCAGCA CTGATGATCA
58151 TGAGGTTTTT GTAAAGCAGT GCTTGAAAAG AGATTGTTGA CCGTTAGCTA
58201 TGATATGAGA TGGGCCCCAG AGAAAGAGGT GGCTGGCGAA GGTGTTTTCC
58251 TTAGTTATGG GGTGAGAGTG GGAGAAAAAT AACATTTTGA CTGAGAATAT
58301 AGGATTTATA TCTCTAAGCC TAAAAATACT GGGTTGGTTT TTTTTTTTTT
58351 TTTTTTTTTT TGGTACAATT CTGGGTAGTC TGCAAGTAAT ATTGAGTCAG
58401 CACATTTTAG GGACATATTA CCCAATATTG AATGGATAAT CATGCTTCAT
58451 GGTTACTGTG ACTCACATAG TAAATTGGTA ATGAAACGTT AACATATTTT
58501 ATACCCTGTC CCACCATAGT CTCTAATCCT AAAATTATAG TATATTTCAG
58551 TAAATGGTGC TGTCTAGGTT ACATCGTCAG CCTTCTTGCA TAGATTCTTA
58601 ACCTTTTAGA CTTAGGAACT TATTTGAGAA TTTGATGAAT CCTGTGGATC
58651 CCCACCTCAG AAATACAGAC ACATGAATAC ACAGATTTCA CTCACAATTT
58701 CAGTGGATAC ATAGATATAC CAGAAGTCCA TCAGATTAAG GACTCCTATT
58751 AGCCACAATT TCAGTGGATG CATGTGTGCC AGAAGCCTGA CAGATTAAGG
58801 ACTCCTATTT TATAGTCTCC TTGCTCAAGC TCATCCACTC ATAGGGCTTT
58851 CATTACAGCC TATTTGCTGA TTATCATAAA TCTGTATTTC CTAGTGGGTC
58901 TCTTTCCTGA GCCCTAGGTT CATTATTTCC AACTGTCTTC TGTATGTGTC
58951 CACCGAAATG CTCTCAAGGA CCTCAAATTC AAAGTCCAAA ATTGAATTTA
59001 TTTTCTAAAC TTGTTCCCTG AGAGGCAGAA GCTAGGTGGA ATTGTTCATT
59051 AAACTGAGCA GGAATCCACC TTGAGAGTGG GGATGATGCT GTGCTCATCT
59101 ATACTTGCGG TACCTATGAG CCAGAGAGCA GATTTGAGGA ACAGAGTCCT
59151 CAGGGCACAT GGCTCAAACC CCAAAACAAT TCAAGAACCT GGTTGCTAAA
59201 GTTAGAGAGC TGAAAAGCAG ATCCAATTTA TGAATGGAAT ATTTAGTTGG
59251 AAACCTGAGT AGATAGTACT GAGGAAGAGC AAGTGATCAA ATGGAAAAGC
59301 ATGTACCAAG GTGCAGAACC CACAGTAACA GACAAGAAGA AACATGAAAA
59351 TGAAGTCAGC TGGGGGACAG GGGTTAGATT AAATCCCTAA ACCAAACAAC
59401 AAAAAGCTGC AGCAGCAGTT GGAATTGATA TTCTTACATT AAAGGTAAAG
59451 CCTGGAATGA ATGCATACTT GTGTTTTCTG GTTCCTATAC TCAGCAAAAA
59501 CTGCTTGTTC CTGTTTTTTT CTATCTCCAT ACATAGCATG CTTATTCACC
59551 CAGTTACCCA AATTAGGTCT CCTCACTTAA AATTCATGAA TGACTCCACT
59601 GTTACTACAG GATAGAGTCT AGACTTCTTA GAATGACATT TACTTTTCTA
59651 GTATTTGGGT ATTTTCTCAT TATCTTTTTG TTGTTGATTT CTAATGTGAC
59701 CATTATGGTC AGAGAACACT CATTATGGTT TGTTTCAGTC CTTTGAAATA
59751 TATTGAATAT TGTTTTATGG CCAGTATATG GTCTTATGTG ATCAGTTGAA
59801 AAAATATGTA TTCTGTGATT GTTGCAGAGT TCTGTAAATA TCAGTGAGGT
59851 CAAGAAATTT TATAGTGTTG TTACAGTCTA AATCTTATTT GATTTTTTGG
59901 TCTGCTTTAT TAATGTTGGG AAAATTATGA ATTTTTCAAA TTTTCCTTAC
59951 ATTTCTAGCA ATTTTGTTTC ATGTATTTAG GATCTATATT ATTGGGAACA
60001 CACCCATTTA GACCTTCTTG AAGAAGTAAC TCTTTTGTAA TTATGAAATA
60051 TTTCTCTTTA TCTCTGCTGT TACCCTCTGA AAGTCTACTT TATCTGATAT
60101 GAATATAGCC CAACAGTGTT TTTATGTATA CTATATACAT GGTATATTTT
60151 CCCGATTCTT TTACTTTTAA TCTGTGTCTT TATATAGCTG GCTTTGTTTG
60201 TTAATCCAGT TTTATAGTCT CTGCCTTTTA AATGGAGAGT TAATCCACTT
60251 ACATTTAATG TAATTATTCA TCTGATTGGA TTTAAAACTA CCATCTTGCT
60301 ATTTGTTTTT TATTTGGATC ATCTATTTTT GTTTCTTTGT TTCTCTTTTC
60351 CTGCCTTCTT TTGGATTAAT CTTTTTTGGT ATTCCATTTT ATATATTATC
60401 TCCTCTTTTT AGCTATACCT CTTCTTTTTG TTTTGTTTTT GCTTATAGTG
60451 GTTACTGTAA GACATGGGCT GCACATTTTT TATATTGTAA AAATCCAGAT
60501 AGTAGGCCGG GTGCAGTGGC TCACACCTGT AATCCCAGCA CTTTGGGAGG
60551 CTGAGGCAGG TGGATCACAA GGTCAGGAGA TCGAGACCAT CCTGGCTAAC
60601 ATGGTGAAAC CCCCGTCTCT ACTAAAAATA CAAAAAGAAT TAGCTGGGCT
60651 TGGTTGTGGG CACCTGTAGT CCCAGCTACT TGGGAGGCTG AGGCAGGAGA
60701 ATGGCATGAA CCTGGGAGGT GGAGCTTGCA GTGAGCTGTG ATCACTCCAC
60751 TGCACTCCAG CCTGGGCAAC AGAGCGAGAC ACCGTCTCAA AAAAAAAAAA
60801 AATCCAGATA GTAAATATAT TATGCTTTGT GGGCCACAGT TGGGCTCTTT
60851 GTTCTTTACT TGAAGATCCA GATTTTCATC TGGCATCATT TCTCTTTAGC
60901 CTGATGCACT TCCTTTAGCA GTTCTTATAG TAAAGACATG TTGACTACTA
60951 ATGCTCTTAG GTTTTTTTTT TTTTTTTTAA TTTGAAAATG TGTTTGTTTT
```

FIGURE 3T

```
61001 TTTTTTAATT TGAGAATATT TTGCTGGACA TAGAGTTCTA GGCTATTGGT
61051 CGTTTTGTAT TTTTTTTAAC TTTCAACATT AAAAAGATAC TATTTTATTG
61101 GCTTCCCATG TTTTTGATGA AAGTCAGCTG ACATTCTTAT GAATGTAATT
61151 TTTTTTCTTT GACTGCTATA AGATTTTTCC CTATTTTTGG TTTTCAGCAG
61201 TTTGATTATA ATATACCAAA TTCGTAGCTC CGTTCTACTG CCATCTCCTG
61251 TGTGGGCCTC AGTTTTGATT AGTTTTTATT AGCCTACCTT TGAATTCATT
61301 GATCCCTTCT TTTTCTGTGT CCAGTCTGCT GTTAAACCCA TCTGGTGACT
61351 TCTTCATTTC AGATCATTTA TTTTTCAGTT CTAGAATTTC CCTTTCTCTG
61401 CTGGAATTCT TTGCTCTTTA CCCATTCTGT TGATCTTTTC CTCTAAATTA
61451 TTTAACATAT TCATAATAAC TTTTAAAGTC TTCATCCACG GATCTCTCCC
61501 TGTTGACTTT GTTTCTTTAT TATGGGTTAT AGGCACACCT TGGAGAGACT
61551 GTGGGTTTGG TTCCAGACCA CCAAAATAAA GTGAATATCC CAATAAAGCA
61601 AGTCACACAT AATTTGGTTT CCCAGTACAT ATAAAAGTTA TACACTACAT
61651 TGTAGTCTGT TCAGTCTGTA GTAGCATTGT GTCAAAAGAA AACACAATGC
61701 ATATGCCTTA ATTTAAAATA CTTTATTGCT AAAAAAAAAA TGCTAGCAAT
61751 CATCCAAGCC TTCAGCAAGT CATAATCATT TTGCTGGTGG AGACTCTTAC
61801 CTCCATGTTG ATGACTGCTA GACCATTCAG GGTGGTGGTT GCTAAAGATT
61851 GGGGTGACTA TAGCAATTTG TTTTGTTATG TAATATTCTA TATCCTTTGC
61901 TGTCTTTTCA ACAATATTCA CAGCATCTTC ACCAGGAGTA GATTCCATCT
61951 CAAGAACCAC TTTCTCTGCT CATTCTTAAG AAGCAACTCA TTCATTCAAG
62001 TTCAATCATA AGATTGTAGC AATTCAACCA CATCTTCAGG CTCACTTCTA
62051 GTTATAGTTC TTTTGCTATT TCTACCACAT CTGCAGTTCC TTCCTCCACT
62101 GAAGTCTTGA ACCTCTCAAT GTCATCCGTC TGATTCTTCC AAATTCCTGT
62151 TAACATTGAA ATTTTGACCT CCTCCCATGA ATTACGAATG TTCTTAATGG
62201 CATCTAAAAT GATGAACCCT TTCCAGAAGG TTTGCAGTTG ACTTTGTGCA
62251 AATCCATCAG AGGAGTTGGT ATCTATGGCA GCTATAGTCT TAAGAAATGT
62301 ATTTCTTAAA TAATAATCTT GACAGGGCCA GGTGCAGTGT CTTAAACCTG
62351 TAATCCCAGC ACTTTGGGAG GCCAAGGTGG ATGGATCACC TGAGGTCAGG
62401 AGTTCAAGAC CAGCCTGGCC AACATGGCGA AACTCCATCT CTACTAAAAA
62451 TACAAAAATT AGCTGGGTGT GGTGGCGCAT GTGTGTAATC CCAGCCACTC
62501 AAGAGGCTGA GGCAAGAGAA TCGCTTGAAC CGGGGAGGGA GAGGTTGCAG
62551 TGAGCCAAGA TTATGCCACT GCACTCCAGC CTGGGTGACA GAGCGAGACT
62601 CCATCTCAAA AAAAAAAACA AAAAACAAAA CCAACTTGAC AGTAGAAATT
62651 ACTCCTTGAT CCGTGGACTA CAGAATGGAT ACTGTGTTAG CAAGCATGAA
62701 AACAGCATTC ATCTCCTTGT ATATCTCTAT CAGAACTCAT GGGTGACAAG
62751 GTGCATTGTC AACGAGCAAT AGTATTTTGT GAGAAATCTT TTTTCCTAAG
62801 CAATAGGTCT CAACAGTGGG CTGAAAATTG CATTTTTATG TTATGGAGAT
62851 AGCTTCTTTC CTTAATCTTC ATAAACAAAC AACCTCTACT AGCCTCCAAC
62901 TTTTCCTCTC ACAGCCTTTA TAAAATTGAA GAGAATTAGG GCCTTGCTCT
62951 GGATTAGGCT TGGCTTAAG GGAATGTCAT GGCTGGCTTT ATCTGTCTAG
63001 TCCACTAAAA CTTTTGCCAT GTCTACAGTA AGACTCTCAC TTTCTTACCA
63051 CTTGTGTGTT CATTGGAGTA GCACTTGAAT TTACTTCAAG AACTTTTCCT
63101 TTGTATTCAC AACTTGACTA TTTGATGCAA GAGGCCTGGC TTTCAGCTTA
63151 TCTTGGCTTT CAACATACCT TCCTCACTAA GCTTGATTGT TTCTAGCTTC
63201 TGACTTAAAG TGAGAGATAT GCGACTATTC CTTTCGTTTG GACACTTAGA
63251 GCCCATTGTT GGATTATTAA TCGGCCTTTT TTCAATATCA ATGTGTCACA
63301 GGAACAGGGG AGGCCCAAGG GAGAGGGAGA GAGATGGGGG AACAAACAGC
63351 CAGTTGGTGT AGCAGTCAGA ACATACACAA CATTGATTAA GTTAATTATG
63401 TTATATGGGC TTAGGATCGT GGCACCCCAA AACAATTACA TGGTAACATC
63451 AAAGATCTCT GATCGCACAT CACCGTAACA GATACAATAA TGAAGAAGGT
63501 TCAAATATTG CAAGAATTAC CACAGTGTCA TAAAGAGACA TGAAGGGAGT
63551 GCATGTTGTT GGAAAAATGT CACCAACAGA CTTGCTCACC ACAGGATTAC
63601 CACACACCTT CAATTTGTAA AAAACACAAC ATCTGCAAAG CACAATGAAA
63651 TGAGGTATGC CTGTACTCAT TTGCTTCTTC ACATGTCTTA GAAGTTTTAA
63701 CTGCATACTG GACCTTTTGT ATAACAGAGG GGTAGAGAAT GAACTAGGTA
63751 ATACTTTTTG TTTTATTTTT GTTAAAGAGA GCAGTTCTTT CCTCCAGCAG
63801 GTAGCTAAGG TGATCACTCA AATTTGACAG TGAATCAAGC TGAGCTGGGG
63851 CTGAGCAGTA GCTTTAATTG ATTTCAGTTT GCCTCTGGAT TCAAATGAGA
63901 TTAAGGAAAT TTGACTTTTA GCCCAACCTT AGCTTTCTAT ATCATTTAGA
63951 CGAGGGGTTC ATTTCTTTGA TTTTAGCAAG ATTGCAGCTG GGAGGCAGTT
64001 GGGTTGAAGA TTAAATTAAT TTACTTTACC TCTGGATTGC AACTATAGCA
```

FIGURE 3U

```
64051 GGGCCCTGGA ACCCAAGCAC CACACAGCAT TGGGAGATCT CTTTCTGTCT
64101 CTCACTGTGC TCCCACCAGC ACTTACTAAG ATTCTCTTGT AGTATTACAT
64151 GTAATTGTCA GGTCAAGAGA TTTGTTTTTA CACTTGGGAC TCTTTCAGAT
64201 TCTAATTAAT CATACCAGTC CACAGTCTCA CTAAAAGTTT GGCTTGTTTC
64251 AGCAAAATCT TTCCACCTAT GGGAGACCTC CTTTTCTGCC CACTTGTACC
64301 CAGACAGGCA ATTGATTCAA GGTAGCTAGA AACAGGCTTT TGTTTCTCTG
64351 TGAAGAACTC ATCCTTCTCC AGAAATTGGC TCAGTTAGAC TTCTTGGCAT
64401 TCATTTACTG CTTTTTCATG GCTTTACAGA AAAGTATGAA GTTTAGTTTA
64451 TCTGGTGTTT TCTTGTTTTG ATGAGAGCAG TGGTCTTTTG GGATCAGCTG
64501 CATTCAAACC AGGTTGGAAC GCTTTAGAAT GATGGCATTA AGATTCTTTG
64551 CCTTCTGCTT TCAACCTTCC TTTTCAACCT CATCTCTTTT TATTCTTTTA
64601 ACCACACCAC AGTGCCTCCC TTTCATTCCC ACAGCACATT GTATACCTCC
64651 ATACCTTTGT TCCTTCTGCC TTGATTGTCC TTCTTCTCAT CTTACAACTT
64701 TGTCCTTTGA AACTCAACTC ACATGACACC TCTTCTGTGC CACAGATCCT
64751 CCTGCTACAA TGTACCTACC TTTACTTGTG TACTTTCACA TTATATTGTG
64801 ATGATTTATA TTATATGCTG CTGCTTTTAA ACTAAGGACA TGCCAGACAT
64851 GCCTTCATCT GAAAATGTTA ATATAGTTCA AAGTGTTGCT ATAGTCTTTG
64901 TTTAGTTAAA GTAACAACTT TCTGGTCTGA AAAAAAAAAG ACTATGCATC
64951 CCTTCAACAG AATAAGATAG TTTTAAAAGT AATGATATGG GAGCATCTCT
65001 TAAGATATGG TCAGTGTTAT GTTTTACCAT TTGTATTTAG AAAAACAGCT
65051 GTGTGTGTAT GTATGTATGT ATGTATGTAT GTATGTATGT ATGTATGTAT
65101 TAATTTATTT TGAAACGGAG TCTCATTCTG TCACCCAGGC TGGAGTTCAG
65151 TGGTGCGATC TCTGCTCACT GCAACCCCCG CCTCCTGGGT TCAAGCAATT
65201 CTCCCACCTC AGCCCCTAGA GTAGCTGGTG TTACAGGTGC ATGCCACCAT
65251 GCCTGGCTAA TTTTTATATT TTTAGTAGTG ACAGGGTTTC ACCAAGTTGC
65301 CCAGGCTGGT CTGAAGCTGC TGACCTCAGG CGATCTGCTC ACCTTGGCCT
65351 CTCAAAGTGC TGGGATTACA GGCGTGAGTC ACTGCACCTG GCTTGTATAT
65401 GTAGTTTTTT AAAAAAATAA ATAAGTAAAG ACTTTTCAAG GACAAAGATA
65451 TCATTTGCAT TTTGTAGCCT GAGTGCCAGT AATACTTGAC AATTACTTGA
65501 TGCTCAATAA AATGATTCTT ATTAGCAAAA TAAACCTTAC ACGTAGAAAA
65551 AGAATATGCC AGGAACCAAG AAAAGGGATA TTCAGATATG AGGCTCTTGG
65601 AGTTACGGCT CAGCTCACAA GGATTCTGCC GTAGGTGAGA AATGCTCCAT
65651 TACCCAGAGG CAAAGCCCCA GAGGTTGTGG CAGCACTTTA TGACTATGTA
65701 TCAGTCTGGG CTCAGTCAGG GAAACATTGA GCCACTGTTA AGTGTTATAG
65751 GAGTGAGGGG TTTAATATAG TAATTAAGGC CTATGCAAAT ATGGGAGGAC
65801 TAGAGAAGTG AAGGTCTGCA CGTTTTTTAT TGTATACTGG ACACGTTGTT
65851 TACAATAGGA GTAGGGAATG AGCTGGATAC AGCTACAGTT GGAAGACCAG
65901 AGGAATAGGC ACTGATGACT GAAACCTGCA GCTCTAGAGA GGGCAGAGAA
65951 GTGCTAGGAA ACTGCCTCTC GCTGCCAAAG TAGGACTCAG TGTGGGATCC
66001 CAAGGAAAGG TCTGTGAAGA CTGCCACGGG GATAAAGTGG AGCTTTAGGA
66051 GAGGCCAGTG GAGCGACTGC ATCTGACTGC CCTGACCTCT TAAAAATAAT
66101 GGCTTCTACT TCATTTCCAC CTTCTAAAAC TCACAGAAGC CTCTGACCCA
66151 GAACCACACA GGGAAAGGAA TTCTGGGAGA CTTAATTTTC TGTCCTAGAC
66201 AACAGTGGTG GTGGTGCCAG TTGACCATCC AGCATAGGCC ATTCCTTTGC
66251 CAGCCTGGCT TACATACACA CCTACTTAAA CCATATTTAA CTGCCAGATA
66301 AAGCTAAATG CTCTGCTTAA CATGTTGTAA CTATCGCTTA GCAAACTGAA
66351 AACATGCTAA GCACTCCCTC AAAGAGGAGA TGCTGTATTT CATATTGTGC
66401 TTTGTACATT TCTGGCTGAT ATGAATGTAT TCCACTAGCT GAGTCACATC
66451 CCCTCTTTGA TATCCTAAAA CTTACATATA CTGAGATACA GAGTTAGCCA
66501 TTTCCTTTTT TTTTTTTTCT TGGCAAGGTC TTGTTCTGTC ACCCAGGCTG
66551 CAGTGCAGTG GCGCCATCAT AGCTCACTGC ATCCAGAATC TCCTGGGCCC
66601 AAGCGATCCG CCTGCCTTAG CTTCTTGACT ATAGGTGTGC ACCACCACAC
66651 CTAGCTAAAT TTTTTTTATT TTTAACTTTT TGTAGAGACA AGAGGTATCA
66701 CTGTGTTGCC CAGGCTGCTC TTGAACTCCT GGCCTCAAGC AATCCTGTTG
66751 CCTTAGCCTC TCAACGTGTT AGGATTATAG GCATGAACCA CCGTGCCCAG
66801 CCAGAGTCAA TACACCTTAT ATTAGAGAGT ATTATTAGAC AGGGAAAAGT
66851 GGAAAAAAGA ATTCGTTAAT ATATTCAGTA TATATTCATA TCAAAGCAAA
66901 GAAGAATATC TGCCAAACTA TTGTAGTTCT CATTTTCTGT ACCTTTCATG
66951 TGATCATGGC AGGTATCTGT CATTTCTTTC TTCCTCTAGC CATTCCATGT
67001 TCCTTTGGTC CTCAGTAGTC ACCTCAGATG GTCTTTGTTC TTTGCCTGGT
67051 GGGGTGGCCT AAACCTTCAT TCTGGGGTGT ATGTACCAAT AAATGGCCAT
```

FIGURE 3V

```
67101 ATTGTTTTGC TCTAATATCC CGTTAACTTT CCATAATAAA CAAGTGTAAT
67151 AGAAAATCCT AGGTTCCAGG CAATTTCTTT CCTTCTTCCA TTGAGTATTT
67201 TTTTCCCATT GTGTATTTTA AACTTGGTTC TTCCTTGATA ATCGGGATCA
67251 ATCAGCCTAG CTATTATAGT ACCTGCCTTA CTTGTCTTTG GCTAAGTGGC
67301 ATGAGGAGCA AGAAGTGCTG AGTTAACAGT CTCAGCTCTC TGTTCAGTGG
67351 AAATAATGTT GTGTCTCCCC CAAAGAAGCA CTTCTCCCTT GAGGATTAAG
67401 ACCTGTAAAC TGGGAGAGCC CACAGCTGCT GCGAGTTTTC TTTTGGGGAA
67451 GGATTTTGAT AATATTTAGT GAATATAGGG CTATTTCGAT TTTCTTGTTC
67501 TTGTATCAAT TTTGATAAAT TGTATTTTTT AAAGTAATTT GGCCATTTCA
67551 CTTAAGTTGT CAAATTTGTT GGCAGGAAGC TGCAGTATTT TCTTAGAGTC
67601 CTTCTAATCT TTGTCAAATT GATAGTGATA ACTTTTCTAT TCCTCATGTG
67651 ATGACCCCTT GATTCCGCCT CTGTCCACAC CTGTTAGTGA TTCCCTCCAC
67701 CTGAATGTGG ACAGGACCTG TGACTTGCTT GGAACGAATA GAATACAACA
67751 AAGGCGATGG GAGATATGTG ATTGCATGAT TATATTATAT AAGATTACAG
67801 CACTGGACTG GCTGGAGTGT GCACGTCTCT CTCTCTCTCT CTCTGGACAT
67851 AAAGACTGTT ATCTTGTATA GACTCTGGGT TCCTTTATAA TACTCTTGTG
67901 AATGCATTTA CTTTTGTTTT AGCAGGCAAT CAACTCAGGT AGGCTGGATT
67951 ATACATTGTT TTGCCTTTTG CAGGCAGTGA TTCAAATCCC AATTCAGTTA
68001 TCAAAGCAAA GCCTTTGCTA AACTGGTTTG GGTTTGTCCT GTGCATGTGT
68051 GATTCAGAGG TTAAGGTGAG ACCCGTGTAG GTGCATACAT AAAAGTGGAG
68101 AGCTCCTTCA CCTGCTGTTT CTGCTCCAGG AGTTTGCTCT GACTCCCTGT
68151 CTTTCTTTGG CTCCTTTCCC TGCTTGCTCT GACCAGAAAG AAAACAATTC
68201 CTATCAGAGT TTTAGCCACC TACGTGTGCT GCTTAGTGAC TGAAGCTGTC
68251 CCACCCTCAA GGAAAAACTT GATGAGAAAA AAATAAACAA ACAGAAAACT
68301 CACCCTGTAA GGTCACTTCT CCAACTTTTT ACTTCCCTCC ACAATCTGCC
68351 TGCTTTTATT TACTTTCCAG ATCCTCATAT AGTTTTTTGT TTTGTTTTGT
68401 TTTGCTGTGT TTTGAGATGG AGTTTCACTC TTGGTGCCCA GGCTGGAGTG
68451 CAGTGGCACA ATCTTGTCTC ACTGAAACCT CCCCCTCCCG GGTTGAAGCG
68501 ACTCTTTTGC CTCAGCCTCC TGAGTAGCTT GGGATTACGG GCAGCCGCCA
68551 CCATGCACGG CTAATTTTTG GTATTTTTAG TAGAGACAGG GTTTCACCAT
68601 GTTGGCCAGG CTGGTCTTGA ACTCCTGACC TCAGGTGTCC CACCCACTTC
68651 AGCCTCCCCA CAGTGCTGGG ATTACAGGTG TGAGCCACCG CGCCTGGCCC
68701 AAGGTAGTTA TTTTTTAAAA GTTTGCTCAA ACTTTATAGT TGTAATTAGA
68751 GGGAGGAACA ACTTTATGGG ATGTAGGTGG CTTAACCTCA CCATAATGGA
68801 ACCAAAACTC CACTTCATTC ACTTTTTTTT TTTAGATGGA GTCTCGCTCT
68851 GTCTGCAGTG ATGAGATCTC GGCTCACTGC AAGGTCCGCC TCCCCGGGTT
68901 CATGCCATTC TCCTGCCTCA GCCTCCTGAG TAGCTGGGAC TACAGGCGTC
68951 TGCCACCACG CCCGGCTAGT TTTTTTGTAT TTTTAGTAGA GACGGGGTTT
69001 CACCGTGTTA GCCAGGATGG TCTCGATCTC TTGACTTCGT GATCCGCCCG
69051 CCTCGGCCTC CCAAAGTGCT GGGATTACAG GTGTGAGCCA CTGCGCCCGG
69101 CCCACTTCAT TCACTTTAAA ATGAAGTACT TGACCAGAAG CAGTACTGTT
69151 TAGAATGCCA TTATGGTGAA TAAGATATTT TGTAAGGGAA AGGATGCTGG
69201 TTTTTGACAG AAATGTTGTG GGCAGAGAAG GAAATCTTCA TTGAGTAAAA
69251 GCAGTGTCCT TTTTAGATGG AAGCGGTCCA GTGTGATCAT CCTGCTACAG
69301 ATGGCTGCCC AGACCCCCTG GGAGCAGCGC TTTATTGGGG CACCATTGTT
69351 GGCCTCTCCT GTTGGCAGGT TGGACACTTA GCCATGATTG TTGCCAGGTC
69401 AGCCTTGACA GGTGGAAGCC TGTGTCACTG AGCACATGCA TGACCTTCAT
69451 TCCTGTTGCT CTCACAGTAG GATATGAACT TTGTTCATTA GCGTTCTGAG
69501 CAAGGGAAAC AGTGGCTGAT AAAATAATGA GTCATTTTGT CCACTTGGTT
69551 ATTGAGAGCC TCCTCTGCTG AGATTATACA TTGGTCATCA TTTACATGGG
69601 ACACAAATAC CCTCACACTT TGTCCTGTTT GAGAATAGTT TATTGACATA
69651 GCTCTTTTCT ATATCTTACC ACAAGTTTCC CAACCTTATT CTAAGTTTCT
69701 GAATTTCCAG TCAAACCATC TGCTGCTGAC CACAAATCAG TGTGGATTCG
69751 TATTTATAGC CATCACTCCT TTGACACAAA ATGTGCAGTC ATGTACACTG
69801 CTTCGAGTGT ATGATGAGCA GCCTAAGCGA CTTGGGCAAC TTGGTAGCCA
69851 GTGGTAAAGT GTTCAGTCCT TACTAAATCC TAGTAGCAAG CAAGGGCTCT
69901 TTCTCAAAAG GGAGAGTAAT GATCTCCAGA AGTTAGCATA GCTTTGCTCT
69951 AAAATCCTAG GGTTCTATAC TGTGATTTAC CTCTAGGGCC TGCCATACCT
70001 CCACACATCA CTCATGAAGT ATCATCCTGT ATCTTAAGTT TTTGTTGGCG
70051 ATACTAATCT CTGCAGTTCC TCTAGGAATG CAGTATTACT TTTGGTGTAA
70101 TATTTTGGTA GAGAGAGGCA GCTCTAATGT AACCCCTGAG GTATGGCTTT
```

FIGURE 3W

```
70151 AGTATGCTAC CCATCTCTGT TAGTCCTAGG GACACCATCA CCAATCAGCC
70201 ACCACCAGAG ATCTCTACAG CTCACACCAT TCTCTTTTCC TACTCTACCT
70251 CTGCGTGTGC TTATAAAGTA TAGCCATGTG CCCATTGTTT CTGTCATGAA
70301 GCGTCACCAG TTGGCTGCTG TGACTCAGAG ATCTTTTCAT CCTTCCCTTG
70351 GGTTCAGGGA ATCTATTTCT CTGACAGCCT TTCCCATTGT TATTTCTAGC
70401 CTGCAGCGAA CAAGCACTAA AGAGCTTTTT AGGGATGTTG TTGCCCCCTT
70451 CACCAATGTA TTTCTCAAAG GCTTGGTAAA GGAGTGAGTT CTCTAGACAT
70501 TCCTGGGATG TAGTTAGGAG ATCAGTGAAC AGATCAGTCA TACGTATTAA
70551 ATACACCCCA GTATTCCTTA TTTTCTAACC TTTTGAATAA ATTTTATTTT
70601 GAGACTGAGT TTTGCTCCTG TTGCCCAAGC TGGAGTGCAA TGGCACTGTC
70651 TCAGCTCATT GCAACCTCTG CCTTCCGGGT TCAAGCACTT CTCCTGCTCA
70701 GTCTCCTCAG TAGCTGGGAT TACAGGTGCC CGACACCATG CCCAGCTAAT
70751 TTTTGTATTT TTAGTAGAGA CAGGGTTTCA CCATGTTGGT CAGGCTGGTC
70801 TTGGAACTCC TGACCTCAGG TGATCCACCC ACCTTGGCCT CCCAAAGTGC
70851 TGGGATTACA GGCATGAGCC ACTGCACCTG GCTTGAACAA CTTTTATTTA
70901 CAGTATACCA AGGAGGTTCT GGCATCTAAG CTTCATTTAA TGTAAGCCAC
70951 TGATGGATCC AGGTTTTGGC CAACCAGGTG AGGAAATTGT TAGAGTTATT
71001 CCCTGATTAC TCAAGCCAAT ATACTGCATC CAAAATATCT GGTTAATGTA
71051 CTCATATATT GATAAATTTG ACCAAGTCCA ACGTTACATT CCTTCTTGTC
71101 TGGTCTAACA TTCTTAGGAT TCATTGCTAC ACACTTCCTA GGTTTCTGCA
71151 AGTACAAATG GGCAAAATCT AGCACAATGA CCCTAGCCCT CTGAGGGTCA
71201 CAGCAGGTTG GTTCAGGAGT AGGAACCTGA CCCAACACAG GCAAATAAAG
71251 GTCTTTCCCT GGGACTGTGA AATGGTACCA AGGGAAGAAA GGTGGTTTCT
71301 CTCTGGTAGG GAGGGCCACT GGATATAAGG CACAGGAACT GTTGCTGGAA
71351 GCGTTAGACA CTGCTGACTG CTTGTTCCTT TTTCCCTGTT AGTAAAGACT
71401 ATTCCTTTAA AAAACCAAAA AAGGTAGATA AAAATGCCAG ATATTCATTT
71451 TCCCATATAC TCTTGTGGGT GGAATGACCA CTTGACCATT TTTTTGTAGC
71501 CAGTGATACA TAAGGAGATT TTTTTTTAAC AGGGAAAAAA AGAGCTTACA
71551 AATTTTATGT GCACATGTGT GCATGGGAGT TATACAATTC TTTTAAAAAA
71601 AAAACTCAAA TGGCTAGATG ATTGACACTT TTGTACCACC CTGAGATACA
71651 GAAAGAATAG GGGCTTGGAT CATGGCCAAA CAAGTTATGG TGGCAAAACA
71701 GGTTATGGGA GGAAGAGAAG ACCACCTTTG CCTGGCTAGC AAAGGTAGTC
71751 TTGAACTCTC ACAGGCAGCA GCCCTCAGAA AGAATGGATA GTAGCCAGTG
71801 ATAAATGTTT CTAGCAGACC TTTAAAGGTG TTAGACTCTC AGTTAATCAT
71851 TCTTAGGTCT GGATAAGGAG ATGTTTGCTA GGGATTTTCT GGGAGAGATT
71901 TAGCTTTCTG AGAAAATAAA GAATTGTGTG AAAAGAGCTT ACTCTTTCCT
71951 TCCTGCTTTT GAACATTGCT GTGAAAGAAC ATTATGCTTA GCCCTGCTGC
72001 AGCCACTTTG TGATCCTAAG AGAAGTTATC ATCAATAACA CACTGAAGGT
72051 GACAGAAGGA AGATTAGGGC AGAGGCTTCC CTTGATTTCT GGGCTTAGGA
72101 CTGTCCATCC ACCTCATGTC TGGACTTCTT GTTATGTGTT TGACATACTT
72151 GTACTCAGTT ATTCTATTAC CGTGTGTTCA CTGCAAATGG GGTCGTGTTC
72201 CTCAGTGTGT AAGGGAATAA AGCCAACCCA TCGAGAGAAG CAGAGCCAAA
72251 GAGGTCAAGG GAGTGTCTGG CAGGGGTTGA GGTCCTGGTT CTGGTTGCCC
72301 ATGAAGATCA TTTCCAGCTC TGCCCTTGCC ACAGTTCCAG GAAACATTTC
72351 CCTTTTTGAC TGTATTACTT GAATTGGGTT TCTGGGCTGT AGTAGGAATA
72401 TTCCAACTAA TACCATACTG GGTAAATTTG AAGTATGATA AATTTTAAGC
72451 TACTTCTCAC TTTATTTCTT GTGCCTAAAT TTGAAGAGTA TTTATTTATT
72501 TATTTATTTA TTTATTTATT TATTTATTTA TGAGACAGGG TCTCGCTCTG
72551 TTGCCCAGAG TGCTCTGGAA TGCAGTGGCA CGATCATAGC TTACTGCAGC
72601 CTTGACTTCT TGGGCTCAGG TGATCCTCCC ACCTTGGCCT CCCAAAGTTC
72651 TGGGATTATA GGCATATAGG CATGAGCCAC TTTGTCTGGC CTAAATTTTA
72701 GTTAAAGAAA TTCTTATCTC ATTCTTTCAG AATTTTCATA GGCCTTCAAA
72751 GCAACAACCA TGGAGTTAAA TTCATTTCCT CAACTTGGCA GGATTTTTTT
72801 TTTCCCCTAT TGAAGTATTT TGTCTTTTTT TTGTGTGTGT GTGACAGGGT
72851 TTCACTCTTC GCTCTGTTGC CCAGGCTGGA GTGCAGTGGC ATGATGATAG
72901 CTCACTGTAG CCTTAAACTC CCCTGGGCTC AAGCCATCCT CCCACCTCAG
72951 CTCCCTGAGT AGCTGAGACC ATAGGCATGC ACCACTATGC CCAACTAATT
73001 ATTGTATTTT TTGTAGAGAC AAGATGTCAC CATATTACCC AGGCTGGCCT
73051 CAAACTCCTG AGCTCAAGTG ATTCACCTGG CCCGGCCTCC CAAAGTGCTG
73101 GGATTACAGG AGTGAGCCAC TGTGCCCAGC CATTTTGTTT TATTTTGAAA
73151 GAAGGCTGAA TTGATTCCTG CAGGCATTCT GTAAAGAATA TATAAGGAAG
```

FIGURE 3X

```
73201 TTCAAAGTAG CACATTTTAC CATCTCTCAG AATACCTCAG TCTTTCTTCT
73251 GATGCATCAC TTTAAGGCTT CGATTATTAA ACAAGCAATT ACTAAACAGT
73301 TGCTTTTTGG AATACTACCT TCTAGTGCTT CAGGAGATGC AAAGATCTGG
73351 CTTGTATCCA GGAAGAAAAT ACAGGTAATT GGATTGGAGA GAGAAGACAT
73401 GCCATAGAAG AAAATGAAAT AATAATAAGA TGGGAGAAGA ATTTTTACTG
73451 TGTTTTAAAG GGTTAAAAAC TGTTGGAAAC CTAAAAATTT GTCCACAGGA
73501 CGAGGCTGAA AGTCTGAGAC TACCCCACAG GAATAGCCTT GTCAAGGCCT
73551 GATTGTGCCC TTTGACTCAT CCTTCAAAGT CAAACCTTTC TCATCTTCTC
73601 TCCCAGCTTT GGCACTGTCA TTCCATAAGT GTATCCCAAT AATTTGTGTT
73651 TTCTGCCAGA AATCCTTTTG GGGCTAATGA GTTTCATGCA CTTGTATTTG
73701 CTGTGTAAAG TAGGTTTTCC TATACTTGTA CTTACCAGAT TAAATGTCAA
73751 AGGATCCAGC TCTTTGTTGG TTTTGTGTAC AAGCACAAAT TGCACTTGCT
73801 CATGCCATTC AGAATTTCGT ACATTTTAGT TGTCTTTTAC AACTGTAATC
73851 CCATCTGAAG GTCTATGGGA AATTCAGTTC CTTAAGAAAT AGGTTCCCCT
73901 CATCCTTCTC TTTCTGCCTT CATTAGTGAG AGTACTTTTT GAGAGCAAGA
73951 GAACATTTGC AGTGAAGAGG TTTAGTTGGA TAGCTATTTA TACAGTTTTC
74001 CTTGGAATTT TAAAGAATGA AATAATTTCT CTTTATGTCA GCAAATGCCT
74051 ATTCTGAACA TTCAGAATGA CTGTTCTGAA CAGTAATGTT TAACTCTTAA
74101 AAAACATGGT ATTTATAAAT GAGAATATAA TAAATCAGTA TTAGAAGTCA
74151 TTTTTTACCC CATGCTCTAA TTCAGGAGAA AATAGGAGAT ACTTATAGGT
74201 TAACTTGGTG TCTGATTACC AGTGCCTGAT ATAATTTCTC CAATTCCCTT
74251 TTTAAAAATC TATTAAAATA TCGTTAATTT AAAAAATCCC TTTAAAATGA
74301 AGATATGAAA AGCTCTATGC TAAAGAATAG GGAAATTTTC CACTAAGTCG
74351 ATCATTGATT GTATTGTGGC TTTTCCTTAA ACCCAAAGAT TACCCAAAGA
74401 TTACTGTAGA AGTGACACTA CGAAAAATCA AATTAATGAT AGGGAGAGTA
74451 TACATTAGAT GCTCTTCCAG AATGTCCAGC AAAAGACCAG AGATGAAGAT
74501 TGATAGATGA GAGAAAATGA TACCTATGAA AGAAAAAAAT AGAGATTTAA
74551 CTGGTGACTA ATAGATGTCT GCAAAGGAGC CAACAGAAGT GGAACAAAAG
74601 CATGGATCAA ATGTCTCATT GTGGAAGACT TTCCAGGGTT GAAAATGACC
74651 TGAAGAATAA AAGAGCTCAC TGTATTCTAA AGAACATTAT GAAAACGTGT
74701 CTGTACCTAG ACATATTTTG CTGGTTTTCT TTTGATTTTA AGGATCCTGA
74751 AAAAAAAAAA AATCCTGCAT ATATCAAGGC ACAAAAAAAT GAGCTTTCAA
74801 CAAAGAAACA AAAATGATGC TGGTAGCCAG GCGCGGTGGC TCATGCCTGT
74851 AATCCCAGCA CTTTGGGTGG CCAAGGTGGG CAGATCACAA GGTTAGGAGT
74901 TTGAGACCAG CCTGGCCAAC ATGGTGAAAC CCTGAATCTA CTGAAAATAC
74951 AAAAAATTAG CTGGGTGTGG TGGCATGTGC CTATAATCCC AGCTACTCGG
75001 GAGGCTGAGG CAGGAGAATC ATTTGAACTC GGGAGGCGGA GGTTGCAGTG
75051 AGCCAAGATC ATGCCATAAC TCTCCAGCTT GGGTGACAGG GCGAGACTTG
75101 ATCTCAAAAA AAATAAAATA ATAAAATAAA ATAAACAAAT TATGCTGGCT
75151 ACAAAATTTT CTTTTGCAAA TACTAAATGT TGGAAAATGA TGGAGCAGTG
75201 GGCAGTGATC CTTAGCTTAT GTGGTCTTTG AACTCCCTGC AGTAATATTT
75251 GGACCTCTAT GTCTTGATGC AAGTTGATTT TCCTGGGAAT AGAATCTATA
75301 TCGTTCCTCA TATTTTCCAG GATTTCATGA AACAAAGAGT TAAGAACTAC
75351 AGTAGTGGAG CAATATTCAT GGTGCTTTTT CTTTTTCTTT TGAAATAATT
75401 AAAAACTTAC AGAAAGGCTG TAAGAATAAT ACAGAGAAAT CCTGTGTATT
75451 CTTTCCCAAA TTCATGTGTT TGTCTTCTCT CTCTTTCTCT CTCCTTATAA
75501 AATATTTCAA TGTTGTTAGT TATCTCAAAA TGGACTTTGT AGTTTTTTTT
75551 TCCTCCCCTA CCAGTACAGG TTTCAGTCTA AGATCACATC ATATATATAG
75601 TTTTATATTG TTTTAGTTTT CTTTATCTGT AACAGTTTCT CAGATGCTCT
75651 CTGTCTTCCA TGATACTGAT ATTTTTTTGA AGAATGCTGG CAGGTTATTT
75701 TACAGTGTTC CTCATTCTGG GTTTGTCTGA TGTTTCCTCT TGATTATTAT
75751 TCGGGTTATG CATATGAGGC CACAATACTA GGTAAATTGT GTGGTTTCAT
75801 TCTCAAGGTA TCCACATCTG AAGGCGTATG ATGTTCATCT GTCACACCGT
75851 TGATGTTAAT TTCGATCTCA TGGTAAATGT GTTTTTTCGG TGTCTCCACT
75901 CTATGGTTAC TTTTTTATCC CTTTCAATTA AAAAACAATC AGTGGTCGGG
75951 CACTGTGGCT CATGCCTATG ATCCCAACAC TTTGGGAGGC AGAGGCAGGA
76001 GGATCGCTTA AGCCCAGGAA CTCAAGACCA GCCTGGGCAA CATAGGGAGA
76051 CCCCATCTCT ACTGGACTGG TGGCATGTGC CTCTTGTCCC AGCTGCAGGA
76101 GGCTGAGGTG GGAGGATTGT CTGAGCCCAG GATGTCAAGC CTGCAGTGAG
76151 CTGAGATTGC ACCACTGCAC TCCAGCCTGA GTGACAGAGT GAGACCCTGT
76201 CTCAAAAATA AATAAATTAA TTAAAAATAA AAACGATCAA TGTGGAAAAA
```

FIGURE 3Y

```
76251 ACTTGAAGAC TGTGCAAATA GCCATATGTT GCTTAACGAT GGGAATACAT
76301 TGTGAAAAAT GTGTTATTAG GTGATTCTGT CATTGTGCAA ACACCATAGG
76351 GTGTACTTAC ATAAATTTAG ATGGTATAGC CTGCTACATA GCTAGGCTAT
76401 ATGGTTTAGC CTATTGTTCT TAGGCTACAA AACTGTACAG CTTGTTACTG
76451 TACTGAATAT TGTAGGCAGT TGTAACACTA TGATAAGTAT TATATAAACA
76501 TGTCTAAACA TAGGAAGATA CAGTAAAAAT ACAGAATTAT AATCTTATGG
76551 GACCACTGTC ATAAGTGTGG TTTATTACTG ACCAAAATGT CATTATGTGG
76601 CACATGGCTG TATCTTGCTT TTCATCAGGC TTTACACTCT AGATGAGCAT
76651 CCATTGATTA TTCTTACCCA CACCAATGGT ACAGTTATGA TAGTTGGAAA
76701 ATGCTGCTTT TTTCCAACTC CACTACTCCC TCCATTTCAT GGTATTCTAA
76751 TGAATGATCA TTGTCACAAA ATTCAACACC TAATTGTATC TGTTATGATA
76801 ATGAAAAGAA ACAAATGACC CATTCAAAAC AGTTCAGTTG AAAAGAGTTT
76851 ATCAAAGGAA TGACTTAACA CGGTGTGGCC ACAGTAAGGG AATCAACAAG
76901 GAATGGTGAA GCACCCAGTA ACTAGCAACA GTGGGAAGCC ATTGCCACCC
76951 TTAGACCTGC GGAGGCAAAG GGAGGGCACA TGGTTATCAG GCTCGTGAAA
77001 CTGGAATTCA TAGAGGAGGA ACCACCTACA GGTGCTGTGT CTCTAGAGAA
77051 AAACAGCCAC TGTCAGCACA GAGGCAAGGT TGAGACAAAG CTGGGGGAAT
77101 CAGCTGAGTT CTTCCTGCTG CTGCTCTGAC CTGTTAGTAG TGCTCACGGT
77151 TGCCCAGTCA TAAGCCAAAG GACAAGAAAG CCTGGGTGAT GCAATCTGGA
77201 GAGCTTGACC TCCTGGGGCA CAGAAGGTGT TGGGGGGTTG TGGGAATGGT
77251 AGTATAACCA GCACACTAGC TAAGATTTTA TTAATGTGAC AAGACAAGAA
77301 AAAGATCTCT GATGCGCAAG AACTGAATGG AGAGTTCAGA TCATGTTCTT
77351 AGATGGGAAG ATTGAATAGT ATAAATATCT TGGTTCTTGC CACATGAATT
77401 TGTCTACTTA ATTCCAACAG TCTAATGGAA TTACGGAGGG AGTAGGGGTG
77451 ATGGTGGGGT AACATTGTTA AAATGATTCT AAGTTCAATC AGGCAAGAAT
77501 AACAAGAAAA AAAAATTCGG GCCAGGTGCG GTAGCACACG CCTGTAATCC
77551 CAGCACTTTG GGAGGCCAAA GCAGGCAGAT CACCTGAGGT CTGGAGTTCG
77601 AGACCAGCCT GACCAACATG GAGAAACCCT GCCTCTACTA AAAATACAAA
77651 ATTAGCCAGG CATGGTAGCA CATGCCTGTA ATCCCAGCTA CTCGGGAGGC
77701 TGAGGCAGGA GAATCGCTTG AACTCAGGAT GCGGAGGTTG CGGTGAGCCA
77751 AATTCATGCC ATTGCACTCC AGCCTGGGCA ACAAGAGTGA AACTCCATCT
77801 CAAAAAAAAA AAAAAAATTC TGATTTCACT GCGTAATTTT AAAAATAATA
77851 TTTTAATTTT GTTTTGAACT AAATATTTTA AAATTATTTG TGTTCATAAA
77901 TTATTTAGAA TTGTTTTTAA GGGTTTTCTA AGTTACATTT TTGTTACTCC
77951 TTTCTGACTT AAATATAATA TAGTTAAAGA ATATTATCTA AATGATACTA
78001 ATTCTGTAAA ATGTTGTTGA AGCTTAATGA TCTAAGACGG GTCAGTTTTT
78051 GTGAATCTTA CTGTGTGTGT GTTCCTGAGA AGGATGTGTA TTCACTAATT
78101 AATGGGTGCT GGGTTTTATT GGTAGGCCAG AAGTCAAACT TGACAGTTAT
78151 GTAGCCCTTA ATTCATGCTA ATGTTTTGTA TCATTGGTCT GTAAATAACT
78201 GAAAGAGCTG TGTTGAAATC TTCCACTTTG TGGATAGATT TGTTCATTTC
78251 TCTCTAAAGT TGTCAAATTT TGCTTTATTT TGAGGCTATT TTTTGAGAGC
78301 TTACAAATTT AGATTCATTA GCATTTTCTA GCAAATTGAA CATTTTATTG
78351 TAACATACGG ACTATCACTA AAAATGCTTT TTGTCTTACA GAGTAGAATT
78401 GCTAAATAAA ATACAGGATG CTCAATTAAA TTTGAATTTC AGATAAATGT
78451 TGAGTACTTT TTTAGTATAA GTATGTTCTA CATATTGCAA AAATTATTCA
78501 TTTTTCACAG GAACAGAAAA CCAGATACCA CGTGTTCTCA CTTATAAGGG
78551 GGCACTAAAT GATGAGAACA CATGGACACA TGGCGGAGAA CAAGACACTG
78601 GGGTGTACTG GAGGGTGGAG GGTGGAGGAG GGAGAGGATC AGGAAACATA
78651 ACTAATGGGT ACTAGGCTTA ATACCTGGGT GATGAAATAA TCTGTACAGC
78701 AAACCCCCAT GACATGAGTT TACCTATAGA ACAAAACTGT ACATGTTCCC
78751 CTGAACTTAA AATAAAAGTT AACAAAAAAA GTCTGGCATG GAAAGACATA
78801 AACATGCGTG GAGCTGGTTG TCTCTGATCT TGCACCACTT GTGATAAAGT
78851 TGTTTGTAGT ATTTAATGAA TGTGTTCAAA AATCTGTATC TTTAGTTATA
78901 TGTACTTCTT GGTCCTAATA TTACTGATTT GTGCTACCTA TACAGTTTTG
78951 GTGGGGGGTT TGCTTATTTG GGGGATAACC TTACTACTGG TTTGTCTCTC
79001 TTATTAGTCT TTTCAAGTAA TACTTTCTTT GGCTGTATTC TGTTGCTCCT
79051 TTTCTAGCTT GTTTAATTGA ACATTTAATT AAATATTCAT CATTCCTTTT
79101 GAAAAAATTG TTGTTTATCT GACATTCAAA TTTAACTAGG CATCCTATGT
79151 TTTGTTTGTT TTTGCTAAAT TTGGGAGCCT ATTTAAAAAC TATTTTGTTT
79201 GATACTAATA TAGCTATCCC CAATATTTTT TGGTTATAAT TTCCCTAGTA
79251 TATCGTTTTT ATAAATTTCA TTCTTTGAGT CTTTGTGTTT TAATGTTTTT
```

FIGURE 3Z

```
79301 TTTTTAATAT CCTATAGTCA GAATTGTTAG TCTAATCTTA CCTATGTTGT
79351 TTTTCTAGGA AGTGTAGGGC TTTTTTATTG GGATTGCAGA CCTATTGTCC
79401 CTTTTTTAAA ACTATATTTT CAAATGCTTT TTATTTTTCC CACTTGTTTT
79451 GTGCTTTTGT GGACTGTTTT CTTTTTGCAT GATTTTAAAA AAATTCCATG
79501 TTCTCTTACT ATTATTTTAG ACATTACACA TATTTATTAT TTTGTTAACC
79551 TTTAAATATT ACTGTCAGGC CAGGCACGGT GGCTCATGCC TGTAATCCCA
79601 TCACTTTGGG AGGCCAAAGC GGGTGGATCA CCTGAGGTCA GGTGTTCCAG
79651 ACCAGCCTGG CCAACATGGC GAAACCCCGT CTCTACTAAA AATATAAAAA
79701 TTAGCCAGGC GGGGTGGCAG GCGCCTATAA TCACAGCTAC TGAGAAGGCT
79751 GAGTCAGGAG AATCGCTTGA ACCTGGAGGC AGAGGTTACA GCGAGCCGAG
79801 ATCATGCCAT TGTACTCGAG CCTCGGCGAC AGAGCAAGAC TCTTTCTCAA
79851 AAATAAATAA ATAAATAAAT ATATATTACT GTTCAAACTC TACTTGATAA
79901 AGTTATTTAA TATTTTTAAA TCCCCACACA AACATCCTAA CTCTGATAAC
79951 TACCCTTTTA ATGCTTATGC TATTACTGAT GAATATTTAA GTTCTTTTTT
80001 TAACACTATA TGTTAGACAT CATCATTACT GTTACTTTAT ATGGACAGTA
80051 TTATGTTTAT GTATATGTTT ACCATTTCCC ATGCTCACAA TTACTTCTTG
80101 CATCTAAGAT CATCTTTCTC AGATTGGTTT CCTTTTTTTT CCCCCAAGTA
80151 CATTCTTCAG AATTTTTTTT TTTTTTTAGA CGAAGTCTCA CTCTGTTGTC
80201 AGGCTGGAGT GCAGTGGCAC GATCTCAGCT CACTGCAACC TCCCCCTCCT
80251 GGGTTCAAGG GATTCTCCTG CCTCAGCCTC CCGAGTAGCT CCTACTACAG
80301 GTGCCCGCCA CCACGCCTGG CCAATTTTTG CATTTTTAGT AGAGATGGGG
80351 TTTCACCATG TTGCCCAGGC TGGTCTCGAT CTCCTGACCA TGTGACTCGC
80401 CGCCTTGGCC TCTCAAAGTG CTGGGAGTAT AGGCGTGAGC CACCACGCCC
80451 AGCCTAGAAG TTTTTTTGGT AAAGGTAAAT TGATGGTAGA CTCAGACTTT
80501 GCATATTTGG GAATATTTTT ACTTCACTCT AATTCTTGAA ATGTTGTTTT
80551 GTTGAATAGA CTAGGTTTAT AGTAATCTTC CATCAGCACT TTGAAGATAT
80601 TTTAACATTT TCTGGGCCCT AGTTTTGCAA TTGAGAAGTT ACTATCAGCG
80651 TAGTTGCTAT TTCTTTGTGG GTGACTTTAC TCTCTGATTT TTAAGGTCTT
80701 CTTTATATAA CTGTATTTTC CAATTTTACT ACAATATAGC TAACTGTGGC
80751 TTTTCTCATT TATTTGTTTT GTTTTGTATA TTTATATGAT TTCCTGTATT
80801 TTATCAGTTC TATAAAATTC TCGACCATTT TTCTTTGAAT ATTTCTTCTT
80851 CTCCGTTCTC TCCATTTTGT CCTTTGAACT CCAGTTATTT GAATATTAAA
80901 ATGTTGCATT CTGTCCTCCA GATAGTTTAA CAACTCTTTC ATGTTTTCTG
80951 CCTTCTTACC TCTATCTGCT AGATAATTTC TTTAGATCAA TTGTCTGATT
81001 CACTCATTCT TTCTTCATCT GTTTCATTTG CTCTTTAACG TGTCCAGTAT
81051 ATTTTAATTA AAAATATATA TGTTGGGTTA TTTTTAGCCT GCCTGCTACT
81101 TTAAAAAAAT ACTCTTTTGT TCCTTTTAAA ACATCAAAAG TTGATCTGAA
81151 GTGTTTCAGC AGTTGAACTC CTAGGTCTTC ATTGTCAGCC TGCTGTACTT
81201 GTTTTCTTCA AGAAGATAGA TATCTCTAAA TGTTGTCATA TCCTTTTTTG
81251 TTATTGAATC AAAGTAGCTG AATTTGATAG AAGTTCAGTG TTGCATTGTC
81301 CAGATACACA GTTTTGAGGT TTGAAAGCTT GAATAAGTGC CAGTGGACTT
81351 CATGCAAATG CTTTATATAT TTTTCACCTA ATATATTTTG AATTTCAACA
81401 AGTAACACAT TCTCTTAAAT ACTGACTTGA TAGGCAAGTG AGCATAGCAA
81451 GCTTCATCTT TTAGTGAAAG TCCATTGATC CTGTTTCGTA ATTGGATGAA
81501 GAGTGTCCAA ACTATTGCCA GTAGCTTTCT GTTTTCCCAT CATTTTTCAA
81551 CCCAGAAATA TTTATTTTTC TTTCCAGGGA GGCATTAGCA GTACCCTGGA
81601 AGCTCCCCTC CTACCCCTCC AAATTATTCC CTCCTCCTCT TTACTTTTCT
81651 CCAAAGATAA TCTCTGTCCT GAATCAAAAA TCGTCCCCGC TTCCTGGTAG
81701 CACCCGATCT GGAAGAAACC CAAAATCACC TAACCAAAAC CTGAATCATA
81751 TAATAGTCTT TTCTAATACT CTTTTACTGA GACATTCCAC AATTCCCAAT
81801 TATATGTGTT ATTCCTTGCT GAAATGAATA ATGAACCCAA CATGTGCAAC
81851 TACAGCTATG TTCCTGGTAA CCTTTGGCTG GGAGGATTGA CAATATTCAT
81901 TTGTGTCTGG TTTCTTTCTT TCTTTTTTTC TTTTTCTTTT TTTTTTTTTT
81951 TTTTTTGAGA CGGAGTCTTG CTCTGTCCCC CAGGCTGGAG TGCAGTGGCA
82001 CAATCTCGGC TCACTGCAAG CTCCACCTCC CGGGTTCACT CCATTCTCCT
82051 GCCTCAGCCT CCCGAGTTGC TGGGACTACA GGCGCCCGCC ACCATGCCTG
82101 GCTAATTTTT TGTATTTTTA GTAGAGGCGG GGTTTCACCA TGTTAGCCAG
82151 GATGGTCTCG ATCTCCTGAC CTTGTGATCT GCCCGCCTCG GCCTCCCAAA
82201 GTGCTGGGAT TACAGGCGTG AGCCACCGCG CCCAGCCTGG TTTCTTTCTT
82251 TTTAACATTT TGTAAGATTC ATGTTTTTGC ATGTAGTCAT AGTTTTTTTT
82301 GTGTGTGTGA TGGAATTTCA CTCTTGTTGC CCAGGCTGGA GTGCAATGGA
```

FIGURE 3AA

82351 GTGATCTCGT CTCACCACAA CCTCCGCCTC CCAGGTTCAA GCGATTCTCC
82401 TGCCTCAGCC TCCCGAGTAG CTGGTATTAC AGACATGTGC CACCACGCCC
82451 GGCTAATTTT GCATTTTTAG TAGAGATGGG GCTTCACCAT GTTGGTCAGG
82501 CTGGTCTCAA ACTCCTGACC TCAGGTGATC TGCCCGCCTC AGCCTCCCAA
82551 AGTGCTGGGA TTACAGTTGT GAGCCACCGT GCCCGGCCTT GTTCATTTTT
82601 GTTATTTAAT ATTATGCTAT AATTACATAA CTATTTGGAA CTTTTTGACT
82651 CTGTTTTAAT GTTGATACAC AGTATCTTTG TACATATCAT TTGGTGAACA
82701 TGAATAATGC ATTTTTGTTG GGAGTATGCC TGGGAGTTAT ATTGGGAGTT
82751 CCCAAGACCA CTCATAGTAA TCAGAAGTTA TGATTATGAT TATAGTTGAT
82801 TACAGCAAAA GGATATGAAG TAAAAGTCAA GAAAGGGAAA AGGCACATGG
82851 GCAAAGTCTG GAAGGAACCA GCTGCTCACT TTCCAATGTG CCCTCTCAGT
82901 GGAGTCAGAC AGGACATGTT TCATTTCCCC AGCAACATGT GTGACAACAC
82951 ACACAAAATG TTTCCAATCA AGGAAGCTCA CCTGAGCTTT TGTGTCCAGA
83001 GTTTTTATTA GGGGTCAGTC ATGACATAGG CATTTGGTAT TACCTGCACA
83051 ACTGACTTCA GGGTCAGGCT CCAGATCCCC AGAGAAAAAG CAGGTGTCAA
83101 CCATAAATCA CATTGTTAGC ATAAACTATC TGGTTAAACC AGTACAGCAT
83151 GGCCCAAGGC CTCAGACACA TGAAACATTT CTTATCAGAC ATAAGATTCT
83201 ATGATAGGAG GCAGCCAATA GCCAGTCCTG AAAACAGGCC TGTCTTGGGA
83251 ATGTGCAACC AGGCCTGCTG AGTTAATAAA CTTTTCCAGC AGAGATTGAA
83301 AAGGATGGGT CAAAGGATAT CTGTAGGTAC AAATTTGAGA GATAGTGCCA
83351 AAGAGTTTTT CAAAGTGATT ATACCTGTTT ACTCTCTAAC CAGCAGATGT
83401 GTAAGAACTT CAGTTCTTCT ACTTTGCCAA TACCTTGTAC AGTTTAATCT
83451 TCTAAAATTG TAATTTTCTT CCTCGTGTCT ATTGATATCT CATTTTGGTT
83501 TACATTTTTA TTTCCTTAGT AACTGAGACT GAGCACCTTT TCATATGTCA
83551 TTGACCAGTA GCCTATGTTG TGAAGTGCCA GTTCAGGTTC TTTGCCTGGT
83601 TTTCTTTTGA ATCATTTGCT TTTTTCTCAT TGATTTTTAG GAATTATTTA
83651 CATGTTTTGA TATGTACACT TCATGTGTGT TTCAAATAAC TTCTCCCATC
83701 TATCTGCCTT GCCTTTTCTC TCTCTTAAGG CTGTCTTTTG AAAAATAGAA
83751 GTTAATTTTA ATGTCTAATT TTGTGATCTT TTTCTTTACT GCTTTTGGCA
83801 TACCATTTAA TAAATCTTTT TTCCAATTCA AGTCCTTGGA TATATCCTCC
83851 TATGTTATCT AATGAAAAGT TTATTGCTTT ACCTTTCTCT TTTAGATCTG
83901 TAACCTGCCT GGAATTGATT TCTTTTCATT GTGGTAAGAA ACACATGACA
83951 TAAAATACTC TCTTAAAGAT TTACAACTGT ACATCTCAGT AGTGTTAAAC
84001 ATATTTACAG TGTTGTAAAA CAGATTCAGA AACTTTTTAT CTTGAAAAAC
84051 GGAAAACTTT ATACTCATTA AACAATAACT CTCCATTCTT CTTCTCCCCA
84101 CTCCCCTCCT TGCTGCTCCT GGCAGTCCCT ATTTTACTTT TGTCTCGATT
84151 TAAGTACCTC ATGTGGCATC AAATAGTATT TGTCTCTTTG TGACTGGCTT
84201 GTTTGAGTTA GCATAATGTC CTCAAGTTTC ATCCATGTTA CAGGATGTGA
84251 CAGGACTTCC TTTTTAAGGC TGCATAGTAT TTCATTGTAT GTCTGTACCA
84301 CATTTTGTTC ATCCATTCAT CTGTTGATCA ATTTGGGTTG CTTCCATTTC
84351 TTGGCTATTG TGAATAGTGC TGCAGTGAAC ATGATGTGCA GATATCTCTT
84401 TGAGTTCTTG CTTTCAGTTA TTTTGTGTAT ACTCAGAAGT GGAATTGCTG
84451 AATTATATGG GAGTTCTATT TTTTATTTTT TCAGGAAGCT GCCGTACTGT
84501 TACTCCATAG CAGCTGCACT ATTTTACATC CCTTCCAGTA GTGCACAAAG
84551 GTTCCAGTTT TCCACAGCTC ACCAACACTT GTTATTTTTT TTATTTTTTT
84601 ATTTTTTATT TTTTTAAATA GTAGCCATTC TAATGGATAT GAATGGTAAC
84651 TCATTATGGT TTTGATTTGC ATTTCTCTGA TGATTAGTGA TGTTGAGCAT
84701 CTTTTCATAT GCTTGTTGTC TATTTATGTA TCATCTTTGG GAAGAAATAC
84751 TTTGTTCATT TTTAATTGGA TTTTTTGATT TTTTGCTGTG AATTGTAGAA
84801 GTTCTTTATG TAATTCTGAA TATTAACCCC ATAGCAGATA CATGACTTGC
84851 AAAATTGTGT TTCTTTAGAG TTGATTTCTT TAACTTTATT TTGATTCTTT
84901 AATTGGGCCA TCTATCCAGA CCAGGCTGGT CTCGGACTCC TGAGCTCAGG
84951 CAATCAACCC GTATCAGCCT TCCAAAGTGC TGGGATTACA GGCGTGAGCC
85001 ACCCTGCCTG GCCGCTGTGG ATTTTTAAAT AAACGTCCTT TATCATGTTA
85051 AAGAAGCTTT CTTCTGTTCT TAGTTTACTA AGTGTTTTGT TATGAAGTGA
85101 TGTTGAGTTT TGCCCAGTGT TTTTTTCTGT GTGTATTGAG ATGATGTGTT
85151 TTTCTTTATA TTTTATTATT ATGTATTACA CTGGATGATT ATCTTACATT
85201 GAACCACCCT AGCATTCCTG AGATAAATCC AAATTGGGCT GCATCGAAAC
85251 TAAAAACTTT TGTATTACAA ATGTTATGAA GAAAGTGAAA AGACAACCCA
85301 CAGATGCTAT CTAGAGATTG GTATCCAGAT TATATAAAGA ATTCTTGCAA
85351 GTCAAATAAT AAAAATTTAC ATCACCCAAT TAGTAGTTTA AGTCAGCCAG

FIGURE 3BB

```
85401 AGTTGGTTCC TCTTGAATCA CCCAATTTGT GGTGAATTGA AACTATAATC
85451 AGATACTACT TCACACCCAC CGGGATGCTT ATAATAAAAA ATACATGGGA
85501 AATAGTACAG TAGTTCCTCA AAAAATTATA GAATTACCAT TTGATCCAGC
85551 AGTTCCACTT CTGTGTATAT ATACAAAAGA GGTCAAAGCA GGGATACAGA
85601 TATTTGTGCA CCAGTGTTCA TAGCAGCACT ATTCACAACA GTCAGAAGGT
85651 GGAAACAACC TAAATGTCCA TCTACAGATG AATGGGTAAA CAAAATGTGG
85701 TAAAGATGGA TCAATAGATC ACAAAGGAAT ATTATTCAGC CTTAAAAAGG
85751 AATGAAATTC TGATACATGC TACAATAAGG ATGAAACTTC AAGACACTGT
85801 GCTGGGTGAA ATAAGCCAGA CACAAAAGGA CAAATGTTGT ATAATTTGAC
85851 TTATGGGGTA CATAGAATAG GTCAATTCAT AGAGATAGAA AGTAGAATGG
85901 AGGTTATCAG GGGTGGGGTA TGATTTCATT CCTGTAAAGT TCAGAGTTAC
85951 TCTTATTGGA GGAAAGGATA CATTATGACT AGAAGGAGGG ACAAGGAAGG
86001 CCACTGGGTC ATCTTCTATT TCTCAATCTG TGTTTACTCC ATAGAATTTG
86051 ATTGAGCTGT TTAGCTGTGG TTTGCACATT TTCCTTTACG TATAAACTTT
86101 TTACATATAT ACTTTTATTA AAATCTACTT AAAATGGGAA AAAAAAAGAT
86151 ATCTAGATTT CAGCTTTTAA ATGCTGGTGC AATGATAGCC ATTTTCGGCT
86201 GGGTGCAGTG GCTCACACCT GTAATCCCAG CACTTTGGGA GGCTGAGGCA
86251 GCTGGATCAC CTGAGGTCAG GAGTTCAAGA CCAGCCTGGC TAACATGGTG
86301 AAACTTTGTC TCTACTAAAA ATTAGCCAAA CCTGGTGGTG GGTTCCTGTA
86351 ATCCCAGCTA CTCGGGAGGC TGAGGAAGGA GAATTGCTTG AACTCGGGAG
86401 GCAGAGGTTT TGCAGTGATC CAAGACTGTG CCACTGCACT CCAGCCTGGG
86451 TGACAGAGTA AGACTCTGTC TCAAAAAAAA AAAAAAAAAA AAAAAAAAAA
86501 AAACAAGACA AAACACTCAT ATCTGAAATG TGGTTTACAT AGAATGTTCT
86551 TCCAGGCAAA AAAAACAAGA TTAAAATTAC TGGTTTTGAA AATGTATTCT
86601 GTTCTTTCTT ATATCAAAGT CTTGATGTTG GTGGCTAGAG AGAACTTCTT
86651 AGGTTTTCTA CCTGTATTAG TCCGTTTTCA TACTGCTATA AAGAACTGCC
86701 CAAGACGGGG TAATTTATAA AGGAAAGAGG TTTAATTGAC TCATAGTTCA
86751 GCATGGCTGG GGAGGCCTCA GGAAACTTAA AATCATAGTA GAAGGTCAAG
86801 AGGAAGCAAG GCACTTTCTT CACAAGTCAC AAAGGAGAAG TGCTAAGTGA
86851 AGGATGAAGA GCCCCATATA AAACCATCAC ATCTCGTGAG AACTCACTCA
86901 CTATCACGAG GACAGCATGG GGGAACCTCT GCCGTGATTC AGTGACTTCC
86951 ACCTGGTCTC TCCCTTGACA CGTGGGGATT ATGGGGATTA TAATTCAAGA
87001 GGAGATTTGG ATGGGGACAC AAAGCCTAAC CATATCACTA CCATTTTTCT
87051 TTTCTTTTTT TTTCATGCCT GGATTTTTTC GTTGTTCCCT CATGAACATT
87101 TTAAAGTGTA ATTAAGCAAA AGAGAATACT ATACAATGGT TTTTAACAAT
87151 TTTTTTAAGT TTCCCCCCTC CCCCCAAGAC AGGGTTTCCC AATGTTGCCT
87201 AGGCTGGTCT CGAACTCCTG GCCTCAAGTG ATTCTCCCAC CTCACCCTCC
87251 TAAGTAGCTG GGACTACAGA CATGTGCCAC TGTGCCCAGC TGCCTATACA
87301 GTGTTTTTAT TTTATTTTAT TTTTTTAAGA TGGAGTCTTG CTTTATCACC
87351 CAGGCTGGAG TGCAGTGGCA TTATCTTGGC TTACCGCAAC CTCTGCCTCC
87401 CGGATTCAAA TGATTCTCCT GCCTAAGCCT CCCAAGTAGC TGGGATTACA
87451 GGCACCCGCC TCCATGCCTG GCTAATTTTT GTATTTTTAG TAGAGACAGG
87501 GTTTCACCAT GTTGGCCAGG CTGGTCTCGA ACTCCTGAGC TCGTGATCTG
87551 CCCGCCTTGG CCTCCCAAAT TGCTGGGGTT ACAGGCGTGA GCCACCATGC
87601 CTGGCCTTTA ATTTTTTTAA AAAGTAAAAC TTCTTTAATT TTCTTCTCGC
87651 AAGAATTGAA TAGAATGATA GAATGAATGC CAGTATTTTA TAATGTTGTA
87701 TCCAGCAGGT TGCAATCAGG GAGGCTCCAA CAGAGTCACT TTTTCTGTCT
87751 TTTTATGTTC AATCTATGCT GTAAATTGGT TTCAGAAACT TCTGTGAGTC
87801 TATCAACTGT AAAAATGGAG ATGACTATGA AAGGATCTTA CGCTTTTATT
87851 CTTCTTTGAT CCACATGTCT GTTTGTTCCT CCATCTAGAA TATAAAGATG
87901 ATTAAGACTC TACCTGTCTC CTTTAAGTCC AGTGAAGAAG ATAGATTTAC
87951 AATTAATGGT AATTCAGTAT AACTGCCGTA AGAACAGGGC ATTCAGAATG
88001 CCCTGTGAGC TCAGAGATGG CGCTACTGTA TTCTCATGTT TAAAGGATAA
88051 GTAAAAGTTC CCCAGTTTGA GAAAAGAGGG GAAAAGGACT CCAGTGAAAG
88101 GAAATTGATG AAATTACTGT TGACTTTACT TGTATATATT AACTGTCTTT
88151 CAGTGTCTCT GAAAACTTGA TTTGGGACTA TTTCCTTTGA ACAGAAATAA
88201 TAGCATTCCT GCCTGATAAA TGTCCTGTGG TCAAATAATA TGATTTCCTA
88251 ATCATTCTGC ACACTAAACT TCCCCCCACC AGGAAATCAA TGCCTTAATG
88301 CTAAATTTCC TCTGTACTAC TTTCTGTAAG AGTAAGAGGT TCCTATTTCA
88351 CAGTCACGAC ACATTCCCAA CTCAATTCAC ATTCCAATCC ATCTTGTCCA
88401 ACTTCATTGA AAGTTGATAC ACTGAACCAT TTCCTTTACT TAAAAGAAAT
```

FIGURE 3CC

```
88451 AGAATTCTTC CTAAATTCTA TCTACTGTTG GAATAGAAAG AATATCATGC
88501 TTCTAGACTG ACTAATTTTT TTTCTTCTTG ATATAAGTAT TGACAACATT
88551 TATTCATTTG TTTCTAGGCA GCACAAGACT GTTGAACTTT CCTAGAACTG
88601 AGTCTGAGAT TTGCAAAGCT GCCAAAATAT TTTGAAACAA ATGAAAATAT
88651 GTAAACATGA ATGTTATCAG CTGTTTTACA GTATTTGTGT TTTAGAGATA
88701 ATGAGCATCT GGTGGACCAC AGGAGCCCAG GGGGATTTCA AACTCCAGAT
88751 TCCTTTTTGT GTAATCATAT CTGGCTGGAG TTATTTGTTT TCTCTGCATG
88801 TGAAACTATC AAGTCATAAT TCTTCAAAGG GGAATGTTTA TTGCATTATT
88851 TAAAAATAAT AAATTATATT ACTAAATAAA TAACAGCAGG CCAGGCATAA
88901 ACCAATGATG AAAGTTTGTC AGAAACTAAG GCTTCTGATT AATTCTGTGC
88951 TCTGGACTAT AATTGGAAGG AAGGATTATA TTAGAGTTTA CAATGAGTTT
89001 ACAGAAAGAA AGGAGAGGGA TAAATTATAT TTAGTTCACA GTAAATCTGA
89051 ATTCAGAACC CCTGGTTGTA AGACTAGTCT TTTAACCTTT AGAGTTAAAA
89101 AATGTATATG TACAGCTGGG TGCAGTGGTT CACGCCTGTA ATCCTAGCAC
89151 TTTGGGAGGC CAAGGTGGGT GGATCGCTTG AACCCAGGAG TTTGAGACCA
89201 GGATGGGCAA AATGGCAAAA CCCTGACTCT ATAAAAAATA CAAAAATTAG
89251 CTAGGTGTGG TGGCAGGTGC CCATAGTCCT AGCTACTCAG GAGGCTGAGG
89301 TGGGAGGATC CCTTGAGTCT GGGAGGTCAA AGCTGCAGTG AGCCGTGATT
89351 GTGCTACTGT ACTCCAGCCT GGGTGACAGA GAAAGACCCT GTCTTAAAAA
89401 AAAAAAAAAG TGCGTGTGTG TGTGTGTGTA TGTACGTTGA AGAAAACTAT
89451 GAGAAAAAGC AAAAATGTAG AGTCCATAAT GCATAATGTT GTGTTAAGCA
89501 CATAGTTTAG TCATTGGTAC ATATTTCTGG AGATGGTCTA AAGATCTATT
89551 TTTTAAAAAC TGATTTTAGT TAAATCAGAG GTTAGCAAAT CACAGCCTGC
89601 AGGCCAAATC TGGCCTATCA TACATTTTGT TTGTCTCTTT GTTGTGTTTT
89651 TGGTGTTTTT TTTTCTTTCT TTTTTTTTTC CTTTCCTTTT TTTTTTTTTT
89701 TTTTTTTTTT TTGGAGACAG AGTCTTGCTC TGTTACCCAG ACCAGGCTGG
89751 AGTGCATTGG TGCGATCTCA GCTCACTGCA ACCTCTGTCT CCCAGGTTCA
89801 AGCAATTCTC CTGCCTCAGC CTCCTGAGTA GCTGGGATTA TAGGTGTGCA
89851 CCACCATGCC CAGCTAATTT TTGTATTTTT AGTAGAGATG GGGTTTTACC
89901 ATGTTGCCCA GGCTGGTCTC AAACTCCTGA GCTCAGGCAA TCTTCTCGCC
89951 CCAGCCTCCC AAAGTGCTGG GATTACAGAC GTGAGCCACC GCGCCTGGCC
90001 CTATCATACA TTTTGGTAAA TAAAGTTTTA TTAGAACATA CTATGCTCAA
90051 TCATTTATAT GTTTTGTGTG GCTGCATTTG CCCTGCAGCA GTAGAGCTGA
90101 GTAGTTGGAA CAGAGACTGT GGTTCATACA ACCTAAAATA TTTACCCTGG
90151 CCTTTGTTAC AGAATAGGTT GCTAACCTCT GAGTTTCTCA GTTTTAGCCC
90201 ATTCACAAAT GAAATAGTTT TTTTTTGTTG TTTTTTTTGA GACAGCCTCA
90251 CTCTGTCGCC CAGGCTGGAG TGCAGTGGCA TGATCTTGGC TCACTGCAAC
90301 CTCTGCCTCT TGGGTTCAAG CAATTCTCTT GCCTAAACCT CCTGAGAAGT
90351 TGGGACTATA GGCACATGCC ACAACGCCTG GCTAATTTTT GTATTTTTAG
90401 TAGAGACCAG GTTTCGCCAT GTTGACCAGG CTGGTCTTGA ACTCCTGGCA
90451 TCAAGTGATC TGCCTGTCTT GGCCTCCCAA AGTGCTGGGA TCCCAGCCTC
90501 TCTCTCTCTC TTTCTCACTC TCTCTCTCTC CCGCTCTCTC TCTCTCTCTC
90551 TCTCTCTCTC TCTCTCTATA TATATATATA TTTTTTTTTT TTTTTTTTTT
90601 TTTTGAGACA GGGTCTCATT CTGTCACCCA GGCTGGAGTG CAGTGGCATA
90651 ATCACAGCTC ACTGCAGCCT CAACCCCACG GGCTCAAGCA ATTCTCCTGC
90701 CTCAGCCTCC CAAGTAGCTG GGATTACAGG TGCGCACAAC CACGCCCAGC
90751 TAATACTTGT ATTTTTTTGT AGAGACGAGG CTTCTCCATG TTGTCCAGGC
90801 TGTTCTCGAG CTCCTGGAAC TCAAGCAATC TGCCTCAGGC AGGAATCCTG
90851 AAATTCTGGG ATTATAGGTG TGAGCCACTT CTCCCTGGCC CACAAATGAC
90901 ATATTCCTTA TAATCTACTA CAGTGAGCTT TGCATGGTTA ATATATTTGT
90951 TGTGTTGAAA CTATCTTCCT GATTTTTTCC AATTTTTTAT AGAGAAACCT
91001 GGAAAGAATA GTACCATAAA TACCTATATA CCCTAACAGA GAATTATTGT
91051 TAAAATTTTG CCATATTTGC TTTATCTTCT CTGTGCATAT GTATACTCAC
91101 ATGGCTTTTT TTTTATTGGT ATTAGTTGAA AGTTGCAGAT ATTATGCTTC
91151 CTCAGCGCAT ATCCCTAAGA ATAAAAGCAT TTTCCTCGAC AACTGATTAT
91201 GTTAAAATTT GAAGACGTGT ATGAGGTTTT TGTTTGTGAG GGCTATATGA
91251 CTGGCGTTTC TCCAGTATAT GACACTTTGT TCATCCCTAT GTTCCTCTTT
91301 ATAAACTGCA GAAATTCTAA ATATAATGCA TTAGTTGTCT ATTGCTTGCA
91351 AGTAGTAGAC TGAATGATGG CTCCATAAAG ATGTCCACTT CCATTAGATA
91401 AAGAAAATGT GTACATATAC ACCATGAAAT ATTGCACAGC CATAACAAAG
91451 AGCGAAATCA TGTTCTTTGC AGCAGTTTGG ATGGCGCTTG AGGCCATTAT
```

FIGURE 3DD

91501 CCTAAGTGAA TTAATGCAGA AACAGAAAAC CAAGTACCTC ATGTTCTCAC
91551 TTGTAAGTGA GAGGTAAACA CTGGGTACAA ATGGACATAA AGATGGGGAC
91601 AGTAGACACT GGGAATACAA GAGGGCAGAA GAGGGAAGGA AAAATAAGGG
91651 TTGAAAAACT ACCTATTGGG TACTGTGCTC ACTACCTGGG TGACAGGTTC
91701 AATCATATCC CAAACTTCAG CATCACACAC TATACCCCTG TAACAAACCT
91751 GCACATGTAC CCCCTGAATC TAAATAAAAG TTGGAAAAAC AAATCAACCC
91801 AGATGGCCAT TTCCTAATCC CTGGGGTCTG TGAATATGTT ACCTTATCTG
91851 GCAAAAGGAA CTTTACAGAT GGAATTAAGG AATTTTAGAT GAGGAGATTA
91901 CCGATCATCT GGTGGGCCTA AAGTAATCAC CAGGGTCCTC ATAAAGGAGA
91951 GGCAAGGGAG TTGAAGGTAG AGAAGGGGCT CTGAAGATGG GAAGCAGAAT
92001 AAGTGTAGGA AATGTGAGCT TGCCACACTG CTAGTGTTGA AGATGGTGAG
92051 GCTAAGAATT TTCACATCCA CTTTCAAAAC CATTGTGTCC TGGCTCCTTT
92101 TAAACCATCT TTCCCTCAAT TTCTCTGTCC TCTTACATCT TATTGTAAAC
92151 ACCAAGAAGA AACCTGGCAG TTAACTTTGC TTGGAAATCT TTTTAGCTAG
92201 ACCATCTAAT TCATTCGGCA CATTTTCTAC CTTCCACATC ACTGTAAAAT
92251 TGGGTTGCTA AACTTTCCAC AACTACCTAA CAGAGATCCC TTGCCTCCAG
92301 TTTCTACTCA GATGTTCCTC ACATTCCTTA AAACTCACAG TCCACCTCCT
92351 AACAATCTAA AATCTACCAA CTATCAATTC CTGGCAATTT AGGCTTTACC
92401 GCTCCTCTCC TGAAAGGCCT TAAAGTATTA GAACTGGGCC CTATTATTAG
92451 AACCTATTTC CCAGTTCTAA TATTCCTCCC ACATTTTTGG TATGTGTGAC
92501 AATGGAACTT TACTCCTGAT ACCAAAATCT GTATGATTTA TATATGAAGC
92551 ATAACAAATT ATTCTAAAAC GTATTAATGG CTTAAATCAA CAAACGTGTT
92601 GTCTCATAGG TTCTGTGGTT CAGGAATCCA GGCAAAGCTA CCTAGATGCT
92651 TCTAGCTCAG GATCTTTCAT GAAGTTGCAG TCAAGCTGTC AGCTGGGCTG
92701 CAGTCATCCA AGGCTCAGCT GGGAGAGGAT CTGCCTTCAA GCTCTCTCAT
92751 GTGACTGTTG GCGGGCCTCA GGTTTTCACT GGCTGTTGGC TGGAGATGCC
92801 AGTTATTTGC CACATGAGCC TCTGTCTACG GCAGTTGACA ACATGCAGCT
92851 GGCCTACCTC AGAGCAAGCA ACCAAGCAAG AGAGCAAGAT AGAGTGCTCA
92901 AGACAAAAGA TAACAGACTT TTTGTAACTT AATCTCAGAA GTAACATCCC
92951 ATCACTTTTG CCAAATTCTG GTTGTTAGAA GCCAGTCACT AGATCTGTCC
93001 CACACTTGAA GAGGGTTAAA CAAGGTCATG TTCTTCATAA GATTAATCCA
93051 AGTACAGAAT TGGCTTAATA ACATTTCTGA CGATTTTTCC TATAACTTGT
93101 AAAACCTTGG CTATCTGAAA CCCTTGGGAA GTGAATCATC CTTAAAAGCT
93151 AAGTTTCTGG ATAGATTTTT ACCATGAAGG GACCAAATCT TAATAATTTG
93201 GAGTAGAATC ACTTCTGCAT TTGATCACAA TATTTCTTGC CTTTTAAAAT
93251 AAATTACTGA TCATTATTTG AAATTTTATT TCATCAAAAG AAAATTAGCA
93301 ATTGTGTGTT ATAAAGAGAA GGTGTCTGTC TTCTCCTTAT GTAGGGTATA
93351 GAACTGTTCA TCTCTTTACT AAAAACTTAA GGCTTCTGTC TGCCTTTTAT
93401 AATTTCTGTT TCTTTCTTTG TTTCATTTGT TACCTCTTAG TTATCAGTAC
93451 TTGCCCATTG CCTTCCTGTT TACTGTATCT AGTAAGTTGC TGCAAAAGTA
93501 ATTGTGATTT TTGTATTAAA ACAAATGGCA TTAGATTCTC ATAGGAGCAC
93551 GAACACTTTT GTGAACTGTG CATGTGAGGC ATCTCGGTTG TTCTTGCCTT
93601 ATGAGACTCT AATGCCTGAT GATCTTTCAC TGTCTCCGAT CACCCCCAGA
93651 TGAGACCCTC TAGTTGCAGG AAAACAAGCT CAGGGCTTCT ACTGATTCTG
93701 CAATATAGTG AGTTGTGTAA TAATTTCACT ATATATTATG ATGTAATAAT
93751 AACAGAAATA AAGTGCACAG TAAACGTAAT GTGCTTGAAT CATCCGGAAA
93801 CCATCCCCTC TGCTGGTCCA TGGAAAGATT GTTTTTCACA AAACCGGCCC
93851 CAAAGTTGGG GACTACTGCT ATAGAGAATT GGATCTGCGG TCTACAAGTA
93901 ATGTTAATGA CATTTATTTT AAGTTGCACT GAGACTTTTG TTTACATCTT
93951 TTTTTTTTTT TTGAGATGAG AGTCTCGTTT GTGTTGCTCA GGCTGGAGTG
94001 CAAGGCACAA TCTCAGCTCA CTGCAACGTC CGTCTCCTGA GTTCAAGCGA
94051 TTCTCCTGCC TCAGCCTCCC GAGTAGCTGG GATTACAGGT GCCCGCCACC
94101 AAGCCCAGCT AATTTTTTGT ATTTTTAATA GAGATGGGGT TTCACCATAC
94151 TGGTTGGCCA GGCTGGTCTT GAACTCCTGA CCTCAGGTGA TCCACCCGCC
94201 TCGGCCTCCC AAAGTGCTAG GATTACAGGC ATGAGCCAAC ATGCCTGGCC
94251 TGTTTACATC TTAATTATGA ATTGTTACTA TAGTCAGCCC TTTGTATCTG
94301 TGGTTTCCAC ATCCATAGAT TCAACTAACC ATGGACTGAA AATATGTGGG
94351 GGGGAAATGA TGCTTACATC TGTACTGAAC GTGACGGACT TTGTCATTAT
94401 TTCCTAAAAA ATACAGGATA ACTATTTACA TAGCATTTGC ATTGTATTAG
94451 GTGTTATAAG CAGTCTAGAG ATGATTTAAA GTATACAGGA GGATATGTGT
94501 ATGTTACGTG CAAATACTAC ACCATTTTAT ATAAGGCACT TGAGCACCTG

FIGURE 3EE

```
94551 TGGATTTTGT TATTCACAGG GGATCCTGGA AACAATCCCC TGTGGATACC
94601 AAGAGATGAC TGTATAGGGG AGGCCGTGGT GACAGATGAA GTGGCACTGG
94651 GCTTAGTAAG GGTAAGAAAG CTAAGAGTGG CCTGAGGACA GATGACAAAC
94701 ATGACATATT GCTCACTTTA GCCAATGCTC AGAATCTCTT AGGTTTTTGA
94751 AACTTCACAA GCAATTTAGG CAAACTCTCC TTTCTTCTCT ATCTCTGTAT
94801 TCTATGTAAT CCCACAGTTG AAGGCTGTTC TTATAGTGGA ATTAATTATA
94851 CCTCACTCCA AAAACTTGAC CCTGATTTCC GTCTACAAAC CCAAAGCAGC
94901 AAATACAATT TACTTTTATA TTTGAATTAT TTTCTTTGTA ATGGTGTCTG
94951 TTGACAGCCA AAGCCTCTTG TATGGAAACA TACCACCACT GCCACAAGTA
95001 AAAGCTATAA AGCAGTGTTA AATACTGTAT ATAGAGCTCA CATTTGTATA
95051 TGCATTTCTT TTAGGTCTTA TGTAGTGTGT GTACTGTGGA AGATCGAGAA
95101 AGTGCGTTAG GTTGTTAGAC AAAAGACCCA GAAGGCCTGC TAGAGATGCC
95151 ACAGGTGGAA CTAAGAAAGC AATCTCTGTG TCACTCAGGC TTTGAGAAAC
95201 TTCCTTCAGA ATCATAAAAC ATTAGAACTG GGAAGGTTAA AAAATCTTTA
95251 GTCTTTTTTT CCCAGCTCCA GTCTCTTGTG AATAATTAAC AGTAAAGTTA
95301 AAGATTATGG GAATTACGTG CCTCCTTTTT TCCCTTGCAC AACATAGAAT
95351 TTGTTTTCTA ATAGTAGTTT ATTTGTTAGC TTTGCATTCC CATAAGTGAT
95401 GGTTTCCAGC CTTGGCAAAC CCTTGCAGCC TCCAGCCACA AGTCCCCTGG
95451 ACCTCAGAGA ATGTATATAC TGTATGTGCA CCCTAATAAC ATGTTTCCTT
95501 AAAACTAGTA CTACTGGATC CTCTAACTTT AGTACATGTC TTTCATGTCC
95551 AACTTTTCAG AGGCCGCCAA ACTAGCAACC CTAAACTCAT TTGTCACTAT
95601 CAAAACATAA TATACGAATA TGGAAAGCTA ATATAAAAAT GGTAAGGGAC
95651 TGAGCCATTT GGAAGGTAAC TTAATGTAAG TGCCTGAAAA ACAGGGATAC
95701 AAAAAAGCAA AGGGACAAGA AGCAAGCCAG TTCACCCTGA ACCCTACAAA
95751 TGTTTGGGAA TTAGAAACAT CAAGTATTAC AAATTAGGGG AAACGGATGA
95801 AGTCTGATAC TAAAAATAGG GAGGTTGACA GTCTGTGTAG GAACAGTTAG
95851 ACTTCCAGAT CCTTATCTCT ATACCCCACC TCCCCCTCTG CAGAAGAGAT
95901 AGATTCCCTT AGGGAGGAAG AAAACTAGAG AAAATAAAGA CACTAGGGGG
95951 AGAGTGTGAT GTCAGCAAGA TAGTGGAATA AAAGATACCT GGCATCACTC
96001 TTCCCACAAA AATGCAACTA GAAATTATTC AGGCTGGGCG CGGTGGCTCA
96051 CTCCTGTAAT CCCAGCATGT TGGGAGGCCG AAACGTGTGG ATCACTTGAG
96101 GTCAGGAGTT CGAGACCAGC CTGGCCAACA TGGTGAAACG CCGTCTCTAC
96151 TAAAAATACA AGCATTAGCT GGGCATGGTG GTGGGTGCCT GTAATCCCAG
96201 CTACTCAGGA GGCTGAGACA GGAGAATTGC TTGAACTCGG GAGTTGGAGG
96251 TTGCAGTGAG CCAAGATCAT GCCACTGCAC TCCAGCCTGG GTGAAAGAGC
96301 GAGACTCCTC TCAAAAAAAA AAAAAAAAGT ATTCAAAGAC AAGAATATCA
96351 ACCTGAGTTC ACCAGAACTT GGGGAAGAAG TGGAGAAACC TCCTGGGCCA
96401 ACAAAATTTT TTGTAAAATA AGTGGTCATT TCAGACTGTG CCACCCCTTC
96451 CCCCCAAGCT GGCATAACAC CACTCAGGGA GAATTTTCCT AGCCCTGCAG
96501 TTTCCAAGGT GAGAGGAAGG AATTGGAGGT GTGTATTCAG TCTCCTCACT
96551 GGTCTGGGAA TCTTCCCAGG GAGCCCACTC CCGTCCCATC AGGGAGAGCC
96601 AGGAGAGCTG AACTATCTGG GGTAAAGTGG GGACAAAGAG CAGGGCACTG
96651 ATTGTAGCAA CTAGTATATG GATCTTGCAG CTACTCTGTA CTCTAATTAG
96701 CCGAGACACC CTATTGACAA GGATGGCCAG TGTCTTAGTG CCACTGGGGT
96751 GTAATCAGTG GGAAGGCCTG AATCCCTGGT CGGATTTTCC ACAAAACTTA
96801 GTGCTCACAT GGAACCTTCC CGTGGCCCAG AAACAGCTAT AAGATTGGGA
96851 TTAAGCTGGG CATGGCAGCT CATTTCTGTA ATCCCATTTT GGGAGGCCAA
96901 GTTGGGTGGA TAATTTGAGC CCAGGAGTTC AAGACCAGCC TGGGCAACAT
96951 AGCAAAATCC CACTTCTACC ACAAAAACAA AAGTTAGCTG CATGTGGTGG
97001 TACGTGCCTG TAATCCCAGC TACTTCAGAG GCTGAAGCAA AGAGTCGCTT
97051 GAGCCTGGGA GACAGAGGTT ACAGTGAGCC AAGATCGCAC CACTGAACGC
97101 CAGCCTGGGC AACAGAGCAA AACTGTGTCT CAAAAAAAAA AAAAAGTTGG
97151 GATTAACTTC CAGTGTACAC TTAAGCACTT AAGACTTTCA CAGACTGGGA
97201 AATGATGACA GGATAGCAAT ATAGTTGGAG AACAATGTTT ACCTTTCGGT
97251 GGTCACTATA AGTCTTCCTG TCTGTGAAAC AATGTCAGGG CAAGTTAGTT
97301 TAGTTTTAGT GCAGTGTTTT GAACGGCAGG GCAAGTTAGT TCTGTTTTAG
97351 TGCAATGTTT TGAATGGCAG GGCAAGTTAG TTTAGTTTTA GTGCAGTGTT
97401 TCAGTTCTGA TGCTCACTGT AAGTCTTCCC CAGAATGGGA AGAAACAATA
97451 GGCCAGTACT TAAGCTCTCA TACTAAGTAA AGGCCCGAAA TCACCAAAGA
97501 ACACCTGCAA AACCTAGAAG AAATGGCTGT GTCCTCAAAT GTGCAAGCAT
97551 CAACATAAAC AAGCAATGAT TATGAAAACT TAGGGAAATA TGACACCACC
```

FIGURE 3FF

97601 AAAAGAAACC AACAAAGCTC CACCAGTGGA CTCAGAAGAA TTGAAGATCT
97651 ATGAAATGTC AGACAGAGAA TTCAGAATAA GCCTCTTTAA AAAGTTCAGT
97701 GAATCTGCCA GGCATGGTGG CTTACGCCTG TAATCCCAGC ACTTTGGGAG
97751 GCCGAGGTGG GCAGATCACG AGGTCAGGGG ATCGAGACCA TCCTGGCTAA
97801 CACGGTGAAA CCCCATTTCT ACTAAAAATA CAAAAAATAA GCAGGGCCTG
97851 GTGGTGGGCA CCTGTAGTCC CAGCTACTCG GGAGGCTGAG GCAGGAGAAT
97901 GGTGTGAACC CAGGAGGCGG AGCTTGCAGT GAGCTGAGAT TGTGCCACTG
97951 CACTCCAGCC TGGGAGACAG AGCAAGACTC CGCCTCAAAA AAAAAAAAAA
98001 TGTTCAGGGA ATCACAAGAA AATAGAGATA GAAAATTAAA TGAAATTTAG
98051 AAAGCAATCC ATGTATGTAG TGAGAAATTT GACAAAGAAA TAGAAACAAG
98101 AAAACAAATA GAAATCCTAT CTATAAACAA TACAGTAACT GAACTGGAAT
98151 AACTCATTGG AAAGCTTTAG CAGCAGACTT AATCAAATAA AAGAATTGGT
98201 GAGCTTCAGG ACAGAACATA TGAAATTACC CATTCAGAGG AGCAAGAATA
98251 AAAAAGGGTA AAGAAGACCT ACAAGAATTG TGGAATACCA TCAAGCAGAC
98301 TAACCTCTGC ATAATAGGAA TTCCTGAAGA TGAGGAAGAA AAGGGTGTAG
98351 AAAGCATACT TAAGCAAATC ATGGCTGAAA AAGTCCCAAA TCTAGAGAAA
98401 GATGACACTG TCTAGGTACA GGAAGCTCAG TGATCAGCAA TTAAAATCAA
98451 CCCAAAGAAG AGATACCTAT GGCACATAAC AATCTGGTTA ACAAAAATCA
98501 AAGACAAAGA AAGATTACTC AAGGCAGCAA GAGAAAAGAA ATGTGTCCCA
98551 TTCAACATAC CCCAATAGAG CTTTCAGCAG ATATCCCAGC AGAAACCCTG
98601 TAGGCCAGCA AAGAGTGGAA TGGTATATTT AGAGTGCTGA AGGAAAAGAA
98651 AAAAACTGCC AAGCAAGAAT ACTGTACCCA GCAAAGTTAC CCTTTATAAA
98701 CACAAAGGCA AGATAAAGAT TTTTCCAGAC AAACAAAAGT TGAGGGAATT
98751 CATCAACACC AGACCTGTCT TACAAAAAAT GCTAAAGGGA GCTGTTCAGT
98801 CAGAAAGTGA AGGATGCTAA TGGGTAAAAA GAAAGCATCT AATGGCATTA
98851 AACTCACCGG CAAAAGAAAG AAAACTCACT GGTAAAAGAA GACTTCTGAA
98901 AAATTCAGAA TATTGTAATA CTGCAAATGG GATGAGTAAA CCACTTATAT
98951 TTTAAGTATG AAGACTAAAA GACAAATTTT TTTTTTTTTT TTTTTTTTTT
99001 TTAAGACAGA GCCTCGCTCT GTCACTCAAG CTGGAGAGTG CAGTGGTGCA
99051 ATCTCAGCTC ACTGCAACCT GCACCTCCTG GGTTGAAGTG ATTCTCATGC
99101 CTCAGCCTCC GAGTAACTGG GATTACAGAT ATGTGCCAAC ACACCTGGCT
99151 TATTTTTGTA TTTTTAGTAG AGACAGTATT TCACAATGTT GGCCAGGCTG
99201 GTCTCGAACT CCTGACCTCA GGTGATCCGC CCACCTCGGC CTCCTGAAGT
99251 GCTGGGATTA CAGGCTTGAG CCACCATGTC CGGCCGACAA AACTATTAAA
99301 AACAGTAACT ACAACGGTTA TTTAGGAGAC AGGACAATTG TTTAAGCAAT
99351 AAAAAGATTA AATCAAAACA TCAAAAAGTC AAAATGGCAA TGGCGGTGTT
99401 AAAGTATAGA GTTTTTGTTA CTTTTCTTTG CAAAGTTAAG TGATTATCAG
99451 TTTAAAATAA CCTATTATAA GATTTTTTTG TAAGCCTCAC AGTAACCATA
99501 AAGCAAAAAC CTATAATAGA TACACTAAAA ATAAATAGCA CAAAATCAAA
99551 GCACGCTGCT AGAGAAAATC ACTTACCATA GAGGAAGACA GTAAGAGAGG
99601 AAAATAGGAA GAAAGAATCT ACAAAGCAAC CAAAAACAAG GAACAGTATG
99651 GCAGTAGTAA ACCCTTACCT GTCAGTAATA ACTTTGAATA TAAATGGATT
99701 AAATTCTTCA ATTAAGAGTG GCAGAATGGA TTAAAAAACA AGACCCATCC
99751 ATATGCTGGC TACAAGAAAC TCACTTCATC TGTAAAGATA AGCACAGACT
99801 GAAAGTGAAG GTATGGAAAA AGATAATTTA TGCAAATGGA AACCAAAAAA
99851 GAGCAAGAGA GCCTATAGTT TTATCACATA AAATAAACTT AAATCAAGAT
99901 GGTTAAAAAA AAGACAAGGC CATTATATAA CGACAAAGGG GTCAGTACAG
99951 CAAGAGGATA TAACAATGGT AAATATATAT ACACCCAACA CCAGAGCACC
100001 CAAATATATA AAGCAAATAT TAATAGACCT AAAGAGAGAG ATAGACTGCA
100051 ATACAGTAAT ACTAGGGAAC ATCCACACTT TCAATGTGAA CAGATCATCC
100101 AGACAGAAAA GAAACAAAGA AACGTAGACA TTAAACTGTA CTCTGGACCA
100151 AATGGACCTA ACAGATATTT ACAGAACATT CCATCCAACA GTTGCAGAAT
100201 ACACATTTTT CTCAACAGCA CATGGAATAT TCTCCAGGAT TGATCATACA
100251 TTAGGTCACA AAACAAGTTT TAACAAATTT TTAAAATTGA AATTATATTT
100301 ATCTTGTCAC AGTGGAATAA AACTAGAAAT CTATAATCAG AGGAACATTG
100351 GAAACAGTAC AAATTAATGG AAATTAAACA ACAAATGGAC CAATGAAGAA
100401 ATTTTAAAGT AAATTTTAAA ATTTCTTGAG ACAAATGAAA ATGGAAACAA
100451 AATACCAAAA CCTATGGGAT ACAGCAAAAG CGGTTCTAAG AGGGAAGTGT
100501 ATAGCAATAA ACGTCTATAT CAAAAAAGTA AAAAGACTTC AAATAACCTA
100551 ACGATACACC TCAAGGAACT AGAAAAGCAA AACCAAACAA ACCCCCAATT
100601 TTTTGTTCTT TTTTTCTCCG TGAAAAAAGG CATCTAAAAA ACAAACCAAT

FIGURE 3GG

```
100651 GTTAATAGAA AGAAATAATA AAAGAGCAGA AGTAAATGAA ACCAAGACTA
100701 AAAGAATACA AAGATCAATG AAATGAAAAT GTTTTTTTGA ATAGGTAATC
100751 AAAATTGGCA AACCTTTCAG AAGACTAAGT GTTGGGGGGT GGTGGGTGGG
100801 GGGAGAAGAA GACCCAAATA AGCAAAACCA GAGGTGAAAA ATGGGACATT
100851 GTAAGTGATA CCACCGATAT ACAAAAAGAT CATTAGAGAC TACTATGAAC
100901 AACTATACAC CAAAAAATTG CAAAGCCTAG AAGGAATGTG TAAATTCTCT
100951 GACACATACA ACCTACCAAG ATTGAATCAG GAAGAAACAA AAGACCTCAA
101001 CAAACCAATA ATGAGTAATG AGATTGAAGC CATATAAAAA AAGTCTCTCA
101051 ACCAAGAAAA GCCCAGGACC TGTTGCTTCA CTGCTAAATT CTGCCAGACA
101101 TTTAAAGAGC TAATACCAAT CCTACTCAAA CTCCTCAAAA CAAAAATTTT
101151 TTTGGAAGAG AAGGGATTAC TTCCCAACTC ATTCTACAAG GGCAACATTA
101201 CCCTGATACC AAAACCAGAC AGGATGCAAC AAGAAAATGA CAGGCCAACA
101251 TCCCTGATGA ACACAGATGC AAAAATCCTC AACAAAATAC TAACAAACCA
101301 AGTGCAACAA TACATTAAAA AGATCATCCT GGGATACGAA GAGGGGAAGA
101351 ACAGACTTAC TTGAGGGTGG GGGGTTGGAG GAAGGAGAGG ATCAGAAAAA
101401 ATACCTATTC GGTACTATGC TTATTACCTG AGTGATGAAA TAATCTGTAC
101451 ACCAAGCCTC TGTGACACAC AGTTTACCCA CATAACAAAC CAGCACATGT
101501 ACCCCTCAAC CTAAAAAAAA AAAAAAAAAA AATCATCATG ATAAAGTGGA
101551 AATCCGAGGG ATGCAAGGAT GATTCAGCAT ACCCAAATCA ATAAACATAG
101601 TACATTACAT TAATACAATC AAGACCAAAA ACCATATGAT GATTTCAATA
101651 GATGCTCAAA AAGCATTCAG TAGAATTCAG CATCCCTTCT TGATAAAAAT
101701 TCTCAACAAA CGGTATAGAA GGAACATACT TCGGTGAGGT GTAGTGGCTC
101751 ATGCCTGTAA TCCCAGCAAT TTGGGAGGCT GAGGTGAGTG GATCCCTTGA
101801 AGTCAGGAGT TTGAGACCAG CCTGGCCCAC ATGGTGAAAC CCCATCTCTA
101851 CTAAAAATAC AAAGCCTGGG TGATAGAGCG AGACTTTATC TCAAAAAAGA
101901 AAAAAAAAAG AAGGAACATA TCTCAAACCA TATATGACAA ACCCACAGCT
101951 AATGTCATGT TCAACAGTGA AAAGCTGAAT AATGAATAAT TTTTCTCTAA
102001 GATTAGGAAC AGACAAGGAT GCCCACTCTA ACCACTTCTG TTCAACTTAG
102051 TACTTGAAGT CCTAGCCCAA GCAATTAGGC AAGAGAAAGA AATAAAGGGT
102101 ACCCAAATTG GAAAGGAAGA AACCACATTA TCTTTATTTG CAGATAACAT
102151 GATCCTGTAT TTAGAAAAAC CTGAAGACTC CTCCAAAAAC TGCTAGAACT
102201 GATAAACAAA TTCACTTAAG TTTCATGATA CAAAATCAAC ATAACAAAAA
102251 TCTGTAGCAT TTCTATACAT CAACAGCAAG CAATCTGAAA AAGAAATCAG
102301 AAAAGCAATC CCATTTACAT AGCTACAAAA AAAATAAAAT ACCTAGGCAT
102351 GAACTTAACC AAATAAGTGA AGAATCTCTG TGATGAAAAC TGTAAAAGAC
102401 TGATGACAGA AATTGAAGAG GACATATAGA AAATGAAAAG ATACTTCATA
102451 CTCATGGATT AGAAGAATTA ATATTGTTAT GGAGTTCGAG ACCAGCCTGG
102501 CCAACATAGT GAAACCCCAT CTCTACTAAA AATAGAAAAA TTAGCCAGGC
102551 CTGGTTGTGG GTGCCTATAA TCCCAGCTAC TCAGGAGGCT GAGGCAGGAG
102601 AATCACTTGA ACCTGGGAGG CAGAGGGTGC ACCAAGCCGA GATCATGCCA
102651 CTGCACTCCA GCCTGGGTGA CAGAGTGAGA CTCCGTCTCA AAAGTCAGTA
102701 TTACCCAAAG TAATCTACAG AGTCAGTATA ATCTCTATCA AAATACCAAT
102751 GACATTTTTC ACAGAAATAG AAAAAACCTA AAATTTGTGT GGAATGACAA
102801 AAGACCTTGA ATACCTAAAG CTATCCTGAG CAGAAAGAAC AAAGTTGGAG
102851 ACATCTCACT GCCTGACTTT GAATACCACA AAGCTATGGT AACCAAAACA
102901 CCATGGTTCT ATATATATGT GCACACATTT TATACACACA TAGGTATATA
102951 AAACACCTAC AAATTTTTGT TTTTTGAGAC AGAGTCTCGC TCTGTTGCCC
103001 AGGCTGGAGT GCAGTGGCAT GATCTTGGCT CACTGCAACC TCCGCCTCCT
103051 GGGTTCAAGC AATTCTCTGC CTCAGCCTCC CAAGTAGCTG GGATTGCAGG
103101 CACCCATCAC AAATGCCTGG CTAATGTTTT TGTATTTTTG GTAGAGATGG
103151 GGTATCACCA TCTTGGTCAG GCTGGTCTTG AACTCCTGAC CTCATGATCC
103201 ACCTGCCTCG GCCTCCCAAA GTGCTGGGAT TCCAGGTGTG AGCCACCGCA
103251 CTCAGCCTAG ACCTACAAAA TTATACTTGG AGAATCCTGA CAAAAAGGCT
103301 GGCTGAGAAA GCACACCCAT AATTATACTC AACTCTCATA TAGAGAACTC
103351 TATTTAACTT TGTAGTGCTT CATAGCCAAG ACTTGCCAGA AATTGGCAGA
103401 ACATCTCTAA CATAAGAGAG ACCAAAAGAA AGAAAAATGT ACCTCGGAGA
103451 TAACAAAAAC AATGTAATAA GCAAAAGAAA TCATAAATGA ACTGTAATTA
103501 ATATTCTTGT AGAGGTGAGG TGAAGGAACA AGAATAAATT GCTATTTTCT
103551 AAAACATTCA GAAAGCTTGG GAACTAAAAA TAGGAGAGCT GAAATTTAAA
103601 ATCAGTGATT GGATAAAGTT GAGAAAATAT CTTAGTAAAA CAAAAAGAAA
103651 AAACAAGAGA TGACTTAGAG AGAAAAGATA AGAAACTTAG AAGCAAAATT
```

FIGURE 3HH

103701 CAAGTTGTCT GATGTTTAAC TGACTGGAAT TCCAGAAAAA GAGAATAGAG
103751 AAAACGAACA GCAGGATGTT ATCAAAATGA CAATATAAGA GTAGATGGAC
103801 ATGTATCTGT TTCCAATACC ACTGAGTGAG GAAAATAAGC CACAGTACCA
103851 TGAAACTGTA GAACACCAAG GACAAAGAGA AGCTGCAAAA ACTGAAAAAT
103901 CAACTCTTCA ATCAGAAAAT TGAGGCTTCA GGGCAAACCA TTCTCCCAAA
103951 AACTGGAGGG AATGGTGCAT ACTGAGAATC ACAGATTACC TCCAGAAACC
104001 TCACCAGATT CTCAGGGTAA AGAGAAAAAT CTCCTCAAGC TTTAGGTAGG
104051 GAGAAGGGGA AATCATCATC TTGAAATAAG CCGTAGCACT CCTTAGCAAT
104101 GGTTTGCTCT CAAAGTAAAC TGTTTAATCA AGCCTAATTG ACATGTGCTT
104151 TACCAGAGCC TAACAGACCT GGAGGAAGAT GTGTTAGTCC ATCTTGCATT
104201 GCTAAAAAAG AATACCTGAG ACTGGTAATT TATAAAGAAG AGGGGTTTAT
104251 TTGGCTCACA TTTCTGCAGA CTGTACAAGA AGCATGGCAC CAGCATCTAT
104301 CTGCTTAGCT TCTGGTGAGG CCTCAGGAAG CTTTCCCTTA TGGTGGAACA
104351 CAAAGGGGAA CAGGCACAGC ACATGGAGAG AGAGAGAGCA AGAGAGAGAG
104401 GGGAGGGAGG TGCCAGACTC TTGAACAACC AGATCTCGCA CCAGGTCTTG
104451 CGTGAACTAT AGTTATAGAG TAAGAACTCA CTCACAAGTG CAGGGACAAC
104501 ATCAAGCCAT TCATGAGGGA TCTGGCCCCA TGACCCAAAC ACTTCCCACT
104551 AGGCCCCACC TTCAACACTG GGAATCACAT TTCAGCATGA GTTGGAGGGG
104601 AAAAATACCC AAAGTGTATC AGAAGGGAAA CACCCAACTG CAGCCCTCTC
104651 TAGCCTTCCT GTCTTACCTA ATTGGGGAGA AGGGAACCTG AGAAGCACTT
104701 GTGAAAGTCA CGGCCCAGGC ACACAGGCTC ACTAAAAGAC TGAGAACTAA
104751 TTATGTGATT ATAAGACACT CCCCCCACCA CACACACCTC ACCACCACAC
104801 CAATCAGTCT CCTGTGTAAT GATAGTGGAT TACTGCTAAA TGAACTAATT
104851 TTCAGACCCT ATTCTATTTT AATAAGGAGT CTTTAGGGAA ACGAAGAAAT
104901 GATAGATACA AAAACAAGGA TGTGATTGTA ACAACGTGGG TACAGCTGGA
104951 GGCCATTATC CTAAGTGAAT TAATGCTGAA ACAAAAAACC AAAAACTACA
105001 TGTTCCGAAC TCATAAGTGG GAGCTAGACA TTGGGTATTC ATGGACATAA
105051 AGATGGGAAC AGTAGACACT GGGTACTGCA AGAGACAGGA GAGAGGGAGG
105101 GGAGAAAGGG TTGAAAAGCT GCCTATTGGG TACTATGCTC ACGACCTGGG
105151 TAGCAGGATC AGTTGTACCC CAGACGTCAG CATCACACAA AATACCCTTG
105201 TAACCTGCAC GTGTACCCCT GAATCTAAAA TAAAAATTGA TTTAAAAAAG
105251 GACACTAAAG GAAATGTAAC CTATACAGCT ACACAAAACA GTAAACACAA
105301 CCCAACTCTT AGCCAGAGAA ACATAAAGCC TCAAACAAGA GGACTTTTTA
105351 CCGCAGTTTC TTCTACCCAG TATATCATGT CTGCTTTCAA CAAAAACTTA
105401 CAAGACATGC TAAAAGGCAA AAATCAAAGT TGCATGAGGC ATAACAAGAA
105451 TCAGAACCAT TGCCAGACTC ATTTATGGCA GCGATTTTTG GAATAATCAG
105501 ACTGGAAATT TTAAATAAGT ATGATTAATA TACTAAAGGC TCTAATGGAA
105551 AAAGTGAACA ACATGCAAGA AAGGTGGGTA ACATAAGCAG ACAATAGAAA
105601 CTCTAAGAAA GAACCCAAAA GAAATACTAG AAATAAGCAA TACTATAACA
105651 GAAATGAAGA ATGCCCTTGG ACTTATTGAT AGAGTGGAAA GGACAATAGA
105701 TAACCTGGGA AAGATTCAAT GAGCTTGAAG ATATGTCAGT AGAAAGTTCC
105751 AAAACTTAAA CTGCAAAGAG AAAAAAGAAT AAATGACAGA ACATGGCAGG
105801 GCCTGGTGGC TCACACTGTA TCTCCACACT TCAGGAGGCC CAGGTGGGAA
105851 GATCACTTGA GACCAAGAGT TGAGGGCCAG CCTAGGCAAC AGAGAGAGAT
105901 CTGTTGACTC CACAAAAAAT AAAAAGGAAA AGAATAGGAT ATCCAAAAAC
105951 TGTGGGACAG TTACAAAATT ATATATATTT AAGTCCTTGC TTTGGCTGAA
106001 CCTAACACTA AAATTGGAAC AATACCAAGA AGATTGCACA ACATGGCCCT
106051 GTGCAAGGAT GATATGTAAG GTCATGAAGC ATAGAAAAAA CATTTCTAAT
106101 TGTTTTTTTT AGATGGAGTC TCACTCTTTC ACCTGAGCTG TAGTGCAGTG
106151 GCATGATCTT GGCTCACTGC AACCTCTGCT GCCCAGATTC AAGCGATTCT
106201 CCTGCCTCAG CCTCCAGAGT AGCTGGGATT ACAGGTGTCT ACCACTGCGC
106251 CTGGCTAATT TTTGTAATTT TAGTGGAGAT GGGGTTTCAC CATCTTGGCC
106301 AAGCTGGTCT TGAACTCCTG ACCTCGTGAT CCACCTGCCT TGGCCTCCCA
106351 AAGTGCTGGG ATTACAGGTG TGAGGCACCT CACCCAGCCA ACATTTCTAA
106401 TTTTTTTTTT TTTTTTTTTT TAGACATAGT CTCACTCTGT CGCCCAGGCT
106451 GGAGTACAGT GGGGCAATCT CGGCTCACTG CAAGCTCCGC CTCCTGGGTT
106501 CATGCCATTC TTCTGCCTCA GCCTCCCTAG TAGCTGGGAC TACAGGTGCC
106551 TGCCAACACA TCCAGCTAAT TTTTTATACT TTTTAGTAGA GACGGGGTTT
106601 CACCATGTTA GCCGGGATGG TCTCGATCTC CTGACCTTGT GATCCGCCCG
106651 CCTCGGCCTC CCAAAGTGCT GGGATTACAG GCGTGAGCCA CCGCGCCTGG
106701 CCAATTTTTT AAAAAATTAA AAAAAATATG TGTATGTAAA ATTGTGTACA

FIGURE 3II

```
106751 CACGATGGGA ATAACAAAGG AAAAGAGAGA AAGGAATAGA AGAACCATTT
106801 GAAGTAATAA TGACTATTTT CAAAACTAAA GACAGATGCC AAACCACAAA
106851 TCCAGTTTAG AAAGTTAAGA AAACAAGCAA GATAAATACC AAATGCCAGG
106901 TGCGGTGGCT CACACCTGTA ATCCCAGCAT TTTGGGAGGC CGAGGTGGGC
106951 AGATCACTTG AGGTCAGGAG TTCAAGACCA GCCTGGCCAA CATGGTGAAA
107001 CCCTGTCTCT ACTAAAAATA GAAAAATTAG GCCTGGTGGC AGGTGCCTGT
107051 AATCCCAGCT ACTCAAGAGA CTGAGGCAGG AGAATTGCTT GAACCTGGGA
107101 GGCAGAGGTT GCAGTGAGCT GGGCACCACT GCACTCCAGC TTGGGCAAAA
107151 GAGTGAGACT CCATCTCCAA AAAAAAAAAA AAAAAAAAAA GATAAATACA
107201 AGAAAGTCTG TACCCAGGCA CCTAGGCATA TCATAATCAA ATTGCAGAAA
107251 ATCAAAGATA ACATCCTGAA AAAACCTAGA GGAAAAAAAA CACCTATGGA
107301 GAGTGGAGTG AAATATCTCT ATATTTATTA TGTCTTTATT ATGTTTTTAA
107351 TTATGTTTTT CATTTATTTT TGTGGTTACC TGGTAGGTGT ATATATTTAT
107401 GGGGTACATG AGATATTTTG ATGCGGGTAT ACAATATGTA ATAATCACAT
107451 CAGGATGAAT GAGGTATCTG TCACCTCAAG CATTTATCAT TTTCTTGTAT
107501 TACAAACCAT CTAGTTATAC TCTAGTTGTT TTTAAATAAA TAGTTAATTA
107551 TTGACTGTAG TCACCGTGTT GTGCTATCAA ATACTAGATT TTATTCCTTC
107601 TATCTAATAA TATTTTTGTA CCCTATAATT ATCCCCTCCC CCACCCACCT
107651 ACCCACTACC CTTCCCAGCC TTTGGTAACC ATTGTTCTAC TCTCTATTTC
107701 CATGAGTTCA ACTGTCTTAA TTTTTAGCTC CCACAAATAA GTGAGAACAT
107751 GTAAAGTTTG TCTTTCTATA CCTGGCTTAT TTTACTTAAC ATAATGACCC
107801 CCACTTCCAT CCATGTTGTT GCAGATGACA GGGTCATTCT TTTCTATGGC
107851 TGAATAGTAC ATATATATAT ATATATAATA TTTCCTTTAT CCATTTATCT
107901 GTTGATGGAC ACTTAGATTG ATCCCAAATC TTGGCTATTG TGAATAGTGC
107951 TGCAGCAAAC GTGAGAATGC AGATATCTCC TTGATTTACT GATTTCCCTT
108001 CTTTTGGGTA TATTCCTAGT AGTGGGATTG CTAGATCATA TGGTAGTTCC
108051 ATTTTTAGTT TTTTGAGGAA CCTCCATACT GTTCTCCATG GTGGTTGTAC
108101 TAATTTATAT TCCCACCAAC AGTGTACCAG GGTTCCCTTT TCTCCACATC
108151 CTCACCAGCA TTCGTTATTG CCTGTCTTTT GGATAAAAGC CATTTTAACT
108201 GGGATGAGAT GATATCTCAT TGTAGTTTTG ATTTGCATCT CCCTGATGGT
108251 CATGACGTAA TATTGAGTAC CTTTTCATAT ACCTGCTTGC CATTTGTATG
108301 TCTACTTTGT AGTAATGTCT ATTCTGATCT TTTGCCCATT TTTTATTGTA
108351 TTATTCGATT TTTTATTGAC TTGTTTGAGC TCTTTATTCT GGTTATTAGT
108401 TTCTTGTCAA ATGGATAGTT TGCAAATATT TTCTTCCATT TGGGGGATTG
108451 TCACTTCCCT TTGTTGATTG TATCCTTTGC TGCATAGAAG TTTTTACACT
108501 TGGCATGATC CCATTTGTCC ATTTTTGCTT TGGGTGCCTG TCTTTGTGGG
108551 GTATTACTCA AGAAATCTTT GCTCAGTGCA ATGTCCTGGA GAGTTTTCCA
108601 AATGTTTTCT TTTAGCAGCT TCATAGTTTG AGGTTTTAGA TTTAAGTATT
108651 TAATTCATTT TGATTTGATT TTTGTATATG GCAAGAGATA GGGGTCTAGT
108701 TTCTTTCTTT CTTCTTTTTT TCCTTTGCTT TACTTTTTTT TTTTTTTTTT
108751 TTTTTTTTTG AGACAGGGTC TCACTCTGTC TCCCAGGCTG GAGTACAGTG
108801 GTGTGATCAC AACTCATTGC AACCTCCACC TCCCAGGTTC AAGTAATTCT
108851 AATGCCTCAG CCTCCTGAGT AGCTGGGATT TCAGGTATAT GCCACCATGC
108901 CTGGCTAATT TTTGTATTTT GAGTAGAGAC GGGGTTTCAC CATGTTGCCC
108951 GGGCTGGTCT CAAACTTCTG GCCTCAAGTG ATCCACTGGC CTTGACTTAC
109001 TAAAGTGCTG GGATTATAGG TGTGAGCCAC CATGTCCAGC AAGTATCTAG
109051 TTTCATTCTA CTACATATGG ATATCCAGTT TTCCCAGCAC CATTTATTGA
109101 AGAGACTGTT CTTTCCCCAA TGTATGTTCT TGGCACATTT GTTGGTAATG
109151 AGTTCTCTGT AGATGTGTGG ATATGTTTCT GGGTTATCTG TTCTTTTCCA
109201 TCAATCTGTG TGTCTATTTT TATGCCAGTA CCATGCTGTT TTGGTTACTA
109251 TAACTCTGTA GTATAATTCG AATTCAGGTA ATGTTACTCC ACCAGTATTA
109301 TTCTTTTTGC TCAGGATAGC TTTGGTTATT CTGGATCTTT TCATGGTTCC
109351 AGGTAAACTT TAGAATTGTT TTTTCTATTT CTGAGTAGAA GAATTTTATT
109401 TTATTCATAG CTATTGTAAA TGGGATTACT TTCTTGACTT CTTTTTCAGA
109451 TTGTTCACTG TTGGCACATA AAAATGCTAC TGATTTTTGT ATGTTGGTTT
109501 TGTCTTCTTC AACTTTCTGA ATTTATTAGT TCTAATAGTT TTTTTGGTGG
109551 AGTCTTTTGG TTTTTCCAAA TATAAGGTTA TATTATCTAT AAACAAGGAT
109601 AATTTGACTT CTTTCTTTCT AGTTTGGATG CCCTTTCTTT CTATTTTCTT
109651 ATTACTGTAA GACTTACAGA ATGAAATATT TAAAGTATTG AAAGAAAAAC
109701 CCCACCAACC TATGGTAACT CCATGTTTCC AGTTGGTAGT TGCTTAGGCA
109751 AAACACCTTG GAGTCATTCT TGATTCTCCT TGTCCCTCAC ATCCCACATC
```

FIGURE 3JJ

```
109801 CTATCTGTTA GGATATCGAG ATGTAATAAG AAAAAAAAAA TTGTAATCCT
109851 CCCCTTCTTA CCACCTCTAT TTCTATCTCC TTGGTCCAAG CCATCATTAT
109901 CTCTTCTCTG GATTATTGCT ATAGACTCCA TACTACAGTC TAAACAGAGC
109951 AACTAGAATG ATTAAAGTCC AATCTAGTAC TACTACAGAA GCTTCCCATT
110001 TCACTACCTG TCTATGAATT ACTTAATTTC TCTGTGTCTC AGTTGCTTCA
110051 TCTGTTAAAA GAGAATAATA CCTCCTCAGG AGATTGTGTG ATTGATGAGG
110101 AGGCACTTAC TTAATACCAA CCTGATGCAC AGAAAATAGT AAAGTTTAGC
110151 GATTTTTTTT ATTATTTTAA TTTCCAATTT GCCCTTCAAA TCAGAAGCTT
110201 AGTTTTGTCT TATTCTTCAG TGCTTGAGGT GGGAGGGTTT GTAGAAACAT
110251 TTGGCTTCTG AATACCTAGC TCATTGCTGT CAAGCAGAAT CCTCCATCTT
110301 TTAGTGCCTG AAAATATTCA GATGTCCAGA AACATTAACC AAAGGAAATT
110351 CCATTTCTAG CTCTGCTGTT TGTATAGGCA ATGTAGTGGG TCAGTTTTCT
110401 GCACTGTGTA GAAATTGCTT TGTCAGTGGA AAATGTTATT TTCGTCGGTT
110451 TTACAGTTCC TAACTTTTGA GGCATTTGTT CCCTGGAGGA TACTAAAAGA
110501 AGGAAATCTT CAGACAGCTG CCCACTGAAT TTTTGCGTGA GCCTTTATTT
110551 GATATTTTAC CCAGACCCCT TTTGGTTTTT TATTACAGTA ACATCGCATA
110601 CCTAGGTTTT TTTTTTCTTC TTCATATAAG CCTTACCTAT CTGGAACTGT
110651 CAGTACTAGG AAGGTACTTA TAGTGTTGAA TGTTCCCACT CATATTTCCT
110701 GTTATGCCTT ATGCTTTTTA TAACAAGCCA AAAAGAGGAA GAAAGATTTC
110751 ACCATAGATT TGCTAAAGGC AATGTGGGAT GCAATGAGTG TGGTTTAATG
110801 GAAGAGCCCT GGGGTGCGGC CTCTGAGCCT TGCTCTGCCA CTGACACCTG
110851 TATGACTGCC TGGGCTTGAG TTAAACGTTC TGCATAAATT CTAGCAGAAG
110901 AGGCTAGCTC AAAGAGGAGA TTCAGTGTCT GAATGTCTGA GAGAGTGTGA
110951 AAATAAGAAA AGTTGGCTGG GCGCCGTGGC TCACACCTGT AATGCAGCAC
111001 TTTGGGAGGC CGAGGCAGGC GGATCACCTG AGGTCAGGAG TTCAAGACCA
111051 GCCTGACCAA CATGGAGAAA CCCTGTCTCT ATTAAAAATT CAAAAAAGTA
111101 GCCAGGCGTG GTGGTGCATG CCTGTAATCC CAGCTACTCA GGAAGCTGAG
111151 GCAGGAGAAG TGCTTGAACC TGGGAGGCAG AGGTTGTGGT GAGCCAAGAT
111201 TGCGCCATTG CACTCCAGCC TGGGTGACAG AGCGAAACTC CGTCTCAAAA
111251 CAACAACAAC AACAACAACA AAGTCAAGTC ACTTGAGACC TCAACCCACT
111301 GACAAGAGAA GAGGGACTGG GGCAGACCCA ACCTGAACTG GTTCTGTAAA
111351 GCAGCCACGG CACAGACCAG AGTGGACTGT GGGCCTGAGC AGTGTATGCC
111401 CCTGGGGCCT GGAAAGTAGG GGCTGGGACT TCATTTCTTG AATAGAGGGA
111451 GAAGGAAAGA CACTTGAGAA TCTGGTAAAA ACAAAAACAA CAACAACAAA
111501 AAACCCAAAA CAAATAAAAC ATTCTAGTAG CTTCAGGCCC TCCACTGGGC
111551 ATGGTGTCTT CTTGACCCAC AGACAATAGG CAGGCAAAGT AGATGGAAGC
111601 AAGTGCTAAC ATGATACACA GCTCCCAGGG CTTAGACACT TCCCACCTCA
111651 GCAAGCTGGA CCCATCCAAG CTGTGGTGTC AGGGTAGAAC AAATGATTCT
111701 TTTTTTCGAG ATGGAGTTTC GCTCTTGTTG CCCAGTCTGG AGTGCAATGC
111751 TGAGATCAGC TCACTGCAGC CTCCGCCTCC CAGGTTTGAG CAATTCACCT
111801 GCCTCAGCCT CCTGAGTAGC TGGGATTACA GGCGCCTGCC AACACGCTCA
111851 GCTAATTTTT TGTATTTTAA GTAGAGATGG GGTTTCACCA TGTTGGCCAG
111901 GCTGGTCTCG AACTCCTGAC CTCAGGTGAT CTGCCCGCCT TCGCCTCCCA
111951 AAATGCTGGG ATTACAGGCA TGAGCTACCG CGCCCAGCCG AACAAATGAT
112001 TCTTATATGT AGATTCTTTA GGGAGCAGCT AAGCCAGCCC CCATTGACTG
112051 GGGGAGATGA TGGTAGCTTT GAGACACTCC TAGCAGCTGC AGTTTTGTTA
112101 TCCTGCACCC TGTTCACTTT CCAGGGCCAT GCACCTCCAC GGAAATACCT
112151 TATCTATAAG CCTTGTGTCT CTACTTCAGT TTAGGTCTCC TAGACTGTAA
112201 CGGAGAACAA AAAAAAAAAA TAGACCAAGT TTTAGGCATT GCAGGAAAAA
112251 AAAGTGTGTT CATTCTCTGA GCCTCCGAAG TAATGCAGCT ATATTTATAA
112301 GTGGATCAGT AAAAGGAGAA ACTTCTTTAG GTTTTTAGAC CTGGGATTCA
112351 GCATTGAGAT TTTCTGTGCT CTGAAGGACT ATCCAGTAAC TGTCCTTCCA
112401 ATAACTTTCC TTAGTTTCTT GTTACAATCG CGATTCCGGT GGTTATCAAA
112451 CTTCTTCCTA GTGGATTGCT TTTCCACTCT TCATTGACAT TACTTGTTCC
112501 CAAGTTTTTT TTTGCTGTTG CAAAGTGTTG AAATAAACAT CTTTGTACTT
112551 AAATGATATA TGTGTAACAG TAAATTTTTA ACATTAAACC ACTGACTTAA
112601 TTCATTTATT GAATTTTGTT GTAGTATATC ACACATACAG TATACCAATC
112651 ATTTATCAAT AACTGATGTG TTCACAAAAT GAACACATGC TCATAATCAC
112701 TACTGATATC AAGACAGAAA ATTACCAGCA CCCTGGAAGC CTCTCTCAGC
112751 TTCTCTCTCT CAATCACTAC CACCTCCTTC CTACCCAGGG CAAACAGTAT
112801 CCTGATTTCT AAGATCATTG ATTTGTTTTA CCTACTTAGT AGCTTTAAAT
```

FIGURE 3KK

```
112851 TTTTTAAATG AAGATGTAGT ATATTATTCT TTGGAATCTG GCTCCCCACC
112901 TCCTCATCAT TATGTTGAGA TTCATCTGTG TTGTTGCTAA TGTAGCAGAG
112951 TTCATTTTTT TGTTACTGTA TAGTGTATCA TTATATGCGT AGATCACGTT
113001 TTTTAATTTA TTCTTTCTCA TTGCACTGTT CTGCAATGCC ACCTTGCCGT
113051 AAACCAGGCA TCTGCATCTG AGGGGCTGTT TCTGGACCTG TCATTCTGTT
113101 TCATCGATAT ATTTATCTAT CCTTGTGCCA AAACCCTACT GTCTTACTTA
113151 TGGCTATATC ATTAACTTAG CTAATGTTTA GAGCTATGTA ATGTAGATAA
113201 TTGTAGCTGT ATAATAGTAA TGTATCGATA TCTGGTAGAA TAAGTTCTTC
113251 TACTTTGTTA TTCTTTTAAA ACTACCTTGA CTATTCTTGG CCCTGTGTAT
113301 TTCCATATAA CTTTTACAAT CAAGTTGAAA TTACTCCCTC CCCTCCAAAA
113351 AAAAAAAAAA AGCATGCTAG AATTTTGATT GGGAATTCTT TGAGGAGAAT
113401 GGCTATCTTT ATTATATTAA ATCTTCCTGT CCCTGAAAGT GGTATGTCTG
113451 TTTATGTGGG TCTTTAATTT CTCTCAATAG TGTTTTATAG TTTTCTGTGT
113501 TAAGGTTTTA TATATCTTTT ATTGATTTAC TCTTACATAT TCAGTGGGCT
113551 TTTAAATGTA ATAAATGGTA TTTATCACAA ATTTATCATA AAGATTCCTA
113601 ATTATTGCAT GTATTAGAAA CATTTTTATA TATTAAAGCA TAGGTTTTTA
113651 ATTATAAGAT TTTATGAGAT TTACGGTTTA TATCATTTTA AGAATCACTT
113701 AATATTCAAA TTCAAATCAC CATGAGAATT CTGGGTAAAT TGAGAAAAGT
113751 AAAGTTGGAT TAAATCCAGG GTTGTATCCT TGGAGAATTC AAAAGGAACC
113801 AGGAAGAGCT TGTTCCTAAA CTGCGTGAGT TCTGTGTTGG TTGCTTGAGA
113851 GAGATTGCCT AGGGCTTGCT TCCTCTCTCA GCTAAAGTGA TTGGGATTTG
113901 GCAGTCAGGG TGCTTTTGTT TTTAGGGTAC CCTGAGCCCT CTCCTAGCCA
113951 GCCCACATTT GTGAGCACTC GGTAAACACA GAGCAGGAGG GAATTACAGT
114001 GAATGGGGAT TTCCCTCAGT GCTGCCCACT GGCTGCTCTT GAACTGACAG
114051 GCTTCTTTCT CATTCTAAAC TCACCAGCAG TGGAGCAGTA AACCCGGCCA
114101 CGGTCAGGCA TGGCACATGT CCTGCAATGA TGGGGACTGG ACCTGTTGCC
114151 TTAAACTCAC GCCTGCTTTG TTTTTCCAGG TCTATAAGGG AGAATTCCAA
114201 CTACCTGACT TTCTTAAAGA AAAACCACAG GTACTGTGTC TGCTTTTTCC
114251 TCCTGATGTA TACTAGATTG GCTCTTGCAT TGAAGTAATA TTTTTAAAGA
114301 GATAATGAAA TTAAAAAGAC AGAAACAAGA AAACCAAAAA GAAAAGAAGA
114351 AAAGGGATAG TGATATGTGC TGGGGAAGAA AGATCAGCGT CTGGGACTTG
114401 TTGATTTTAA CAATAATTTA ACACAGTCTT AATTTCAGAG AGCTCAGTGT
114451 CTCCCAAAAC CAGGGAAATA CTTTATTGAT AACCAAATTC TGATTGCTTG
114501 AGGTCCTGCA CAAGCCGCCC AGTGGGTAAA GCTGCTCCAG CGTTCCAGTG
114551 CCTAATTTGA AATAAAAATG TTCAGCGACC CTCTCTGTTC CTACTCTGTG
114601 TACTGTACAT CCTTGCCCCT TTGACTTTTC TCATTTGGAG CCCAGATGAC
114651 TTATATATAC ACATAGTCAC TGGCCCCTGG GAAGGACAGT GAGAGTTTGA
114701 AGGATTAAAG CCAGCATGGT GGCTCATGCC TGTAATCCCA GCAATTTGTG
114751 AGACCGAGGT TGGCAGATCA CTTGAAGTCG GGAGTTCAAG ACCAGCATGG
114801 CCAACATGGT GAAACCTCAT CTCTACTGAA AATATAAAAA TTAGCCGAGT
114851 ATTGCAGAAT TTGCCTGTAA TCCCAGCTAC TTGGGAGGCT GAGGGAGAAT
114901 CACATGAACC GGGAGTTGGA GGTTGCTGAG CCAAGATTAC ACCACTGCAC
114951 TACAGCCTGT GTGACAGAAC AAGACTGCCT CAAAAAAAGA AAAAATTAGC
115001 TAGGCATGGT GGCGAGGCCT CTGGTCCCAG CTACTTGGGA GGCTGAGGCA
115051 GGAGGATCGC TTGAGCCCAT GAGGTGGAGG TTGCCATGAG TTTAGATTGT
115101 GCCACTGCAC TCCAGCCTGG GTGACAGAGT GAGACCCTGT CTCAAAAATA
115151 AAAAAAATTA AGCAGATTCA GAGTTTTCCC TGTAACGTCT TCTCTCACTG
115201 ACTTGCATTC CAATCCTGTT TCCTGGGTTG GAAAGAAACA GGGAGTCTCA
115251 CGGCTGACAT GCCTAGAGGA GCCCGGCATC CTGCCTCTGG GCATCACTGT
115301 CATGCCCATA TGGAAGTCAG AAAAAATGGA CACTCATGGC CTGAGTGCAG
115351 CCGACTTCCC TTTCCAGCAA GGCGATGATG CATGTTGCCT CCAGGCTGCT
115401 GCTGTCAGTG ATTAGCTTGT CAATAGGAAG AGGAGACTCA GTTTTGAACT
115451 CAGTTTCTGA AAGCGTTCCA GATAGAGGTT GGTGAAGCAA CAGCACCTCA
115501 GAGACTTGTG TGAAGTCCAG TTGCCTGATG CAAGCCTGGA GTAAATGGGC
115551 TGCCCTCTCT GAGGGAAGCC ATGTCTCACA CCAGAGTTGA AGCCTCTTCC
115601 TTCCTGACCC TTTTCTGAAA ACACTTAGCC GCCAGTAATT GATACATATG
115651 ACTTGAGTGT TTCAAAGTAC TTTCAAGGCA TATTCTTATT CACATATATT
115701 TACTATTCAT CCATTCATTC ACTTATTCAC CAATTGTTTA CCCAGTGTCT
115751 ACTATGGTGA GGAATTAGAG TAAGTCCTCA GGAGTCACGG GGGAAAGAAA
115801 GACCTCAAGG AGCTCCTGAT TTATCCAGAA GAATCCGACC ACCTCGTGCA
115851 GACAAGGGGA CACAGAGCTC TGGGCCCAGG CTGGGCATGA TGTCCCAGAA
```

FIGURE 3LL

```
115901 ACCTGGGCAG ATTCATGAAC AGACTGACAC CGGCTGTGGA AATTGGAGCC
115951 AGAGAATATT CCAAGAGGCT GTCTTGAAGG AATATAAAAT CCAAAAGCGC
116001 CCAGGTGCGG TGGTTCACGC CTGTAATCCC AGCACTTTGG GAGGCCCAGG
116051 TGGGTGGATT GCCTGAGGTC AGGAGTTCAA GATCTGTTTA GCCAACACAG
116101 TGACACCCCG TCTCTACTAA AAATATAAAA TAATTAGCAA GACTTGGTGG
116151 TGTGCGCCTG TAATCCCAGC CTGGGTGACA GAGCGAGAGT CTGTCTCAAA
116201 AAAAAAAAAA AAAAAAAAAA AAAATTCCAA AAGCCGGTTT GCATAACAAA
116251 TCTGAAGAAG TCAAGAAAAG GTATTTGAGA CTAAAACTAA AGGGACACTC
116301 CTGCTTCACA ACATACCTAA AAATATTTCC AAATGGATTG CACACCTAAA
116351 TGTGAAAGGC AAAATAATGA AAGTTGTTAG AGGATATAGA AGAGCCAGGC
116401 ATGAGGCTCA CGCTTGTAAT CCCAGCACTT TGGGAGGCAG GCAGATTGCT
116451 TGAGTCCAGG CATTCAAAAC CAGCCTGGGA AACATAGCCA AACCTCATCT
116501 CTACTAAAAA TACAAAAAAT TAGCTGGGTG TGGTGCATGC CTGTAGTCCC
116551 AGCTACTTGG GAGGCTGAGG TGGGAGGATC ACCTGAGCCC CA  (SEQ ID NO:3)
```

FEATURES:

Start: 2104
Exon: 2104-2948
Intron: 2949-48176
Exon: 48177-48375
Intron: 48376-114179
Exon: 114180-114263
Stop: 114264

CHROMOSOME MAP POSITION:

Chromosome 7

ALLELIC VARIANTS (SNPs):

| DNA Position | Major | Minor | Domain |
|---|---|---|---|
| 1304 | A | G | Beyond ORF(5') |
| 1365 | A | G | Beyond ORF(5') |
| 1725 | A | C | Beyond ORF(5') |
| 3505 | C | T | Intron |
| 11936 | G | A | Intron |
| 12627 | A | T | Intron |
| 15410 | A | G | Intron |
| 17211 | A | C | Intron |
| 17579 | A | G | Intron |
| 18134 | G | A | Intron |
| 21381 | A | C | Intron |
| 23624 | A | G | Intron |
| 27555 | A | G | Intron |
| 27889 | C | T | Intron |
| 28550 | G | A | Intron |
| 29808 | C | T | Intron |
| 31295 | - | T | Intron |
| 31480 | A | G | Intron |
| 32739 | T | G | Intron |
| 32879 | A | G | Intron |
| 38304 | T | C | Intron |
| 39702 | G | T | Intron |
| 39887 | C | T | Intron |
| 40477 | G | A | Intron |
| 44465 | G | A | Intron |
| 45032 | T | A | Intron |
| 45757 | T | C | Intron |
| 46030 | - | T | Intron |

FIGURE 3MM

| | | | |
|---|---|---|---|
| 46179 | C | T | Intron |
| 46652 | A | G | Intron |
| 46843 | G | A | Intron |
| 56450 | T | A | Intron |
| 56906 | G | C | Intron |
| 56974 | C | T | Intron |
| 57923 | - | C | Intron |
| 60974 | - | T | Intron |
| 61352 | C | A | Intron |
| 61353 | T | A | Intron |
| 61679 | G | A | Intron |
| 64709 | A | G | Intron |
| 65783 | A | G | Intron |
| 66506 | T | - | Intron |
| 66589 | T | C | Intron |
| 67336 | C | T | Intron |
| 68176 | G | C | Intron |
| 69456 | T | C | Intron |
| 70557 | C | T | Intron |
| 72833 | G | T | Intron |
| 75250 | T | G | Intron |
| 76502 | G | A | Intron |
| 78350 | A | G | Intron |
| 78359 | G | A | Intron |
| 79720 | G | A | Intron |
| 81763 | C | T | Intron |
| 87250 | C | T | Intron |
| 87345 | A | G | Intron |
| 87393 | C | G | Intron |
| 90448 | G | A | Intron |
| 91485 | C | A | Intron |
| 94099 | T | C | Intron |
| 95236 | G | A | Intron |
| 95493 | G | A | Intron |
| 96594 | A | G | Intron |
| 96887 | T | C | Intron |
| 97803 | C | T | Intron |
| 101109 | G | A | Intron |
| 101298 | C | T | Intron |
| 104790 | C | T | Intron |
| 105798 | G | A | Intron |
| 110536 | C | T | Intron |
| 114916 | G | T | Beyond ORF(3') |

Context:

DNA
Position

1304
ATTACATGCTCCTTTTCATTATGCTCCCATTGTCCCTTTGCGTATTTCCACGGAGGCACT
CATCACATTTTATTGTTATTGTTTACATATCTGTCTGTCAAAAGGCTTTGTTTTCCAACA
GCAGAAGTTACTATACTGTTTTCCTTTTCAAAGTTGGTCCTCAGTCGAGCCTATCTGGTC
TGTAGTACCTAAATAAATTGTGGGATAATAAACTGAATCTCTGTTAAAGATTTGGAAGTT
GTTTCATATTTCTTCTATAATTTCTCATTGTTAGAATGTGGAGATAATGACTGCTTGGAG
[A,G]
TAAAGCAAGTCTGAATAGCAGAGATCAGCCTTGGGTTGGACTCCAGACATTCTTGGGCTT
ATTAAATATTTGGTTGACTCACTGATAGAAATAGTTTTATTTATTTTCCATTCTTTACCA
GGTACATAGCTTCAAAATTACTTCATTAACAAAAGCTGTTTCTGATTATAAACATTGATT
TATTTTTACTCAAATTTGTATATACTGTATATACTGAGTAAAACAAATTTTACTCATTTG
TTTTTGTTTTGTTTTGTTTTGTTTTGTTTTTTTGAGACAGAGTCTTGCTTTGTTGCCTAG

1365
ATCACATTTTATTGTTATTGTTTACATATCTGTCTGTCAAAAGGCTTTGTTTTCCAACAG

FIGURE 3NN

CAGAAGTTACTATACTGTTTTCCTTTTCAAAGTTGGTCCTCAGTCGAGCCTATCTGGTCT
GTAGTACCTAAATAAATTGTGGGATAATAAACTGAATCTCTGTTAAAGATTTGGAAGTTG
TTTCATATTTCTTCTATAATTTCTCATTGTTAGAATGTGGAGATAATGACTGCTTGGAGA
TAAAGCAAGTCTGAATAGCAGAGATCAGCCTTGGGTTGGACTCCAGACATTCTTGGGCTT
[A,G]
TTAAATATTTGGTTGACTCACTGATAGAAATAGTTTTATTTATTTTCCATTCTTTACCAG
GTACATAGCTTCAAAATTACTTCATTAACAAAAGCTGTTTCTGATTATAAACATTGATTT
ATTTTTACTCAAATTTGTATATACTGTATATACTGAGTAAAACAAATTTTACTCATTTGT
TTTTGTTTTGTTTTGTTTTGTTTTGTTTTTTTGAGACAGAGTCTTGCTTTGTTGCCTAGG
CTGGAGTGCAGTGGCATGATCTCAGCTCACTGCAAGCTCTGCCTCCTGGATTCATGCCAT

1725 GGTACATAGCTTCAAAATTACTTCATTAACAAAAGCTGTTTCTGATTATAAACATTGATT
TATTTTTACTCAAATTTGTATATACTGTATATACTGAGTAAAACAAATTTTACTCATTTG
TTTTTGTTTTGTTTTGTTTTGTTTTGTTTTTTTGAGACAGAGTCTTGCTTTGTTGCCTAG
GCTGGAGTGCAGTGGCATGATCTCAGCTCACTGCAAGCTCTGCCTCCTGGATTCATGCCA
TTCTCCTGCCTCAGCCTCCCGAGTAGCTGGGACTACAGGCACCCGCCACCATGCCCAGCT
[A,C]
ATTTTTTTGTATTTTTTTTAGTAGAGATGGGGTTTCACCGTGTTGGCCGGGATGGTCT
CCATCTCCTGACCTCGTGATCCGCCCGCCTCGGCCTCCCAAAGTGCTGGGATTACAGGTG
TGAGCCACCGCGCCCGGTCTCAATTTTGTTTTAAGAATATCAAAGAATCCAAGACTGTTT
CAGCTTCTTTCTACCTAAAATGCAGTGGTGATAACTGGTGACTGATTTGTAAGCAATCTC
AATGTAATGATAAATAACCTTTTCCTTTCTCTACTAGATGTTGGTTATCTTTCTGAAGTA

3505 TGATGGATACAAACCCACCTTACAGGCGGTGAAAAGCCTTCTTCAGGGTCTCAGACCTTA
ATGCCAATCATTCAGTTTTAGTGGCTTCTGATTTCTAATTTCTAGATATTGTTGTTAATG
AGGATAGTTGGCTTTTGTGTGGATTAAGGTTAAAATCAGGAAGTGCATATATCATGTTAA
TGAGCACATAGTGAATTATAAGCATTTTGAAATTTTTAGTGGTAGAGAAAAAATAAAAGCT
TCGTCTAACCTAATCTCTTCATTTTATGGACAAGAAGACTGAGTCACAGTAAGATTAAAA
[C,T]
GATTTGTTCAGATTTAGATGGCAAGGCCAGAATTCGAATCTGTGCCTTGGTCTCAATGAG
GTCGTGCTTTTCTCCGTGGCATTTTACTACGTGTTGTGCTTCCTTTGTCATCTGAAGGAT
ATAACCTCTCTTATTTTTTACAAAAGGCTAGAGAATCTCCAAAATTTGGAAGCCTAATCC
ATACAAGAAGTTCCTTGGATTCAAAACTTCTCAAATGATGATTTTTAGCATTTTGCTTCT
TTTCTTATGAAGTGACAACTAGTATACCCTCTAACCTGTCTTGATGACTTATATACCTGG

11936 TGGCAAATGGAAAAGGGTTGATACTTTGAAGCTGGCTAGACTTTGTTTAAAGTCTTTCAT
TGACACTAACTGGTTTTGTAACATTGCATCAAATACTATCTCTCTCCGTGTCTCCATTTT
CTTATCTATAAAACAGGGAAGATGGTGATGATGGTAATGATACCATCCAACATCTACTGA
ACATTTGTTATGTGCCAGGCAGTATGCTGAGCTCTCTGTGTGCCTTATCTCATTTAGTTT
TTATATTTACCCTTTCACACTCACCCATAGGTGCCTTAAACATCTTAATTTTATAGATGA
[G,A]
GGACTTGAGGCTCCCAGAAGTTGAGGAGCTTGTCCTCCGTCCCACAGTTGGAAGATGGTA
GAGCCAGGCTGTGGACTCAGGTCTTTGTCTTCATCTATACTTTTAGCTCTTGTTGTATAT
ACTTACAGCATTTATGAAGACAAACTAAAACAGTGTGACAGTGGCTAAGCACACGTTTTA
GAGTCAGACAGACATAGGTTCAAATCCTAGCACTGTCCTTTATTGATTATGTGACCTTGA
GTGAGTTATTTGGTTTTGTCTAGTCTTGGTTATCTCATCTTTCCTTTAGTTTTCTTATCC

12627 TACCGAGCCCTATATATACTATGTTTTTTCCTGTGCATATATACCTGTGGTTAATTTATA
AATCAAGCACAGTAAGATTAACAGCAGTAACTAATTATAAAGTAGAACAATTATAACAAT
ATGCCAGTATTACTACTTTTGAGCTTTATGGCCATGATTAAGTTAAACAAGAGTTACTTC
AACGTAAGCACTGCGATACTGCTACAGTCCATCTGATAACAGAGGGCTACTAAGTGACTA
ATGGTGGGTAGTGAGTGTACATTGCATGGACGTGTTGAACAAAGGGATGATTTACATCCC
[A,T]
GTCTAGACAGAGTGAGACAATGTTAGATTTCATCATGCTACTGAGAATGACATGCAATTT
AAAACTTATGAGTTGTTTATTTCTGGAGTTTCCCATTTAATGTTTTCAGACCACAGTTGA
CTGCAGAGAACTACCTGAAACTGTGGATAAAGGCTTACTGAAATAGTATCCATTAAGGAT
GATAATAATAACTATCCATAGGGTTGTCGTGAGGATTTAGTTAGAATGACTATAAAGCCC
TTAGCCAAGTGCCTGGTATATAATGAGAGGTTGAAAATGTTACCTGTTGTCTTTATTATT

15410 GCACGATCTCAGCTCACTGCAACCTCCGCCTCCTGGGTTCAAGCGATTCTCATGCCTCAA
TTCTCCCGAGTAGCTGGGACTACAGGCGTGTGCCACCATGCCTGGCTAATTTTTTGTATT

FIGURE 3OO

TTTAGTAGAGACGGGATTTCACCGTGTTAACCAGGATGGTCTCTCTCTCCTGACCTTGTG
ATCCGCCCACCCTGGCCTCCCAAAGTGCTGGGATTACAGGCATGAGCCACTGCACCCAGT
CAAGAAATCCTTCTTCACTTAGTCTATCCTAATGCCATATACCACTCTATTTTAATTACT
[A,G]
CAGTTTTAGAAAATGTCTTCGAGTTAGCCAGGCGCGGTGGCTTATGCCTATAATCCCAGC
ACTTTGGGAGGCTGAGGTGGGCGGATCACTTGAGGTAAGGAGTTATACCCCAGCCTGGCC
AACACGGTGAAACGCCATCATTACCAAAAAATAAAAATTAGCTGGGCATGGTAGCGGGCA
CCTTTAGTCCCAGGGAATGGAGGCAGAAGTTGCAGTGATCCAAGATTGTACCACTGCACT
CCAGCCTGGTTGACAGAGTGAGACTCTGTTTCAAAAAAAAAAAAAAAAAAAAAAGAAAGAA

17211 TGGTCATCACAGTTGGGGAAGTGGAGGTGATACTGCTGGCCTCAAATAGAAAGAGGCCAG
GGTGTTGCTAAACATCCTGCAATTATAGGACAGCTACTACAACAAAGAATTTATTCAGCC
CCAAATGTCAGCTGTGCCAAGGTTGAGAAACTGTATTTTAAAGGGAATGCCTTAAACAAT
ATTTTATTATTATGCAGAATTCCAAACACAAAAATAAATTGGTAAACAGAATTCCCAATA
CCAACAGTTAACTATTGTAGGCCAGTATTTAACTCCTTTCCTTCCCCCAACTTCTGCTGA
[A,C]
TTATTTTAAAACAAATACAAGATATCACATCATTCCATCTGTAAATACTTCTCTGTGTGT
CACTAAAGTAGAGGTTCCCAAATTATGGTTTCAGAATACCCAAAAAATCCTTCAGACCCT
CCCAGAAGATCTCCAAGGCTAAAACTATTTTCACAATGGTACTAAGATGTTATTTGAATT
TTCATTCTGTTGACATTTGTGCTGATAGTGCAAAAGAGTTGAAAATTGTGGATGCCTTAG
CACAAATCAAGGCTCTGGCACCAAACTGTACTTAGTGGTCATTGTACTTTTAGTACTGTC

17579 GTAGAGGTTCCCAAATTATGGTTTCAGAATACCCAAAAAATCCTTCAGACCCTCCCAGAA
GATCTCCAAGGCTAAAACTATTTTCACAATGGTACTAAGATGTTATTTGAATTTTCATTC
TGTTGACATTTGTGCTGATAGTGCAAAAGAGTTGAAAATTGTGGATGCCTTAGCACAAAT
CAAGGCTCTGGCACCAAACTGTACTTAGTGGTCATTGTACTTTTAGTACTGTCAAATTCT
CTTCTGCTTAAAAAAAAAACCAACTAGATTTAAGTAAGAATGTGATTCATGAAGCAGTAC
[A,G]
GTTTTTTTTAGTCTTCTACCTAATGGTTTTAGTGATCATTGATGAATCATTGCCCAGACC
TACTATTTTATTAAGTCTGGCCAAATGGTGGTAGTCTAATTTAAAATTTCCTTCTGTATT
CATTAATGATATTTTTCTATAAAGAAGACTGTGCTTATACCAACTGTTTAGTTACTCCTA
AATATCCTTTGTGTAGGAAATGGAGGAAAATGATTTATTTATTTTTTCCCAGAACAGAGT
TCACTCTAAAGGGAATATGTTTAATGAATTTTGTTGTATTTATTTTAATGTACATTATTG

18134 ATATGTTTAATGAATTTTGTTGTATTTATTTTAATGTACATTATTGGTATATGCTGTTAG
TTTTCTTTCTCTTTGTTGATATCTTTTATCAAGTTAAAGAATTTCTCTTCTATTTCTAGT
TCACTAAGAGTTTTCAAAGTTAATGGATATTGTATTCATTTTCCATTGCTGTGTAGTAAG
TTACCCCAGAATTTAGTGGCTGAAAACAACAAACATAAAAGTTTCTGTGTGTCAGGAATA
TGGACACAGCATAGCTGGATCTTCTGCTTCAGAGTCCCTCACAAGGCTGCATCAGGGCTC
[G,A]
ACTGGGGAAGGAATGATTTCCTAGTTCATGTGGTATTTGGCAAGATTCAGTTCCTTCTCT
GTCTTAGGTGGAGGGCCTTAGTTTCTTGCTGTGTGTTTCTGTATATGGCTACTTAACATG
GCAGCAGGCAAACAAGAAGAGCCAGAGAAAGTAAAGAAGATGGAAGTTACATCTTTTCCA
GCCTTATCTCAGAAGTGACATCCTATCACTTTTGCCATATTCATGAGAATCAAATTCCTA
GGCCCAGCTAAAATCAAGTAGACGGGATTACACGAAGGTAGGAATATCAGGAGTTGGGAA

21381 TAATTTTTACTTGGAACGTGTTGAGCTCTTTGGATCAGTGAGTTTTATAGTTTATATAAA
ATTTGGAAAATTGTGTACTTTTTTTTTCCAAATTTTTTTTCTCTTCTTTCTCCTTTCCTT
CAGGACTCCAATTACACATATATGAGACTGTTGGAAATGTTTCCATAGTTCACTGATTTT
TTTCAATTTTATTTTCAAAAATAGGCTTTGTTTTTTATAGCAGTTCTGGATTCATGGCAA
ACTTGAACAGAAAGTGTAGAGAGTTCCCATATATGACTTATCCACACACATGCACTGCCT
[A,C]
CCCCAATATCAGTATCCTACTGGTATATTTATTACAATCGATGAATTTATATTGACACAT
TATTATAACCCAAAGTCCATAGTTTACATTAACGTTCACTCTTGGCATTGTATATTCTGT
GGGTTTTGACAAATGTATACTACCATATATCTACCATTTTAGTATCATACAGAATATTTT
AACTGTCCTAAAAATCCTCCGTGTTCCCCCTATTTATCCTTTCCTTTTTCAGCCCCTTGG
CAACCACTGATTTTTTATTCTAGCCATAGTTTTGCCTTTTCCAGAATGTCATGGAGTTGG

23624 TTAAAAAAATATATTTAATACATGTATTTTTCCATAAAATATATGTTGTCATATTGGGTT
CAGATCTTGGCTTTACCACTTACTGACTGTGGGACCTTGAATCAGATACCTAACCTTTGT
ATGCCTCATTTTCTTCATGTGTAAAATGGTGATAGTAATGGCATTTACGTCATAGGGTTG

FIGURE 3PP

TTAATAAGGTTTAAATGCATTAATAATATGTAAAGAGCTTAGGATAGTATCTGGCATCTA
AGTGCTATAAATGTGTGTTAGCTCTTATTATTTTTACCACAACTACCACCACCACTGCAT
[A,G]
TATTACTGCTAGTGTCCATGCCAGGAGAACCATGTCTGTTCCCTAGGTGGCATATGGGTG
TGTGTATGTAAAGATGAGGTGACTGTGTGGTCTTGTGCTGCTCTCTCTGAGCCCTCCTTG
GCCTCTGGAGTAATAGTATTGCTGTCCACCTGGTCAATGTGTCCTGCTGATAAGTGCTGT
TGCAGTCTGTGGTCAGCAAATGGTCCAGTGGTTCTCCTTGCTTCACTGGCCTCACCTTGG
CTCATGCTGACTCTGAGGTTTGGGTGTCATATTCTTTAAGCCCTGGACCTGGGCAGTAAG

27555
AAAAAAGGGAAAGGGAAGTGAAATAGTGGCTAAAACCCCAAATTTGATGGAAAAGCATGC
ATTTATGCATACAAGAAGCTCAGTAAACTCCAAGCAGGATAAAACCAGAGATTCACAGCT
AGACACATCATAATCAAACTGTTGAAAGCCAAAGATAGAATCTTTAAAGCGGCAAGAGAA
AAGCAGCTCATCATGTACAGGGTAACCTCAGTAAGATGAACAGCAGACTTCTCACCAGAA
ACTATGGTGCCCAGAAGGCAATGGGTTGATGTACTCACATCCCTGAAAGGAAAAAGCCCA
[A,G]
CAAAAACTACCATATCTGGCAAAACTCCCCTTGAGAAATGAAAGAGAAAGAAGATATTCC
TCATAAACCAAAACTGTGAGAATTGTAGCTAGCAGACCTGCCTACAACAAATGCTAAGGG
GAATTCTTCCAGCTGAAATCAAGATGCACTAGATGGTAACTCAAATCTGCATGAAAGAAT
AAAGAACATGGGTCAAGTTAACTACATCGGTTAACTTAGCACTGGCCCAAGCTGGTTCCC
AGAAAAAGGAGACCGTCCAATAATCAACTGCCAGAGGACAGGAAGGATGAAACCATATTT

27889
AGAAATGAAAGAGAAAGAAGATATTCCTCATAAACCAAAACTGTGAGAATTGTAGCTAGC
AGACCTGCCTACAACAAATGCTAAGGGGAATTCTTCCAGCTGAAATCAAGATGCACTAGA
TGGTAACTCAAATCTGCATGAAAGAATAAAGAACATGGGTCAAGTTAACTACATCGGTTA
ACTTAGCACTGGCCCAAGCTGGTTCCCAGAAAAAGGAGACCGTCCAATAATCAACTGCCA
GAGGACAGGAAGGATGAAACCATATTTTTCTCTCCTCTTCACTTTCAGGAGCCCTGCACA
[C,T]
TTCCCATATTTCAGTATATAATTTTTGAGTAAATTAGCAAGGTGAGATCTTTTCACCAGT
CTAATTCTACTAAAAAAAAAAAAAAAGTAGGCTTAGTATTATTAGTCCATAGGGAATGCAG
TTTAAAACCACAGTGAGATACCCCTCTATATTCACCAGAATGGTTAATATTAAATGAATG
GACATTACAGAGTAATGGCAAGGATAATGTTGGTAGGAGTTAAACTAGTATAACCATTTG
GGGAAACTATATATTATGGCTACTTAGCAAAACATGCCTAGCTTATAACCCTACAAATCC

28550
TTACAGAAGAATATTTATAGCAGCACTATTCATAGTAATAGCTGAAAGCTAGAAATGGAT
CCAAGTACCTATCAACAGGGGGATGTATAAATAAAATACATTATATTCATGCAATTAGAT
ATTACTCAGCAATAAAAAGAAGCAAACCAGTGATACATACAACATGGTTGAAGCTCAGAA
ATATACTAAGTGTACACAGCCAGCTGCAAATAAGTATATACTGTAGGTTTCCATTTATAT
GAAGTTCAAAAGTAGCTAAAACCAATCTTTTGTGATAGTAGTTAGAATAGTGGTTATTCT
[G,A]
GGGGGCTGACTGGGAGGCAACACAAAAGAGACTGTTGAGGGGCTAGAAATGATCACTGTC
CTATCTAGGTGGTGGTTACATGGCTGTATATATAAAATTTTGAGTTACACACTTCAGACA
GTGTTGCTGTTAAGATCTGTGTATACTCCATATTATGAAAGATAATTTTTAGGATCTTAA
AAAAAATCTTGATTGCTCTGTCAGTGTTATTGAAATCAAGGATGTATAATATTATCAAGT
TCAATCATCCTAAAAGGAAATTCAATTATAGTTTCATTTTTGTAACTGTTAAAAGCATTA

29808
CATATATTGGGGGAGGGGGTGTGGCAGAAATGCATACACATATTGTACATGTAGCAATGA
GGTTAGATTAGATGGCTACTTTTTCTCTTTCTTTCCTTCTTTCCTTCCTTTCCTTCCTTT
CCTTCCTTCCTTTCGTCCTTTTTTTTTGACAGGGTTTCCATCTATCACCCAGGCTGGAGT
GCAGTGGTACAGTCTTGGCTCACTGCAACCTCCTCCTCTCGGGCTGAAGTGATTCTCCTA
CCTCAGCCTCCCAAGTAGCTGGGATTACAGGCATGTGCCACCACGCCCAGCTAATTTTTA
[C,T]
ATTTTTAGTAGAGATGAGGTTTTGCCATGTTGCCCAGGCTGGTCTTGAACTCCTGACCTC
AAGTGATCCACCCACCTCAGCCTCTCAAAGTGCTGGGATTACAGGTGTGAGCCACTGCAC
CCGGCCAAGGTGGCTACTTTTTAAAGTATGCCATAGTTTAGCCTTCAACTATATATGCCT
TATGGAACCTCCAGTTTAATGCTGCTGTTGATACCCCTCTTAGATTTTCTAATGAGACCT
TCCTCAGCACTTTAATAATGAAATCTACTATATGACTCAAGGTTGATGTGTCTTACTCAG

31295
TTAGTTTTCTTATGCATGCAGATGCTAAAACCATAAATAAAATACCAGTAAATAGAATTC
AGCAGTGTAGCAAAAACTGATCAGCTATTATGACCAAATAGTTTTTATTTCAGCAACAAA
AGAATAGTTCACTACTAGAAAAATCTGTCAACAGAATGTACTACATCAATAAATTAAAGG
AGAAAACCATATGATCATATCATTCAGTGCTGAAAAGGCTCTGGGTACAATTCAGTTGTC

FIGURE 3QQ

ATTCATAATAAAAGCTCTTAAGAAGGAACAGGAAAAACACTACCTAGATATAGTAAAGAC
[-,T]
GCACTCAACATGTTTTTACTAAGCATCCATTATATGCCCAGTAATATTCCAGCAGTTAAC
AGACAAAACATTTAGAGCCATCTCATTTTTTAAAAAAGAAGGAGTTGAATGTTTAGTTTG
TCAGATGGTAATAAGCGCTTTGAAATAAGAAATAAAGCAGGGAATAGGAGGTTGCCAAGA
GCTGAGATGTAGGAATTGTCAGGGAAGGACTCATTGGTAAGGTGATATTTGAGTAGAGAA
CTGTAGGAGAGCAAGTCAACAAAGCAGGCAAAAATTCCAGCCATCATGTATCCTACGGTC

31480 ACCATATGATCATATCATTCAGTGCTGAAAAGGCTCTGGGTACAATTCAGTTGTCATTCA
TAATAAAAGCTCTTAAGAAGGAACAGGAAAAACACTACCTAGATATAGTAAAGACTGCAC
TCAACATGTTTTTACTAAGCATCCATTATATGCCCAGTAATATTCCAGCAGTTAACAGAC
AAAACATTTAGAGCCATCTCATTTTTTAAAAAAGAAGGAGTTGAATGTTTAGTTTGTCAG
ATGGTAATAAGCGCTTTGAAATAAGAAATAAAGCAGGGAATAGGAGGTTGCCAAGAGCTG
[A,G]
GATGTAGGAATTGTCAGGGAAGGACTCATTGGTAAGGTGATATTTGAGTAGAGAACTGTA
GGAGAGCAAGTCAACAAAGCAGGCAAAAATTCCAGCCATCATGTATCCTACGGTCTCATG
GTGGGGGAGGGGGCAATACAAAAAACATGATAAAAACATATAGCATATTAGAAGGTTATA
GTGGAAAAAAGGAAAAACAGAGGAAAGTAAAGGGGACCAGGGCCCAGAGGATTTTGAAGG
TCAGATTATAAAGTTAGTAGTCTCATTGAGAAGGTGATATCTGAGCAAAGTCTCAAAGGA

32739 ATTGATCGCTGAGCCCAGAGGCTTAATCACACTCAAGGTCTTATTTGGTGAGGCTATATA
CATTATGTGTGGTTGTCATTTTTCTTGTGATTTTAGCAGCCATTGATCCTCAGTGCCTAG
ATTCATCAATTTGTTGACTATTGTAAAGTGCTGATATTCTAATTCTGATCTCTTTTCTAC
ATCTTACTTGGAACAATTTTATGAAGAGACATATCCTTGCCTCTATATTTTTTGGTTGCC
CAGGGTTACAGCTTTTCATATACAAAAAGCATAATAAATACTTGATTCTTTTGCTTTTTT
[T,G]
GGGCCAGTTTTCAAGATAATGGTTTGGTTCCTTTTCATCTTCCCAAGAGACCAATTTTAT
ATGTTTCTATCTGTTGCAATTAGCATTTTTATTGAGTTCAAATTGTTCCTTCTCTGGCCA
CTAGATGCTTCTACACATTACCTCCTGAGTACTTTTGCTGTGACCTCAGTTGTGTCTGAT
AGCTTCCTTGCTACCTGGTATGATAACATCTGGTGTGACAAGATAGTACATGCTCAGCTG
AGCTTAGTGATCAGCTGGGACTACAGGTGCCCGCCGCCACGCCCGGCTAATTTTTGTATT

32879 TTGTAAAGTGCTGATATTCTAATTCTGATCTCTTTTCTACATCTTACTTGGAACAATTTT
ATGAAGAGACATATCCTTGCCTCTATATTTTTTGGTTGCCCAGGGTTACAGCTTTTCATA
TACAAAAAGCATAATAAATACTTGATTCTTTTGCTTTTTTGGGGCCAGTTTTCAAGATAA
TGGTTTGGTTCCTTTTCATCTTCCCAAGAGACCAATTTTATATGTTTCTATCTGTTGCAA
TTAGCATTTTTATTGAGTTCAAATTGTTCCTTCTCTGGCCACTAGATGCTTCTACACATT
[A,G]
CCTCCTGAGTACTTTTGCTGTGACCTCAGTTGTGTCTGATAGCTTCCTTGCTACCTGGTA
TGATAACATCTGGTGTGACAAGATAGTACATGCTCAGCTGAGCTTAGTGATCAGCTGGGA
CTACAGGTGCCCGCCGCCACGCCCGGCTAATTTTTGTATTTTTAGTAGAGACGGGGTTTC
ACCCTGTTAGCCAGGATCATCTTGATCTCCTGATCTCGTGATCTGCCCGCCTCAGCTTCC
CAAAGTGCTGGGATTACAGGCGTGAGCCACCGTGCCTGGCTTGTTTATTTTATATCAGTG

38304 ATTTCTTCTTAAATTTTAAAAACATTTCATATATATATATATATGTATTTTTTTGAGGCA
GAGCCTCACTTTGTCTCCCAGGCTGGAGTGCAGTGGTGTGATCTCGGCTCATTGCAACCT
CTGCCTCCTGGGTTCAAGTGATTCTCCTGCGTCAGCCTCTCAAGTAGCTGCGAGTACAGG
CATGTGCCATCATGCCTGGCTAATATCTTCTATTTTCAATTAGTTTAAATTGGAAAGCTT
TTAAATCTTTGAAGGCATTCTATTTCACTTATAATTTCTTTTAAGATTCTCTTGTATTTA
[T,C]
TAACTCTTGTCTTCCTTCTAGTTTAGTTTATTTTTGTAATGATTTTTCCTTCCATTTCTA
AATTCCTGAGCTCTATCACCTTATTTCTAATATGATTTATGTATCATTTTCTCAGTGTCT
TTTAGCTTGTTTTAAAATAGTAAGTTACAATTTTAATGTTTTGTGGGCATGTCTTTTTTT
CTCTATAGGAATGTTCTTCTTCTTCTCTGTTTTCTTTTAACAACTCTTTATGGTATTTGA
CCAAATACTTTTTTGTCACTCATTTTTACTGAAAAACAGTTTTCTCAAGCTTTTGGGAGG

39702 GGATTTTGAGCAATGGAGTGACATGACCTGACTGGTGTTTTAAAGGCTCTGTCTGGTGAT
AGACTGAGAATAGACCATAGAAATGTAGAGGAAGAAGTAGGGGGACCTATTAGAAGAATG
TTGCAGAAATAGGCTGGGTGGATCACTTGAGGTCAGGAGTTTGAGACCAGCCTGGCCAAC
ATGGCGAAACCCTGTCTCTACTAAAAATACAAAAATTAGCTGGGTGTGGTAGTGGGTGCC
TGTAATCCCAGCTACTCAGGAGGCTGAGGCTGGAGAATTGCTTGAGCCCATGAGGTGGAC

FIGURE 3RR

[G,T]
TTGCAGTGTGCTGAGATTGTGCCACTGCACTCCAGCCTGGGCAACAAGAATGTGACTCCA
TCTCAAAAAAAAAAAAAAAAAAAAAAAAAAAAATTGCAGAAATCCAGGTGAGAGATGTTT
GCTTGGACTTGGGGAGCAGCAGTGGAGTTAATGAGAAGTGGCCAGATTTGCATATATTTT
GAGGTATAGTTGATAAGATTTCCTGATGGATTTGATGTGAAGTATGAGAGAATGTAGTTG
AAAAATAACTCTGGTTTTGTCCTGAGCAACTGTAAGAATGGAGTTGCTTTTAACTGAGAT

39887 GAAACCCTGTCTCTACTAAAAATACAAAAATTAGCTGGGTGTGGTAGTGGGTGCCTGTAA
TCCCAGCTACTCAGGAGGCTGAGGCTGGAGAATTGCTTGAGCCCATGAGGTGGACGTTGC
AGTGTGCTGAGATTGTGCCACTGCACTCCAGCCTGGGCAACAAGAATGTGACTCCATCTC
AAAAAAAAAAAAAAAAAAAAAAAAAAAAATTGCAGAAATCCAGGTGAGAGATGTTTGCTT
GGACTTGGGGAGCAGCAGTGGAGTTAATGAGAAGTGGCCAGATTTGCATATATTTTGAGG
[C,T]
ATAGTTGATAAGATTTCCTGATGGATTTGATGTGAAGTATGAGAGAATGTAGTTGAAAAA
TAACTCTGGTTTTGTCCTGAGCAACTGTAAGAATGGAGTTGCTTTTAACTGAGATTAGAA
GGCTGAGGCTGCCGTGCGGGTAAGGTAGACTTTAGGGGTGACATAAAGAGCTCAGTTTGG
ACTATGTTGAGCTTGAGATAGTTATTAGACTTCTGAGTGAAGATACTCTTCGTGATTCTG
CGAGTCCCATGACAGCATGAGGTAAAAAAAGAAAGACATTGGGCCGGGCGCAGTGGCTCA

40477 GCAGTGGCTCACGCCTGTAATCCCAGCACTTTGGGAGGTCGAGGTGGGCGGATCACGAGG
TCAGGAGATTGAGACCATCCTAGCTAACACGGTGAAACCCCATTTCTACTAAATATACAA
AAAGTAGCTGGGCTTGGTGGCGGGCGCCTGTAGTCCCAGCTACTGGGAGGCTGAGGCAG
GAGAATGGCGTGAACCTGGGAGGCGGAGCTTGCAGGGAGCCGAGATCGCACCACTGCACT
CCAGCCCACTGCACTCCAGCCTGGGTGGCAGAACGAGATTCCGTCTCAAAAAAAAAAAA
[G,A]
TTTATCATAGAAAATTGGAAAATATGGATAAGTTAGGTAAGAAAATAAAAATCATGCTGC
ATTGTAAACATTCTGATATGATTCTAAACATACATATAACATGCATTTAGAACACATCGC
TTTTTTCTTTCCAACTTTTAGGTTCAGGGAGTACATGCACAGGTTTGCTACCGGTAAATT
GTCTGTCACGGGGGTTTGGTGTACAGATTGTTTCATCACCCAGGTAATAAGCATAGTACT
CTATGGGTAGTTTTTCGATCCTCACCTTCCTCCCACCCTCGACCCTTAAGTAGGCCCAAG

44465 TTTTGGAAACTGTGTCTCCGTCTGTTAGTGGTCATTATCCTCAGTCTCTTAGGATCAGAG
TTTTTCTTAGATTACAAAACTGGATCATACAGACCTGACTTCCAGGTCTGCGTTCTCTCC
ACTACACTTTGCTGCCTCTTAGAAAAACATAAGCTAAATAACTAGAACCCATGGAAAGAG
GGAAAAGTGAAGCCCAGAGAGCTGATGCGGGACTAAGAGGCAACTCTGAGAGTTTCAATG
TGGAATGTTTGTGTGGCTCCCCAACCAGACCGTGACCTCCTTGAAGATTGGGACTGCATC
[G,A]
TATCTTGTTCTCATTTTCTATTTTATTTTAATGATCTATCCTTTGGGTTGAACGAATGTG
TTTCTTGAACCCGATAAGTGCAACACTGAGTAAACACTTGTTTCTTTTCTCCCTTCCATC
CTCCCAACTTAGTAGCTTCAATACATTCTTAGCTCTCCTCACTTGCTATTCTCTAACCAT
ACCACGTGGCTGGGCACGGTGGCTCATGCCTGTAGTCCCAGCACTTTGGGAAGCCGAGGT
GGGCAGATCACCTGAGGTCAGGAGTTCAAGACCAGCCTGGCCAATGTGGCAAAACCCCAC

45032 CAAGACCAGCCTGGCCAATGTGGCAAAACCCCACTAAAAATACAAAAATTAACTGGGTAT
GGTGGTGGCCTGTAATCCCCAGCTACTCAGGAGGCTGAGGCAGGAGAATCGCTTGAACCC
AGGAGGCAGAGGTTATAGTGTGCTGAGATTGCGTCACTGCACTCCAGCCTGGGTGACAGA
GCAAGAGTCCGTCTCAAAAAACAAAAACAAAAAAAACCCCAGGTTATCTCCATGAATGTG
AATATTGATGTGGTCCTTCTGTCAGGAAGACATCACCTGAGACCACACACAGAAAGCCTA
[T,A]
TTTTCCTTAGGATACAGTCCTACATCAGGGTTGACAAAGTTTTTTTGTAAGGGTTAGATA
GTAAATATTTTAGATTTTGCAAGCCATATGGTCTCTTCCTCAGCTACTCAACTCTGCCGT
TGTACTACAAGAGCAGCCATAGACAATCTATACATGAATGAGTGTGGCTGTGTTCCAGTA
AACTTTACTTATGGATATTGATACTCAGATTTCACATGATTTTCATGTGTAATGAAATGT
GATTATTTTTATTTAAAACATTAAAAATGTAAAAGCCATTTTTTGCTTGCAGGCCAGACA

45757 ATATTGTCTCTAACCTCTGTCATTTCATTTATGATGCTATGTATTATGTGTACCTTTGTC
TCTCTTGCTGGATTCTGAGTATCTTGAGAGGTAGGCCATGGCCTAGTCAGTCATCTTTGT
ATCCTTAATATCAAACCCACATAGTGGGTATTTAAGAAGTGACTGTTGAATTTGAATTTT
ATGCTTGATATATATAAAATGTCATTTCTGCTGATCTTAAAGAGAAACACTTGACTGATA
TGCATAGGTTTCCCATGTTCTTCCCCTTGAGAGGCCATAGTTAACTGCATTTGCTGCTAG
[T,C]

FIGURE 3SS

GGCTCTTGTAAACTCAGTGGTTATACAGCAAAGCCTTTGCAAAGTCTTTTATTTTAGAGC
TCTTTTTCAGACAAGAAATGATTATACTTTTTCTTCAAATCATTTATTCAATCATAATGA
TAAATATGGCTTTCACTATTCTGATGAAGCAGAGCTACCATCAGTGTGAAATAATAATAG
CCGTTGTTTAGTGAGCATCTACTACATTCCAGTCAATTCAGATTTTTTCTCTAGATTTTT
GGTGACCTTCTGATTACTATTAATTTACATTTTTTTTTATTGTTCTCTACATGTCAAACA

46030 GCCATAGTTAACTGCATTTGCTGCTAGCGGCTCTTGTAAACTCAGTGGTTATACAGCAAA
GCCTTTGCAAAGTCTTTTATTTTAGAGCTCTTTTTCAGACAAGAAATGATTATACTTTTT
CTTCAAATCATTTATTCAATCATAATGATAAATATGGCTTTCACTATTCTGATGAAGCAG
AGCTACCATCAGTGTGAAATAATAATAGCCGTTGTTTAGTGAGCATCTACTACATTCCAG
TCAATTCAGATTTTTTCTCTAGATTTTTGGTGACCTTCTGATTACTATTAATTTACATTT
[-,T]
TTTTTATTGTTCTCTACATGTCAAACAAAACAAAGCAACAATATCAAAAACCCACATGCT
TTTTCTTCATACTGTCTATATTATTGAATGACAGACAAACATCTGTCCTTCAAGTCAAAT
ATTAATTAATCATAGACTCCTTTCTCTTCTTCTTCACCCCGCCTTATCTAATTGGCCACT
GTCTTAGCTTTTTTTTTTTTTTTTTTTTTAAAGATGGAGTCTTACCCTGTTGCCTAGTCT
GGAGTGCAGTGGTGTGATCTCGGTTCACCGCAACCTCCATCTCCTGGGTTCAAGCAATTC

46179 AAATATGGCTTTCACTATTCTGATGAAGCAGAGCTACCATCAGTGTGAAATAATAATAGC
CGTTGTTTAGTGAGCATCTACTACATTCCAGTCAATTCAGATTTTTTCTCTAGATTTTTG
GTGACCTTCTGATTACTATTAATTTACATTTTTTTTTATTGTTCTCTACATGTCAAACAA
AACAAAGCAACAATATCAAAAACCCACATGCTTTTTCTTCATACTGTCTATATTATTGAA
TGACAGACAAACATCTGTCCTTCAAGTCAAATATTAATTAATCATAGACTCCTTTCTCTT
[C,T]
TTCTTCACCCCGCCTTATCTAATTGGCCACTGTCTTAGCTTTTTTTTTTTTTTTTTTTTT
AAAGATGGAGTCTTACCCTGTTGCCTAGTCTGGAGTGCAGTGGTGTGATCTCGGTTCACC
GCAACCTCCATCTCCTGGGTTCAAGCAATTCTCCTGCCTCAGCCTCCCAAGTAGCTGGGA
TTACAGACATGCACCACCACACCTGGCTAATTTTTGTATTTTTAGTAGAGATGGGATTTC
GCCATGTTGGCCAGGATGGTCTCGAACTCCTGACCTCAAATAATCCACCCACTTTGGTCT

46652 AGCTGGGATTACAGACATGCACCACCACACCTGGCTAATTTTTGTATTTTTAGTAGAGAT
GGGATTTCGCCATGTTGGCCAGGATGGTCTCGAACTCCTGACCTCAAATAATCCACCCAC
TTTGGTCTCCCAGTGTCTTAGCAGTTTTAAAAATTATCTTTGGAATTTGTCTCATCTCTA
TTTCTAATTCATTTAATCTAATTGAAGCCTTAATCATTTCTTTTCTTCCAACATGTTGAG
CATCTGTTCTGATTTTCCTGACCCCACTTGCCTCATTCTCCAATTATTCTTCCCATAGTT
[A,G]
TCAGCACTGAATGCTAATAATAATACTTTGTTCATATCAGTTGTTATTAAAACTCTTCAC
TTATTCCTTATTATCTTCAAGGTAAGCCCAGCTTCCCAGTCATGACATACAAGACTCTAT
GTGTGACCCCAATACTTAACACAGATGTGTTTCAGAATTCAGAATTTTTTGGATTTTAGA
AAAGTAATACGGTTTATGCAATACATATATAACATCCTCTGCTCATTCCTGAACACTGAT
GGGAGTGAATGGCAGGTGCTTTTAATAATTACGCTGAGGTAAATTATGCTAGGTGTAAAC

46843 TTTAATCTAATTGAAGCCTTAATCATTTCTTTTCTTCCAACATGTTGAGCATCTGTTCTG
ATTTTCCTGACCCCACTTGCCTCATTCTCCAATTATTCTTCCCATAGTTATCAGCACTGA
ATGCTAATAATAATACTTTGTTCATATCAGTTGTTATTAAAACTCTTCACTTATTCCTTA
TTATCTTCAAGGTAAGCCCAGCTTCCCAGTCATGACATACAAGACTCTATGTGTGACCCC
AATACTTAACACAGATGTGTTTCAGAATTCAGAATTTTTTGGATTTTAGAAAAGTAATAC
[G,A]
GTTTATGCAATACATATATAACATCCTCTGCTCATTCCTGAACACTGATGGGAGTGAATG
GCAGGTGCTTTTAATAATTACGCTGAGGTAAATTATGCTAGGTGTAAACTGGACCTGTCC
TGGGCAAACGAGGATGTTCTTTACACAGTTTAAGAATGTCAAGCAAAGAACATTAGGGAT
GAAGCAATACAGGGAGAATAGATAGAGTGAAGGGAGCAGTGGGTTAAGTGGAGTCCTGGA
GAAATATTTGAAAAGGGAGAAAGGAATGTGGCTCCTGAGGTAGGAGGGAAACCTGGAGCA

56450 TTCCCCTTTTCAATTCATTATTAGCAGCTATATGGGAAGAGCTGCCTTCTTGTAAACCAT
CACATATGAGGGCAAATTAAAAAAAACAATAATCGCTATCCTCTTTACACTTTTTATATA
TATATAAATATTTCCATTATAAAAATATAAGCTCATTATATGAAACTTACAAAATTCAAA
GGATAAGAGAATAAAAATCACCTGTAATGTTCCCACCTAGACACATACACATATTATTCT
TTTTTATTTTCTTATTTATTTACACATATTATTCTTAATATTTTGATGTATTTTCTCTCC
[T,A]
CTGCATTATGTTAAACAAAGGTAAGATTACGTATATCATCTTACCTTTATATACACAGTT

FIGURE 3TT

TTGTATCCAGTCCTTTTAATATTCACGAGCATTTTCCCATTGTGTGCATGCTTTTTAAAC
ATAATTTTTATAGTTATAAACCTTCATAGAAGCCACCTTAAATTCTTTCTGAAGCACAGT
AGTAAATGAATGAATAAATCAACAAACAAAATACATTTCCCTGGTAGATGTTCTACAATT
GATTTTACCATTTTGTTGTTTACCGTTTTCTCTTTGACAAATTGTGCTGCAGTGAACATC

56906
CCTTAAATTCTTTCTGAAGCACAGTAGTAAATGAATGAATAAATCAACAAACAAAATACA
TTTCCCTGGTAGATGTTCTACAATTGATTTTACCATTTTGTTGTTTACCGTTTTCTCTTT
GACAAATTGTGCTGCAGTGAACATCTTTGCAGATACTCAATTTTAGGATTTTTTTTTTAA
GGTAGGATCAATAAAAATAGAACTAAACCAGGGTAAAGTATCTGAGATTTTTAAAAGGTG
TTTGATATCTATTGATACTAAAAAACCTTTGGGCTGGCCACAGTGGCTCACGCCTGTAAT
[G,C]
CCAGCATTTTGGGAGGCTGAGGTGGGTGGATCACTTGAGCTCAGGAGTTCAAGACCAGCC
TGGACAACGTGGCAAAACCCCATCTCTACAAAAAATACAAAAGTTAGCCAGGTGTGGTGG
CACATGCCTCTGGTTTCAGCTGCTTGGGAGGCTGAGGTGAGAGGATTGCTTGAGCCCAGA
ATTTTGAGGTTACAGTGAGCTGAGATTGTGCCACTGCACTCCAGCCTGGGTGATGGAGCG
AGATCCTGTCTCAAGAAAACAAAAACAAAAAACAAACAAACAAAAAACCTTTGAACTGCC

56974
GTAGATGTTCTACAATTGATTTTACCATTTTGTTGTTTACCGTTTTCTCTTTGACAAATT
GTGCTGCAGTGAACATCTTTGCAGATACTCAATTTTAGGATTTTTTTTTTAAGGTAGGAT
CAATAAAAATAGAACTAAACCAGGGTAAAGTATCTGAGATTTTTAAAAGGTGTTTGATAT
CTATTGATACTAAAAAACCTTTGGGCTGGCCACAGTGGCTCACGCCTGTAATGCCAGCAT
TTTGGGAGGCTGAGGTGGGTGGATCACTTGAGCTCAGGAGTTCAAGACCAGCCTGGACAA
[C,T]
GTGGCAAAACCCCATCTCTACAAAAAATACAAAAGTTAGCCAGGTGTGGTGGCACATGCC
TCTGGTTTCAGCTGCTTGGGAGGCTGAGGTGAGAGGATTGCTTGAGCCCAGAATTTTGAG
GTTACAGTGAGCTGAGATTGTGCCACTGCACTCCAGCCTGGGTGATGGAGCGAGATCCTG
TCTCAAGAAAACAAAAACAAAAAACAAACAAACAAAAAACCTTTGAACTGCCAGCATAAT
TGAGGTAATTTATTTTAGATTTTTGTTGGTTTTAATAGATTTCATTGATTAATGTAATTG

57923
AGCTCTTTGTAATTGGTAATTCATAGCTATCTCCTTTGCACAATAGTGAAAGGGTTTTTT
ATTACCAAGATACATGTACAATGCTATTTTGAGGGTTCTTAGGCAGTAGACATTATAGTT
TTCCTACATGCAAATTGGCTTGGCTAGATTATCCTTTGCTTTCTTGAGTGGTGGGTTGGG
AAGAATGCTATGGTTTGAATCCATGTGACTAAAGAATCTATTTCATACACACTTGTGGTT
TTTGAAAGGATTTCAAAATACCCACTGAAATAAAAAAACACCCACCCTTTCCCCCCCCCC
[-,C]
CCCCGTCTCTGCCTATCTTTAAAGTGACAGATAATTTTGAGGAAGAAAAGATGAAGTGTG
AACTATAGTGGTGTTTTTGGGCCTTTTGTGGTAATGCATACAAACTGACAGTCTTGTCTT
GTGAGGGTAGGTTTCATAAGACCTTTTTGCAAACTAAATCCTGTGTATCTTCAAAGCTTT
TTTGCCTGTAATAAGTCAGATGCTAATGTATCCAGCACTGATGATCATGAGGTTTTTGTA
AAGCAGTGCTTGAAAAGAGATTGTTGACCGTTAGCTATGATATGAGATGGGCCCCAGAGA

60974
AGCTACTTGGGAGGCTGAGGCAGGAGAATGGCATGAACCTGGGAGGTGGAGCTTGCAGTG
AGCTGTGATCACTCCACTGCACTCCAGCCTGGGCAACAGAGCGAGACACCGTCTCAAAAA
AAAAAAAAATCCAGATAGTAAATATATTATGCTTTGTGGGCCACAGTTGGGCTCTTTGTT
CTTTACTTGAAGATCCAGATTTTCATCTGGCATCATTTCTCTTTAGCCTGATGCACTTCC
TTTAGCAGTTCTTATAGTAAAGACATGTTGACTACTAATGCTCTTAGGTTTTTTTTTTTT
[-,T]
TTTTAATTTGAAAATGTGTTTGTTTTTTTTTTAATTTGAGAATATTTTGCTGGACATAGA
GTTCTAGGCTATTGGTCGTTTTGTATTTTTTTTAACTTTCAACATTAAAAAGATACTATT
TTATTGGCTTCCCATGTTTTTGATGAAAGTCAGCTGACATTCTTATGAATGTAATTTTTT
TTCTTTGACTGCTATAAGATTTTTCCCTATTTTTGGTTTTCAGCAGTTTGATTATAATAT
ACCAAATTCGTAGCTCCGTTCTACTGCCATCTCCTGTGTGGGCCTCAGTTTTGATTAGTT

61352
GTTTTGTATTTTTTTTAACTTTCAACATTAAAAAGATACTATTTTATTGGCTTCCCATGT
TTTTGATGAAAGTCAGCTGACATTCTTATGAATGTAATTTTTTTTCTTTGACTGCTATAA
GATTTTTCCCTATTTTTGGTTTTCAGCAGTTTGATTATAATATACCAAATTCGTAGCTCC
GTTCTACTGCCATCTCCTGTGTGGGCCTCAGTTTTGATTAGTTTTTATTAGCCTACCTTT
GAATTCATTGATCCCTTCTTTTTCTGTGTCCAGTCTGCTGTTAAACCCATCTGGTGACTT
[C,A]
TTCATTTCAGATCATTTATTTTTCAGTTCTAGAATTTCCCTTTCTCTGCTGGAATTCTTT
GCTCTTTACCCATTCTGTTGATCTTTTCCTCTAAATTATTTAACATATTCATAATAACTT

FIGURE 3UU

TTAAAGTCTTCATCCACGGATCTCTCCCTGTTGACTTTGTTTCTTTATTATGGGTTATAG
GCACACCTTGGAGAGACTGTGGGTTTGGTTCCAGACCACCAAAATAAAGTGAATATCCCA
ATAAAGCAAGTCACACATAATTTGGTTTCCCAGTACATATAAAAGTTATACACTACATTG

61353 TTTTGTATTTTTTTTAACTTTCAACATTAAAAAGATACTATTTTATTGGCTTCCCATGTT
TTTGATGAAAGTCAGCTGACATTCTTATGAATGTAATTTTTTTTCTTTGACTGCTATAAG
ATTTTTCCCTATTTTTGGTTTTCAGCAGTTTGATTATAATATACCAAATTCGTAGCTCCG
TTCTACTGCCATCTCCTGTGTGGGCCTCAGTTTTGATTAGTTTTTATTAGCCTACCTTTG
AATTCATTGATCCCTTCTTTTTCTGTGTCCAGTCTGCTGTTAAACCCATCTGGTGACTTC
[T,A]
TCATTTCAGATCATTTATTTTTCAGTTCTAGAATTTCCCTTTCTCTGCTGGAATTCTTTG
CTCTTTACCCATTCTGTTGATCTTTTCCTCTAAATTATTTAACATATTCATAATAACTTT
TAAAGTCTTCATCCACGGATCTCTCCCTGTTGACTTTGTTTCTTTATTATGGGTTATAGG
CACACCTTGGAGAGACTGTGGGTTTGGTTCCAGACCACCAAAATAAAGTGAATATCCCAA
TAAAGCAAGTCACACATAATTTGGTTTCCCAGTACATATAAAAGTTATACACTACATTGT

61679 TTCTAGAATTTCCCTTTCTCTGCTGGAATTCTTTGCTCTTTACCCATTCTGTTGATCTTT
TCCTCTAAATTATTTAACATATTCATAATAACTTTTAAAGTCTTCATCCACGGATCTCTC
CCTGTTGACTTTGTTTCTTTATTATGGGTTATAGGCACACCTTGGAGAGACTGTGGGTTT
GGTTCCAGACCACCAAAATAAAGTGAATATCCCAATAAAGCAAGTCACACATAATTTGGT
TTCCCAGTACATATAAAAGTTATACACTACATTGTAGTCTGTTCAGTCTGTAGTAGCATT
[G,A]
TGTCAAAAGAAAACACAATGCATATGCCTTAATTTAAAATACTTTATTGCTAAAAAAAAA
ATGCTAGCAATCATCCAAGCCTTCAGCAAGTCATAATCATTTTGCTGGTGGAGACTCTTA
CCTCCATGTTGATGACTGCTAGACCATTCAGGGTGGTGGTTGCTAAAGATTGGGGTGACT
ATAGCAATTTGTTTTGTTATGTAATATTCTATATCCTTTGCTGTCTTTTCAACAATATTC
ACAGCATCTTCACCAGGAGTAGATTCCATCTCAAGAACCACTTTCTCTGCTCATTCTTAA

64709 TGCTTTTTCATGGCTTTACAGAAAAGTATGAAGTTTAGTTTATCTGGTGTTTTCTTGTTT
TGATGAGAGCAGTGGTCTTTTGGGATCAGCTGCATTCAAACCAGGTTGGAACGCTTTAGA
ATGATGGCATTAAGATTCTTTGCCTTCTGCTTTCAACCTTCCTTTTCAACCTCATCTCTT
TTTATTCTTTTAACCACACCACAGTGCCTCCCTTTCATTCCCACAGCACATTGTATACCT
CCATACCTTTGTTCCTTCTGCCTTGATTGTCCTTCTTCTCATCTTACAACTTTGTCCTTT
[A,G]
AAACTCAACTCACATGACACCTCTTCTGTGCCACAGATCCTCCTGCTACAATGTACCTAC
CTTTACTTGTGTACTTTCACATTATATTGTGATGATTTATATTATATGCTGCTGCTTTTA
AACTAAGGACATGCCAGACATGCCTTCATCTGAAAATGTTAATATAGTTCAAAGTGTTGC
TATAGTCTTTGTTTAGTTAAAGTAACAACTTTCTGGTCTGAAAAAAAAAAGACTATGCAT
CCCTTCAACAGAATAAGATAGTTTTAAAAGTAATGATATGGGAGCATCTCTTAAGATATG

65783 TACTTGACAATTACTTGATGCTCAATAAAATGATTCTTATTAGCAAAATAAACCTTACAC
GTAGAAAAAGAATATGCCAGGAACCAAGAAAAGGGATATTCAGATATGAGGCTCTTGGAG
TTACGGCTCAGCTCACAAGGATTCTGCCGTAGGTGAGAAATGCTCCATTACCCAGAGGCA
AAGCCCCAGAGGTTGTGGCAGCACTTTATGACTATGTATCAGTCTGGGCTCAGTCAGGGA
AACATTGAGCCACTGTTAAGTGTTATAGGAGTGAGGGGTTTAATATAGTAATTAAGGCCT
[A,G]
TGCAAATATGGGAGGACTAGAGAAGTGAAGGTCTGCACGTTTTTTATTGTATACTGGACA
CGTTGTTTACAATAGGAGTAGGGAATGAGCTGGATACAGCTACAGTTGGAAGACCAGAGG
AATAGGCACTGATGACTGAAACCTGCAGCTCTAGAGAGGGCAGAGAAGTGCTAGGAAACT
GCCTCTCGCTGCCAAAGTAGGACTCAGTGTGGGATCCCAAGGAAAGGTCTGTGAAGACTG
CCACGGGGATAAAGTGGAGCTTTAGGAGAGGCCAGTGGAGCGACTGCATCTGACTGCCCT

66506 TGGTGGTGGTGCCAGTTGACCATCCAGCATAGGCCATTCCTTTGCCAGCCTGGCTTACAT
ACACACCTACTTAAACCATATTTAACTGCCAGATAAAGCTAAATGCTCTGCTTAACATGT
TGTAACTATCGCTTAGCAAACTGAAAACATGCTAAGCACTCCCTCAAAGAGGAGATGCTG
TATTTCATATTGTGCTTTGTACATTTCTGGCTGATATGAATGTATTCCACTAGCTGAGTC
ACATCCCCTCTTTGATATCCTAAAACTTACATATACTGAGATACAGAGTTAGCCATTTCC
[T,-]
TTTTTTTTTTTTCTTGGCAAGGTCTTGTTCTGTCACCCAGGCTGCAGTGCAGTGGCGCCA
TCATAGCTCACTGCATCCAGAATCTCCTGGGCCCAAGCGATCCGCCTGCCTTAGCTTCTT
GACTATAGGTGTGCACCACCACACCTAGCTAAATTTTTTTTATTTTTAACTTTTTGTAGA

FIGURE 3VV

GACAAGAGGTATCACTGTGTTGCCCAGGCTGCTCTTGAACTCCTGGCCTCAAGCAATCCT
GTTGCCTTAGCCTCTCAACGTGTTAGGATTATAGGCATGAACCACCGTGCCCAGCCAGAG

66589 AACTGCCAGATAAAGCTAAATGCTCTGCTTAACATGTTGTAACTATCGCTTAGCAAACTG
AAAACATGCTAAGCACTCCCTCAAAGAGGAGATGCTGTATTTCATATTGTGCTTTGTACA
TTTCTGGCTGATATGAATGTATTCCACTAGCTGAGTCACATCCCCTCTTTGATATCCTAA
AACTTACATATACTGAGATACAGAGTTAGCCATTTCCTTTTTTTTTTTTTTCTTGGCAAGG
TCTTGTTCTGTCACCCAGGCTGCAGTGCAGTGGCGCCATCATAGCTCACTGCATCCAGAA
[T,C]
CTCCTGGGCCCAAGCGATCCGCCTGCCTTAGCTTCTTGACTATAGGTGTGCACCACCACA
CCTAGCTAAATTTTTTTTATTTTTAACTTTTTGTAGAGACAAGAGGTATCACTGTGTTGC
CCAGGCTGCTCTTGAACTCCTGGCCTCAAGCAATCCTGTTGCCTTAGCCTCTCAACGTGT
TAGGATTATAGGCATGAACCACCGTGCCCAGCCAGAGTCAATACACCTTATATTAGAGAG
TATTATTAGACAGGGAAAAGTGGAAAAAAGAATTCGTTAATATATTCAGTATATATTCAT

67336 TGTTCTTTGCCTGGTGGGGTGGCCTAAACCTTCATTCTGGGGTGTATGTACCAATAAATG
GCCATATTGTTTTGCTCTAATATCCCGTTAACTTTCCATAATAAACAAGTGTAATAGAAA
ATCCTAGGTTCCAGGCAATTTCTTTCCTTCTTCCATTGAGTATTTTTTTCCCATTGTGTA
TTTTAAACTTGGTTCTTCCTTGATAATCGGGATCAATCAGCCTAGCTATTATAGTACCTG
CCTTACTTGTCTTTGGCTAAGTGGCATGAGGAGCAAGAAGTGCTGAGTTAACAGTCTCAG
[C,T]
TCTCTGTTCAGTGGAAATAATGTTGTGTCTCCCCCAAAGAAGCACTTCTCCCTTGAGGAT
TAAGACCTGTAAACTGGGAGAGCCCACAGCTGCTGCGAGTTTTCTTTTGGGGAAGGATTT
TGATAATATTTAGTGAATATAGGGCTATTTCGATTTTCTTGTTCTTGTATCAATTTTGAT
AAATTGTATTTTTTAAAGTAATTTGGCCATTTCACTTAAGTTGTCAAATTTGTTGGCAGG
AAGCTGCAGTATTTTCTTAGAGTCCTTCTAATCTTTGTCAAATTGATAGTGATAACTTTT

68176 TGGGTTCCTTTATAATACTCTTGTGAATGCATTTACTTTTGTTTTAGCAGGCAATCAACT
CAGGTAGGCTGGATTATACATTGTTTTGCCTTTTGCAGGCAGTGATTCAAATCCCAATTC
AGTTATCAAAGCAAAGCCTTTGCTAAACTGGTTTGGGTTTGTCCTGTGCATGTGTGATTC
AGAGGTTAAGGTGAGACCCGTGTAGGTGCATACATAAAAGTGGAGAGCTCCTTCACCTGC
TGTTTCTGCTCCAGGAGTTTGCTCTGACTCCCTGTCTTTCTTTGGCTCCTTTCCCTGCTT
[G,C]
CTCTGACCAGAAAGAAAACAATTCCTATCAGAGTTTTAGCCACCTACGTGTGCTGCTTAG
TGACTGAAGCTGTCCCACCCTCAAGGAAAAACTTGATGAGAAAAAAATAAACAAACAGAA
AACTCACCCTGTAAGGTCACTTCTCCAACTTTTTACTTCCCTCCACAATCTGCCTGCTTT
TATTTACTTTCCAGATCCTCATATAGTTTTTTGTTTTGTTTTGTTTTGCTGTGTTTTGAG
ATGGAGTTTCACTCTTGGTGCCCAGGCTGGAGTGCAGTGGCACAATCTTGTCTCACTGAA

69456 TGCCATTATGGTGAATAAGATATTTTGTAAGGGAAAGGATGCTGGTTTTTGACAGAAATG
TTGTGGGCAGAGAAGGAAATCTTCATTGAGTAAAAGCAGTGTCCTTTTTAGATGGAAGCG
GTCCAGTGTGATCATCCTGCTACAGATGGCTGCCCAGACCCCCTGGGAGCAGCGCTTTAT
TGGGGCACCATTGTTGGCCTCTCCTGTTGGCAGGTTGGACACTTAGCCATGATTGTTGCC
AGGTCAGCCTTGACAGGTGGAAGCCTGTGTCACTGAGCACATGCATGACCTTCATTCCTG
[T,C]
TGCTCTCACAGTAGGATATGAACTTTGTTCATTAGCGTTCTGAGCAAGGGAAACAGTGGC
TGATAAAATAATGAGTCATTTTGTCCACTTGGTTATTGAGAGCCTCCTCTGCTGAGATTA
TACATTGGTCATCATTTACATGGGACACAAATACCCTCACACTTTGTCCTGTTTGAGAAT
AGTTTATTGACATAGCTCTTTTCTATATCTTACCACAAGTTTCCCAACCTTATTCTAAGT
TTCTGAATTTCCAGTCAAACCATCTGCTGCTGACCACAAATCAGTGTGGATTCGTATTTA

70557 GTGCTTATAAAGTATAGCCATGTGCCCATTGTTTCTGTCATGAAGCGTCACCAGTTGGCT
GCTGTGACTCAGAGATCTTTTCATCCTTCCCTTGGGTTCAGGGAATCTATTTCTCTGACA
GCCTTTCCCATTGTTATTTCTAGCCTGCAGCGAACAAGCACTAAAGAGCTTTTTAGGGAT
GTTGTTGCCCCCTTCACCAATGTATTTCTCAAAGGCTTGGTAAAGGAGTGAGTTCTCTAG
ACATTCCTGGGATGTAGTTAGGAGATCAGTGAACAGATCAGTCATACGTATTAAATACAC
[C,T]
CCAGTATTCCTTATTTTCTAACCTTTTGAATAAATTTTATTTTGAGACTGAGTTTTGCTC
CTGTTGCCCAAGCTGGAGTGCAATGGCACTGTCTCAGCTCATTGCAACCTCTGCCTTCCG
GGTTCAAGCACTTCTCCTGCTCAGTCTCCTCAGTAGCTGGGATTACAGGTGCCCGACACC
ATGCCCAGCTAATTTTTGTATTTTTAGTAGAGACAGGGTTTCACCATGTTGGTCAGGCTG

FIGURE 3WW

GTCTTGGAACTCCTGACCTCAGGTGATCCACCCACCTTGGCCTCCCAAAGTGCTGGGATT

72833 AGACAGGGTCTCGCTCTGTTGCCCAGAGTGCTCTGGAATGCAGTGGCACGATCATAGCTT
ACTGCAGCCTTGACTTCTTGGGCTCAGGTGATCCTCCCACCTTGGCCTCCCAAAGTTCTG
GGATTATAGGCATATAGGCATGAGCCACTTTGTCTGGCCTAAATTTTAGTTAAAGAAATT
CTTATCTCATTCTTTCAGAATTTTCATAGGCCTTCAAAGCAACAACCATGGAGTTAAATT
CATTTCCTCAACTTGGCAGGATTTTTTTTTTCCCCTATTGAAGTATTTTGTCTTTTTTTT
[G,T]
TGTGTGTGTGACAGGGTTTCACTCTTCGCTCTGTTGCCCAGGCTGGAGTGCAGTGGCATG
ATGATAGCTCACTGTAGCCTTAAACTCCCCTGGGCTCAAGCCATCCTCCCACCTCAGCTC
CCTGAGTAGCTGAGACCATAGGCATGCACCACTATGCCCAACTAATTATTGTATTTTTTG
TAGAGACAAGATGTCACCATATTACCCAGGCTGGCCTCAAACTCCTGAGCTCAAGTGATT
CACCTGGCCCGGCCTCCCAAAGTGCTGGGATTACAGGAGTGAGCCACTGTGCCCAGCCAT

75250 CAAAAAATTAGCTGGGTGTGGTGGCATGTGCCTATAATCCCAGCTACTCGGGAGGCTGAG
GCAGGAGAATCATTTGAACTCGGGAGGCGGAGGTTGCAGTGAGCCAAGATCATGCCATAA
CTCTCCAGCTTGGGTGACAGGGCGAGACTTGATCTCAAAAAAAATAAAATAATAAAATAA
AATAAACAAATTATGCTGGCTACAAAATTTTCTTTTGCAAATACTAAATGTTGGAAAATG
ATGGAGCAGTGGGCAGTGATCCTTAGCTTATGTGGTCTTTGAACTCCCTGCAGTAATATT
[T,G]
GGACCTCTATGTCTTGATGCAAGTTGATTTTCCTGGGAATAGAATCTATATCGTTCCTCA
TATTTTCCAGGATTTCATGAAACAAAGAGTTAAGAACTACAGTAGTGGAGCAATATTCAT
GGTGCTTTTTCTTTTTCTTTTGAAATAATTAAAAACTTACAGAAAGGCTGTAAGAATAAT
ACAGAGAAATCCTGTGTATTCTTTCCCAAATTCATGTGTTTGTCTTCTCTCTCTTTCTCT
CTCCTTATAAAATATTTCAATGTTGTTAGTTATCTCAAAATGGACTTTGTAGTTTTTTTT

76502 TCAAAAATAAATAAATTAATTAAAAATAAAAACGATCAATGTGGAAAAAACTTGAAGACT
GTGCAAATAGCCATATGTTGCTTAACGATGGGAATACATTGTGAAAAATGTGTTATTAGG
TGATTCTGTCATTGTGCAAACACCATAGGGTGTACTTACATAAATTTAGATGGTATAGCC
TGCTACATAGCTAGGCTATATGGTTTAGCCTATTGTTCTTAGGCTACAAAACTGTACAGC
TTGTTACTGTACTGAATATTGTAGGCAGTTGTAACACTATGATAAGTATTATATAAACAT
[G,A]
TCTAAACATAGGAAGATACAGTAAAAATACAGAATTATAATCTTATGGGACCACTGTCAT
AAGTGTGGTTTATTACTGACCAAAATGTCATTATGTGGCACATGGCTGTATCTTGCTTTT
CATCAGGCTTTACACTCTAGATGAGCATCCATTGATTATTCTTACCCACACCAATGGTAC
AGTTATGATAGTTGGAAAATGCTGCTTTTTTCCAACTCCACTACTCCCTCCATTTCATGG
TATTCTAATGAATGATCATTGTCACAAAATTCAACACCTAATTGTATCTGTTATGATAAT

78350 TGTGAATCTTACTGTGTGTGTGTTCCTGAGAAGGATGTGTATTCACTAATTAATGGGTGC
TGGGTTTTATTGGTAGGCCAGAAGTCAAACTTGACAGTTATGTAGCCCTTAATTCATGCT
AATGTTTTGTATCATTGGTCTGTAAATAACTGAAAGAGCTGTGTTGAAATCTTCCACTTT
GTGGATAGATTTGTTCATTTCTCTCTAAAGTTGTCAAATTTTGCTTTATTTTGAGGCTAT
TTTTTGAGAGCTTACAAATTTAGATTCATTAGCATTTTCTAGCAAATTGAACATTTTATT
[A,G]
TAACATACGGACTATCACTAAAAATGCTTTTTGTCTTACAGAGTAGAATTGCTAAATAAA
ATACAGGATGCTCAATTAAATTTGAATTTCAGATAAATGTTGAGTACTTTTTTAGTATAA
GTATGTTCTACATATTGCAAAAAATTATTCATTTTTCACAGGAACAGAAAACCAGATACCA
CGTGTTCTCACTTATAAGGGGGCACTAAATGATGAGAACACATGGACACATGGCGGAGAA
CAAGACACTGGGGTGTACTGGAGGGTGGAGGGTGGAGGAGGGAGAGGATCAGGAAACATA

78359 TACTGTGTGTGTGTTCCTGAGAAGGATGTGTATTCACTAATTAATGGGTGCTGGGTTTTA
TTGGTAGGCCAGAAGTCAAACTTGACAGTTATGTAGCCCTTAATTCATGCTAATGTTTTG
TATCATTGGTCTGTAAATAACTGAAAGAGCTGTGTTGAAATCTTCCACTTTGTGGATAGA
TTTGTTCATTTCTCTCTAAAGTTGTCAAATTTTGCTTTATTTTGAGGCTATTTTTTGAGA
GCTTACAAATTTAGATTCATTAGCATTTTCTAGCAAATTGAACATTTTATTGTAACATAC
[G,A]
GACTATCACTAAAAATGCTTTTTGTCTTACAGAGTAGAATTGCTAAATAAAATACAGGAT
GCTCAATTAAATTTGAATTTCAGATAAATGTTGAGTACTTTTTTAGTATAAGTATGTTCT
ACATATTGCAAAAAATTATTCATTTTTCACAGGAACAGAAAACCAGATACCACGTGTTCTC
ACTTATAAGGGGGCACTAAATGATGAGAACACATGGACACATGGCGGAGAACAAGACACT
GGGGTGTACTGGAGGGTGGAGGGTGGAGGAGGGAGAGGATCAGGAAACATAACTAATGGG

FIGURE 3XX

79720 TCAAATGCTTTTTATTTTTCCCACTTGTTTTGTGCTTTTGTGGACTGTTTTCTTTTTGCA
TGATTTTAAAAAAATTCCATGTTCTCTTACTATTATTTTAGACATTACACATATTTATTA
TTTTGTTAACCTTTAAATATTACTGTCAGGCCAGGCACGGTGGCTCATGCCTGTAATCCC
ATCACTTTGGGAGGCCAAAGCGGGTGGATCACCTGAGGTCAGGTGTTCCAGACCAGCCTG
GCCAACATGGCGAAACCCCGTCTCTACTAAAAATATAAAAATTAGCCAGGCGGGGTGGCA
[G,A]
GCGCCTATAATCACAGCTACTGAGAAGGCTGAGTCAGGAGAATCGCTTGAACCTGGAGGC
AGAGGTTACAGCGAGCCGAGATCATGCCATTGTACTCGAGCCTCGGCGACAGAGCAAGAC
TCTTTCTCAAAAATAAATAAATAAATAAATATATATTACTGTTCAAACTCTACTTGATAA
AGTTATTTAATATTTTTAAATCCCCACACAAACATCCTAACTCTGATAACTACCCTTTTA
ATGCTTATGCTATTACTGATGAATATTTAAGTTCTTTTTTTAACACTATATGTTAGACAT

81763 AGTGAAAGTCCATTGATCCTGTTTCGTAATTGGATGAAGAGTGTCCAAACTATTGCCAGT
AGCTTTCTGTTTTCCCATCATTTTTCAACCCAGAAATATTTATTTTTCTTTCCAGGGAGG
CATTAGCAGTACCCTGGAAGCTCCCCTCCTACCCCTCCAAATTATTCCCTCCTCCTCTTT
ACTTTTCTCCAAAGATAATCTCTGTCCTGAATCAAAAATCGTCCCCGCTTCCTGGTAGCA
CCCGATCTGGAAGAAACCCAAAATCACCTAACCAAAACCTGAATCATATAATAGTCTTTT
[C,T]
TAATACTCTTTTACTGAGACATTCCACAATTCCCAATTATATGTGTTATTCCTTGCTGAA
ATGAATAATGAACCCAACATGTGCAACTACAGCTATGTTCCTGGTAACCTTTGGCTGGGA
GGATTGACAATATTCATTTGTGTCTGGTTTCTTTCTTTCTTTTTTTCTTTTTCTTTTTTT
TTTTTTTTTTTTGAGACGGAGTCTTGCTCTGTCCCCCAGGCTGGAGTGCAGTGGCACAA
TCTCGGCTCACTGCAAGCTCCACCTCCCGGGTTCACTCCATTCTCCTGCCTCAGCCTCCC

87250 ATTTGGATGGGGACACAAAGCCTAACCATATCACTACCATTTTTCTTTTCTTTTTTTTTC
ATGCCTGGATTTTTTCGTTGTTCCCTCATGAACATTTTAAAGTGTAATTAAGCAAAAGAG
AATACTATACAATGGTTTTTAACAATTTTTTAAGTTTCCCCCCTCCCCCCAAGACAGGG
TTTCCCAATGTTGCCTAGGCTGGTCTCGAACTCCTGGCCTCAAGTGATTCTCCCACCTCA
CCCTC
[C,T]
TAAGTAGCTGGGACTACAGACATGTGCCACTGTGCCCAGCTGCCTATACAGTGTTTTTAT
TTTATTTTATTTTTTTAAGATGGAGTCTTGCTTTATCACCCAGGCTGGAGTGCAGTGGCA
TTATCTTGGCTTACCGCAACCTCTGCCTCCCGGATTCAAATGATTCTCCTGCCTAAGCCT
CCCAAGTAGCTGGGATTACAGGCACCCGCCTCCATGCCTGGCTAATTTTTGTATTTTTAG
TAGAGACAGGGTTTCACCATGTTGGCCAGGCTGGTCTCGAACTCCTGAGCTCGTGATCTG

87345 TTTTCTTTTCTTTTTTTTTCATGCCTGGATTTTTTCGTTGTTCCCTCATGAACATTTTAA
AGTGTAATTAAGCAAAAGAGAATACTATACAATGGTTTTTAACAATTTTTTAAGTTTCC
CCCCTCCCCCCAAGACAGGGTTTCCCAATGTTGCCTAGGCTGGTCTCGAACTCCTGGCCT
CAAGTGATTCTCCCACCTCACCCTCCTAAGTAGCTGGGACTACAGACATGTGCCACTGTG
CCCAGCTGCCTATACAGTGTTTTTATTTTATTTTATTTTTTTAAGATGGAGTCTTGCTTT
[A,G]
TCACCCAGGCTGGAGTGCAGTGGCATTATCTTGGCTTACCGCAACCTCTGCCTCCCGGAT
TCAAATGATTCTCCTGCCTAAGCCTCCCAAGTAGCTGGGATTACAGGCACCCGCCTCCAT
GCCTGGCTAATTTTTGTATTTTTAGTAGAGACAGGGTTTCACCATGTTGGCCAGGCTGGT
CTCGAACTCCTGAGCTCGTGATCTGCCCGCCTTGGCCTCCCAAATTGCTGGGGTTACAGG
CGTGAGCCACCATGCCTGGCCTTTAATTTTTTTAAAAAGTAAAACTTCTTTAATTTTCTT

87393 TGAACATTTTAAAGTGTAATTAAGCAAAAGAGAATACTATACAATGGTTTTTAACAATTT
TTTTAAGTTTCCCCCCTCCCCCCAAGACAGGGTTTCCCAATGTTGCCTAGGCTGGTCTCG
AACTCCTGGCCTCAAGTGATTCTCCCACCTCACCCTCCTAAGTAGCTGGGACTACAGACA
TGTGCCACTGTGCCCAGCTGCCTATACAGTGTTTTTATTTTATTTTATTTTTTTAAGATG
GAGTCTTGCTTTATCACCCAGGCTGGAGTGCAGTGGCATTATCTTGGCTTACCGCAACCT
[C,G]
TGCCTCCCGGATTCAAATGATTCTCCTGCCTAAGCCTCCCAAGTAGCTGGGATTACAGGC
ACCCGCCTCCATGCCTGGCTAATTTTTGTATTTTTAGTAGAGACAGGGTTTCACCATGTT
GGCCAGGCTGGTCTCGAACTCCTGAGCTCGTGATCTGCCCGCCTTGGCCTCCCAAATTGC
TGGGGTTACAGGCGTGAGCCACCATGCCTGGCCTTTAATTTTTTTAAAAAGTAAAACTTC
TTTAATTTTCTTCTCGCAAGAATTGAATAGAATGATAGAATGAATGCCAGTATTTTATAA

FIGURE 3YY

90448 TGGCCTTTGTTACAGAATAGGTTGCTAACCTCTGAGTTTCTCAGTTTTAGCCCATTCACA
AATGAAATAGTTTTTTTTTGTTGTTTTTTTTGAGACAGCCTCACTCTGTCGCCCAGGCTG
GAGTGCAGTGGCATGATCTTGGCTCACTGCAACCTCTGCCTCTTGGGTTCAAGCAATTCT
CTTGCCTAAACCTCCTGAGAAGTTGGGACTATAGGCACATGCCACAACGCCTGGCTAATT
TTTGTATTTTTAGTAGAGACCAGGTTTCGCCATGTTGACCAGGCTGGTCTTGAACTCCTG
[G,A]
CATCAAGTGATCTGCCTGTCTTGGCCTCCCAAAGTGCTGGGATCCCAGCCTCTCTCTCTC
TCTTTCTCACTCTCTCTCTCTCCCGCTCTCTCTCTCTCTCTCTCTCTCTCTCTCTCTCTA
TATATATATATATTTTTTTTTTTTTTTTTTTTTTTTTGAGACAGGGTCTCATTCTGTCACC
CAGGCTGGAGTGCAGTGGCATAATCACAGCTCACTGCAGCCTCAACCCCACGGGCTCAAG
CAATTCTCCTGCCTCAGCCTCCCAAGTAGCTGGGATTACAGGTGCGCACAACCACGCCCA

91485 CTCGACAACTGATTATGTTAAAATTTGAAGACGTGTATGAGGTTTTTGTTTGTGAGGGCT
ATATGACTGGCGTTTCTCCAGTATATGACACTTTGTTCATCCCTATGTTCCTCTTTATAA
ACTGCAGAAATTCTAAATATAATGCATTAGTTGTCTATTGCTTGCAAGTAGTAGACTGAA
TGATGGCTCCATAAAGATGTCCACTTCCATTAGATAAAGAAAATGTGTACATATACACCA
TGAAATATTGCACAGCCATAACAAAGAGCGAAATCATGTTCTTTGCAGCAGTTTGGATGG
[C,A]
GCTTGAGGCCATTATCCTAAGTGAATTAATGCAGAAACAGAAAACCAAGTACCTCATGTT
CTCACTTGTAAGTGAGAGGTAAACACTGGGTACAAATGGACATAAAGATGGGGACAGTAG
ACACTGGGAATACAAGAGGGCAGAAGAGGGAAGGAAAAATAAGGGTTGAAAAACTACCTA
TTGGGTACTGTGCTCACTACCTGGGTGACAGGTTCAATCATATCCCAAACTTCAGCATCA
CACACTATACCCCTGTAACAAACCTGCACATGTACCCCCTGAATCTAAATAAAAGTTGGA

94099 AACCATCCCCTCTGCTGGTCCATGGAAAGATTGTTTTTCACAAAACCGGCCCCAAAGTTG
GGGACTACTGCTATAGAGAATTGGATCTGCGGTCTACAAGTAATGTTAATGACATTTATT
TTAAGTTGCACTGAGACTTTTGTTTACATCTTTTTTTTTTTTTTGAGATGAGAGTCTCGT
TTGTGTTGCTCAGGCTGGAGTGCAAGGCACAATCTCAGCTCACTGCAACGTCCGTCTCCT
GAGTTCAAGCGATTCTCCTGCCTCAGCCTCCCGAGTAGCTGGGATTACAGGTGCCCGCCA
[T,C]
CAAGCCCAGCTAATTTTTTGTATTTTTAATAGAGATGGGGTTTCACCATACTGGTTGGCC
AGGCTGGTCTTGAACTCCTGACCTCAGGTGATCCACCCGCCTCGGCCTCCCAAAGTGCTA
GGATTACAGGCATGAGCCAACATGCCTGGCCTGTTTACATCTTAATTATGAATTGTTACT
ATAGTCAGCCCTTTGTATCTGTGGTTTCCACATCCATAGATTCAACTAACCATGGACTGA
AAATATGTGGGGGGGAAATGATGCTTACATCTGTACTGAACGTGACGGACTTTGTCATTA

95236 TTGTAATGGTGTCTGTTGACAGCCAAAGCCTCTTGTATGGAAACATACCACCACTGCCAC
AAGTAAAAGCTATAAAGCAGTGTTAAATACTGTATATAGAGCTCACATTTGTATATGCAT
TTCTTTTAGGTCTTATGTAGTGTGTGTACTGTGGAAGATCGAGAAAGTGCGTTAGGTTGT
TAGACAAAAGACCCAGAAGGCCTGCTAGAGATGCCACAGGTGGAACTAAGAAAGCAATCT
CTGTGTCACTCAGGCTTTGAGAAACTTCCTTCAGAATCATAAAACATTAGAACTGGGAAG
[G,A]
TTAAAAAATCTTTAGTCTTTTTTTCCCAGCTCCAGTCTCTTGTGAATAATTAACAGTAAA
GTTAAAGATTATGGGAATTACGTGCCTCCTTTTTTCCCTTGCACAACATAGAATTTGTTT
TCTAATAGTAGTTTATTTGTTAGCTTTGCATTCCCATAAGTGATGGTTTCCAGCCTTGGC
AAACCCTTGCAGCCTCCAGCCACAAGTCCCCTGGACCTCAGAGAATGTATATACTGTATG
TGCACCCTAATAACATGTTTCCTTAAAACTAGTACTACTGGATCCTCTAACTTTAGTACA

95493 TGAGAAACTTCCTTCAGAATCATAAAACATTAGAACTGGGAAGGTTAAAAAATCTTTAGT
CTTTTTTTCCCAGCTCCAGTCTCTTGTGAATAATTAACAGTAAAGTTAAAGATTATGGGA
ATTACGTGCCTCCTTTTTTCCCTTGCACAACATAGAATTTGTTTTCTAATAGTAGTTTAT
TTGTTAGCTTTGCATTCCCATAAGTGATGGTTTCCAGCCTTGGCAAACCCTTGCAGCCTC
CAGCCACAAGTCCCCTGGACCTCAGAGAATGTATATACTGTATGTGCACCCTAATAACAT
[G,A]
TTTCCTTAAAACTAGTACTACTGGATCCTCTAACTTTAGTACATGTCTTTCATGTCCAAC
TTTTCAGAGGCCGCCAAACTAGCAACCCTAAACTCATTTGTCACTATCAAAACATAATAT
ACGAATATGGAAAGCTAATATAAAAATGGTAAGGGACTGAGCCATTTGGAAGGTAACTTA
ATGTAAGTGCCTGAAAAACAGGGATACAAAAAAGCAAAGGGACAAGAAGCAAGCCAGTTC
ACCCTGAACCCTACAAATGTTTGGGAATTAGAAACATCAAGTATTACAAATTAGGGGAAA

96594 AAAGAGCGAGACTCCTCTCAAAAAAAAAAAAAAAAAGTATTCAAAGACAAGAATATCAACC

FIGURE 3ZZ

TGAGTTCACCAGAACTTGGGGAAGAAGTGGAGAAACCTCCTGGGCCAACAAAATTTTTTG
TAAAATAAGTGGTCATTTCAGACTGTGCCACCCCTTCCCCCCAAGCTGGCATAACACCAC
TCAGGGAGAATTTTCCTAGCCCTGCAGTTTCCAAGGTGAGAGGAAGGAATTGGAGGTGTG
TATTCAGTCTCCTCACTGGTCTGGGAATCTTCCCAGGGAGCCCACTCCCGTCCCATCAGG
[A,G]
AGAGCCAGGAGAGCTGAACTATCTGGGGTAAAGTGGGGACAAAGAGCAGGGCACTGATTG
TAGCAACTAGTATATGGATCTTGCAGCTACTCTGTACTCTAATTAGCCGAGACACCCTAT
TGACAAGGATGGCCAGTGTCTTAGTGCCACTGGGGTGTAATCAGTGGGAAGGCCTGAATC
CCTGGTCGGATTTTCCACAAAACTTAGTGCTCACATGGAACCTTCCCGTGGCCCAGAAAC
AGCTATAAGATTGGGATTAAGCTGGGCATGGCAGCTCATTTCTGTAATCCCATTTTGGGA

96887 CATCAGGGAGAGCCAGGAGAGCTGAACTATCTGGGGTAAAGTGGGGACAAAGAGCAGGGC
ACTGATTGTAGCAACTAGTATATGGATCTTGCAGCTACTCTGTACTCTAATTAGCCGAGA
CACCCTATTGACAAGGATGGCCAGTGTCTTAGTGCCACTGGGGTGTAATCAGTGGGAAGG
CCTGAATCCCTGGTCGGATTTTCCACAAAACTTAGTGCTCACATGGAACCTTCCCGTGGC
CCAGAAACAGCTATAAGATTGGGATTAAGCTGGGCATGGCAGCTCATTTCTGTAATCCCA
[T,C]
TTTGGGAGGCCAAGTTGGGTGGATAATTTGAGCCCAGGAGTTCAAGACCAGCCTGGGCAA
CATAGCAAAATCCCACTTCTACCACAAAAACAAAAGTTAGCTGCATGTGGTGGTACGTGC
CTGTAATCCCAGCTACTTCAGAGGCTGAAGCAAAGAGTCGCTTGAGCCTGGGAGACAGAG
GTTACAGTGAGCCAAGATCGCACCACTGAACGCCAGCCTGGGCAACAGAGCAAAACTGTG
TCTCAAAAAAAAAAAAAAGTTGGGATTAACTTCCAGTGTACACTTAAGCACTTAAGACTT

97803 ACCTGCAAAACCTAGAAGAAATGGCTGTGTCCTCAAATGTGCAAGCATCAACATAAACAA
GCAATGATTATGAAAACTTAGGGAAATATGACACCACCAAAAGAAACCAACAAAGCTCCA
CCAGTGGACTCAGAAGAATTGAAGATCTATGAAATGTCAGACAGAGAATTCAGAATAAGC
CTCTTTAAAAAGTTCAGTGAATCTGCCAGGCATGGTGGCTTACGCCTGTAATCCCAGCAC
TTTGGGAGGCCGAGGTGGGCAGATCACGAGGTCAGGGGATCGAGACCATCCTGGCTAACA
[C,T]
GGTGAAACCCCATTTCTACTAAAAATACAAAAAATAAGCAGGGCCTGGTGGTGGGCACCT
GTAGTCCCAGCTACTCGGGAGGCTGAGGCAGGAGAATGGTGTGAACCCAGGAGGCGGAGC
TTGCAGTGAGCTGAGATTGTGCCACTGCACTCCAGCCTGGGAGACAGAGCAAGACTCCGC
CTCAAAAAAAAAAAAAATGTTCAGGGAATCACAAGAAAATAGAGATAGAAAATTAAATGA
AATTTAGAAAGCAATCCATGTATGTAGTGAGAAATTTGACAAAGAAATAGAAACAAGAAA

101109 AAGACCCAAATAAGCAAAACCAGAGGTGAAAAATGGGACATTGTAAGTGATACCACCGAT
ATACAAAAAGATCATTAGAGACTACTATGAACAACTATACACCAAAAAATTGCAAAGCCT
AGAAGGAATGTGTAAATTCTCTGACACATACAACCTACCAAGATTGAATCAGGAAGAAAC
AAAAGACCTCAACAAACCAATAATGAGTAATGAGATTGAAGCCATATAAAAAAAGTCTCT
CAACCAAGAAAAGCCCAGGACCTGTTGCTTCACTGCTAAATTCTGCCAGACATTTAAAGA
[G,A]
CTAATACCAATCCTACTCAAACTCCTCAAAACAAAAATTTTTTTGGAAGAGAAGGGATTA
CTTCCCAACTCATTCTACAAGGGCAACATTACCCTGATACCAAAACCAGACAGGATGCAA
CAAGAAAATGACAGGCCAACATCCCTGATGAACACAGATGCAAAAATCCTCAACAAAATA
CTAACAAACCAAGTGCAACAATACATTAAAAAGATCATCCTGGGATACGAAGAGGGGAAG
AACAGACTTACTTGAGGGTGGGGGGTTGGAGGAAGGAGAGGATCAGAAAAAATACCTATT

101298 CAACAAACCAATAATGAGTAATGAGATTGAAGCCATATAAAAAAAGTCTCTCAACCAAGA
AAAGCCCAGGACCTGTTGCTTCACTGCTAAATTCTGCCAGACATTTAAAGAGCTAATACC
AATCCTACTCAAACTCCTCAAAACAAAAATTTTTTTGGAAGAGAAGGGATTACTTCCCAA
CTCATTCTACAAGGGCAACATTACCCTGATACCAAAACCAGACAGGATGCAACAAGAAAA
TGACAGGCCAACATCCCTGATGAACACAGATGCAAAAATCCTCAACAAAATACTAACAAA
[C,T]
CAAGTGCAACAATACATTAAAAAGATCATCCTGGGATACGAAGAGGGGAAGAACAGACTT
ACTTGAGGGTGGGGGGTTGGAGGAAGGAGAGGATCAGAAAAAATACCTATTCGGTACTAT
GCTTATTACCTGAGTGATGAAATAATCTGTACACCAAGCCTCTGTGACACACAGTTTACC
CACATAACAAACCAGCACATGTACCCCTCAACCTAAAAAAAAAAAAAAAAAAAAATCATCA
TGATAAAGTGGAAATCCGAGGGATGCAAGGATGATTCAGCATACCCAAATCAATAAACAT

104790 GCAGGGACAACATCAAGCCATTCATGAGGGATCTGGCCCCATGACCCAAACACTTCCCAC
TAGGCCCCACCTTCAACACTGGGAATCACATTTCAGCATGAGTTGGAGGGGAAAAATACC

FIGURE 3AAA

CAAAGTGTATCAGAAGGGAAACACCCAACTGCAGCCCTCTCTAGCCTTCCTGTCTTACCT
AATTGGGGAGAAGGGAACCTGAGAAGCACTTGTGAAAGTCACGGCCCAGGCACACAGGCT
CACTAAAAGACTGAGAACTAATTATGTGATTATAAGACACTCCCCCCACCACACACACCT
[C,T]
ACCACCACACCAATCAGTCTCCTGTGTAATGATAGTGGATTACTGCTAAATGAACTAATT
TTCAGACCCTATTCTATTTTAATAAGGAGTCTTTAGGGAAACGAAGAAATGATAGATACA
AAAACAAGGATGTGATTGTAACAACGTGGGTACAGCTGGAGGCCATTATCCTAAGTGAAT
TAATGCTGAAACAAAAAACCAAAAACTACATGTTCCGAACTCATAAGTGGGAGCTAGACA
TTGGGTATTCATGGACATAAAGATGGGAACAGTAGACACTGGGTACTGCAAGAGACAGGA

105798 CAGACTGGAAATTTTAAATAAGTATGATTAATATACTAAAGGCTCTAATGGAAAAAGTGA
ACAACATGCAAGAAAGGTGGGTAACATAAGCAGACAATAGAAACTCTAAGAAAGAACCCA
AAAGAAATACTAGAAATAAGCAATACTATAACAGAAATGAAGAATGCCCTTGGACTTATT
GATAGAGTGGAAAGGACAATAGATAACCTGGGAAAGATTCAATGAGCTTGAAGATATGTC
AGTAGAAAGTTCCAAAACTTAAACTGCAAAGAGAAAAAAGAATAAATGACAGAACATGGC
[G,A]
GGGCCTGGTGGCTCACACTGTATCTCCACACTTCAGGAGGCCCAGGTGGGAAGATCACTT
GAGACCAAGAGTTGAGGGCCAGCCTAGGCAACAGAGAGAGATCTGTTGACTCCACAAAAA
ATAAAAAGGAAAAGAATAGGATATCCAAAAACTGTGGGACAGTTACAAAATTATATATAT
TTAAGTCCTTGCTTTGGCTGAACCTAACACTAAAATTGGAACAATACCAAGAAGATTGCA
CAACATGGCCCTGTGCAAGGATGATATGTAAGGTCATGAAGCATAGAAAAAACATTTCTA

110536 GGTTTGTAGAAACATTTGGCTTCTGAATACCTAGCTCATTGCTGTCAAGCAGAATCCTCC
ATCTTTTAGTGCCTGAAAATATTCAGATGTCCAGAAACATTAACCAAAGGAAATTCCATT
TCTAGCTCTGCTGTTTGTATAGGCAATGTAGTGGGTCAGTTTTCTGCACTGTGTAGAAAT
TGCTTTGTCAGTGGAAAATGTTATTTTCGTCGGTTTTACAGTTCCTAACTTTTGAGGCAT
TTGTTCCCTGGAGGATACTAAAAGAAGGAAATCTTCAGACAGCTGCCCACTGAATTTTTG
[C,T]
GTGAGCCTTTATTTGATATTTTACCCAGACCCCTTTTGGTTTTTTATTACAGTAACATCG
CATACCTAGGTTTTTTTTTTCTTCTTCATATAAGCCTTACCTATCTGGAACTGTCAGTAC
TAGGAAGGTACTTATAGTGTTGAATGTTCCCACTCATATTTCCTGTTATGCCTTATGCTT
TTTATAACAAGCCAAAAAGAGGAAGAAAGATTTCACCATAGATTTGCTAAAGGCAATGTG
GGATGCAATGAGTGTGGTTTAATGGAAGAGCCCTGGGGTGCGGCCTCTGAGCCTTGCTCT

FIGURE 3BBB

114916 CCCCTTTGACTTTTCTCATTTGGAGCCCAGATGACTTATATATACACATAGTCACTGGCC
CCTGGGAAGGACAGTGAGAGTTTGAAGGATTAAAGCCAGCATGGTGGCTCATGCCTGTAA
TCCCAGCAATTTGTGAGACCGAGGTTGGCAGATCACTTGAAGTCGGGAGTTCAAGACCAG
CATGGCCAACATGGTGAAACCTCATCTCTACTGAAAATATAAAAATTAGCCGAGTATTGC
AGAATTTGCCTGTAATCCCAGCTACTTGGGAGGCTGAGGGAGAATCACATGAACCGGGAG
[G,T]
TGGAGGTTGCTGAGCCAAGATTACACCACTGCACTACAGCCTGTGTGACAGAACAAGACT
GCCTCAAAAAAAGAAAAAATTAGCTAGGCATGGTGGCGAGGCCTCTGGTCCCAGCTACTT
GGGAGGCTGAGGCAGGAGGATCGCTTGAGCCCATGAGGTGGAGGTTGCCATGAGTTTAGA
TTGTGCCACTGCACTCCAGCCTGGGTGACAGAGTGAGACCCTGTCTCAAAAATAAAAAAA
ATTAAGCAGATTCAGAGTTTTCCCTGTAACGTCTTCTCTCACTGACTTGCATTCCAATCC

FIGURE 3CCC

ISOLATED NUCLEIC ACID MOLECULES ENCODING TRANSFERASE ENZYMES

FIELD OF THE INVENTION

The present invention is in the field of enzyme proteins that are related to the transferase enzyme subfamily, recombinant DNA molecules, and protein production. The present invention specifically provides novel peptides and proteins that effect protein phosphorylation and nucleic acid molecules encoding such peptide and protein molecules, all of which are useful in the development of human therapeutics and diagnostic compositions and methods.

BACKGROUND OF THE INVENTION

Many human enzymes serve as targets for the action of pharmaceutically active compounds. Several classes of human enzymes that serve as such targets include helicase, steroid esterase and sulfatase, convertase, synthase, dehydrogenase, monoxygenase, transferase, kinase, glutanase, decarboxylase, isomerase and reductase. It is therefore important in developing new pharmaceutical compounds to identify target enzyme proteins that can be put into high-throughput screening formats. The present invention advances the state of the art by providing novel human drug target enzymes related to the transferase subfamily.

Transferases

The novel human protein, and encoding gene, provided by the present invention is related to transferases in general, specifically sulfotransferases and tyrosylprotein sulfotransferases in particular. Furthermore, the protein of the present invention may be an alternative splice form of tyrosylprotein sulfotransferase 1 (Genbank gi4507665); see the amino acid sequence alignment provided in FIG. 2. The C-terminal sequence is not covered by the genomic sequence, suggesting an additional coding exon.

Tyrosylprotein sulfotransferases are important for catalyzing tyrosine O-sulfation, which is a widespread posttranslational modification that occurs in all multicellular organisms and tissues. The tyrosine O-sulfation reaction involves transferring sulfate from 3'-phosphoadenosine 5'-phosphosulfate to tyrosine residues within acidic motifs of polypeptides (Ouyang et al, *Proc Natl Acad Sci U S A Mar.* 17, 1998;95(6):2896–901). Tyrosine O-sulfation is important in protein-protein interactions in a wide variety of physiological systems, particularly those systems involved in inflammation and hemostasis (Ouyang et al., *Proc Natl Acad Sci U S A Mar.* 17, 1998;95(6):2896–901). Sulfation of tyrosine residues in P-selectin glycoprotein ligand 1 (PSGL-1), a leukocyte adhesion molecule, is required for binding of PSGL-1 to P-selectin on activated endothelium (Ouyang et al., *Proc Natl Acad Sci U S A Mar.* 17, 1998;95(6):2896–901). Tyrosylprotein sulfotransferases are integral membrane glycoproteins that are located in the trans-Golgi network with the catalytic site oriented towards the trans-Golgi network lumen. This position allows tyrosylprotein sulfotransferases to catalyze the tyrosine O-sulfation reaction on proteins that pass through the trans-Golgi network, such as plasma membrane and secretory proteins. Tyrosine O-sulfation facilitates protein-protein interactions between such proteins as secretory proteins, cell surface receptors, and plasma membrane proteins. For a further review of tyrosylprotein sulfotransferases, see Beisswanger et al., *Proc. Nat. Acad. Sci.* 95: 11134–11139, 1998.

Due to their importance in regulating protein-protein interactions, particularly in inflammation, hemostasis, and other important physiological processes, novel human tyrosylprotein sulfotransferase proteins/genes, such as provided by the present invention, are valuable as potential targets for the development of therapeutics to treat inflammatory, hemological, and other disorders. Furthermore, SNPs in tyrosylprotein sulfotransferase genes, such as provided by the present invention, are valuable markers for the diagnosis, prognosis, prevention, and/or treatment of such disorders.

Using the information provided by the present invention, reagents such as probes/primers for detecting the SNPs or the expression of the protein/gene provided herein may be readily developed and, if desired, incorporated into kit formats such as nucleic acid arrays, primer extension reactions coupled with mass spec detection (for SNP detection), or TaqMan PCR assays (Applied Biosystems, Foster City, Calif.).

Enzyme proteins, particularly members of the transferase enzyme subfamily, are a major target for drug action and development. Accordingly, it is valuable to the field of pharmaceutical development to identify and characterize previously unknown members of this subfamily of enzyme proteins. The present invention advances the state of the art by providing previously unidentified human enzyme proteins, and the polynucleotides encoding them, that have homology to members of the transferase enzyme subfamily. These novel compositions are useful in the diagnosis, prevention and treatment of biological processes associated with human diseases.

SUMMARY OF THE INVENTION

The present invention is based in part on the identification of amino acid sequences of human enzyme peptides and proteins that are related to the transferase enzyme subfamily, as well as allelic variants and other mammalian orthologs thereof. These unique peptide sequences, and nucleic acid sequences that encode these peptides, can be used as models for the development of human therapeutic targets, aid in the identification of therapeutic proteins, and serve as targets for the development of human therapeutic agents that modulate enzyme activity in cells and tissues that express the enzyme. Experimental data as provided in FIG. 1 indicates expression in humans in the placenta, neuroblastoma cells, liver, brain, T-cells from T-cell leukemia, hippocampus, and fetus.

DESCRIPTION OF THE FIGURE SHEETS

FIGS. 1A through 1B provides the nucleotide sequence of a cDNA molecule that encodes the enzyme protein of the present invention. (SEQ ID NO: 1) In addition, structure and functional information is provided, such as ATG start, stop and tissue distribution, where available, that allows one to readily determine specific uses of inventions based on this molecular sequence. Experimental data as provided in FIG. 1 indicates expression in humans in the placenta, neuroblastoma cells, liver, brain, T-cells from T-cell leukemia, hippocampus, and fetus.

FIGS. 2A through 2C provides the predicted amino acid sequence of the enzyme of the present invention. (SEQ ID NO:2) In addition structure and functional information such as protein family, function, and modification sites is provided where available, allowing one to readily determine specific uses of inventions based on this molecular sequence.

FIGS. 3A through 3CCC provides genomic sequences that span the gene encoding the enzyme protein of the present invention. (SEQ ID NO:3) In addition structure and functional information, such as intron/exon structure, promoter location, etc., is provided where available, allowing one to readily determine specific uses of inventions based on this molecular sequence. As illustrated in FIG. 3, SNPs were identified at 71 different nucleotide positions.

DETAILED DESCRIPTION OF THE INVENTION

General Description

The present invention is based on the sequencing of the human genome. During the sequencing and assembly of the human genome, analysis of the sequence information revealed previously unidentified fragments of the human genome that encode peptides that share structural and/or sequence homology to protein/peptide/domains identified and characterized within the art as being a enzyme protein or part of a enzyme protein and are related to the transferase enzyme subfamily. Utilizing these sequences, additional genomic sequences were assembled and transcript and/or cDNA sequences were isolated and characterized. Based on this analysis, the present invention provides amino acid sequences of human enzyme peptides and proteins that are related to the transferase enzyme subfamily, nucleic acid sequences in the form of transcript sequences, cDNA sequences and/or genomic sequences that encode these enzyme peptides and proteins, nucleic acid variation (allelic information), tissue distribution of expression, and information about the closest art known protein/peptide/domain that has structural or sequence homology to the enzyme of the present invention.

In addition to being previously unknown, the peptides that are provided in the present invention are selected based on their ability to be used for the development of commercially important products and services. Specifically, the present peptides are selected based on homology and/or structural relatedness to known enzyme proteins of the transferase enzyme subfamily and the expression pattern observed. Experimental data as provided in FIG. 1 indicates expression in humans in the placenta, neuroblastoma cells, liver, brain, T-cells from T-cell leukemia, hippocampus, and fetus. The art has clearly established the commercial importance of members of this family of proteins and proteins that have expression patterns similar to that of the present gene. Some of the more specific features of the peptides of the present invention, and the uses thereof, are described herein, particularly in the Background of the Invention and in the annotation provided in the Figures, and/or are known within the art for each of the known transferase family or subfamily of enzyme proteins.

Specific Embodiments

Peptide Molecules

The present invention provides nucleic acid sequences that encode protein molecules that have been identified as being members of the enzyme family of proteins and are related to the transferase enzyme subfamily (protein sequences are provided in FIG. 2, transcript/cDNA sequences are provided in FIG. 1 and genomic sequences are provided in FIG. 3). The peptide sequences provided in FIG. 2, as well as the obvious variants described herein, particularly allelic variants as identified herein and using the information in FIG. 3, will be referred herein as the enzyme peptides of the present invention, enzyme peptides, or peptides/proteins of the present invention.

The present invention provides isolated peptide and protein molecules that consist of, consist essentially of, or comprise the amino acid sequences of the enzyme peptides disclosed in the FIG. 2, (encoded by the nucleic acid molecule shown in FIG. 1, transcript/cDNA or FIG. 3, genomic sequence), as well as all obvious variants of these peptides that are within the art to make and use. Some of these variants are described in detail below.

As used herein, a peptide is said to be "isolated" or "purified" when it is substantially free of cellular material or free of chemical precursors or other chemicals. The peptides of the present invention can be purified to homogeneity or other degrees of purity. The level of purification will be based on the intended use. The critical feature is that the preparation allows for the desired function of the peptide, even if in the presence of considerable amounts of other components (the features of an isolated nucleic acid molecule is discussed below).

In some uses, "substantially free of cellular material" includes preparations of the peptide having less than about 30% (by dry weight) other proteins (i.e., contaminating protein), less than about 20% other proteins, less than about 10% other proteins, or less than about 5% other proteins. When the peptide is recombinantly produced, it can also be substantially free of culture medium, i.e., culture medium represents less than about 20% of the volume of the protein preparation.

The language "substantially free of chemical precursors or other chemicals" includes preparations of the peptide in which it is separated from chemical precursors or other chemicals that are involved in its synthesis. In one embodiment, the language "substantially free of chemical precursors or other chemicals" includes preparations of the enzyme peptide having less than about 30% (by dry weight) chemical precursors or other chemicals, less than about 20% chemical precursors or other chemicals, less than about 10% chemical precursors or other chemicals, or less than about 5% chemical precursors or other chemicals.

The isolated enzyme peptide can be purified from cells that naturally express it, purified from cells that have been altered to express it (recombinant), or synthesized using known protein synthesis methods. Experimental data as provided in FIG. 1 indicates expression in humans in the placenta, neuroblastoma cells, liver, brain, T-cells from T-cell leukemia, hippocampus, and fetus. For example, a nucleic acid molecule encoding the enzyme peptide is cloned into an expression vector, the expression vector introduced into a host cell and the protein expressed in the host cell. The protein can then be isolated from the cells by an appropriate purification scheme using standard protein purification techniques. Many of these techniques are described in detail below.

Accordingly, the present invention provides proteins that consist of the amino acid sequences provided in FIG. 2 (SEQ ID NO:2), for example, proteins encoded by the transcript/cDNA nucleic acid sequences shown in FIG. 1 (SEQ ID NO: 1) and the genomic sequences provided in FIG. 3 (SEQ ID NO:3). The amino acid sequence of such a protein is provided in FIG. 2. A protein consists of an amino acid sequence when the amino acid sequence is the final amino acid sequence of the protein.

The present invention further provides proteins that consist essentially of the amino acid sequences provided in FIG. 2 (SEQ ID NO:2), for example, proteins encoded by the transcript/cDNA nucleic acid sequences shown in FIG. 1 (SEQ ID NO:1) and the genomic sequences provided in FIG. 3 (SEQ ID NO:3). A protein consists essentially of an amino acid sequence when such an amino acid sequence is present with only a few additional amino acid residues, for example from about 1 to about 100 or so additional residues, typically from 1 to about 20 additional residues in the final protein.

The present invention further provides proteins that comprise the amino acid sequences provided in FIG. 2 (SEQ ID NO:2), for example, proteins encoded by the transcript/cDNA nucleic acid sequences shown in FIG. 1 (SEQ ID NO: 1) and the genomic sequences provided in FIG. 3 (SEQ ID NO:3). A protein comprises an amino acid sequence when the amino acid sequence is at least part of the final amino acid sequence of the protein. In such a fashion, the protein can be only the peptide or have additional amino acid molecules, such as amino acid residues (contiguous encoded sequence) that are naturally associated with it or heterologous amino acid residues/peptide sequences. Such a protein can have a few additional amino acid residues or can comprise several hundred or more additional amino acids. The preferred classes of proteins that are comprised of the enzyme peptides of the present invention are the naturally occurring mature proteins. A brief description of how various types of these proteins can be made/isolated is provided below.

The enzyme peptides of the present invention can be attached to heterologous sequences to form chimeric or fusion proteins. Such chimeric and fusion proteins comprise a enzyme peptide operatively linked to a heterologous protein having an amino acid sequence not substantially homologous to the enzyme peptide. "Operatively linked" indicates that the enzyme peptide and the heterologous protein are fused in-frame. The heterologous protein can be fused to the N-terminus or C-terminus of the enzyme peptide.

In some uses, the fission protein does not affect the activity of the enzyme peptide per se. For example, the fusion protein can include, but is not limited to, enzymatic fusion proteins, for example beta-galactosidase fusions, yeast two-hybrid GAL fusions, poly-His fusions, MYC-tagged, HI-tagged and Ig fusions. Such fusion proteins, particularly poly-His fusions, can facilitate the purification of recombinant enzyme peptide. In certain host cells (e.g., mammalian host cells), expression and/or secretion of a protein can be increased by using a heterologous signal sequence.

A chimeric or fusion protein can be produced by standard recombinant DNA techniques. For example, DNA fragments coding for the different protein sequences are ligated together in-frame in accordance with conventional techniques. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and re-amplified to generate a chimeric gene sequence (see Ausubel et al., *Current Protocols in Molecular Biology,* 1992). Moreover, many expression vectors are commercially available that already encode a fusion moiety (e.g., a GST protein). A enzyme peptide-encoding nucleic acid can be cloned into such an expression vector such that the fusion moiety is linked in-frame to the enzyme peptide.

As mentioned above, the present invention also provides and enables obvious variants of the amino acid sequence of the proteins of the present invention, such as naturally occurring mature forms of the peptide, allelic/sequence variants of the peptides, non-naturally occurring recombinantly derived variants of the peptides, and orthologs and paralogs of the peptides. Such variants can readily be generated using art-known techniques in the fields of recombinant nucleic acid technology and protein biochemistry. It is understood, however, that variants exclude any amino acid sequences disclosed prior to the invention.

Such variants can readily be identified/made using molecular techniques and the sequence information disclosed herein. Further, such variants can readily be distinguished from other peptides based on sequence and/or structural homology to the enzyme peptides of the present invention. The degree of homology/identity present will be based primarily on whether the peptide is a functional variant or non-functional variant, the amount of divergence present in the paralog family and the evolutionary distance between the orthologs.

To determine the percent identity of two amino acid sequences or two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, at least 30%, 40%, 50%, 60%, 70%, 80%, or 90% or more of the length of a reference sequence is aligned for comparison purposes. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The comparison of sequences and determination of percent identity and similarity between two sequences can be accomplished using a mathematical algorithm. (*Computational Molecular Biology*, Lesk, A. M., ed., Oxford University Press, New York, 1988*; Biocomputing: Informatics and Genome Projects*, Smith, D. W., ed., Academic Press, New York, 1993*; Computer Analysis of Sequence Data, Part* 1, Griffin, A. M., and Griffin, H. G., eds., Humana Press, New Jersey, 1994*; Sequence Analysis in Molecular Biology*, von Heinje, G., Academic Press, 1987; and *Sequence Analysis Primer*, Gribskov, M. and Devereux, J., eds., M Stockton Press, New York, 1991). In a preferred embodiment, the percent identity between two amino acid sequences is determined using the Needleman and Wunsch (*J. Mol. Biol.* (48):444–453 (1970)) algorithm which has been incorporated into the GAP program in the GCG software package (available at http://www.gcg.com), using either a Blossom 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package (Devereux, J., et al., *Nucleic Acids Res.* 12(1):387 (1984)) (available at http://www.gcg.com), using a NWSgapdna.CMP matrix and a gap weight of 40, 50, 60, 70, or 80 and a length weight of 1, 2, 3, 4, 5, or 6. In another embodiment, the percent identity between two amino acid or nucleotide sequences is determined using the algorithm of E. Myers and W. Miller (CABIOS, 4:11–17 (1989)) which has been incorporated into the ALIGN program (version 2.0), using a PAM120 weight residue table, a gap length penalty of 12 and a gap penalty of 4.

The nucleic acid and protein sequences of the present invention can further be used as a "query sequence" to perform a search against sequence databases to, for example, identify other family members or related sequences. Such searches can be performed using the NBLAST and XBLAST programs (version 2.0) of Altschul, et al. (*J. Mol.*

*Biol.* 215:403–10 (1990)). BLAST nucleotide searches can be performed with the NBLAST program, score=100, wordlength=12 to obtain nucleotide sequences homologous to the nucleic acid molecules of the invention. BLAST protein searches can be performed with the XBLAST program, score=50, wordlength=3 to obtain amino acid sequences homologous to the proteins of the invention. To obtain gapped alignments for comparison purposes, Gapped BLAST can be utilized as described in Altschul et al. (*Nucleic Acids Res.* 25(17):3389–3402 (1997)). When utilizing BLAST and gapped BLAST programs, the default parameters of the respective programs (e.g., XBLAST and NBLAST) can be used.

Full-length pre-processed forms, as well as mature processed forms, of proteins that comprise one of the peptides of the present invention can readily be identified as having complete sequence identity to one of the enzyme peptides of the present invention as well as being encoded by the same genetic locus as the enzyme peptide provided herein. The gene encoding the novel enzyme of the present invention is located on a genome component that has been mapped to human chromosome 7 (as indicated in FIG. 3), which is supported by multiple lines of evidence, such as STS and BAC map data.

Allelic variants of a enzyme peptide can readily be identified as being a human protein having a high degree (significant) of sequence homology/identity to at least a portion of the enzyme peptide as well as being encoded by the same genetic locus as the enzyme peptide provided herein. Genetic locus can readily be determined based on the genomic information provided in FIG. 3, such as the genomic sequence mapped to the reference human. The gene encoding the novel enzyme of the present invention is located on a genome component that has been mapped to human chromosome 7 (as indicated in FIG. 3), which is supported by multiple lines of evidence, such as STS and BAC map data. As used herein, two proteins (or a region of the proteins) have significant homology when the amino acid sequences are typically at least about 70–80%, 80–90%, and more typically at least about 90–95% or more homologous. A significantly homologous amino acid sequence, according to the present invention, will be encoded by a nucleic acid sequence that will hybridize to a enzyme peptide encoding nucleic acid molecule under stringent conditions as more fully described below.

FIG. 3 provides information on SNPs that have been found in the gene encoding the enzyme of the present invention. SNPs were identified at 71 different nucleotide positions. Some of these SNPs that are located outside the ORF and in introns may affect gene transcription.

Paralogs of a enzyme peptide can readily be identified as having some degree of significant sequence homology/identity to at least a portion of the enzyme peptide, as being encoded by a gene from humans, and as having similar activity or function. Two proteins will typically be considered paralogs when the amino acid sequences are typically at least about 60% or greater, and more typically at least about 70% or greater homology through a given region or domain. Such paralogs will be encoded by a nucleic acid sequence that will hybridize to a enzyme peptide encoding nucleic acid molecule under moderate to stringent conditions as more fully described below.

Orthologs of a enzyme peptide can readily be identified as having some degree of significant sequence homology/identity to at least a portion of the enzyme peptide as well as being encoded by a gene from another organism. Preferred orthologs will be isolated from mammals, preferably primates, for the development of human therapeutic targets and agents. Such orthologs will be encoded by a nucleic acid sequence that will hybridize to a enzyme peptide encoding nucleic acid molecule under moderate to stringent conditions, as more fully described below, depending on the degree of relatedness of the two organisms yielding the proteins.

Non-naturally occurring variants of the enzyme peptides of the present invention can readily be generated using recombinant techniques. Such variants include, but are not limited to deletions, additions and substitutions in the amino acid sequence of the enzyme peptide. For example, one class of substitutions are conserved amino acid substitution. Such substitutions are those that substitute a given amino acid in a enzyme peptide by another amino acid of like characteristics. Typically seen as conservative substitutions are the replacements, one for another, among the aliphatic amino acids Ala, Val, Leu, and Ile; interchange of the hydroxyl residues Ser and Thr; exchange of the acidic residues Asp and Glu; substitution between the amide residues Asn and Gln; exchange of the basic residues Lys and Arg; and replacements among the aromatic residues Phe and Tyr. Guidance concerning which amino acid changes are likely to be phenotypically silent are found in Bowie et al., *Science* 247:1306–1310 (1990).

Variant enzyme peptides can be fully functional or can lack function in one or more activities, e.g. ability to bind substrate, ability to phosphorylate substrate, ability to mediate signaling, etc. Fully functional variants typically contain only conservative variation or variation in non-critical residues or in non-critical regions. FIG. 2 provides the result of protein analysis and can be used to identify critical domains/regions. Functional variants can also contain substitution of similar amino acids that result in no change or an insignificant change in function. Alternatively, such substitutions may positively or negatively affect function to some degree.

Non-functional variants typically contain one or more non-conservative amino acid substitutions, deletions, insertions, inversions, or truncation or a substitution, insertion, inversion, or deletion in a critical residue or critical region.

Amino acids that are essential for function can be identified by methods known in the art, such as site-directed mutagenesis or alanine-scanning mutagenesis (Cunningham et al., *Science* 244:1081–1085 (1989)), particularly using the results provided in FIG. 2. The latter procedure introduces single alanine mutations at every residue in the molecule. The resulting mutant molecules are then tested for biological activity such as enzyme activity or in assays such as an in vitro proliferative activity. Sites that are critical for binding partner/substrate binding can also be determined by structural analysis such as crystallization, nuclear magnetic resonance or photoaffinity labeling (Smith et al., *J. Mol. Biol.* 224:899–904 (1992); de Vos et al. *Science* 255:306–312 (1992)).

The present invention further provides fragments of the enzyme peptides, in addition to proteins and peptides that comprise and consist of such fragments, particularly those comprising the residues identified in FIG. 2. The fragments to which the invention pertains, however, are not to be construed as encompassing fragments that may be disclosed publicly prior to the present invention.

As used herein, a fragment comprises at least 8, 10, 12, 14, 16, or more contiguous amino acid residues from a enzyme peptide. Such fragments can be chosen based on the ability to retain one or more of the biological activities of the enzyme peptide or could be chosen for the ability to perform a function, e.g. bind a substrate or act as an immunogen. Particularly important fragments are biologically active fragments, peptides that are, for example, about 8 or more amino acids in length. Such fragments will typically comprise a domain or motif of the enzyme peptide, e.g., active site, a transmembrane domain or a substrate-binding domain. Further, possible fragments include, but are not limited to, domain or motif containing fragments, soluble peptide fragments, and fragments containing immunogenic structures. Predicted domains and functional sites are readily identifiable by computer programs well known and readily available to those of skill in the art (e.g., PROSITE analysis). The results of one such analysis are provided in FIG. 2.

Polypeptides often contain amino acids other than the 20 amino acids commonly referred to as the 20 naturally occurring amino acids. Further, many amino acids, including the terminal amino acids, may be modified by natural processes, such as processing and other post-translational modifications, or by chemical modification techniques well known in the art. Common modifications that occur naturally in enzyme peptides are described in basic texts, detailed monographs, and the research literature, and they are well known to those of skill in the art (some of these features are identified in FIG. 2).

Known modifications include, but are not limited to, acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent crosslinks, formation of cystine, formation of pyroglutamate, formylation, gamma carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination.

Such modifications are well known to those of skill in the art and have been described in great detail in the scientific literature. Several particularly common modifications, glycosylation, lipid attachment, sulfation, gamma-carboxylation of glutamic acid residues, hydroxylation and ADP-ribosylation, for instance, are described in most basic texts, such as *Proteins—Structure and Molecular Properties,* 2nd Ed., T. E. Creighton, W. H. Freeman and Company, New York (1993). Many detailed reviews are available on this subject, such as by Wold, F., *Posttranslational Covalent Modification of proteins*, B. C. Johnson, Ed., Academic Press, New York 1–12 (1983); Seifter et al. (*Meth. Enzymol.* 182: 626–646 (1990)) and Rattan et al (*Ann. N. Y Acad. Sci.* 663:48–62 (1992)).

Accordingly, the enzyme peptides of the present invention also encompass derivatives or analogs in which a substituted amino acid residue is not one encoded by the genetic code, in which a substituent group is included, in which the mature enzyme peptide is fused with another compound, such as a compound to increase the half-life of the enzyme peptide (for example, polyethylene glycol), or in which the additional amino acids are fused to the mature enzyme peptide, such as a leader or secretory sequence or a sequence for purification of the mature enzyme peptide or a pro-protein sequence.

Protein/Peptide Uses

The proteins of the present invention can be used in substantial and specific assays related to the functional information provided in the Figures; to raise antibodies or to elicit another immune response; as a reagent (including the labeled reagent) in assays designed to quantitatively determine levels of the protein (or its binding partner or ligand) in biological fluids; and as markers for tissues in which the corresponding protein is preferentially expressed (either constitutively or at a particular stage of tissue differentiation or development or in a disease state). Where the protein binds or potentially binds to another protein or ligand (such as, for example, in a enzyme-effector protein interaction or enzyme-ligand interaction), the protein can be used to identify the binding partner/ligand so as to develop a system to identify inhibitors of the binding interaction. Any or all of these uses are capable of being developed into reagent grade or kit format for commercialization as commercial products.

Methods for performing the uses listed above are well known to those skilled in the art. References disclosing such methods include "Molecular Cloning: A Laboratory Manual", 2d ed., Cold Spring Harbor Laboratory Press, Sambrook, J., E. F. Fritsch and T. Maniatis eds., 1989, and "Methods in Enzymology: Guide to Molecular Cloning Techniques", Academic Press, Berger, S. L. and A. R. Kimmel eds., 1987.

The potential uses of the peptides of the present invention are based primarily on the source of the protein as well as the class/action of the protein. For example, enzymes isolated from humans and their human/mammalian orthologs serve as targets for identifying agents for use in mammalian therapeutic applications, e.g. a human drug, particularly in modulating a biological or pathological response in a cell or tissue that expresses the enzyme. Experimental data as provided in FIG. 1 indicates that the enzymes of the present invention are expressed in humans in the placenta, neuroblastoma cells, liver, brain, T-cells from T-cell leukemia, and fetus, as indicated by virtual northern blot analysis. In addition, PCR-based tissue screening panels indicate expression in the hippocampus. A large percentage of pharmaceutical agents are being developed that modulate the activity of enzyme proteins, particularly members of the transferase subfamily (see Background of the Invention). The structural and functional information provided in the Background and Figures provide specific and substantial uses for the molecules of the present invention, particularly in combination with the expression information provided in FIG. 1. Experimental data as provided in FIG. 1 indicates expression in humans in the placenta, neuroblastoma cells, liver, brain, T-cells from T-cell leukemia, hippocampus, and fetus. Such uses can readily be determined using the information provided herein, that which is known in the art, and routine experimentation.

The proteins of the present invention (including variants and fragments that may have been disclosed prior to the present invention) are useful for biological assays related to enzymes that are related to members of the transferase subfamily. Such assays involve any of the known enzyme functions or activities or properties useful for diagnosis and treatment of enzyme-related conditions that are specific for the subfamily of enzymes that the one of the present invention belongs to, particularly in cells and tissues that express the enzyme. Experimental data as provided in FIG. 1 indicates that the enzymes of the present invention are expressed in humans in the placenta, neuroblastoma cells, liver, brain, T-cells from T-cell leukemia, and fetus, as indicated by virtual northern blot analysis. In addition, PCR-based tissue screening panels indicate expression in the hippocampus.

The proteins of the present invention are also useful in drug screening assays, in cell-based or cell-free systems.

Cell-based systems can be native, i.e., cells that normally express the enzyme, as a biopsy or expanded in cell culture. Experimental data as provided in FIG. 1 indicates expression in humans in the placenta, neuroblastoma cells, liver, brain, T-cells from T-cell leukemia, hippocampus, and fetus. In an alternate embodiment, cell-based assays involve recombinant host cells expressing the enzyme protein.

The polypeptides can be used to identify compounds that modulate enzyme activity of the protein in its natural state or an altered form that causes a specific disease or pathology associated with the enzyme. Both the enzymes of the present invention and appropriate variants and fragments can be used in high-throughput screens to assay candidate compounds for the ability to bind to the enzyme. These compounds can be further screened against a functional enzyme to determine the effect of the compound on the enzyme activity Further, these compounds can be tested in animal or invertebrate systems to determine activity/effectiveness. Compounds can be identified that activate (agonist) or inactivate (antagonist) the enzyme to a desired degree.

Further, the proteins of the present invention can be used to screen a compound for the ability to stimulate or inhibit interaction between the enzyme protein and a molecule that normally interacts with the enzyme protein, e.g. a substrate or a component of the signal pathway that the enzyme protein normally interacts (for example, another enzyme). Such assays typically include the steps of combining the enzyme protein with a candidate compound under conditions that allow the enzyme protein, or fragment, to interact with the target molecule, and to detect the formation of a complex between the protein and the target or to detect the biochemical consequence of the interaction with the enzyme protein and the target, such as any of the associated effects of signal transduction such as protein phosphorylation, cAMP turnover, and adenylate cyclase activation, etc.

Candidate compounds include, for example, 1) peptides such as soluble peptides, including Ig-tailed fusion peptides and members of random peptide libraries (see, e.g., Lam et al., *Nature* 354:82–84 (1991); Houghten et al., *Nature* 354:84–86 (1991)) and combinatorial chemistry-derived molecular libraries made of D- and/or L-configuration amino acids; 2) phosphopeptides (e.g., members of random and partially degenerate, directed phosphopeptide libraries, see, e.g., Songyang et al, *Cell* 72:767–778 (1993)); 3) antibodies (e.g., polyclonal, monoclonal, humanized, anti-idiotypic, chimeric, and single chain antibodies as well as Fab, $F(ab')_2$, Fab expression library fragments, and epitope-binding fragments of antibodies); and 4) small organic and inorganic molecules (e.g., molecules obtained from combinatorial and natural product libraries).

One candidate compound is a soluble fragment of the receptor that competes for substrate binding. Other candidate compounds include mutant enzymes or appropriate fragments containing mutations that affect enzyme function and thus compete for substrate. Accordingly, a fragment that competes for substrate, for example with a higher affinity, or a fragment that binds substrate but does not allow release, is encompassed by the invention.

The invention further includes other end point assays to identify compounds that modulate (stimulate or inhibit) enzyme activity. The assays typically involve an assay of events in the signal transduction pathway that indicate enzyme activity. Thus, the phosphorylation of a substrate, activation of a protein, a change in the expression of genes that are up- or down-regulated in response to the enzyme protein dependent signal cascade can be assayed.

Any of the biological or biochemical functions mediated by the enzyme can be used as an endpoint assay. These include all of the biochemical or biochemical/biological events described herein, in the references cited herein, incorporated by reference for these endpoint assay targets, and other functions known to those of ordinary skill in the art or that can be readily identified using the information provided in the Figures, particularly FIG. 2. Specifically, a biological function of a cell or tissues that expresses the enzyme can be assayed. Experimental data as provided in FIG. 1 indicates that the enzymes of the present invention are expressed in humans in the placenta, neuroblastoma cells, liver, brain, T-cells from T-cell leukemia, and fetus, as indicated by virtual northern blot analysis. In addition, PCR-based tissue screening panels indicate expression in the hippocampus.

Binding and/or activating compounds can also be screened by using chimeric enzyme proteins in which the amino terminal extracellular domain, or parts thereof the entire transmembrane domain or subregions, such as any of the seven transmembrane segments or any of the intracellular or extracellular loops and the carboxy terminal intracellular domain, or parts thereof, can be replaced by heterologous domains or subregions. For example, a substrate-binding region can be used that interacts with a different substrate then that which is recognized by the native enzyme. Accordingly, a different set of signal transduction components is available as an end-point assay for activation. This allows for assays to be performed in other than the specific host cell from which the enzyme is derived.

The proteins of the present invention are also useful in competition binding assays in methods designed to discover compounds that interact with the enzyme (e.g. binding partners and/or ligands). Thus, a compound is exposed to a enzyme polypeptide under conditions that allow the compound to bind or to otherwise interact with the polypeptide. Soluble enzyme polypeptide is also added to the mixture. If the test compound interacts with the soluble enzyme polypeptide, it decreases the amount of complex formed or activity from the enzyme target. This type of assay is particularly useful in cases in which compounds are sought that interact with specific regions of the enzyme. Thus, the soluble polypeptide that competes with the target enzyme region is designed to contain peptide sequences corresponding to the region of interest.

To perform cell free drug screening assays, it is sometimes desirable to immobilize either the enzyme protein, or fragment, or its target molecule to facilitate separation of complexes from uncomplexed forms of one or both of the proteins, as well as to accommodate automation of the assay.

Techniques for immobilizing proteins on matrices can be used in the drug screening assays. In one embodiment, a fusion protein can be provided which adds a domain that allows the protein to be bound to a matrix. For example, glutathione-S-transferase fusion proteins can be adsorbed onto glutathione sepharose beads (Sigma Chemical, St. Louis, Mo.) or glutathione derivatized microtitre plates, which are then combined with the cell lysates (e.g., $^{35}S$-labeled) and the candidate compound, and the mixture incubated under conditions conducive to complex formation (e.g., at physiological conditions for salt and pH). Following incubation, the beads are washed to remove any unbound label, and the matrix immobilized and radiolabel determined directly, or in the supernatant after the complexes are dissociated. Alternatively, the complexes can be dissociated from the matrix, separated by SDS-PAGE, and the level of enzyme-binding protein found in the bead fraction quantitated from the gel using standard electrophoretic techniques. For example, either the polypeptide or its target molecule can be immobilized utilizing conjugation of biotin and streptavidin using techniques well known in the art. Alternatively, antibodies reactive with the protein but which do not interfere with binding of the protein to its target molecule can be derivatized to the wells of the plate, and the protein trapped in the wells by antibody conjugation. Preparations of a enzyme-binding protein and a candidate compound are incubated in the enzyme protein-presenting wells and the amount of complex trapped in the well can be quantitated. Methods for detecting such complexes, in addition to those described above for the GST-immobilized complexes, include immunodetection of complexes using antibodies reactive with the enzyme protein target molecule, or which are reactive with enzyme protein and compete with the target molecule, as well as enzyme-linked assays which rely on detecting an enzymatic activity associated with the target molecule.

Agents that modulate one of the enzymes of the present invention can be identified using one or more of the above assays, alone or in combination. It is generally preferable to use a cell-based or cell free system first and then confirm activity in an animal or other model system. Such model systems are well known in the art and can readily be employed in this context.

Modulators of enzyme protein activity identified according to these drug screening assays can be used to treat a subject with a disorder mediated by the enzyme pathway, by treating cells or tissues that express the enzyme. Experimental data as provided in FIG. 1 indicates expression in humans in the placenta, neuroblastoma cells, liver, brain, T-cells from T-cell leukemia, hippocampus, and fetus. These methods of treatment include the steps of administering a modulator of enzyme activity in a pharmaceutical composition to a subject in need of such treatment, the modulator being identified as described herein.

In yet another aspect of the invention, the enzyme proteins can be used as "bait proteins" in a two-hybrid assay or three-hybrid assay (see, e.g., U.S. Pat. No. 5,283,317; Zervos et al. (1993) *Cell* 72:223–232; Madura et al. (1993) *J. Biol. Chem.* 268:12046–12054; Bartel et al. (1993) *Biotechniques* 14:920–924; Iwabuchi et al. (1993) *Oncogene* 8:1693–1696; and Brent WO94/10300), to identify other proteins, which bind to or interact with the enzyme and are involved in enzyme activity. Such enzyme-binding proteins are also likely to be involved in the propagation of signals by the enzyme proteins or enzyme targets as, for example, downstream elements of a enzyme-mediated signaling pathway. Alternatively, such enzyme-binding proteins are likely to be enzyme inhibitors.

The two-hybrid system is based on the modular nature of most transcription factors, which consist of separable DNA-binding and activation domains. Briefly, the assay utilizes two different DNA constructs. In one construct, the gene that codes for a enzyme protein is fused to a gene encoding the DNA binding domain of a known transcription factor (e.g., GAL-4). In the other construct, a DNA sequence, from a library of DNA sequences, that encodes an unidentified protein ("prey" or "sample") is fused to a gene that codes for the activation domain of the known transcription factor. If the "bait" and the "prey" proteins are able to interact, in vivo, forming a enzyme-dependent complex. the DNA-binding and activation domains of the transcription factor are brought into close proximity. This proximity allows transcription of a reporter gene (e.g., LacZ) which is operably linked to a transcriptional regulatory site responsive to the transcription factor. Expression of the reporter gene can be detected and cell colonies containing the functional transcription factor can be isolated and used to obtain the cloned gene which encodes the protein which interacts with the enzyme protein.

This invention further pertains to novel agents identified by the above-described screening assays. Accordingly, it is within the scope of this invention to further use an agent identified as described herein in an appropriate animal model. For example, an agent identified as described herein (e.g., a enzyme-modulating agent, an antisense enzyme nucleic acid molecule, a enzyme-specific antibody, or a enzyme-binding partner) can be used in an animal or other model to determine the efficacy, toxicity, or side effects of treatment with such an agent. Alternatively, an agent identified as described herein can be used in an animal or other model to determine the mechanism of action of such an agent. Furthermore, this invention pertains to uses of novel agents identified by the above-described screening assays for treatments as described herein.

The enzyme proteins of the present invention are also useful to provide a target for diagnosing a disease or predisposition to disease mediated by the peptide. Accordingly, the invention provides methods for detecting the presence, or levels of, the protein (or encoding MRNA) in a cell, tissue, or organism. Experimental data as provided in FIG. 1 indicates expression in humans in the placenta, neuroblastoma cells, liver, brain, T-cells from T-cell leukemia, hippocampus, and fetus. The method involves contacting a biological sample with a compound capable of interacting with the enzyme protein such that the interaction can be detected. Such an assay can be provided in a single detection format or a multi-detection format such as an antibody chip array.

One agent for detecting a protein in a sample is an antibody capable of selectively binding to protein. A biological sample includes tissues, cells and biological fluids isolated from a subject, as well as tissues, cells and fluids present within a subject.

The peptides of the present invention also provide targets for diagnosing active protein activity, disease, or predisposition to disease, in a patient having a variant peptide, particularly activities and conditions that are known for other members of the family of proteins to which the present one belongs. Thus, the peptide can be isolated from a biological sample and assayed for the presence of a genetic mutation that results in aberrant peptide. This includes amino acid substitution, deletion, insertion, rearrangement, (as the result of aberrant splicing events), and inappropriate post-translational modification. Analytic methods include altered electrophoretic mobility, altered tryptic peptide digest, altered enzyme activity in cell-based or cell-free assay, alteration in substrate or antibody-binding pattern, altered isoelectric point, direct amino acid sequencing, and any other of the known assay techniques useful for detecting mutations in a protein. Such an assay can be provided in a single detection format or a multi-detection format such as an antibody chip array.

In vitro techniques for detection of peptide include enzyme linked immunosorbent assays (ELISAs), Western blots, immunoprecipitations and immunofluorescence using a detection reagent, such as an antibody or protein binding agent. Alternatively, the peptide can be detected in vivo in a subject by introducing into the subject a labeled anti-peptide antibody or other types of detection agent. For example, the antibody can be labeled with a radioactive marker whose presence and location in a subject can be detected by standard imaging techniques. Particularly useful are methods that detect the allelic variant of a peptide expressed in a subject and methods which detect fragments of a peptide in a sample.

The peptides are also useful in pharmiacogenomic analysis. Pharmacogenomics deal with clinically significant hereditary variations in the response to drugs due to altered drug disposition and abnormal action in affected persons. See, e.g., Eichelbaum, M. (*Clin. Exp. Pharmacol. Physiol.* 23(10–11):983–985 (1996)), and Linder, M. W. (*Clin. Chem.* 43(2):254–266 (1997)). The clinical outcomes of these variations result in severe toxicity of therapeutic drugs in certain individuals or therapeutic failure of drugs in certain individuals as a result of individual variation in metabolism. Thus, the genotype of the individual can determine the way a therapeutic compound acts on the body or the way the body metabolizes the compound. Further, the activity of drug metabolizing enzymes effects both the intensity and duration of drug action. Thus, the pharmacogenomics of the individual permit the selection of effective compounds and effective dosages of such compounds for prophylactic or therapeutic treatment based on the individual's genotype. The discovery of genetic polymorphisms in some drug metabolizing enzymes has explained why some patients do not obtain the expected drug effects, show an exaggerated drug effect, or experience serious toxicity from standard drug dosages. Polymorphisms can be expressed in the phenotype of the extensive metabolizer and the phenotype of the poor metabolizer. Accordingly, genetic polymorphism may lead to allelic protein variants of the enzyme protein in which one or more of the enzyme functions in one population is different from those in another population. The peptides thus allow a target to ascertain a genetic predisposition that can affect treatment modality. Thus, in a ligand-based treatment, polymorphism may give rise to amino terminal extracellular domains and/or other substrate-binding regions that are more or less active in substrate binding, and enzyme activation. Accordingly, substrate dosage would necessarily be modified to maximize the therapeutic effect within a given population containing a polymorphism. As an alternative to genotyping, specific polymorphic peptides could be identified.

The peptides are also useful for treating a disorder characterized by an absence of, inappropriate, or unwanted expression of the protein. Experimental data as provided in FIG. 1 indicates expression in humans in the placenta, neuroblastoma cells, liver, brain, T-cells from T-cell leukemia, hippocampus, and fetus. Accordingly, methods for treatment include the use of the enzyme protein or fragments.

Antibodies

The invention also provides antibodies that selectively bind to one of the peptides of the present invention, a protein comprising such a peptide, as well as variants and fragments thereof. As used herein, an antibody selectively binds a target peptide when it binds the target peptide and does not significantly bind to unrelated proteins. An antibody is still considered to selectively bind a peptide even if it also binds to other proteins that are not substantially homologous with the target peptide so long as such proteins share homology with a fragment or domain of the peptide target of the antibody. In this case, it would be understood that antibody binding to the peptide is still selective despite some degree of cross-reactivity.

As used herein, an antibody is defined in terms consistent with that recognized within the art: they are multi-subunit proteins produced by a mammalian organism in response to an antigen challenge. The antibodies of the present invention include polyclonal antibodies and monoclonal antibodies, as well as fragments of such antibodies, including, but not limited to, Fab or $F(ab')_2$, and Fv fragments.

Many methods are known for generating and/or identifying antibodies to a given target peptide. Several such methods are described by Harlow, Antibodies, Cold Spring Harbor Press, (1989).

In general, to generate antibodies, an isolated peptide is used as an immunogen and is administered to a mammalian organism, such as a rat, rabbit or mouse. The full-length protein, an antigenic peptide fragment or a fusion protein can be used. Particularly important fragments are those covering functional domains, such as the domains identified in FIG. 2, and domain of sequence homology or divergence amongst the family, such as those that can readily be identified using protein alignment methods and as presented in the Figures.

Antibodies are preferably prepared from regions or discrete fragments of the enzyme proteins. Antibodies can be prepared from any region of the peptide as described herein. However, preferred regions will include those involved in function/activity and/or enzyme/binding partner interaction. FIG. 2 can be used to identify particularly important regions while sequence alignment can be used to identify conserved and unique sequence fragments.

An antigenic fragment will typically comprise at least 8 contiguous amino acid residues. The antigenic peptide can comprise, however, at least 10, 12, 14, 16 or more amino acid residues. Such fragments can be selected on a physical property, such as fragments correspond to regions that are located on the surface of the protein, e.g., hydrophilic regions or can be selected based on sequence uniqueness (see FIG. 2).

Detection on an antibody of the present invention can be facilitated by coupling (i.e., physically linking) the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoeyrthrin; an example of a luminescent material includes luminol; examples of bioluminescent materials include luciferase, luciferin, and aequorin, and examples of suitable radioactive material include $^{125}I$, $^{131}I$, $^{35}S$ or $^{3}H$.

Antibody Uses

The antibodies can be used to isolate one of the proteins of the present invention by standard techniques, such as affinity chromatography or immunoprecipitation. The antibodies can facilitate the purification of the natural protein from cells and recombinantly produced protein expressed in host cells. In addition, such antibodies are useful to detect the presence of one of the proteins of the present invention in cells or tissues to determine the pattern of expression of the protein among various tissues in an organism and over the course of normal development. Experimental data as provided in FIG. 1 indicates that the enzymes of the present invention are expressed in humans in the placenta, neuroblastoma cells, liver, brain, T-cells from T-cell leukemia, and fetus, as indicated by virtual northern blot analysis. In addition, PCR-based tissue screening panels indicate expression in the hippocampus. Further, such antibodies can be used to detect protein in situ, in vitro, or in a cell lysate or supernatant in order to evaluate the abundance and pattern of expression. Also, such antibodies can be used to assess abnormal tissue distribution or abnormal expression during development or progression of a biological condition. Antibody detection of circulating fragments of the full length protein can be used to identify turnover.

Further, the antibodies can be used to assess expression in disease states such as in active stages of the disease or in an individual with a predisposition toward disease related to the protein's function. When a disorder is caused by an inappropriate tissue distribution, developmental expression, level of expression of the protein, or expressed/processed form, the antibody can be prepared against the normal protein. Experimental data as provided in FIG. 1 indicates expression in humans in the placenta, neuroblastoma cells, liver, brain, T-cells from T-cell leukemia, hippocampus, and fetus. If a disorder is characterized by a specific mutation in the protein, antibodies specific for this mutant protein can be used to assay for the presence of the specific mutant protein.

The antibodies can also be used to assess normal and aberrant subcellular localization of cells in the various tissues in an organism. Experimental data as provided in FIG. 1 indicates expression in humans in the placenta, neuroblastoma cells, liver, brain, T-cells from T-cell leukemia, hippocampus, and fetus. The diagnostic uses can be applied, not only in genetic testing, but also in monitoring a treatment modality. Accordingly, where treatment is ultimately aimed at correcting expression level or the presence of aberrant sequence and aberrant tissue distribution or developmental expression, antibodies directed against the protein or relevant fragments can be used to monitor therapeutic efficacy.

Additionally, antibodies are useful in pharmacogenomic analysis. Thus, antibodies prepared against polymorphic proteins can be used to identify individuals that require modified treatment modalities. The antibodies are also useful as diagnostic tools as an immunological marker for aberrant protein analyzed by electrophoretic mobility, isoelectric point, tryptic peptide digest, and other physical assays known to those in the art.

The antibodies are also useful for tissue typing Experimental data as provided in FIG. 1 indicates expression in humans in the placenta, neuroblastoma cells, liver, brain, T-cells from T-cell leukemia, hippocampus, and fetus. Thus, where a specific protein has been correlated with expression in a specific tissue, antibodies that are specific for this protein can be used to identify a tissue type.

The antibodies are also useful for inhibiting protein function, for example, blocking the binding of the enzyme peptide to a binding partner such as a substrate. These uses can also be applied in a therapeutic context in which treatment involves inhibiting the protein's function. An antibody can be used, for example, to block binding, thus modulating (agonizing or antagonizing) the peptides activity. Antibodies can be prepared against specific fragments containing sites required for function or against intact protein that is associated with a cell or cell membrane. See FIG. 2 for structural information relating to the proteins of the present invention.

The invention also encompasses kits for using antibodies to detect the presence of a protein in a biological sample. The kit can comprise antibodies such as a labeled or labelable antibody and a compound or agent for detecting protein in a biological sample; means for determining the amount of protein in the sample; means for comparing the amount of protein in the sample with a standard; and instructions for use. Such a kit can be supplied to detect a single protein or epitope or can be configured to detect one of a multitude of epitopes, such as in an antibody detection array. Arrays are described in detail below for nuleic acid arrays and similar methods have been developed for antibody arrays.

Nucleic Acid Molecules

The present invention further provides isolated nucleic acid molecules that encode a enzyme peptide or protein of the present invention (cDNA, transcript and genomic sequence). Such nucleic acid molecules will consist of, consist essentially of, or comprise a nucleotide sequence that encodes one of the enzyme peptides of the present invention, an allelic variant thereof, or an ortholog or paralog thereof.

As used herein, an "isolated" nucleic acid molecule is one that is separated from other nucleic acid present in the natural source of the nucleic acid. Preferably, an "isolated" nucleic acid is free of sequences which naturally flank the nucleic acid (i.e., sequences located at the 5' and 3' ends of the nucleic acid) in the genomic DNA of the organism from which the nucleic acid is derived. However, there can be some flanking nucleotide sequences, for example up to about 5 KB, 4 KB, 3 KB, 2 KB, or 1 KB or less, particularly contiguous peptide encoding sequences and peptide encoding sequences within the same gene but separated by introns in the genomic sequence. The important point is that the nucleic acid is isolated from remote and unimportant flanking sequences such that it can be subjected to the specific manipulations described herein such as recombinant expression, preparation of probes and primers, and other uses specific to the nucleic acid sequences.

Moreover, an "isolated" nucleic acid molecule, such as a transcript/cDNA molecule, can be substantially free of other cellular material, or culture medium when produced by recombinant techniques, or chemical precursors or other chemicals when chemically synthesized. However, the nucleic acid molecule can be fused to other coding or regulatory sequences and still be considered isolated.

For example, recombinant DNA molecules contained in a vector are considered isolated. Further examples of isolated DNA molecules include recombinant DNA molecules maintained in heterologous host cells or purified (partially or substantially) DNA molecules in solution. Isolated RNA molecules include in vivo or in vitro RNA transcripts of the isolated DNA molecules of the present invention. Isolated nucleic acid molecules according to the present invention further include such molecules produced synthetically.

Accordingly, the present invention provides nucleic acid molecules that consist of the nucleotide sequence shown in FIG. 1 or 3 (SEQ ID NO: 1, transcript sequence and SEQ ID NO:3, genomic sequence), or any nucleic acid molecule that encodes the protein provided in FIG. 2, SEQ ID NO:2. A nucleic acid molecule consists of a nucleotide sequence when the nucleotide sequence is the complete nucleotide sequence of the nucleic acid molecule.

The present invention further provides nucleic acid molecules that consist essentially of the nucleotide sequence shown in FIG. 1 or 3 (SEQ ID NO:1, transcript sequence and SEQ ID NO:3, genomic sequence), or any nucleic acid molecule that encodes the protein provided in FIG. 2, SEQ ID NO:2. A nucleic acid molecule consists essentially of a nucleotide sequence when such a nucleotide sequence is present with only a few additional nucleic acid residues in the final nucleic acid molecule.

The present invention further provides nucleic acid molecules that comprise the nucleotide sequences shown in FIG. 1 or 3 (SEQ ID NO:1, transcript sequence and SEQ ID NO:3, genomic sequence), or any nucleic acid molecule that encodes the protein provided in FIG. 2, SEQ ID NO:2. A nucleic acid molecule comprises a nucleotide sequence when the nucleotide sequence is at least part of the final nucleotide sequence of the nucleic acid molecule. In such a fashion, the nucleic acid molecule can be only the nucleotide sequence or have additional nucleic acid residues, such as nucleic acid residues that are naturally associated with it or heterologous nucleotide sequences. Such a nucleic acid molecule can have a few additional nucleotides or can comprises several hundred or more additional nucleotides. A brief description of how various types of these nucleic acid molecules can be readily made/isolated is provided below.

In FIGS. 1 and 3, both coding and non-coding sequences are provided. Because of the source of the present invention, humans genomic sequence (FIG. 3) and cDNA/transcript sequences (FIG. 1), the nucleic acid molecules in the Figures will contain genomic intronic sequences, 5' and 3' non-coding sequences, gene regulatory regions and non-coding intergenic sequences. In general such sequence features are either noted in FIGS. 1 and 3 or can readily be identified using computational tools known in the art. As discussed below, some of the non-coding regions, particularly gene regulatory elements such as promoters, are useful for a variety of purposes, e.g. control of heterologous gene expression, target for identifying gene activity modulating compounds, and are particularly claimed as fragments of the genomic sequence provided herein.

The isolated nucleic acid molecules can encode the mature protein plus additional amino or carboxyl-terminal amino acids, or amino acids interior to the mature peptide (when the mature form has more than one peptide chain, for instance). Such sequences may play a role in processing of a protein from precursor to a mature form, facilitate protein trafficking, prolong or shorten protein half-life or facilitate manipulation of a protein for assay or production, among other things. As generally is the case in situ, the additional amino acids may be processed away from the mature protein by cellular enzymes.

As mentioned above, the isolated nucleic acid molecules include, but are not limited to, the sequence encoding the enzyme peptide alone, the sequence encoding the mature peptide and additional coding sequences, such as a leader or secretory sequence (e.g., a pre-pro or pro-protein sequence), the sequence encoding the mature peptide, with or without the additional coding sequences, plus additional non-coding sequences, for example introns and non-coding 5' and 3' sequences such as transcribed but non-translated sequences that play a role in tanscription, mRNA processing (including splicing and polyadenylation signals), ribosome binding and stability of mRNA. In addition, the nucleic acid molecule may be fused to a marker sequence encoding, for example, a peptide that facilitates purification.

Isolated nucleic acid molecules can be in the form of RNA, such as mRNA, or in the form DNA, including cDNA and genomic DNA obtained by cloning or produced by chemical synthetic techniques or by a combination thereof. The nucleic acid, especially DNA, can be double-stranded or single-stranded. Single-stranded nucleic acid can be the coding strand (sense strand) or the non-coding strand (anti-sense strand).

The invention further provides nucleic acid molecules that encode fragments of the peptides of the present invention as well as nucleic acid molecules that encode obvious variants of the enzyme proteins of the present invention that are described above. Such nucleic acid molecules may be naturally occurring, such as allelic variants (same locus), paralogs (different locus), and orthologs (different organism), or may be constructed by recombinant DNA methods or by chemical synthesis. Such non-naturally occurring variants may be made by mutagenesis techniques, including those applied to nucleic acid molecules, cells, or organisms. Accordingly, as discussed above, the variants can contain nucleotide substitutions, deletions, inversions and insertions. Variation can occur in either or both the coding and non-coding regions. The variations can produce both conservative and non-conservative amino acid substitutions.

The present invention further provides non-coding fragments of the nucleic acid molecules provided in FIGS. 1 and 3. Preferred non-coding fragments include, but are not limited to, promoter sequences, enhancer sequences, gene modulating sequences and gene termination sequences. Such fragments are useful in controlling heterologous gene expression and in developing screens to identify gene-modulating agents. A promoter can readily be identified as being 5' to the ATG start site in the genomic sequence provided in FIG. 3.

A fragment comprises a contiguous nucleotide sequence greater than 12 or more nucleotides. Further, a fragment could at least 30, 40, 50, 100, 250 or 500 nucleotides in length. The length of the fragment will be based on its intended use. For example, the fragment can encode epitope bearing regions of the peptide, or can be useful as DNA probes and primers. Such fragments can be isolated using the known nucleotide sequence to synthesize an oligonucleotide probe. A labeled probe can then be used to screen a cDNA library, genomic DNA library, or mRNA to isolate nucleic acid corresponding to the coding region. Further, primers can be used in PCR reactions to clone specific regions of gene.

A probe/primer typically comprises substantially a purified oligonucleotide or oligonucleotide pair. The oligonucleotide typically comprises a region of nucleotide sequence that hybridizes under stringent conditions to at least about 12, 20, 25, 40, 50 or more consecutive nucleotides.

Orthologs, homologs, and allelic variants can be identified using methods well known in the art. As described in the Peptide Section, these variants comprise a nucleotide sequence encoding a peptide that is typically 60–70%, 70–80%, 80–90%, and more typically at least about 90–95% or more homologous to the nucleotide sequence shown in the Figure sheets or a fragment of this sequence. Such nucleic acid molecules can readily be identified as being able to hybridize under moderate to stringent conditions, to the nucleotide sequence shown in the Figure sheets or a fragment of the sequence. Allelic variants can readily be determined by genetic locus of the encoding gene. The gene encoding the novel enzyme of the present invention is located on a genome component that has been mapped to human chromosome 7 (as indicated in FIG. 3), which is supported by multiple lines of evidence, such as STS and BAC map data FIG. 3 provides information on SNPs that have been found in the gene encoding the enzyme of the present invention. SNPs were identified at 71 different nucleotide positions. Some of these SNPs that are located outside the ORF and in introns may affect gene transcription.

As used herein, the term "hybridizes under stringent conditions" is intended to describe conditions for hybridization and washing under which nucleotide sequences encoding a peptide at least 60–70% homologous to each other typically remain hybridized to each other. The conditions can be such that sequences at least about 60%, at least about 70%, or at least about 80% or more homologous to each other typically remain hybridized to each other. Such stringent conditions are known to those skilled in the art and can be found in *Current Protocols in Molecular Biology*, John Wiley & Sons, N.Y. (1989), 6.3.1–6.3.6. One example of stringent hybridization conditions are hybridization in 6×sodium chloride/sodium citrate (SSC) at about 45 C., followed by one or more washes in 0.2×SSC, 0.1% SDS at 50–65 C. Examples of moderate to low stringency hybridization conditions are well known in the art.

Nucleic Acid Molecule Uses

The nucleic acid molecules of the present invention are useful for probes, primers, chemical intermediates, and in biological assays. The nucleic acid molecules are useful as a hybridization probe for messenger RNA, transcript/cDNA and genomic DNA to isolate full-length cDNA and genomic clones encoding the peptide described in FIG. 2 and to isolate cDNA and genomic clones that correspond to variants (alleles, orthologs, etc.) producing the same or related peptides shown in FIG. 2. As illustrated in FIG. 3, SNPs were identified at 71 different nucleotide positions.

The probe can correspond to any sequence along the entire length of the nucleic acid molecules provided in the Figures. Accordingly, it could be derived from 5' noncoding regions, the coding region, and 3' noncoding regions. However, as discussed, fragments are not to be construed as encompassing fragments disclosed prior to the present invention. The nucleic acid molecules are also useful as primers for PCR to amplify any given region of a nucleic acid molecule and are useful to synthesize antisense molecules of desired length and sequence.

The nucleic acid molecules are also useful for constructing recombinant vectors. Such vectors include expression vectors that express a portion of, or all of, the peptide sequences. Vectors also include insertion vectors, used to integrate into another nucleic acid molecule sequence, such as into the cellular genome, to alter in situ expression of a gene and/or gene product. For example, an endogenous coding sequence can be replaced via homologous recombination with all or part of the coding region containing one or more specifically introduced mutations.

The nucleic acid molecules are also useful for expressing antigenic portions of the proteins.

The nucleic acid molecules are also useful as probes for determining the chromosomal positions of the nucleic acid molecules by means of in situ hybridization methods. The gene encoding the novel enzyme of the present invention is located on a genome component that has been mapped to human chromosome 7 (as indicated in FIG. 3), which is supported by multiple lines of evidence, such as STS and BAC map data The nucleic acid molecules are also useful in making vectors containing the gene regulatory regions of the nucleic acid molecules of the present invention.

The nucleic acid molecules are also useful for designing ribozymes corresponding to all, or a part, of the mRNA produced from the nucleic acid molecules described herein.

The nucleic acid molecules are also useful for making vectors that express part, or all, of the peptides.

The nucleic acid molecules are also useful for constructing host cells expressing a part, or all, of the nucleic acid molecules and peptides.

The nucleic acid molecules are also useful for constructing transgenic animals expressing all, or a part, of the nucleic acid molecules and peptides.

The nucleic acid molecules are also useful as hybridization probes for determining the presence, level, form and distribution of nucleic acid expression. Experimental data as provided in FIG. 1 indicates that the enzymes of the present invention are expressed in humans in the placenta, neuroblastoma cells, liver, brain, T-cells from T-cell leukemia, and fetus, as indicated by virtual northern blot analysis. In addition, PCR-based tissue screening panels indicate expression in the hippocampus. Accordingly, the probes can be used to detect the presence of, or to determine levels of, a specific nucleic acid molecule in cells, tissues, and in organisms. The nucleic acid whose level is determined can be DNA or RNA. Accordingly, probes corresponding to the peptides described herein can be used to assess expression and/or gene copy number in a given cell, tissue, or organism. These uses are relevant for diagnosis of disorders involving an increase or decrease in enzyme protein expression relative to normal results.

In vitro techniques for detection of mRNA include Northern hybridizations and in situ hybridizations. In vitro techniques for detecting DNA includes Southern hybridizations and in situ hybridization.

Probes can be used as a part of a diagnostic test kit for identifying cells or tissues that express a enzyme protein, such as by measuring a level of a enzyme-encoding nucleic acid in a sample of cells from a subject e.g., mRNA or genomic DNA, or determining if a enzyme gene has been mutated. Experimental data as provided in FIG. 1 indicates that the enzymes of the present invention are expressed in humans in the placenta, neuroblastoma cells, liver, brain, T-cells from T-cell leukemia, and fetus, as indicated by virtual northern blot analysis. In addition, PCR-based tissue screening panels indicate expression in the hippocampus.

Nucleic acid expression assays are useful for drug screening to identify compounds that modulate enzyme nucleic acid expression.

The invention thus provides a method for identifying a compound that can be used to treat a disorder associated with nucleic acid expression of the enzyme gene, particularly biological and pathological processes that are mediated by the enzyme in cells and tissues that express it. Experimental data as provided in FIG. 1 indicates expression in humans in the placenta, neuroblastoma cells, liver, brain, T-cells from T-cell leukemia, hippocampus, and fetus. The method typically includes assaying the ability of the compound to modulate the expression of the enzyme nucleic acid and thus identifying a compound that can be used to treat a disorder characterized by undesired enzyme nucleic acid expression. The assays can be performed in cell-based and cell-free systems. Cell-based assays include cells naturally expressing the enzyme nucleic acid or recombinant cells genetically engineered to express specific nucleic acid sequences.

The assay for enzyme nucleic acid expression can involve direct assay of nucleic acid levels, such as mRNA levels, or on collateral compounds involved in the signal pathway. Further, the expression of genes that are up- or down-regulated in response to the enzyme protein signal pathway can also be assayed. In this embodiment the regulatory regions of these genes can be operably linked to a reporter gene such as luciferase.

Thus, modulators of enzyme gene expression can be identified in a method wherein a cell is contacted with a candidate compound and the expression of mRNA determined. The level of expression of enzyme mRNA in the presence of the candidate compound is compared to the level of expression of enzyme mRNA in the absence of the candidate compound. The candidate compound can then be identified as a modulator of nucleic acid expression based on this comparison and be used, for example to treat a disorder characterized by aberrant nucleic acid expression. When expression of mRNA is statistically significantly greater in the presence of the candidate compound than in its absence, the candidate compound is identified as a stimulator of nucleic acid expression. When nucleic acid expression is statistically significantly less in the presence of the candidate compound than in its absence, the candidate compound is identified as an inhibitor of nucleic acid expression.

The invention further provides methods of treatment, with the nucleic acid as a target, using a compound identified through drug screening as a gene modulator to modulate enzyme nucleic acid expression in cells and tissues that express the enzyme. Experimental data as provided in FIG. 1 indicates that the enzymes of the present invention are expressed in humans in the placenta, neuroblastoma cells, liver, brain, T-cells from T-cell leukemia, and fetus, as indicated by virtual northern blot analysis. In addition, PCR-based tissue screening panels indicate expression in the hippocampus. Modulation includes both up-regulation (i.e. activation or agonization) or down-regulation (suppression or antagonization) or nucleic acid expression.

Alternatively, a modulator for enzyme nucleic acid expression can be a small molecule or drug identified using the screening assays described herein as long as the drug or small molecule inhibits the enzyme nucleic acid expression in the cells and tissues that express the protein. Experimental data as provided in FIG. 1 indicates expression in humans in the placenta, neuroblastoma cells, liver, brain, T-cells from T-cell leukemia, hippocampus, and fetus.

The nucleic acid molecules are also useful for monitoring the effectiveness of modulating compounds on the expression or activity of the enzyme gene in clinical trials or in a treatment regimen. Thus, the gene expression pattern can serve as a barometer for the continuing effectiveness of treatment with the compound, particularly with compounds to which a patient can develop resistance. The gene expression pattern can also serve as a marker indicative of a physiological response of the affected cells to the compound. Accordingly, such monitoring would allow either increased administration of the compound or the administration of alternative compounds to which the patient has not become resistant. Similarly, if the level of nucleic acid expression falls below a desirable level, administration of the compound could be commensurately decreased.

The nucleic acid molecules are also useful in diagnostic assays for qualitative changes in enzyme nucleic acid expression, and particularly in qualitative changes that lead to pathology. The nucleic acid molecules can be used to detect mutations in enzyme genes and gene expression products such as mRNA. The nucleic acid molecules can be used as hybridization probes to detect naturally occurring genetic mutations in the enzyme gene and thereby to determine whether a subject with the mutation is at risk for a disorder caused by the mutation. Mutations include deletion, addition, or substitution of one or more nucleotides in the gene, chromosomal rearrangement, such as inversion or transposition, modification of genomic DNA, such as aberrant methylation patterns or changes in gene copy number, such as amplification. Detection of a mutated form of the enzyme gene associated with a dysfunction provides a diagnostic tool for an active disease or susceptibility to disease when the disease results from overexpression, underexpression, or altered expression of a enzyme protein.

Individuals carrying mutations in the enzyme gene can be detected at the nucleic acid level by a variety of techniques. FIG. 3 provides information on SNPs that have been found in the gene encoding the enzyme of the present invention. SNPs were identified at 71 different nucleotide positions. Some of these SNPs that are located outside the ORF and in introns may affect gene transcription. The gene encoding the novel enzyme of the present invention is located on a genome component that has been mapped to human chromosome 7 (as indicated in FIG. 3), which is supported by multiple lines of evidence, such as STS and BAC map data. Genomic DNA can be analyzed directly or can be amplified by using PCR prior to analysis. RNA or cDNA can be used in the same way. In some uses, detection of the mutation involves the use of a probe/primer in a polymerase chain reaction (PCR) (see, e.g. U.S. Pat. Nos. 4,683,195 and 4,683,202), such as anchor PCR or RACE PCR, or, alternatively, in a ligation chain reaction (LCR) (see, e.g., Landegran et al., *Science* 241:1077–1080 (1988); and Nakazawa et al, *PNAS* 91:360–364 (1994)), the latter of which can be particularly useful for detecting point mutations in the gene (see Abravaya et. al., *Nucleic Acids Res.* 23:675–682 (1995)). This method can include the steps of collecting a sample of cells from a patient, isolating nucleic acid (e.g., genomic, mRNA or both) from the cells of the sample, contacting the nucleic acid sample with one or more primers which specifically hybridize to a gene under conditions such that hybridization and amplification of the gene (if present) occurs, and detecting the presence or absence of an amplification product, or detecting the size of the amplification product and comparing the length to a control sample. Deletions and insertions can be detected by a change in size of the amplified product compared to the normal genotype. Point mutations can be identified by hybridizing amplified DNA to normal RNA or antisense DNA sequences.

Alternatively, mutations in a enzyme gene can be directly identified, for example,. by alterations in restriction enzyme digestion patterns determined by gel electrophoresis Further, sequence-specific ribozymes (U.S. Pat. No. 5,498,531) can be used to score for the presence of specific mutations by development or loss of a ribozyme cleavage site. Perfectly matched sequences can be distinguished from mismatched sequences by nuclease cleavage digestion assays or by differences in melting temperature.

Sequence changes at specific locations can also be assessed by nuclease protection assays such as RNase and S1 protection or the chemical cleavage method. Furthermore, sequence differences between a mutant enzyme gene and a wild-type gene can be determined by direct DNA sequencing. A variety of automated sequencing procedures can be utilized when performing the diagnostic assays (Naeve, C. W., (1995) *Biotechniques* 19:448), including sequencing by mass spectrometry (see, e.g., PCT International Publication No. WO 94116101; Cohen et al., *Adv. Chromatogr.* 36:127–162 (1996); and Griffin et al., *Appl. Biochem. Biotechnol.* 38:147–159 (1993)).

Other methods for detecting mutations in the gene include methods in which protection from cleavage agents is used to detect mismatched bases in RNA/RNA or RNA/DNA duplexes (Myers et al., *Science* 230:1242 (1985)); Cotton et al., *PNAS* 85:4397 (988); Saleeba et al, *Meth. Enzymol.* 217:286–295 (1992)), electrophoretic mobility of mutant and wild type nucleic acid is compared (Orita et al., *PNAS* 86:2766 (1989); Cotton et al, *Mutat. Res.* 285:125–144 (1993); and Hayashi et al., *Genet. Anal Tech. Appl.* 9:73–79 (992)), and movement of mutant or wild-type fragments in polyacrylamide gels containing a gradient of denaturant is assayed using denaturing gradient gel electrophoresis (Myers et al., *Nature* 313:495 (1985)). Examples of other techniques for detecting point mutations include selective oligonucleotide hybridization, selective amplification, and selective primer extension.

The nucleic acid molecules are also useful for testing an individual for a genotype that while not necessarily causing the disease, nevertheless affects the treatment modality. Thus, the nucleic acid molecules can be used to study the relationship between an individual's genotype and the individual's response to a compound used for treatment (pharmacogenomic relationship). Accordingly, the nucleic acid molecules described herein can be used to assess the mutation content of the enzyme gene in an individual in order to select an appropriate compound or dosage regimen for treatment. FIG. 3 provides information on SNPs that have been found in the gene encoding the enzyme of the present invention. SNPs were identified at 71 different nucleotide positions. Some of these SNPs that are located outside the ORF and in introns may affect gene transcription.

Thus nucleic acid molecules displaying genetic variations that affect treatment provide a diagnostic target that can be used to tailor treatment in an individual. Accordingly, the production of recombinant cells and animals containing these polymorphisms allow effective clinical design of treatment compounds and dosage regimens.

The nucleic acid molecules are thus useful as antisense constructs to control enzyme gene expression in cells, tissues, and organisms. A DNA antisense nucleic acid molecule is designed to be complementary to a region of the gene involved in transcription, preventing transcription and hence production of enzyme protein. An antisense RNA or DNA nucleic acid molecule would hybridize to the mRNA and thus block translation of MRNA into enzyme protein.

Alternatively, a class of antisense molecules can be used to inactivate mRNA in order to decrease expression of enzyme nucleic acid Accordingly, these molecules can treat a disorder characterized by abnormal or undesired enzyme nucleic acid expression. This technique involves cleavage by means of ribozymes containing nucleotide sequences complementary to one or more regions in the mRNA that attenuate the ability of the mRNA to be translated. Possible regions include coding regions and particularly coding regions corresponding to the catalytic and other functional activities of the enzyme protein, such as substrate binding.

The nucleic acid molecules also provide vectors for gene therapy in patients containing cells that are aberrant in enzyme gene expression. Thus, recombinant cells, which include the patient's cells that have been engineered ex vivo and returned to the patient, are introduced into an individual where the cells produce the desired enzyme protein to treat the individual.

The invention also encompasses kits for detecting the presence of a enzyme nucleic acid in a biological sample. Experimental data as provided in FIG. 1 indicates that the enzymes of the present invention are expressed in humans in the placenta, neuroblastoma cells, liver, brain, T-cells from T-cell leukemia, and fetus, as indicated by virtual northern blot analysis. In addition, PCR-based tissue screening panels indicate expression in the hippocampus. For example, the kit can comprise reagents such as a labeled or labelable nucleic acid or agent capable of detecting enzyme nucleic acid in a biological sample; means for determining the amount of enzyme nucleic acid in the sample; and means for comparing the amount of enzyme nucleic acid in the sample with a standard. The compound or agent can be packaged in a suitable container. The kit can further comprise instructions for using the kit to detect enzyme protein mRNA or DNA.

Nucleic Acid Arrays

The present invention further provides nucleic acid detection kits, such as arrays or microarrays of nucleic acid molecules that are based on the sequence information provided in FIGS. 1 and 3 (SEQ ID NOS:1 and 3).

As used herein "Arrays" or "Microarrays" refers to an array of distinct polynucleotides or oligonucleotides synthesized on a substrate, such as paper, nylon or other type of membrane, filter, chip, glass slide, or any other suitable solid support. In one embodiment, the microarray is prepared and used according to the methods described in U.S. Pat. No. 5,837,832, Chee et al., PCT application WO95/11995 (Chee et al.), Lockhart, D. J. et al. (1996; Nat. Biotech. 14: 1675–1680) and Schena, M. et al. (1996; Proc. Natl. Acad. Sci. 93: 10614–10619), all of which are incorporated herein in their entirety by reference. In other embodiments, such arrays are produced by the methods described by Brown et al., U.S. Pat. No. 5,807,522.

The microarray or detection kit is preferably composed of a large number of unique, single-stranded nucleic acid sequences, usually either synthetic antisense oligonucleotides or fragments of cDNAs, fixed to a solid support. The oligonucleotides are preferably about 6–60 nucleotides in length, more preferably 15–30 nucleotides in length, and most preferably about 20–25 nucleotides in length. For a certain type of microarray or detection kit, it may be preferable to use oligonucleotides that are only 7–20 nucleotides in length. The microarray or detection kit may contain oligonucleotides that cover the known 5', or 3', sequence, sequential oligonucleotides which cover the full length sequence; or unique oligonucleotides selected from particular areas along the length of the sequence. Polynucleotides used in the microarray or detection kit may be oligonucleotides that are specific to a gene or genes of interest.

In order to produce oligonucleotides to a known sequence for a microarray or detection kit, the gene(s) of interest (or an ORF identified from the contigs of the present invention) is typically examined using a computer algorithm which starts at the 5' or at the 3' end of the nucleotide sequence. Typical algorithms will then identify oligomers of defined length that are unique to the gene, have a GC content within a range suitable for hybridization, and lack predicted secondary structure that may interfere with hybridization. In certain situations it may be appropriate to use pairs of oligonucleotides on a microarray or detection kit. The "pairs" will be identical, except for one nucleotide that preferably is located in the center of the sequence. The second oligonucleotide in the pair (mismatched by one) serves as a control. The number of oligonucleotide pairs may range from two to one million. The oligomers are synthesized at designated areas on a substrate using a light-directed chemical process. The substrate may be paper, nylon or other type of membrane, filter, chip, glass slide or any other suitable solid support.

In another aspect, an oligonucleotide may be synthesized on the surface of the substrate by using a chemical coupling procedure and an ink jet application apparatus, as described in PCT application WO95/251116 (Baldeschweiler et al.) which is incorporated herein in its entirety by reference. In another aspect, a "gridded" array analogous to a dot (or slot) blot may be used to arrange and link cDNA fragments or oligonucleotides to the surface of a substrate using a vacuum system, thermal, UV, mechanical or chemical bonding procedures. An array, such as those described above, may be produced by hand or by using available devices (slot blot or dot blot apparatus), materials (any suitable solid support), and machines (including robotic instruments), and may contain 8, 24, 96, 384, 1536, 6144 or more oligonucleotides, or any other number between two and one million which lends itself to the efficient use of commercially available instrumentation.

In order to conduct sample analysis using a microarray or detection kit, the RNA or DNA from a biological sample is made into hybridization probes. The mRNA is isolated, and cDNA is produced and used as a template to make antisense RNA (aRNA). The aRNA is amplified in the presence of fluorescent nucleotides, and labeled probes are incubated with the microarray or detection kit so that the probe sequences hybridize to complementary oligonucleotides of the microarray or detection kit. Incubation conditions are adjusted so that hybridization occurs with precise complementary matches or with various degrees of less complementarity. After removal of nonhybridized probes, a scanner is used to determine the levels and patterns of fluorescence. The scanned images are examined to determine degree of complementarity and the relative abundance of each oligonucleotide sequence on the microarray or detection kit. The biological samples may be obtained from any bodily fluids (such as blood, urine, saliva, phlegm, gastric juices, etc.), cultured cells, biopsies, or other tissue preparations. A detection system may be used to measure the absence, presence, and amount of hybridization for all of the distinct sequences simultaneously. This data may be used for large-scale correlation studies on the sequences, expression patterns, mutations, variants, or polymorphisms among samples.

Using such arrays, the present invention provides methods to identify the expression of the enzyme proteins/peptides of the present invention. In detail, such methods comprise incubating a test sample with one or more nucleic acid molecules and assaying for binding of the nucleic acid molecule with components within the test sample. Such assays will typically involve arrays comprising many genes, at least one of which is a gene of the present invention and or alleles of the enzyme gene of the present invention. FIG. 3 provides information on SNPs that have been found in the gene encoding the enzyme of the present invention. SNPs were identified at 71 different nucleotide positions. Some of these SNPs that are located outside the ORF and in introns may affect gene transcription.

Conditions for incubating a nucleic acid molecule with a test sample vary. Incubation conditions depend on the format employed in the assay, the detection methods employed, and the type and nature of the nucleic acid molecule used in the assay. One skilled in the art will recognize that any one of the commonly available hybridization, amplification or array assay formats can readily be adapted to employ the novel fragments of the Human genome disclosed herein. Examples of such assays can be found in Chard, T, *An Introduction to Radioimmunoassay and Related Techniques*, Elsevier Science Publishers, Amsterdam, The Netherlands (1986); Bullock, G. R. et al., *Techniques in Immunocytochemistry*, Academic Press, Orlando, Fla. Vol. 1 (1982), Vol. 2 (1983), Vol. 3 (1985); Tijssen, P., *Practice and Theory of Enzyme Immunoassays: Laboratory Techniques in Biochemistry and Molecular Biology*, Elsevier Science Publishers, Amsterdam, The Netherlands (1985).

The test samples of the present invention include cells, protein or membrane extracts of cells. The test sample used in the above-described method will vary based on the assay format, nature of the detection method and the tissues, cells or extracts used as the sample to be assayed. Methods for preparing nucleic acid extracts or of cells are well known in the art and can be readily be adapted in order to obtain a sample that is compatible with the system utilized.

In another embodiment of the present invention, kits are provided which contain the necessary reagents to carry out the assays of the present invention.

Specifically, the invention provides a compartmentalized kit to receive, in close confinement, one or more containers which comprises: (a) a first container comprising one of the nucleic acid molecules that can bind to a fragment of the Human genome disclosed herein; and (b) one or more other containers comprising one or more of the following: wash reagents, reagents capable of detecting presence of a bound nucleic acid.

In detail, a compartmentalized kit includes any kit in which reagents are contained in separate containers. Such containers include small glass containers, plastic containers, strips of plastic, glass or paper, or arraying material such as silica. Such containers allows one to efficiently transfer reagents from one compartment to another compartment such that the samples and reagents are not cross-contaminated, and the agents or solutions of each container can be added in a quantitative fashion from one compartment to another. Such containers will include a container which will accept the test sample, a container which contains the nucleic acid probe, containers which contain wash reagents (such as phosphate buffered saline, Tris-buffers, etc.), and containers which contain the reagents used to detect the bound probe. One skilled in the art will readily recognize that the previously unidentified enzyme gene of the present invention can be routinely identified using the sequence information disclosed herein can be readily incorporated into one of the established kit formats which are well known in the art, particularly expression arrays.

Vectors/Host Cells

The invention also provides vectors containing the nucleic acid molecules described herein. The term "vector" refers to a vehicle, preferably a nucleic acid molecule, which can transport the nucleic acid molecules. When the vector is a nucleic acid molecule, the nucleic acid molecules are covalently linked to the vector nucleic acid. With this aspect of the invention, the vector includes a plasmid, single or double stranded phage, a single or double stranded RNA or DNA viral vector, or artificial chromosome, such as a BAC, PAC, YAC, OR MAC.

A vector can be maintained in the host cell as an extrachromosomal element where it replicates and produces additional copies of the nucleic acid molecules. Alternatively, the vector may integrate into the host cell genome and produce additional copies of the nucleic acid molecules when the host cell replicates.

The invention provides vectors for the maintenance (cloning vectors) or vectors for expression (expression vectors) of the nucleic acid molecules. The vectors can function in prokaryotic or eukaryotic cells or in both (shuttle vectors).

Expression vectors contain cis-acting regulatory regions that are operably linked in the vector to the nucleic acid molecules such that transcription of the nucleic acid molecules is allowed in a host cell. The nucleic acid molecules can be introduced into the host cell with a separate nucleic acid molecule capable of affecting transcription. Thus, the second nucleic acid molecule may provide a trans-acting factor interacting with the cis-regulatory control region to allow transcription of the nucleic acid molecules from the vector. Alternatively, a trans-acting factor may be supplied by the host cell. Finally, a trans-acting factor can be produced from the vector itself. It is understood, however, that in some embodiments, transcription and/or translation of the nucleic acid molecules can occur in a cell-free system.

The regulatory sequence to which the nucleic acid molecules described herein can be operably linked include promoters for directing mRNA transcription. These include, but are not limited to, the left promoter from bacteriophage λ, the lac, TRP, and TAC promoters from *E. coli*, the early and late promoters from SV40, the CMV immediate early promoter, the adenovirus early and late promoters, and retrovirus long-terminal repeats.

In addition to control regions that promote transcription, expression vectors may also include regions that modulate transcription, such as repressor binding sites and enhancers. Examples include the SV40 enhancer, the cytomegalovirus immediate early enhancer, polyoma enhancer, adenovirus enhancers, and retrovirus LTR enhancers.

In addition to containing sites for transcription initiation and control, expression vectors can also contain sequences necessary for transcription termination and, in the transcribed region a ribosome binding site for translation. Other regulatory control elements for expression include initiation and termination codons as well as polyadenylation signals. The person of ordinary skill in the art would be aware of the numerous regulatory sequences that are useful in expression vectors. Such regulatory sequences are described, for example, in Sambrook et al., *Molecular Cloning: A Laboratory Manual.* 2nd. ed., Cold Spring Harbor Laboratory Press, Cold Spring Harbor, N.Y., (1989).

A variety of expression vectors can be used to express a nucleic acid molecule. Such vectors include chromosomal, episomal, and virus-derived vectors, for example vectors derived from bacterial plasmids, from bacteriophage, from yeast episomes, from yeast chromosomal elements, including yeast artificial chromosomes, from viruses such as baculoviruses, papovaviruses such as SV40, Vaccinia viruses, adenoviruses, poxviruses, pseudorabies viruses, and retroviruses. Vectors may also be derived from combinations of these sources such as those derived from plasmid and bacteriophage genetic elements, e.g. cosmids and phagemids. Appropriate cloning and expression vectors for prokaryotic and eukaryotic hosts are described in Sambrook et al., *Molecular Cloning: A Laboratory Manual.* 2nd. ed., Cold Spring Harbor Laboratory Press, Cold Spring Harbor, N.Y., (1989).

The regulatory sequence may provide constitutive expression in one or more host cells (i.e. tissue specific) or may provide for inducible expression in one or more cell types such as by temperature, nutrient additive, or exogenous factor such as a hormone or other ligand. A variety of vectors providing for constitutive and inducible expression in prokaryotic and eukaryotic hosts are well known to those of ordinary skill in the art.

The nucleic acid molecules can be inserted into the vector nucleic acid by well-known methodology. Generally, the DNA sequence that will ultimately be expressed is joined to an expression vector by cleaving the DNA sequence and the expression vector with one or more restriction enzymes and then ligating the fragments together. Procedures for restriction enzyme digestion and ligation are well known to those of ordinary skill in the art.

The vector containing the appropriate nucleic acid molecule can be introduced into an appropriate host cell for propagation or expression using well-known techniques. Bacterial cells include, but are not limited to, *E. coli*, Streptomyces, and *Salmonella typhimurium*. Eukaryotic cells include, but are not limited to, yeast, insect cells such as Drosophila, animal cells such as COS and CHO cells, and plant cells.

As described herein, it may be desirable to express the peptide as a fusion protein. Accordingly, the invention provides fusion vectors that allow for the production of the peptides. Fusion vectors can increase the expression of a recombinant protein, increase the solubility of the recombinant protein, and aid in the purification of the protein by acting for example as a ligand for affinity purification. A proteolytic cleavage site may be introduced at the junction of the fusion moiety so that the desired peptide can ultimately be separated from the fusion moiety. Proteolytic enzymes include, but are not limited to, factor Xa, thrombin, and enteroenzyme. Typical fusion expression vectors include pGEX (Smith et al, *Gene* 67:31–40 (1988)), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein. Examples of suitable inducible non-fusion *E. coli* expression vectors include pTrc (Amann et al., *Gene* 69:301–315 (1988)) and pET 11d (Studier et al., *Gene Expression Technology: Methods in Enzymology* 185:60–89 (1990)).

Recombinant protein expression can be maximized in host bacteria by providing a genetic background wherein the host cell has an impaired capacity to proteolytically cleave the recombinant protein. (Gottesman, S., *Gene Expression Technology: Methods in Enzymology* 185, Academic Press, San Diego, Calif. (1990) 119–128). Alternatively, the sequence of the nucleic acid molecule of interest can be altered to provide preferential codon usage for a specific host cell, for example *E. coli*. (Wada et al., *Nucleic Acids Res.* 20:2111–2118 (1992)).

The nucleic acid molecules can also be expressed by expression vectors that are operative in yeast. Examples of vectors for expression in yeast e.g., *S. cerevisiae* include pYepSec1 (Baldari, et al., *EMBO J.* 6:229–234 (1987)), pMFa (Kurjan et al., *Cell* 30:933–943(1982)), pJRY88 (Schultz et al., *Gene* 54:113–123 (1987)), and pYES2 (Invitrogen Corporation, San Diego, Calif.).

The nucleic acid molecules can also be expressed in insect cells using, for example, baculovirus expression vectors. Baculovirus vectors available for expression of proteins in cultured insect cells (e.g., Sf 9 cells) include the pAc series (Smith et al., *Mol. Cell Biol.* 3:2156–2165 (1983)) and the pVL series (Lucklow et al., *Virology* 170:31–39 (1989)).

In certain embodiments of the invention, the nucleic acid molecules described herein are expressed in mammalian cells using mammalian expression vectors. Examples of mammalian expression vectors include pCDM8 (Seed, B. *Nature* 329:840(1987)) and pMT2PC (Kaufman et al., *EMBO J.* 6:187–195 (1987)).

The expression vectors listed herein are provided by way of example only of the well-known vectors available to those of ordinary skill in the art that would be useful to express the nucleic acid molecules. The person of ordinary skill in the art would be aware of other vectors suitable for maintenance propagation or expression of the nucleic acid molecules described herein. These are found for example in Sambrook, J., Fritsh, E. F., and Maniatis, *T. Molecular Cloning. A Laboratory Manual.* 2nd, ed, Cold Spring Harbor Laboratory, Cold Spring Harbor Laboratory Press, Cold Spring Harbor, N.Y., 1989.

The invention also encompasses vectors in which the nucleic acid sequences described herein are cloned into the vector in reverse orientation, but operably linked to a regulatory sequence that permits transcription of antisense RNA. Thus, an antisense transcript can be produced to all, or to a portion, of the nucleic acid molecule sequences described herein, including both coding and non-coding regions. Expression of this antisense RNA is subject to each of the parameters described above in relation to expression of the sense RNA (regulatory sequences, constitutive or inducible expression, tissue-specific expression).

The invention also relates to recombinant host cells containing the vectors described herein. Host cells therefore include prokaryotic cells, lower eukaryotic cells such as yeast, other eukaryotic cells such as insect cells, and higher eukaryotic cells such as mammalian cells.

The recombinant host cells are prepared by introducing the vector constructs described herein into the cells by techniques readily available to the person of ordinary skill in the art. These include, but are not limited to, calcium phosphate transfection, DEAE-dextran-mediated transfection, cationic lipid-mediated transfection, electroporation, transduction, infection, lipofection, and other techniques such as those found in Sambrook, et al. (*Molecular Cloning: A Laboratory Manual.* 2nd, ed, Cold Spring Harbor Laboratory, Cold Spring Harbor Laboratory Press, Cold Spring Harbor, N.Y., 1989).

Host cells can contain more than one vector. Thus, different nucleotide sequences can be introduced on different vectors of the same cell. Similarly, the nucleic acid molecules can be introduced either alone or with other nucleic acid molecules that are not related to the nucleic acid molecules such as those providing trans-acting factors for expression vectors. When more than one vector is introduced into a cell, the vectors can be introduced independently, co-introduced or joined to the nucleic acid molecule vector.

In the case of bacteriophage and viral vectors, these can be introduced into cells as packaged or encapsulated virus by standard procedures for infection and transduction. Viral vectors can be replication-competent or replication-defective. In the case in which viral replication is defective, replication will occur in host cells providing functions that complement the defects.

Vectors generally include selectable markers that enable the selection of the subpopulation of cells that contain the recombinant vector constructs. The marker can be contained in the same vector that contains the nucleic acid molecules described herein or may be on a separate vector. Markers include tetracycline or ampicillin-resistance genes for prokaryotic host cells and dihydrofolate reductase or neomycin resistance for eukaryotic host cells. However, any marker that provides selection for a phenotypic trait will be effective.

While the mature proteins can be produced in bacteria, yeast, mammalian cells, and other cells under the control of the appropriate regulatory sequences, cell-free transcription and translation systems can also be used to produce these proteins using RNA derived from the DNA constructs described herein.

Where secretion of the peptide is desired, which is difficult to achieve with multi-transmembrane domain containing proteins such as enzymes, appropriate secretion signals are incorporated into the vector. The signal sequence can be endogenous to the peptides or heterologous to these peptides.

Where the peptide is not secreted into the medium, which is typically the case with enzymes, the protein can be isolated from the host cell by standard disruption procedures, including freeze thaw, sonication, mechanical disruption, use of lysing agents and the like. The peptide can then be recovered and purified by well-known purification methods including ammonium sulfate precipitation, acid extraction, anion or cationic exchange chromatography, phosphocellulose chromatography, hydrophobic-interaction chromatography, affinity chromatography, hydroxylapatite chromatography, lectin chromatography, or high performance liquid chromatography.

It is also understood that depending upon the host cell in recombinant production of the peptides described herein, the peptides can have various glycosylation patterns, depending upon the cell, or maybe non-glycosylated as when produced in bacteria. In addition, the peptides may include an initial modified methionine in some cases as a result of a host-mediated process.

Uses of Vectors and Host Cells

The recombinant host cells expressing the peptides described herein have a variety of uses. First, the cells are useful for producing a enzyme protein or peptide that can be further purified to produce desired amounts of enzyme protein or fragments. Thus, host cells containing expression vectors are useful for peptide production.

Host cells are also useful for conducting cell-based assays involving, the enzyme protein or enzyme protein fragments, such as those described above as well as other formats known in the art. Thus, a recombinant host cell expressing a native enzyme protein is useful for assaying compounds that stimulate or inhibit enzyme protein function.

Host cells are also useful for identifying enzyme protein mutants in which these functions are affected. If the mutants naturally occur and give rise to a pathology, host cells containing the mutations are useful to assay compounds that have a desired effect on the mutant enzyme protein (for example, stimulating or inhibiting function) which may not be indicated by their effect on the native enzyme protein.

Genetically engineered host cells can be further used to produce non-human transgenic animals. A transgenic animal is preferably a mammal, for example a rodent, such as a rat or mouse, in which one or more of the cells of the animal include a transgene. A transgene is exogenous DNA which is integrated into the genome of a cell from which a transgenic animal develops and which remains in the genome of the mature animal in one or more cell types or tissues of the transgenic animal. These animals are useful for studying the function of a enzyme protein and identifying and evaluating modulators of enzyme protein activity. Other examples of transgenic animals include non-human primates, sheep, dogs, cows, goats, chickens, and amphibians.

A transgenic animal can be produced by introducing nucleic acid into the male pronuclei of a fertilized oocyte, e.g., by microinjection, retroviral infection, and allowing the oocyte to develop in a pseudopregnant female foster animal. Any of the enzyme protein nucleotide sequences can be introduced as a transgene into the genome of a non-human animal, such as a mouse.

Any of the regulatory or other sequences useful in expression vectors can form part of the transgenic sequence. This includes intronic sequences and polyadenylation signals, if not already included. A tissue-specific regulatory sequence (s) can be operably linked to the transgene to direct expression of the enzyme protein to particular cells.

Methods for generating transgenic animals via embryo manipulation and microinjection, particularly animals such as mice, have become conventional in the art and are described, for example, in U.S. Pat. Nos. 4,736,866 and 4,870,009, both by Leder et al., U.S. Pat. No. 4,873,191 by Wagner et al. and in Hogan, B., *Manipulating the Mouse Embryo*, (Cold Spring Harbor Laboratory Press, Cold Spring Harbor, N.Y., 1986). Similar methods are used for production of other transgenic animals. A transgenic founder animal can be identified based upon the presence of the transgene in its genome and/or expression of transgenic mRNA in tissues or cells of the animals. A transgenic founder animal can then be used to breed additional animals carrying the transgene. Moreover, transgenic animals carrying a transgene can further be bred to other transgenic animals carrying other transgenes. A transgenic animal also includes animals in which the entire animal or tissues in the animal have been produced using the homologously recombinant host cells described herein.

In another embodiment, transgenic non-human animals can be produced which contain selected systems that allow for regulated expression of the transgene. One example of such a system is the cre/loxP recombinase system of bacteriophage P1. For a description of the cre/loxP recombinase system, see, e.g., Lakso et al. *PNAS*89:6232–6236 (1992). Another example of a recombinase system is the FLP recombinase system of *S. cerevisiae* (O'Corman et al. *Science* 251:1351–1355 (1991). If a cre/IoxP recombinase system is used to regulate expression of the transgene, animals containing transgenes encoding both the Cre recombinase and a selected protein is required. Such animals can be provided through the construction of "double" transgenic animals, e.g., by mating two transgenic animals, one containing a transgene encoding a selected protein and the other containing a transgene encoding a recombinase.

Clones of the non-human transgenic animals described herein can also be produced according to the methods described in Wilmut, 1. et al. *Nature* 385:810–813 (1997) and PCT International Publication Nos. WO 97/07668 and WO 97/07669. In brief, a cell, e.g., a somatic cell, from the transgenic animal can be isolated and induced to exit the growth cycle and enter $G_o$ phase. The quiescent cell can then be fused, e.g., through the use of electrical pulses, to an enucleated oocyte from an animal of the same species from which the quiescent cell is isolated. The reconstructed oocyte is then cultured such that it develops to morula or blastocyst and then transferred to pseudopregnant female foster animal. The offspring born of this female foster animal will be a clone of the animal from which the cell, e.g., the somatic cell, is isolated.

Transgenic animals containing recombinant cells that express the peptides described herein are useful to conduct the assays described herein in an in vivo context. Accordingly, the various physiological factors that are present in vivo and that could effect substrate binding, enzyme protein activation, and signal transduction, may not be evident from in vitro cell-free or cell-based assays. Accordingly, it is useful to provide non-human transgenic animals to assay in vivo enzyme protein function, including substrate interaction. the effect of specific mutant enzyme proteins on enzyme protein function and substrate interaction, and the effect of chimeric enzyme proteins. It is also possible to assess the effect of null mutations, that is, mutations that substantially or completely eliminate one or more enzyme protein functions.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed various modifications of the above-described modes for carrying out the invention which are obvious to those skilled in the field of molecular biology or related fields are intended to be within the scope of the following claims.

That which is claimed is:

1. An isolated nucleic acid molecule consisting of a nucleotide sequence selected from the group consisting of:

(a) a nucleotide sequence that encodes a polypeptide comprising the amino acid sequence of SEQ ID NO:2;

(b) a nucleotide sequence consisting of SEQ ID NO:1;

(c) a nucleotide sequence consisting of SEQ ID NO:3; and (d) a nucleotide sequence that is completely complementary to a nucleotide sequence of (a)–(c).

2. A nucleic acid vector comprising the nucleic acid molecule of claim 1.

3. An isolated non-human host cell containing the vector of claim 2.

4. A process for producing a polypeptide comprising culturing the host cell of claim 3 under conditions sufficient for the production of said polypeptide, and recovering said polypeptide.

5. A vector according to claim 2, wherein said vector is selected from the group consisting of a plasmid, a virus, and a bacteriophage.

6. A vector according to claim 2, wherein said isolated nucleic acid molecule is inserted into said vector in proper orientation and correct reading frame to express a polypeptide comprising SEQ ID NO:2.

7. A vector according to claim 6, wherein said isolated nucleic acid molecule is operatively linked to a promoter sequence.

8. An isolated polynucleotide consisting of the nucleotide sequence set forth in SEQ ID NO:1.

9. An isolated polynucleotide consisting of the nucleotide sequence set forth in SEQ ID NO:3.

10. An isolated nucleic acid molecule comprising a nucleotide sequence selected from the group consisting of:

(a) a nucleotide sequence that encodes SEQ ID NO:2;

(b) the nucleotide sequence of SEQ ID NO:1;

(c) the nucleotide sequence of nucleotides 241–1368 of SEQ ID NO:1;

(d) the nucleotide sequence of SEQ ID NO:3; and (e) a nucleotide sequence that is completely complementary to a nucleotide sequence of (a)–(d).

11. A nucleic acid vector comprising the nucleic acid molecule of claim 10.

12. An isolated non-human host cell containing the vector of claim 11.

13. A process for producing a polypeptide comprising culturing the host cell of claim 12 under conditions sufficient for the production of said polypeptide, and recovering said polypeptide.

14. A vector according to claim 11, wherein said vector is selected from the group consisting of a plasmid, a virus, and a bacteriophage.

15. A vector according to claim 11, wherein said isolated nucleic acid molecule is inserted into said vector in proper orientation and correct reading frame to express a polypeptide comprising SEQ ID NO:2.

16. A vector according to claim 15, wherein said isolated nucleic acid molecule is operatively linked to a promoter sequence.

17. An isolated nucleic acid molecule consisting of a nucleotide sequence selected from the group consisting of:

(a) a nucleotide sequence that encodes an amino acid sequence having at least 99% sequence identity to SEQ ID NO:2;

(b) a nucleotide sequence having at least 99% sequence identity to SEQ ID NO:1; and (c) a nucleotide sequence having at least 99% sequence identity to SEQ ID NO:3;

(d) a nucleotide sequence that is completely complementary to a nucleotide sequence of (a)–(c).

18. A nucleic acid vector comprising the nucleic acid molecule of claim 17.

19. An isolated non-human host cell containing the vector of claim 18.

20. A process for producing a polypeptide comprising culturing the host cell of claim 19 under conditions sufficient for the production of said polypeptide, and recovering said polypeptide.

21. A vector according to claim 18, wherein said vector is selected from the group consisting of a plasmid, a virus, and a bacteriophage.

22. A vector according to claim 18, wherein said isolated nucleic acid molecule is inserted into said vector in proper orientation and correct reading frame to express a polypeptide having at least 99% sequence identity to SEQ ID NO:2.

23. A vector according to claim 22, wherein said isolated nucleic acid molecule is operatively linked to a promoter sequence.

* * * * *

SEQUENCE LISTING

<160> NUMBER OF SEQ ID NOS: 4

<210> SEQ ID NO 1
<211> LENGTH: 1781
<212> TYPE: DNA
<213> ORGANISM: Human

<400> SEQUENCE: 1
ggcggcttcg gttgcgggtc ggaacggcgc tgctctgcgg ggccggtcca ggctggcagc 60
tgccggcgct tggcggtgag ggcgggctcc cgagtggccc cccaccgaag gcggcgcggc 120
ggctcctcac tcatcccaga tgttggttat ctttctgaag tagactgtcc atggcctgaa 180
cattttccga aaatcatttt gagcaaaata tctgtttaat aacaagataa ccacatcaag 240
atggttggaa agctgaagca gaacttacta ttggcatgtc tggtgattag ttctgtgact 300
gtgttttacc tgggccagca tgccatggaa tgccatcacc ggatagagga acgtagccag 360
ccagtcaaat tggagagcac aaggaccact gtgagaactg gcctggacct caaagccaac 420
aaaacctttg cctatcacaa agatatgcct ttaatattta ttggaggtgt gcctcggagt 480
ggaaccacac tcatgagggc catgctggac gcacatcctg acattcgctg tggagaggaa 540
accagggtca ttccccgaat cctggccctg aagcagatgt ggtcacggtc aagtaaagag 600
aagatccgcc tggatgaggc tggtgttact gatgaagtgc tggattctgc catgcaagcc 660
ttcttactag aaattatcgt taagcatggg gagccagccc cttatttatg taataaagat 720
ccttttgccc tgaaatcttt aacttacctt tctaggttat tccccaatgc caaatttctc 780

-continued

```
ctgatggtcc gagatggccg ggcatcagta cattcaatga tttctcgaaa agttactata    840

gctggatttg atctgaacag ctatagggac tgtttgacaa agtggaatcg tgctatagag    900

accatgtata accagtgtat ggaggttggt tataaaaagt gcatgttggt tcactatgaa    960

caacttgtct tacatcctga acggtggatg agaacactct taaagttcct ccagattcca   1020

tggaaccact cagtattgca ccatgaagag atgattggga aagctggggg agtgtctctg   1080

tcaaaagtgg agagatctac agaccaagta atcaagccag tcaatgtagg agctctatca   1140

aaatgggttg ggaagatacc gccagatgtt ttacaagaca tggcagtgat tgctcctatg   1200

cttgccaagc ttggatatga cccatatgcc aacccaccta actacggaaa acctgatccc   1260

aaaattattg aaaacactcg aagggtctat aagggagaat tccaactacc tgactttctt   1320

aaagaaaaac cacaggtact gtgtctgctt tttcctcctg atgtatacta gattggctct   1380

tgcattgaag taatattttt aaagagataa tgaaattaaa aagacagaaa caagaaaacc   1440

aaaaagaaaa gaagaaaagg gatagtgata tgtgctgggg aagaaagatc agcgtctggg   1500

acttgttgat tttaacaata atttaacaca gtcttaattt cagagagctc agtgtctccc   1560

aaaaccaggg aaatacttta ttgataacca aattctgatt gcttgaggtc ctgcacaagc   1620

cgcccagtgg gtaaagctgc tccagcgttc cagtgcctaa tttgaaataa aaatgttcag   1680

cgaccctctc tgttcctaaa aaaaaaaaaa aaaaaaaaaa aaaaaaaaaa aaaaaaaaaa   1740

aaaaaaaaaa aaaaaaaaaa aaaaaaaaaa aaaaaaaaaa a                       1781


<210> SEQ ID NO 2
<211> LENGTH: 376
<212> TYPE: PRT
<213> ORGANISM: Human

<400> SEQUENCE: 2

Met Val Gly Lys Leu Lys Gln Asn Leu Leu Leu Ala Cys Leu Val Ile
 1               5                  10                  15

Ser Ser Val Thr Val Phe Tyr Leu Gly Gln His Ala Met Glu Cys His
            20                  25                  30

His Arg Ile Glu Glu Arg Ser Gln Pro Val Lys Leu Glu Ser Thr Arg
        35                  40                  45

Thr Thr Val Arg Thr Gly Leu Asp Leu Lys Ala Asn Lys Thr Phe Ala
    50                  55                  60

Tyr His Lys Asp Met Pro Leu Ile Phe Ile Gly Gly Val Pro Arg Ser
65                  70                  75                  80

Gly Thr Thr Leu Met Arg Ala Met Leu Asp Ala His Pro Asp Ile Arg
                85                  90                  95

Cys Gly Glu Glu Thr Arg Val Ile Pro Arg Ile Leu Ala Leu Lys Gln
            100                 105                 110

Met Trp Ser Arg Ser Ser Lys Glu Lys Ile Arg Leu Asp Glu Ala Gly
        115                 120                 125

Val Thr Asp Glu Val Leu Asp Ser Ala Met Gln Ala Phe Leu Leu Glu
    130                 135                 140

Ile Ile Val Lys His Gly Glu Pro Ala Pro Tyr Leu Cys Asn Lys Asp
145                 150                 155                 160

Pro Phe Ala Leu Lys Ser Leu Thr Tyr Leu Ser Arg Leu Phe Pro Asn
                165                 170                 175

Ala Lys Phe Leu Leu Met Val Arg Asp Gly Arg Ala Ser Val His Ser
            180                 185                 190

Met Ile Ser Arg Lys Val Thr Ile Ala Gly Phe Asp Leu Asn Ser Tyr
```

-continued

```
        195                 200                 205

Arg Asp Cys Leu Thr Lys Trp Asn Arg Ala Ile Glu Thr Met Tyr Asn
    210                 215                 220

Gln Cys Met Glu Val Gly Tyr Lys Lys Cys Met Leu Val His Tyr Glu
225                 230                 235                 240

Gln Leu Val Leu His Pro Glu Arg Trp Met Arg Thr Leu Leu Lys Phe
                245                 250                 255

Leu Gln Ile Pro Trp Asn His Ser Val Leu His His Glu Glu Met Ile
            260                 265                 270

Gly Lys Ala Gly Gly Val Ser Leu Ser Lys Val Glu Arg Ser Thr Asp
        275                 280                 285

Gln Val Ile Lys Pro Val Asn Val Gly Ala Leu Ser Lys Trp Val Gly
    290                 295                 300

Lys Ile Pro Pro Asp Val Leu Gln Asp Met Ala Val Ile Ala Pro Met
305                 310                 315                 320

Leu Ala Lys Leu Gly Tyr Asp Pro Tyr Ala Asn Pro Pro Asn Tyr Gly
                325                 330                 335

Lys Pro Asp Pro Lys Ile Ile Glu Asn Thr Arg Arg Val Tyr Lys Gly
            340                 345                 350

Glu Phe Gln Leu Pro Asp Phe Leu Lys Glu Lys Pro Gln Val Leu Cys
        355                 360                 365

Leu Leu Phe Pro Pro Asp Val Tyr
    370                 375


<210> SEQ ID NO 3
<211> LENGTH: 116592
<212> TYPE: DNA
<213> ORGANISM: Human
<220> FEATURE:
<221> NAME/KEY: misc_feature
<222> LOCATION: (1)...(116592)
<223> OTHER INFORMATION: n = A,T,C or G

<400> SEQUENCE: 3

nnnnnnnnnn nnnnnnnnnn nnnnnnnnnn nnnnnnnnnn nnnnnnnnnn nnnnnnnnnn     60

nnnnnnnnnn nnnnnnnnnn nnnnnnnnnn nnnnnnnnnn nnnnnnnnnn nnnnnnnnnn    120

nnnnnnnnnn nnnnnnnnnn nnnnnnnnnn nnnnnnnnnn nnnnnnnnnn nnnnnnnnnn    180

nnnnnnnnnn nnnnnnnnnn agattctgct cggtagcagg ctggacacac aggcagggtt    240

tctatgttgt agttcttttc caggaaacct cagtctttgc tcttaaagcc tttacctgtt    300

agatgaggcc ttcctgtatt atggagggta atccacttta ctagaaatct gttgatttaa    360

gtgttaatca catctaaaat ataccttcac agacatatct agattggtgt ttgatcaaac    420

aactggacac caaagtctag ccaagttgac acataaaatt aactgtcaca cttgccttct    480

gaggattcag ggtaaattat tttggtgtac atgtagtctg gttgctgtct gtttcccact    540

gtataccctt gctctagcta aactagcagc tccagctgtt tcatatacat gcttctgctt    600

ttgcacatcc atgtctttgg tcatagtgta cctgcagcat ggagtgcttc ctgtgtccag    660

atcttacctg tccttctgag gattagatca cagatactta tacatacaat tttgtttgca    720

gcctatacac tagctttcct aaacttcttc ctgtcaccta attatgctgt gttctgtctt    780

gccattgtgc ttttgcacac aagttccttt ggtttagaat atccctccct ctgtcttttc    840

tttcttaaag agacagggtc tcagtgtggg ctggtctcga actcctgagc tcaaatgatc    900

ctcccatctc ggtctcccaa agagctgtga ttacaggcgt aagctgctgc acctggtcct    960
```

-continued

```
tccttcctac tttctgtaaa acttttacag cttcctcagg tcaattacat gctccttttc   1020
attatgctcc cattgtccct ttgcgtattt ccacggaggc actcatcaca ttttattgtt   1080
attgtttaca tatctgtctg tcaaaaggct ttgttttcca acagcagaag ttactatact   1140
gttttccttt tcaaagttgg tcctcagtcg agcctatctg gtctgtagta cctaaataaa   1200
ttgtgggata ataaactgaa tctctgttaa agatttggaa gttgtttcat atttcttcta   1260
taatttctca ttgttagaat gtggagataa tgactgcttg gagataaagc aagtctgaat   1320
agcagagatc agccttgggt tggactccag acattcttgg gcttattaaa tatttggttg   1380
actcactgat agaaatagtt ttatttattt tccattcttt accaggtaca tagcttcaaa   1440
attacttcat taacaaaagc tgtttctgat tataaacatt gatttatttt tactcaaatt   1500
tgtatatact gtatatactg agtaaaacaa attttactca tttgtttttg ttttgttttg   1560
ttttgttttg tttttttgag acagagtctt gctttgttgc ctaggctgga gtgcagtggc   1620
atgatctcag ctcactgcaa gctctgcctc ctggattcat gccattctcc tgcctcagcc   1680
tcccgagtag ctgggactac aggcacccgc caccatgccc agctaatttt ttttgtattt   1740
tttttagta gagatggggt ttcaccgtgt tggccgggat ggtctccatc tcctgacctc    1800
gtgatccgcc cgcctcggcc tcccaaagtg ctgggattac aggtgtgagc caccgcgccc   1860
ggtctcaatt ttgttttaag aatatcaaag aatccaagac tgtttcagct tctttctacc   1920
taaaatgcag tggtgataac tggtgactga tttgtaagca atctcaatgt aatgataaat   1980
aacctttcc tttctctact agatgttggt tatctttctg aagtagactg tccatggcct    2040
gaacattttc cgaaaatcat tttgagcaaa atatctgttt aataacaaga taaccacatc   2100
aagatggttg gaaagctgaa gcagaactta ctattggcat gtctggtgat tagttctgtg   2160
actgtgtttt acctgggcca gcatgccatg gaatgccatc accggataga ggaacgtagc   2220
cagccagtca aattggagag cacaaggacc actgtgagaa ctggcctgga cctcaaagcc   2280
aacaaaacct ttgcctatca caaagatatg cctttaatat ttattggagg tgtgcctcgg   2340
agtggaacca cactcatgag ggccatgctg gacgcacatc ctgacattcg ctgtggagag   2400
gaaaccaggg tcattccccg aatcctggcc ctgaagcaga tgtggtcacg gtcaagtaaa   2460
gagaagatcc gcctggatga ggctggtgtt actgatgaag tgctggattc tgccatgcaa   2520
gccttcttac tagaaattat cgttaagcat ggggagccag ccccttattt atgtaataaa   2580
gatcctttg ccctgaaatc tttaacttac ctttctaggt tattccccaa tgccaaattt    2640
ctcctgatgg tccgagatgg ccgggcatca gtacattcaa tgatttctcg aaaagttact   2700
atagctggat ttgatctgaa cagctatagg gactgtttga caaagtggaa tcgtgctata   2760
gagaccatgt ataaccagtg tatggaggtt ggttataaaa agtgcatgtt ggttcactat   2820
gaacaacttg tcttacatcc tgaacggtgg atgagaacac tcttaaagtt cctccagatt   2880
ccatggaacc actcagtatt gcaccatgaa gagatgattg ggaaagctgg gggagtgtct   2940
ctgtcaaagt gagtagaaga tacgtttttt attttgactc tatatttagc taataatgat   3000
ctatacatat gtatgtatgt gttttatgta tatatgtgtg tatgttcctg tgtgtatata   3060
tagaaactga agaccttttc tggaacagat acagcttcat tgatgaggtt tcttttttta   3120
ttaattctct actagtttat tacagatgtt cacttattta tacttcattt tttcatttat   3180
atatcgtggc cctctttatt tgtttgatgg atacaaaccc accttacagg cggtgaaaag   3240
ccttcttcag ggtctcagac cttaatgcca atcattcagt tttagtggct tctgatttct   3300
aatttctaga tattgttgtt aatgaggata gttggctttt gtgtggatta aggttaaaat   3360
```

-continued

```
caggaagtgc atatatcatg ttaatgagca catagtgaat tataagcatt ttgaaatttt   3420
tagtggtaga gaaaaataaa agcttcgtct aacctaatct cttcatttta tggacaagaa   3480
gactgagtca cagtaagatt aaaacgattt gttcagattt agatggcaag gccagaattc   3540
gaatctgtgc cttggtctca atgaggtcgt gcttttctcc gtggcatttt actacgtgtt   3600
gtgcttcctt tgtcatctga aggatataac ctctcttatt ttttacaaaa ggctagagaa   3660
tctccaaaat ttggaagcct aatccataca agaagttcct tggattcaaa acttctcaaa   3720
tgatgatttt tagcattttg cttcttttct tatgaagtga caactagtat accctctaac   3780
ctgtcttgat gacttatata cctggaatga ggatataaaa atggaaacta ctattaaatt   3840
caggtagcat ctcttcatga agaagagttg gctataacta aattttattt ttgttttttt   3900
tcttttatca aagtaatata taacacctgt aaaaaagaaa tatataaggt gttatatata   3960
catatataaa aagaaatata aaaggtgtta tatatacttt ttatcaaagt aatatataac   4020
acctgtaaaa aatactttcc ttgtgtgccc ttcttacttt caccaaggaa tatctgctta   4080
attttttttt gctgtataga acttgtatag taaatagatt tcttatgtag ataatctcaa   4140
aggaacagct gcctgcctgt accaagcttt caattattga ttataagtta tgacatacca   4200
tcattgtagt ggctctaggt tgtttttatt gattcaaaga aaatttcagc tctggctact   4260
ctgattgcag tttattatta tttccagata atagactata attgattttt aatcacctgt   4320
attaggtatt tcagtctttg tgcttgtatg ttggcccggc accgatgcca cctacatctg   4380
ctaatataaa aggaggccat tagaccacca gcctcttcag tagggattaa agagatatgc   4440
ttaagttaaa ttttggtgct aatcaggaag agaacatttt gtgtatatac ttgctatgtt   4500
taaggtaaac ataaaggcca agaaaattca tagaaattat attatgaatt aatgaatttt   4560
agaaagtaaa gagatgttac ttagcatttc agtatgtgga atggaggccc tgtaaggctc   4620
tatgtttttt caaaaattaa catgtcacaa tcatgagtag aacctaccat gcttattcca   4680
agatttttgc attggggtct ttctagtttg gggctattat ggatcaaagt tgctaagaac   4740
gttcttgtac attactttg gtggatatag cattcatttc ttttaggtat ataccaatga   4800
atagaattgc tggatgacaa ggggtgtgtg tgtgtgtgtg tgtgtttgtg tgtgtgtgtg   4860
tgtgtttaac agatactttc taacagtttt ccaaagtgtc tctatcattc atgtatggct   4920
gtactgtaaa tgaacatgtt ctagttgcct cacatcttta ccaacacttg gtattttagt   4980
cttttctggt aggctacaat tgttttttaa aacttaaaag caaaataata tttgaacccc   5040
tttttgaaag aaaatcttac ccagaattcc aatataaaac aagagctgct ttggttgagg   5100
tgagtctaaa ctagaccata tttccttctt ttgtttttga gatggagtct ctctgtgtca   5160
tccaggctgg agtgcagtgg catgatctct gctcactgca acctccatct cccaggctca   5220
ggtgatcctc ccatctcagc ctcccgagta gctgggatta caggcacgca tcaccatgcc   5280
cagctaattt tttttttttt ttttttgtat ttttggtaga gccccatgtt ggccagactg   5340
gtctcaaact cctgagttca ggcaatccat gtacctcagc ctcccagagt actggggtta   5400
caggtgtgag ccactatgcc tggccagcca tacttctttt ttaaagattg aatccctact   5460
ctcaaaaact gctttttggg gaataaggca gaaaatacaa aattattaca tagtgccaag   5520
ttgtaaatat cccatgttca ttataataaa gaatttattg cccacagtca gtcatcctgt   5580
gtgcttttcg ttttttaaac atttttattc tgggaaattt tttttttttt ttttttttct   5640
tcgagacgga gtcttgctct gtcgcccagg ctggagtgca gtggcatgat ctcggctcac   5700
```

-continued

```
tgcgagctcg gcctcccagg ttcacgccat tctcctgcct cagcctcctg agtaggtggg   5760
actataggtg ccccccacca cgcccagcta atttttttat ttttattttt agtggagaca   5820
gggtttcgcc atgttagcca ggatggtctc gatctcctga cctcgtgatc tgcctgcctc   5880
ggcctcccaa agtgctggga ttacaggcgt gagccaccgc gcctggccga aaattgttta   5940
aagtaaatat tttaatactt agttcagtat tacttagtat tacaatactt aaatatttag   6000
gcagccttga aggtttgaag atgtcaccag atggcctagg gatacttgta gaagctgttg   6060
aaaatagaga tatcaggaga ccttcacagt tctgcctctt atcttgttaa tttttgagag   6120
ttaaccttta ctttgcttag aaatttccag ttatttacag tcagggtggc atctcttgcg   6180
tctctgggct gttccagtta cagaaaagtc agaggctcct gctcaagtat cttgaaaaga   6240
aagcagaagt aaagtttgag gctatttacg ttgccctctt ctcatggttt gtggaatttt   6300
ttgtggaatt ttagttgtct ccatcaggga acttttggga agttacaaga gcgtacagtt   6360
acttctgtta ttaaactcat tatgatacca tgaaattacg tggaacaaat aaaagtcaag   6420
tttgctaggt caaaagagca aatccagaaa agcagattaa tgtaacagtg acgcttagac   6480
aacaagtaca ggaatcacaa ctacaattca gagacgagtt cttatctaca cttagggcag   6540
aaagagaata tagcaactat taaacacaaa taaattagaa tgaaaaagat aatagtagtg   6600
ataagtacaa gagaacaaat aagaacatga aaactgacac cctacagctt ctaataagta   6660
aagcagacaa aaaatcctct aaatcagatc aaaagcaaag aaagactgaa taaatgagtg   6720
aaaataatgt aaaaaggttt ttggaaatgg agacattttt gaggaagtag gaagaataat   6780
tagtaattta ttaaattcat aactttcttt ttaatataga aagtgaaatt tagttttgtt   6840
aaagaaaaaa ttattcagtg atacctgcta aggcatgagg cagtgtttat ttagcaccac   6900
tgcaggaggt acagggacca ctgcagtcgg gtcttgcagt ggggaataga gattggactt   6960
aactctgaat acagcatggg caagtgagaa tttgtagcca gagagtaagg tgagggtcag   7020
tggatggaaa attactacga ggaaacatca ggggtcaggg gcattctggc taaatttacc   7080
tgataggatt ctcactgaag acaggccggg gtgatcagac atcacctgga gggtggtgga   7140
ggatgagaaa cccgatcaga tcctgagagt gattagatat caagggtagg aggttgcttg   7200
ctaaactgcc ttagcagggt tactttgcta aaactggatt ttataaagaa gtgcacagat   7260
ggtcctagga gaaggttcag gagcctgact gaagtttggt cacacaaaga atctttgtca   7320
gtttggaaac ttaaaattct tatgtcttat gggattaaca gaaagataac tcaatagcca   7380
cttgaaattc ttctgaaatt taaggataac aagaatattt tgagcaagtg aagagaatga   7440
cagaccatat tcacaaagat atgagcatta atagcatgga aaattaacag caggcaaatt   7500
aggatcacct gagctctact agctcagtct gaaatatccc agaagaattt tataaatatt   7560
acatgtggtg ttttgttttt gtttttgttt tcatgaagct atcagagaac aagtctgttt   7620
atttgtgaaa acttctcctt tgtgaagcac tgcctaagga tgctattggg ctattggggt   7680
tgggtctttt ttggtttttt ttttggagac agggtcttgc tccatcaccc aggctggagt   7740
atagtggcaa gattgtagct cactgcagcc ttgaactcct gggttcaaat gatcttccca   7800
ccttagcttc ctgttagtag ctgggattac aggtgcatgc catcatgcct ggctaatttt   7860
tttttttttt tttttttttt ttttttgggg gagacagggt ctcactatgt gttacccagg   7920
ctggattcga actcctggcc tcaagcagtc ttcctgccat ggcctcccaa agtgctggga   7980
ttaccgctgt gagctgccat gcccagcctc cttttacaag ctatattgaa gagagaagtg   8040
actgagacat cttagctgga gaggaggaat tgaataaaca agggatacaa gtgacagagt   8100
```

-continued

```
aaaatgggct gtgaaaggaa atcagagagc tgatgaaaca ttgcatttca aagtgtgtca   8160
gggaaagatt gagaagaagc agaaccagaa catgaattaa taaggcaaca tttgtacttt   8220
tcttggagaa tatagcaatt ggtagcaaaa attagaagtt ggatatcaga tcatttatta   8280
gtttgattag atttctctac aaatagtaga gatccaaaat aacaaagatt tccaaataat   8340
gactactatg tagaaggcag accagggctg ctttgtcagc tttgcagtca tctggcattt   8400
aggctgcttc cagcttttgt ctccatcatc cccaggatcc aagttggagc gccagtcatt   8460
tcatctacat tctaagcagc acagcagggg tggatgtgtg taaaacaaat ggcgtttagt   8520
attttttgag gatatttctt agaagcttcc aggtagtact tcttgctttt cactggccat   8580
aactggggtt ccttttacta agaaaaatca attggatatt gggataggca gatagtagtc   8640
tctgctacat tattgagcac ctactatgtg ccagacactg tgttagctcc ttgagataaa   8700
aggtctttgc cttaaaggaa catatgatct aatagaagac ttagattcat atataatgca   8760
gggttaagaa ctatggtcac cactgcttct tcattggtga ataattaaaa acaaacaaaa   8820
agaggccagg cacccagtgg ctcacacctg taatcccagc actttgggag gctggggtgg   8880
gcagatcacc tgagggcagt agttcaagac cagcctgacc aacatggtga aaccccatct   8940
ctactaaaaa tacaaaaatt agccaggggt ggtggcccat gcctgtaaac ccagctactc   9000
gggaggctga ggcaggagaa tcacttgaac ctgggaggtg gaggttccag tgagctgagg   9060
tcgtgccact gcactccagc ctgggtgaca gagcaaaact ctgaacaaca acaacaacaa   9120
caaagaacta tggaaaacca aggagaggtg cctaacccag tctgaggtgt tcagagaggt   9180
catcttgggc aatgtgtcat gaaactgagc cctaaagaag ggtttcctca agcttggtat   9240
gacattttag tcagataatt atttgttgtg gcagccatcc aagatgatca acagataaag   9300
ggaagcgcat ttagttttga cttagggaat attgtgctcc ctgggtgacc catggttaag   9360
gcgctgtagt tcttccttga ctgtccagaa tgtctttcct tttccttagc caatgagcca   9420
cccaagaaat gttactcctg ggagaagcct gtgcctaact gtggtttaca gaattcaaag   9480
ggaagaggta gtatggagga ctccttgtgg cttcactcct ggcccaaccc agggcctcaa   9540
aaggacctaa ggaacaacta cgccctgtta tgcctgacct atggacccta ccctcttgac   9600
catataatgg aagtcagcta agcttagtcc cacctggacc tagaacatgg tgtttgtttc   9660
ccataggtga atatattttt gaaaaatata tttttgaaaa ataagtaaaa caaaaccaaa   9720
tcaggaaata atcattgaga agttacaata tgaacacctt aacaaagatg agtaacaatg   9780
tggtgttttt tgctagagag ttcatttcca ggcaggaagt agtgtgaaac aaggtttgag   9840
agaaatgatg cggaccaggc tttggagggc cttatatttt aagctaaaga tattgaattt   9900
taagccagtt gccttcagac ttctcttatt agtggagcac cctttttttc aagtgaaatc   9960
ttgttcggaa ccttggtaga tgatgtactt ggaagtgaag tggccctcct ttaggcagca  10020
tttaattttg gttggattta acaaagaaaa ctgaagtgaa gctcatggaa ttgcaaaact  10080
acaattttgt ttttaaaaga aaaacattga ttgtaatgtg taaaatttac aaaactgata  10140
cacttttaat tgggattata ttggtttata aaaacattta gtgttttttt tttttttttt  10200
tgagacagag tctcgcactg tcttctgggc tggagtgcaa tggcatgatc tcggctcact  10260
gcaacctctg cctcacgagt tcaagtgact cttctgcctc agcttcctga gtagctggga  10320
ttgcaggtgc gtgccaccac acccagctaa tttttttttt gtgtgtgtgt ttttaataga  10380
gatggggttt caccatgtta gccaggatgg ccttgatctc ctgacctcat gatccgcctg  10440
```

-continued

```
cctcggcctc ccaaagtgct gggattatag gcgtgagcca ccgtgcctgg ctcaaaacat  10500
ttagttttaa taggcatttt agggtatgtc ttagtccatt tgggctgcta taacaaaata  10560
ccacaaactg ggttcttaca aacacagaag ttgatttctc gcagttttgg aggctgggat  10620
gtccaagatc aggcactgat ggattcagca tctagtaagg gcctgctgtc tggttcatag  10680
atggcacctt gtgtcctcac atggtaaagg aggtgaagaa tctctccctg gcctcttttg  10740
taagtgcact aataaggaca cttcccaagt tcccatctcc taatacagtc acattggtga  10800
ttaggtttta acatgaattt ggggggacac aaacattcag tccataatga ggtataaaac  10860
ttagaagatt cctgtttttt ttaaaaaaat tctttttttt ttttaagatt taaaatgtaa  10920
gcctagttca gagtattttg ccaagatgaa gtgtagggca aattggatct ttaagtagag  10980
taacctatta cattgattaa ctactgtcaa agaaaagcca agcacatcaa gggaattatg  11040
gttggtaccc atccagatat tatacatgaa ttcatggttc ctccttggtc cttttctgaa  11100
ttacctgtct aatgaagaat tatttcattg tttttgaaaa catccttaca tttcctcatt  11160
gctgaaaatc atgttttcaa acatcaacca ttcatcacaa tcacatacag aacctttaaa  11220
agacctaaaa tttctgattc aggaggtctg ggataggccc aagaacttgc gcttctaaca  11280
ggtttcccgg tgatgctaat gttcctggcc tgatttcact ttgagaacca ctgcttaaaa  11340
tcatgctacg ttttgtttgc ttcatttgtg gactcagact ttcttgcccc tacagcctgg  11400
gctgcagcca cactgaaata attgtagcta caattattgc cacaccattt atttaatcag  11460
ttcctttgaa tgtgttgttt cctgtgcctg caacaccttt ctctcacttc atttcttcat  11520
ctgaccaact catggttgta tttcaagatt tagttcaggt ttcctttccc taaggaagat  11580
ctctccaagg ccccctctg tctgggatgt acttcctatg ctttcatgag acacttggca  11640
aatggaaaag ggttgatact ttgaagctgg ctagactttg tttaaagtct ttcattgaca  11700
ctaactggtt ttgtaacatt gcatcaaata ctatctctct ccgtgtctcc attttcttat  11760
ctataaaaca gggaagatgg tgatgatggt aatgatacca tccaacatct actgaacatt  11820
tgttatgtgc caggcagtat gctgagctct ctgtgtgcct tatctcattt agtttttata  11880
tttacccttt cacactcacc cataggtgcc ttaaacatct taattttata gatgagggac  11940
ttgaggctcc cagaagttga ggagcttgtc ctccgtccca cagttggaag atggtagagc  12000
caggctgtgg actcaggtct ttgtcttcat ctatactttt agctcttgtt gtatatactt  12060
acagcattta tgaagacaaa ctaaaacagt gtgacagtgg ctaagcacac gttttagagt  12120
cagacagaca taggttcaaa tcctagcact gtcctttatt gattatgtga ccttgagtga  12180
gttatttggt tttgtctagt cttggttatc tcatctttcc tttagttttc ttatcctgga  12240
aatgggaatg ataatatgtt agatccccct tatctgcaga tgatatgttc caagacccca  12300
gtggatgccc gaaaccccac tgatggtacc gagccctata tatactatgt tttttcctgt  12360
gcatatatac ctgtggttaa tttataaatc aagcacagta agattaacag cagtaactaa  12420
ttataaagta gaacaattat aacaatatgc cagtattact acttttgagc tttatggcca  12480
tgattaagtt aaacaagagt tacttcaacg taagcactgc gatactgcta cagtccatct  12540
gataacagag ggctactaag tgactaatgg tgggtagtga gtgtacattg catggacgtg  12600
ttgaacaaag ggatgattta catcccagtc tagacagagt gagacaatgt tagatttcat  12660
catgctactg agaatgacat gcaatttaaa acttatgagt tgtttatttc tggagtttcc  12720
catttaatgt tttcagacca cagttgactg cagagaacta cctgaaactg tggataaagg  12780
cttactgaaa tagtatccat taaggatgat aataataact atccataggg ttgtcgtgag  12840
```

-continued

```
gatttagtta gaatgactat aaagccctta gccaagtgcc tggtatataa tgagaggttg  12900
aaaatgttac ctgttgtctt tattattata ataataagga tgataataat accgattgca  12960
gatgatggta agtagtattt atagagttgt gagaattaaa ttactacaaa gcctttagaa  13020
tagcacctgg cacatagaaa ttgttcaaag tggtacttat tagtatgtta tttttattgt  13080
cgaacgctta tgcactgttc ccctccctct ccccatccca aaataatgag tgtgaaacac  13140
ctaggttagt agcaagtgca ccacaggctt ttgttaatgt tcttacacat gctcctgtaa  13200
gcttgtttag ggcaaaggta gtcttgaagt catgaaatgt ttgtctcaat gaagcaaagt  13260
aagcacccga tttgaatagc tctagtagga aactaacatg gcaggttggg aatgctggca  13320
ttacagtaac aataatctct gaaactactt ggaggtgacc tttgatattt cattgtcatg  13380
ttttcccttt ttcctttgtt tctttgttta gtttgcctgt tggtaaactt tatataaatg  13440
ggatcatggt ctgtgttttt ttcggtcagg ttcttttttt ttttctctgg cctaacattt  13500
tcttttgaga tttacctgtg ttgtggtata tagctatatc atcagtttta attgccaaaa  13560
tactattctc tggtataata tagattattt atacattttt actattgatg aacatttgga  13620
ttgtttttag tttggagcta aggacatttt tgaaggtgtt tccttcaaga gtttctctaa  13680
gatatacact ttggattaga atagctggat tatgagcagt atgcatattc cacttgtttt  13740
tctttttgt tttttgagat ggagtctcgc tctgtcgccc aggctagagt gcagtggtgc  13800
gatctcggct cactgcaagc tccgcctccc gggttcacgc cattctcctg cctcagcctc  13860
ccaagtagct gggactacag gcgcctgcca ccacacccgg ctattttttt gtatttttta  13920
gtagagacag ggtttcactg tgttaatcag gatggtctcg atctcctgac ctcgtgatct  13980
acccgcctcg gcctcccaaa gtgctgggat tacaggcttg agccaccgcg cccagccttt  14040
tttttttttt tttgagacgg agtctcgctc tgtcgcccag gctggagtgc agtggcgcga  14100
tctctgccca ctgcaagctc acaccattct cctgcctcag tctcccaagt agcagggact  14160
gcaggcgccc accaccatgc ccggctaatt ttttgtattt ttagtagaga cggggtgtta  14220
gccaggatga tctcgatctc ctgaccttgt gatccgccca cctcggcctc ccaaagtgct  14280
gggattacag gcgtgagcca ccgtgcccgg ccagtagctt atcttttaac ttccttttta  14340
atatcttttt tgtcaatgac ctcactttaa cagaattaag aaaaataaga aaaatctttt  14400
gatgaattta agttttaaac ttgtatttac caatcttttt ctttagaatt ttttgtaaaa  14460
aaattcttcc atactctgag gtcataaaaa tagtttccca tgttttttcc aaaacttaaa  14520
acaaatttct tttcatgtta atctggaatt tattaatcaa tatggaattt attttcttgt  14580
gtgaggtgca gattcatttt catatttttt ctataaagat gaccagtttc ccggaaccat  14640
ctatggaaat acagtcagta ctttggatcc atgggttcca catccataga ttcaactaac  14700
ctcaggtcaa aaacattcag gggggaaaaa ttccacagag ttcccaaaat tacaacttga  14760
gcttgccatg tgctgaatac tacattgaat ctacgtgaat gaagtgatgt gtgggcatcg  14820
ttaggttagg tattataagt aatctagaga tgatttaaag tataagggaa gatgtatgta  14880
ggttatatgt aaatactgtg ccattttata tgagagattt gggcatctgt ggattttggc  14940
atttgtgggg agtccagaaa cctaggggat tgtcctaatg acatgcagta ccagctaggt  15000
taaacatcag gtttccatgt atgcattatt cttttagtga gatcgctttc tttttttttt  15060
tttttttga gacagagtct cactctgttg cccacgctgg agtgcagtgg cacgatctca  15120
gctcactgca acctccgcct cctgggttca agcgattctc atgcctcaat tctcccgagt  15180
```

-continued

```
agctgggact acaggcgtgt gccaccatgc ctggctaatt ttttgtattt ttagtagaga  15240
cgggatttca ccgtgttaac caggatggtc tctctctcct gaccttgtga tccgcccacc  15300
ctggcctccc aaagtgctgg gattacaggc atgagccact gcacccagtc aagaaatcct  15360
tcttcactta gtctatccta atgccatata ccactctatt ttaattactg cagttttaga  15420
aaatgtcttc gagttagcca ggcgcggtgg cttatgccta taatcccagc actttgggag  15480
gctgaggtgg gcggatcact tgaggtaagg agttataccc cagcctggcc aacacggtga  15540
aacgccatca ttaccaaaaa ataaaaatta gctgggcatg gtagcgggca cctttagtcc  15600
cagggaatgg aggcagaagt tgcagtgatc caagattgta ccactgcact ccagcctggt  15660
tgacagagtg agactctgtt tcaaaaaaaa aaaaaaaaaa aaagaaagaa agaaaatggc  15720
ttagaatcta atagggtaat ctccctgctt agttcttctc taggaatgtc taggctgttt  15780
ttaaaccctt tggtcctccg tatatatttt aaaatcaact tgcctgattt catgaaaaat  15840
cagactaaat ttacattgaa cctgtaggta atttggggga ggattgccat tcttaaaata  15900
ttaagccatt ctatccataa tacagtgggc ctctcctttt atttaggtcg tctacaatat  15960
cctttgatgg tattgtattt tataatgttc ttcataaaag tattgtactt tatttgataa  16020
gtttattatt cagtaccttc ttttcattgg taatgtaaat atgtgtattg tttttattta  16080
tttaagttat tcatttattc ttttgggatg gagtctcact gtgttgccca gggtagagtg  16140
cagtggtgcg atctcagctc actgcaacct ccgcctcccg gattcaggag attctcctgc  16200
ctcagcctcc cgagtcgctg ggattgcaag tgtgagccac caagcctggc taatttttgt  16260
atttttagta gagacagggt tttgccatgt tttccaggct ggtctcaaac tactgaactc  16320
aggtgatgca ctcgcctcag cctcccaaag cgttgggatt ataggcacaa gccaccatgc  16380
ccagccagat atgtgtattg tttttaaatg ttcttttagt tgctggtgta tataattgta  16440
aatgactttt gtatatctat atcccgcagc tttcctaatg ttttgtggtt ttgcctaggc  16500
taggacttct aatagtagta agcaacctta ttttaaaaca gttgttgttg ccaggcgtgg  16560
tggctcacgc ctgtaatccc agcactttgg gaggccaagg cgggtggatc acgaggtcag  16620
gagatcgaga ccatcctggc taacatggtg aaaccccgtc tctactaaaa atacaaaaaa  16680
ttagccgggc gtggtggcgg gcgcctgtag tcccagctac tcgggaggct gaggcaggag  16740
aatggagtga acccaggagg cggagcttgc agtgagcgga gatcatgcca tgcactccag  16800
cctgggtgac agagcgagac aacgtctcaa aaaaaaaaaa aaaaaaaagt tgtttttaag  16860
tggggacagt ttgttcccta ggggacattt ggcaatgtct ggagactttt tggtcatcac  16920
agttggggaa gtggaggtga tactgctggc ctcaaataga aagaggccag ggtgttgcta  16980
aacatcctgc aattatagga cagctactac aacaaagaat ttattcagcc ccaaatgtca  17040
gctgtgccaa ggttgagaaa ctgtatttta aagggaatgc cttaaacaat attttattat  17100
tatgcagaat tccaaacaca aaaataaatt ggtaaacaga attcccaata ccaacagtta  17160
actattgtag gccagtattt aactcctttc cttcccccaa cttctgctga attattttaa  17220
aacaaataca agatatcaca tcattccatc tgtaaatact tctctgtgtg tcactaaagt  17280
agaggttccc aaattatggt ttcagaatac ccaaaaaatc cttcagaccc tcccagaaga  17340
tctccaaggc taaaactatt ttcacaatgg tactaagatg ttatttgaat tttcattctg  17400
ttgacatttg tgctgatagt gcaaaagagt tgaaaattgt ggatgcctta gcacaaatca  17460
aggctctggc accaaactgt acttagtggt cattgtactt ttagtactgt caaattctct  17520
tctgcttaaa aaaaaaacca actagattta agtaagaatg tgattcatga agcagtacag  17580
```

-continued

```
ttttttttag tcttctacct aatggtttta gtgatcattg atgaatcatt gcccagacct  17640
actattttat taagtctggc caaatggtgg tagtctaatt taaaatttcc ttctgtattc  17700
attaatgata tttttctata aagaagactg tgcttatacc aactgtttag ttactcctaa  17760
atatcctttg tgtaggaaat ggaggaaaat gatttattta ttttttccca gaacagagtt  17820
cactctaaag ggaatatgtt taatgaattt tgttgtattt attttaatgt acattattgg  17880
tatatgctgt tagttttctt tctctttgtt gatatctttt atcaagttaa agaatttctc  17940
ttctatttct agttcactaa gagttttcaa agttaatgga tattgtattc attttccatt  18000
gctgtgtagt aagttacccc agaatttagt ggctgaaaac aacaaacata aaagtttctg  18060
tgtgtcagga atatggacac agcatagctg gatcttctgc ttcagagtcc ctcacaaggc  18120
tgcatcaggg ctcgactggg gaaggaatga tttcctagtt catgtggtat ttggcaagat  18180
tcagttcctt ctctgtctta ggtggagggc cttagtttct tgctgtgtgt ttctgtatat  18240
ggctacttaa catggcagca ggcaaacaag aagagccaga gaaagtaaag aagatggaag  18300
ttacatcttt tccagcctta tctcagaagt gacatcctat cacttttgcc atattcatga  18360
gaatcaaatt cctaggccca gctaaaatca agtagacggg attacacgaa ggtaggaata  18420
tcaggagttg ggaaccatca ggtgctattt tagaagcagc cttccagcct gccctgtggc  18480
ccccaatgac tcatgtctct tgcatatggc cctcttaatt tgccccttcc tccaggtctc  18540
caaaagtctc attctgttac agcatcagct caaagtccag aatcttgtca tctaaatcag  18600
gtccagttgt gagtgaggct tatgggtgaa gtttcttttt tttcttgaga cagcatctca  18660
ctctgttgcc taggctggag tgcagtggcg cagtcatggc tcactgcagt ctcaacctcc  18720
tgggttcaag tgatcctcct gccccagcct cctgagtagc tgggattaca gttgtgtgcc  18780
accacacctg gctaattttt ttatttttag tggagatagg gtttcgctat gttgcccagg  18840
ctggtttcaa actcctgggc tcagcccccc aaagtgctag gattacaggt gtgagccact  18900
gcacctggcc aaagttttta aaatacagtt ccttgtgtac agttccattc agtctgtaga  18960
aatgtgacat taaagataca agttatcctc ccttccctat atccagtata caagggtgga  19020
acaggcatgg gataatagac attcctgttt aaaggaggga aaataggagg cacagaagtg  19080
ttactagtcc atatcaattc tgaaatccag ccaggatgtt agaagttcct tgattccacc  19140
tctgagttat tcttcctttt tcatgaaagg tagcatgtgt tagcagctgt gtagtttttt  19200
attagtctgc ttcctgccag tagaattttg ggagtctagt gacctctttt cgtgttatac  19260
tatttctggg tttttttggt ccagcctggc agtgttgctg ctgatataat tttctcaaaa  19320
actttgtcag tcctttgtga aactcactgg tgttcattcc attgggtaat agtcacaccc  19380
acgaatctaa ggtacaccct tctttacttt gtgatctttc tcagatggct gagggacaat  19440
gttcttaagt ttcctagagc ccctgttgtt gagtcgcgag gacctattag gcacaccctt  19500
aatttcttta aagagccctt tgtatgacag aattactggg aaccattttc caagtagccc  19560
accacaaagg ttgtattttg tcaaattgaa ggagtcatct gactttcctt aatcataagc  19620
tacaaatata ataagctaca ttaatagatt ttctaatatt tatttaactt tgaatttctg  19680
gaaaaaaccc aacttggtaa tgatttatca tctgagcttt gtttttggct ttggtatgct  19740
aatttttggc ttaggatttt tatatctatt tcatgagtga cactgacctg taattttccc  19800
ttttcttact ctctatgtct gttttttttt aatatagtta tgcttccctt acaaattact  19860
tttgattgtc ttttccctca attttggatc acattttcct gatgctctca tttgagtaat  19920
```

-continued

```
tttggagtta tattttgtgt ttctaagtcc tgttaaaatc cttggaagaa tgctgatttt  19980
atttttgttt tggtagactg tcaggctggt taggttctaa accacaagtt ttctcacctg  20040
tgaatagtat ttccagtatc agttcaaaga ctgtgctatg ctactttggg tctttcctat  20100
ccacagacca tttattagtt agtttggagc tttggcaaca gtttatattt taatttattc  20160
tcagagcctt tgctgtgctt ccctgaatct ctcttatgtg tgagctagaa gttgtgctgg  20220
ttcatgtgca aaattacggg aaaccctttc tctggctcat cttttcctgg attccccaca  20280
tctctctggc tcacagaggc tcctttcatt gttattctag tcagacgttt ggatttcttt  20340
cagagcttta gctgcctgcg atgcgtttct gtatggctgg tgccaccctt agggtgaaga  20400
gctcagaaaa agtgttaaaa ataatgagaa tgattcttac gctccttaga ccactgtggt  20460
ctttcccaat tatttttgcc tgaaatgagg ggttttgccc agagtttttg ctgctcacat  20520
ttgtgcatag tgtggactta tggttctaat tttattctaa ggatctttat atttctcagg  20580
gttttttgtt ttgtttttttg aaaaagtctt agtttcttag caggttattt ttggtttatt  20640
taattctggg ttggcaataa ttttctctta gtgttttgaa gatattattc caccatccac  20700
tagttgcagt ggttgctgtt gaaaaacctg ctgtcaataa ttgtcaggcc tttgttatat  20760
gtcatttctc tgaccacttt aagctcttta tcttttgtgt attttgtttt tattactgta  20820
ttttgtgagt aggtgtggat tcctttttttt gtttagcttg gtaaatgctc ttcttgtaaa  20880
tataatttta gtttctttag acaacatagg gctatttaaa ttgtttctta agtgagcttt  20940
ggtagtttgt ctttcaagga atttgttcat ttcctctaag ttgttgaatt tatgggcata  21000
aagttgttca taatccttat tatcattttc aatccataga atctgtagtg atctgtagaa  21060
ccttgcattc ctgaaatcag taatttttac ttggaacgtg ttgagctctt tggatcagtg  21120
agttttatag tttatataaa atttggaaaa ttgtgtactt tttttttcca aattttttttt  21180
ctcttctttc tcctttcctt caggactcca attacacata tatgagactg ttggaaatgt  21240
ttccatagtt cactgatttt tttcaatttt attttcaaaa ataggctttg ttttttatag  21300
cagttctgga ttcatggcaa acttgaacag aaagtgtaga gagttcccat atatgactta  21360
tccacacaca tgcactgcct accccaatat cagtatccta ctggtatatt tattacaatc  21420
gatgaattta tattgacaca ttattataac ccaaagtcca tagtttacat taacgttcac  21480
tcttggcatt gtatattctg tgggttttga caaatgtata ctaccatata tctaccattt  21540
tagtatcata cagaatattt taactgtcct aaaaatcctc cgtgttcccc ctatttatcc  21600
tttccttttt cagccccttg gcaaccactg attttttatt ctagccatag ttttgccttt  21660
tccagaatgt catggagttg gaatcataca gtatgtattc ttttcagatt gggctctttc  21720
acttagtaat atgctcttta ctccatgtcg tctcatgtct tgatagttta tttcttttta  21780
gcactgctgt caatacagct taagtatctc ttatccgaaa tgcttggact agaagtgttt  21840
ccaattttgg attattttgg attttgaaat atttgcatat acctgattag atctacttga  21900
gaatgggata taagtctaaa tatgaaattc atttatgttt catattacac cttatgcaca  21960
tagcccaagg tgattttata caatattttg aataattttg ttaatgaaac aaagtctgtg  22020
ttaagtatgt gtggaatttc ccacttgtgg agtcaatgtg aatgtcacaa aatttcgtat  22080
tttggagcat ttcagatttt tagattaggg atgctcaacg tgtacttgaa tgactgtact  22140
ccataataac tgtggaataa tctgtggaat aactgtttta atgcatttgg taattctaac  22200
atctgtgtta tttaaaaatg agtatttttc tcattacgag ttgtgtttcc ctgtttattt  22260
gcatgcctga taatatttgg atgccagatg ttgtaaattt tactttttttg gttgctggat  22320
```

-continued

```
atttttgtt tgttttattt ttgtttgctg gatatttttg tagttctgca aatattcttg  22380
agctttgttc tgggatgcag ttaacttact tgaccagttt gatctttggg gtttttgctt  22440
ttatgatttg ttaggtgagt ctgaagaaat acttagtctg tgcctgatta ttccctatta  22500
ctgagtcaag acctggctga gtactctact aatatccaat aaattatgag tttgtccact  22560
ctgggtggta agagcaagca ctattccttg ttctatgtga gttctgggca cagttccctg  22620
taaattcgtt ctttccattt agcacatctc cagaattctc tctgtataca gctctctcct  22680
ctttgattct ctggcctgaa aactccaacc aggactttca gctccatttc tcaacttaga  22740
gtctgctggg ctctgcctgg gacccccttc ttataccaca gtctggatat tttctcaagg  22800
cagtaagctg gggcaattat ggggatcact tttttcccca tttctcggga aacagtcttc  22860
ttcattgccc ctaatatcca gtgttttgaa aattgttgtg caacgtatat tgtctttttt  22920
tttttttttt ttggttcttt cgggttggat tactttgaag cctttcattt atagatattt  22980
caatatggtc ctttgaaaga taagcactct ttactttttt ctgaaacctt ttatattatc  23040
tgaactcatc acgtgtgggc agcactgtgt tgctgtgttc atgaaacatt tataagttat  23100
gtactagttt gctttatttc ccagtatatc agttttgttc agtaacaatc atttgataga  23160
ttagtgctca cctttaaatt ttttaaaatt ttgggcagct gatggctatg tgtgttatct  23220
cctatttctt tatgttatcc tggattcaga gccatagaat actacctaga ttctttagga  23280
aagtctttgt gtgcctgaca ttctgtttat cattttcata tatttaaaaa aatatattta  23340
atacatgtat ttttccataa aatatatgtt gtcatattgg gttcagatct tggctttacc  23400
acttactgac tgtgggacct tgaatcagat acctaacctt tgtatgcctc attttcttca  23460
tgtgtaaaat ggtgatagta atggcattta cgtcataggg ttgttaataa ggtttaaatg  23520
cattaataat atgtaaagag cttaggatag tatctggcat ctaagtgcta taaatgtgtg  23580
ttagctctta ttatttttac cacaactacc accaccactg catatattac tgctagtgtc  23640
catgccagga gaaccatgtc tgttccctag gtggcatatg ggtgtgtgta tgtaaagatg  23700
aggtgactgt gtggtcttgt gctgctctct ctgagccctc cttggcctct ggagtaatag  23760
tattgctgtc cacctggtca atgtgtcctg ctgataagtg ctgttgcagt ctgtggtcag  23820
caaatggtcc agtggttctc cttgcttcac tggcctcacc ttggctcatg ctgactctga  23880
ggtttgggtg tcatattctt taagccctgg acctgggcag taagacaaat agcccttagt  23940
tactgaatct ctttgcctcc cctggggcaa aaccctgtcc ttcagtgatt ttgctagcag  24000
aatccccacc tcccttcctc ttctttcatt gggcatacag aaaatttggg atgcctttta  24060
tgccttgtgg gagccagaga actctggata actaaatcca tgccctcctt cctcctaacc  24120
cttctatgtt gatgattccg cccccacatt ttcattaagg gtcatcttgt gtagcagtct  24180
cctcccagaa ccccaaatgg gagatggatc aaagatgcct gttttttag ctttttcttc  24240
catctgccta gcatgtcttt tcccttttgg aactctatcc tggagagagg agatgagaac  24300
agacttgtgt cactgctgct tccttcccac tgttctcttc tcctgtcatg aagacaccag  24360
aagtctaggc cgggtagact ttccatttcc tcttccactt tcctttgggc atgatggcag  24420
gtgtgatact gggaaggggg aatctgcttg ctgataagga aatgtgtgtt gggagatatt  24480
ttaaaaaata taatccttgg ctgggtgcgg tggctcatgc ctgtaatccc agcactttgg  24540
gaggccgagg tgggcagatc acctgaggtc aggagttcaa gaccagcctg gccaacatgg  24600
tgaaacccca tctctgctaa aaatacaaaa aaattagcca ggtgtggtgg catgtgcctg  24660
```

-continued

```
tagtcccagc tactggggag gctgaggtac tagaatcgct tgaacctgag tggtggaggt  24720
tgcagtgagc ccagatcgtg ccactgcact ccagcctggg tgacagagtg agactccatc  24780
tccataaaaa aataaaaaat aaaaaaataa aaaaataaaa taaaatatta tccttgttaa  24840
acaggttaaa gggaaaaaga atattttagg gtaaaggtgg gggtgccagt ttagatggga  24900
attagggaag gtttctctga ggacataaca cttgaacaat ttcaaggctg ttttgtagta  24960
ttgacaaaat ttaatactag gatcaagatt gcttgtgcac aaagccaaaa gatgggctct  25020
cttatgccct cttcttccca tactgcagtt agtacattct gttttctgca gtggtaactc  25080
tttctggcct aattgctcag tttctcgtac tagtctctgt aacacattta ttctgcttat  25140
cactatagag tcctagtatg tagaggctga caaaaacctg aggcaatatt tcttcaagca  25200
agctaccggt ttcagaacca tctggaacac ttaaaattgc tcctctcgaa cccactccag  25260
tgtcataatt actaacagtt tcatttggaa tctgatactg ttgaatttat catattactt  25320
gaggacgagc agtttgttat tgttatcttt ttagccacac agcattgtaa attctaagta  25380
aatgcttgat aaattgattt attaggaagc taggagagag gcatttcaag tggtttaaaa  25440
agttttgcta tttgggggtg acatcagcaa aagcggcaca gtaaagaagt gtaaaatttt  25500
acccttccat aagagcgaca gaagaactgg caacacctgt cagaatcaac tttttcagaa  25560
ctctagaaat taaccaaaga cttgaaaaaa agtgtgaaga gtgctcattc acaaaaaatg  25620
gctgaatctt agtaagaata gtgagcttac ccaagcccca ttccctgttc catgtgtcag  25680
ctggggctga aataacagcc tgtgtttctg tactggaggg agcagaacag acctcattgt  25740
aagtatttgt tttgccttct taggtggatc cctggatgaa tgacttcaaa accttgtctc  25800
tatttctcct gactcagaac tgccctactt ctgagatcgg ggaggacagt agttatcaag  25860
aaacatttac agacaaataa tttagtcatt gcttcctgaa tcaagaaata acaatggggg  25920
caaacagtag actaactaaa gagcctagga gcagagattg ggaatgagat gtctatgaga  25980
gctttgaaaa gcttcacata ttcccaagaa tgtagaaggc cacatgcttg gcaaggactg  26040
tatgcatgcc cagggaagac ttctacctct cgctgatctt gaggctctgt gaaagcagga  26100
agtgaagcct aaggcagagt tagaagctac ctggctaagt agtgaaggtg tatcccaaac  26160
ctacccagag cccttctgca aagacagaca ggttttttgg ttccaagcat ttaaggcagt  26220
ctgttcagtt gttagctggc cattaagcta acagaataga gactccagtg actgcacata  26280
acaaggaata cagattttac agaattagtt ttgataagtc ttgaaacaaa caactacaac  26340
aataagcagc aacaaaaaat tctggagagg ggagagaatc tgattcccag agttgccaca  26400
ttataagatt taaaatgtct agtgtttaac aaaaaagtgt aagatatgaa acacaacaag  26460
aaaaaaagcc atgaatagaa attgtccctg aggaagccca gacgttagaa tttctagaca  26520
aacactttat attagctatt taaaataatt cttcaagagc taaagaaaac catatcttaa  26580
acaaaacaaa acaaaacaaa aaacccaaaa acctaactga aagtttgaga acagtgtctc  26640
accaattgag aatatcaaca aaaagataga aattatgaac taaaccagat agacaagcat  26700
ggtaactgaa atgaaaaatt tgcttctagg gcccatcagg agatttgaac aggaagaaga  26760
aagaaatttg aaggtagttc tattgacttt atctaatttg aagaacagaa aaggaaaaaa  26820
gtaattagga aatataaata gagcctaaag agacctgtgg gataccatca agtgtaccaa  26880
catacacatg acaggaatct cagaaggaga ggagagatgg tggggcagaa ggatatttga  26940
agaaataatg ggccaggtgc agtggctcat gcctgtaatc ccagaacttt gggagaccaa  27000
aacaggcagg tctcttgagc ccaagagttt gagaccagcc tgcgcaacag cgtgaaaccc  27060
```

-continued

```
tgtctctaca aaaaatacaa aaattaacca tacgtgatga catgtgcctg tagtcccagc  27120
tactcaggag gctgaggttg gaggatcact taagcccagg aggccatggc tgcagtgagc  27180
tgtgattgca ctactgcact gcagactgga cgacagtgtg gaaccctgtc tcaaaaaaaa  27240
aaaaagaaaa aagaaaaaaa gggaaaggga agtgaaatag tggctaaaac cccaaatttg  27300
atggaaaagc atgcatttat gcatacaaga agctcagtaa actccaagca ggataaaacc  27360
agagattcac agctagacac atcataatca aactgttgaa agccaaagat agaatcttta  27420
aagcggcaag agaaaagcag ctcatcatgt acagggtaac ctcagtaaga tgaacagcag  27480
acttctcacc agaaactatg gtgcccagaa ggcaatgggt tgatgtactc acatccctga  27540
aaggaaaaag cccaacaaaa actaccatat ctggcaaaac tccccttgag aaatgaaaga  27600
gaaagaagat attcctcata aaccaaaact gtgagaattg tagctagcag acctgcctac  27660
aacaaatgct aaggggaatt cttccagctg aaatcaagat gcactagatg gtaactcaaa  27720
tctgcatgaa agaataaaga acatgggtca agttaactac atcggttaac ttagcactgg  27780
cccaagctgg ttcccagaaa aaggagaccg tccaataatc aactgccaga ggacaggaag  27840
gatgaaacca tatttttctc tcctcttcac tttcaggagc cctgcacact tcccatattt  27900
cagtatataa tttttgagta aattagcaag gtgagatctt ttcaccagtc taattctact  27960
aaaaaaaaaa aaaagtaggc ttagtattat tagtccatag ggaatgcagt ttaaaaccac  28020
agtgagatac ccctctatat tcaccagaat ggttaatatt aaatgaatgg acattacaga  28080
gtaatggcaa ggataatgtt ggtaggagtt aaactagtat aaccatttgg ggaaactata  28140
tattatggct acttagcaaa acatgcctag cttataaccc tacaaatcca ctcctacata  28200
tattcacaac ataaagaagt tatacacttt aaaaattaca ctaaaagact tacagaagaa  28260
tatttatagc agcactattc atagtaatag ctgaaagcta gaaatggatc caagtaccta  28320
tcaacagggg gatgtataaa taaaatacat tatattcatg caattagata ttactcagca  28380
ataaaaagaa gcaaaccagt gatacataca acatggttga agctcagaaa tatactaagt  28440
gtacacagcc agctgcaaat aagtatatac tgtaggtttc catttatatg aagttcaaaa  28500
gtagctaaaa ccaatctttt gtgatagtag ttagaatagt ggttattctg gggggctgac  28560
tgggaggcaa cacaaaagag actgttgagg ggctagaaat gatcactgtc ctatctaggt  28620
ggtggttaca tggctgtata tataaaattt tgagttacac acttcagaca gtgttgctgt  28680
taagatctgt gtatactcca tattatgaaa gataattttt aggatcttaa aaaaaatctt  28740
gattgctctg tcagtgttat tgaaatcaag gatgtataat attatcaagt tcaatcatcc  28800
taaaaggaaa ttcaattata gtttcatttt tgtaactgtt aaaagcatta agatataaac  28860
atgttaaaca attctccttt gagacataaa cataaaaaca ggtctactga tgagtctgtt  28920
gattacccta ttgcatttta gccaatgttt aaatatttgg tcatgtatgt tattcttgaa  28980
gtgcagaatg tgcttagggt aattattagc aacatttaac caaattggtt ctgttatttc  29040
acgctggagg accagagcag gatgagtcag taaggggact tttgagaaat gaaatgtcag  29100
tgtttttgca accatttgta ggccataaaa aaaaaaaatc agatttgttc ttacaaagaa  29160
tgcaggactg gccaaacacc aagatgttgc tacacagaga gaataaaaca accagagaca  29220
aaaccacagc agaactgctt tcatccccaa attgcagaat aagtactgag atatgaccga  29280
gaaacagggg agagaaaggg taaacagtgg aggaaagaga tttttttgac cttatgctaa  29340
ctattaatct gaagctagaa atgctgattt tatctgaaaa attagagctt tccacagtta  29400
```

-continued

```
ttcatttatt caacaaatat ttgttaaact tccattatgt acctagaatc atcctgggcg  29460
cataagatgg agcagcagac aaaacaaaaa ttcctgccct tatggaacat atattggggg  29520
agggggtgtg gcagaaatgc atacacatat tgtacatgta gcaatgaggt tagattagat  29580
ggctactttt tctctttctt tccttctttc cttcctttcc ttcctttcct tccttccttt  29640
cgtccttttt ttttgacagg gtttccatct atcacccagg ctggagtgca gtggtacagt  29700
cttggctcac tgcaacctcc tcctctcggg ctgaagtgat tctcctacct cagcctccca  29760
agtagctggg attacaggca tgtgccacca cgcccagcta atttttacat ttttagtaga  29820
gatgaggttt tgccatgttg cccaggctgg tcttgaactc ctgacctcaa gtgatccacc  29880
cacctcagcc tctcaaagtg ctgggattac aggtgtgagc cactgcaccc ggccaaggtg  29940
gctacttttt aaagtatgcc atagtttagc cttcaactat atatgcctta tggaacctcc  30000
agtttaatgc tgctgttgat acccctctta gattttctaa tgagaccttc ctcagcactt  30060
taataatgaa atctactata tgactcaagg ttgatgtgtc ttactcagtg gcaaagaaca  30120
gaataagaaa tagatccaaa catatcggaa tttaagacag tggaatgata tcttacagaa  30180
aggagtcagg gtattgggtc ctaaaatcaa cacagatcaa agctgaaatt aataaaatag  30240
agaaaaatag aataggataa ataaaaacca aaatcaattc tttgggatgg tcagtagaaa  30300
tgtaaaccct ttgcaatatt gatgaaaata aaagtgaata tgtatcataa aggatgagga  30360
aagagaaata atcacaactg taaacgattt tttttttttt tgagacagaa tcttactctg  30420
ttgcccaggc tggagtgcct ggctcactgc aacctctgcc tctcaggttc aattgattct  30480
cctgccttag cctcctgagt agctgggatt acaggcacgc gccaccacgc ctagctaatt  30540
tttgtatttt tagtagagac aggatttcac catgttggcc aggctgaact cctgacttca  30600
ggtgatccgc ctgccttggc ctcccaaagt gctgaggtta caggggcgtg agccaccacg  30660
cccggcctat aaaagacatt tttaaaaaat gataggagaa tacaagaaag tacatttgta  30720
atacatttga aagtctagaa acagtggctg atttttgaag atagatggag agcttcagta  30780
ggttgattag caccaaagag attaaacggt gattaagaga tatcatttaa aaaggaagag  30840
atgatacaca actgaattat ttctaatcag tggagaacag atgagtccga tgctatttaa  30900
gctattttag tagatggaaa actccccatt cattttccaa agctatgatt taatgtcaga  30960
acccaataga aattacataa aagaaaactt tagattagtt ttcttatgca tgcagatgct  31020
aaaaccataa ataaaatacc agtaaataga attcagcagt gtagcaaaaa ctgatcagct  31080
attatgacca aatagttttt atttcagcaa caaaagaata gttcactact agaaaaatct  31140
gtcaacagaa tgtactacat caataaatta aaggagaaaa ccatatgatc atatcattca  31200
gtgctgaaaa ggctctgggt acaattcagt tgtcattcat aataaaagct cttaagaagg  31260
aacaggaaaa acactaccta gatatagtaa agactgcact caacatgttt ttactaagca  31320
tccattatat gcccagtaat attccagcag ttaacagaca aaacatttag agccatctca  31380
ttttttaaaa aagaaggagt tgaatgttta gtttgtcaga tggtaataag cgctttgaaa  31440
taagaaataa agcagggaat aggaggttgc caagagctga gatgtaggaa ttgtcaggga  31500
aggactcatt ggtaaggtga tatttgagta gagaactgta ggagagcaag tcaacaaagc  31560
aggcaaaaat tccagccatc atgtatccta cggtctcatg gtgggggagg gggcaataca  31620
aaaaacatga taaaaacata tagcatatta gaaggttata gtggaaaaaa ggaaaaacag  31680
aggaaagtaa aggggaccag ggcccagagg attttgaagg tcagattata aagttagtag  31740
tctcattgag aaggtgatat ctgagcaaag tctcaaagga ggtgagggag ttagccaagt  31800
```

-continued

```
agatattaca ggaaggagtg ctccaggcag agagaagagt cacagtaaag tagctatcaa  31860
gagaccacgc ctggcctagt caaggaccta caaagatgtc aataggactg gagtagagtg  31920
aacaagggag tgtgtgaagg tcaggttatt ttatgtggga ccttgtagac cactggaagg  31980
actattttaa aaattacctt aatgaatttt tataaggcaa acactcttat aactattacc  32040
catgttaaga aatagaacca tatcagtcag tccagaagct ttttcatgta ccctatccca  32100
aactaagtcc cctcctcttc tcccaaacta tccactattt tggcaccttt agaaatcact  32160
tactctgctt ctttatactt ttattaccca aatgtgcatt tagacattgt agcttattct  32220
tactcattaa aaataatttg acaagtcttc tcttttaatc gacagatttc caagtgatcc  32280
attcctttct ttaccataca ctatttttg aagaacccaa gctatttagc ctgtaaagtt  32340
attcacaatc tgaattttgc tgattggaaa attgtgcagt tttgcaatcg aactgctgat  32400
tatccagcat gttcttctga attctctact tcctgtaaat tgatcgctga gcccagaggc  32460
ttaatcacac tcaaggtctt atttggtgag gctatataca ttatgtgtgg ttgtcatttt  32520
tcttgtgatt ttagcagcca ttgatcctca gtgcctagat tcatcaattt gttgactatt  32580
gtaaagtgct gatattctaa ttctgatctc ttttctacat cttacttgga acaattttat  32640
gaagagacat atccttgcct ctatattttt tggttgccca gggttacagc ttttcatata  32700
caaaaagcat aataaatact tgattctttt gctttttgg ggccagtttt caagataatg  32760
gtttggttcc ttttcatctt cccaagagac caattttata tgtttctatc tgttgcaatt  32820
agcattttta ttgagttcaa attgttcctt ctctggccac tagatgcttc tacacattac  32880
ctcctgagta cttttgctgt gacctcagtt gtgtctgata gcttccttgc tacctggtat  32940
gataacatct ggtgtgacaa gatagtacat gctcagctga gcttagtgat cagctgggac  33000
tacaggtgcc cgccgccacg cccggctaat ttttgtattt ttagtagaga cggggtttca  33060
ccctgttagc caggatcatc ttgatctcct gatctcgtga tctgcccgcc tcagcttccc  33120
aaagtgctgg gattacaggc gtgagccacc gtgcctggct tgtttatttt atatcagtgc  33180
aagttggtac cctttgacct acatctcccc atttcctccc atttctgccc ctggtaacca  33240
ccatcctact ctgctttgat gtgttttact tttttagatt ctgcatataa gtgagatcat  33300
acagtatttg tctttctgtg tctaatttat ttcacttagc ataatgtcct ccaggtttat  33360
ccatgttgtt acaaatggca gtgtctcctt tttaaaggct gcataatatt tcattgtgag  33420
tatatattaa tccatatata tgtatatatc catatccata tcgtatatgt atcaccattt  33480
ctttagccat tcatccctac attttaggat tttttttttt cattttagga cattttcaaa  33540
ggattgtaaa aattctaaaa agagaatacg caacagatta ttctttggat tatagagcct  33600
aaactatttg ctgtctagtc ttttacagaa aaaatttgct gacatacact ctagtagatt  33660
cttcagaaag tgtctgtggg aacaatattc tctgagtttg taactttgat aacagctgct  33720
ctgtgccttt tatactttta caagtcattt ttcctggatg taagattctt ggcttatttt  33780
tcttccatat gtatattaaa tagattgttc aatttcttct gggggaaaaa agtattgata  33840
ttctacaaga aaagaaaatt agaagccagt atttctggtg aatatagatg caaaaatcct  33900
caacaaaata ttaggaaaca aaattcatca gcacatttat aaggatcatt caccataatc  33960
aaatgggact tatatttggg atacaaaggt gattcaaaat aatgcaaatt aataaatgcg  34020
atataccaca tttacagaat gaaggacaaa aatcgtatga tcacctcaat agatgcagaa  34080
aaggcatttg acaaaattca gcatcttttc atgataaaaa ctctcaacca aattagatac  34140
```

-continued

```
agaaggaagg tatgtcaaca caataaagac tatcataagc ccacagctga catcatcctc  34200
agtggtgaaa agttgaaagc ttttcctgca agatcaggaa caagacagaa tacccactct  34260
caccccaatt cttttttttt tttttttct gagacatggt ttcactctgt tgcccaggtt  34320
ggaaggcagt agtgcaatca cagctcactg cacctcctcc tccgggctca agcaatcctt  34380
ccacctcagc ctcccaagta gctgggacta caggcacata ccctcatgcc tggctaattt  34440
ttgtatattt tatagagttg gggttttgcc atgttgccca ggctagtctt aaactcctag  34500
gctcaagcag tccactcacc ttgccctcct aaagtgctgg gattacgggt gtgagccact  34560
gtgcttggcc ttactctcac cacttctgtt cagtacagta ctggagtcct agccagagca  34620
attaagcaag agacagaaat aaaaggcatc cacatcagaa aggaagaaac taaattgtct  34680
ctatttgctg atgacatgat cttacatata gaaagtccta aagactccac caaaaattgt  34740
tagaactagt taatgaattc agtaaaattt caagatacaa agtcaacatt caaaaatcag  34800
tagtgtttct atacactaac aatgaactgt ccaaaaaaga aatgatgaaa acaatctcat  34860
tcacaatagc taccaaaaaa aagacttatg aataaattta aaatttaatc aaggaggtga  34920
aagacttgta cactaagaac tataaaacac tgatgaaaga aactgaacac actaataaat  34980
ggaaacatat cctgtattcg tggattggaa tattgtttaa atggccacac tacctaaaat  35040
gatctataga tttcaataca atccctatca aaatttcaat gacattttca cagaaataga  35100
aaaagcactt gtaaaattta tgtagaacta caaaaagccc caaatagtca aagcaatctt  35160
gatagaaaag aacaaagctg gatgcatcac agtatttgac ttcaaaatat actgtaaagc  35220
tatagtaatc agaatagcat ggtactggca taaaaacaga catataaacg aatggaactg  35280
aatagagagc ccccagaaat aaacccacat atttatggtc agttgatctt aagggtgcca  35340
agaatacaca atagggaaaa gacagtctct taaataatgt tgggaaaact ggatatccac  35400
atgagaagaa tgaagttaga ctcttacctc acatcatata caacaaccaa ctcaaaatgg  35460
atcaaagttt tatcttggaa aaaaaaaatt tttttttct tttgagacag ggtctcactc  35520
tgtcacccag gctggagtgc agtggtgtga tcttggctca ctgcaacctc cgccttctgg  35580
gttcaagcga ttctctcacc tgagccttcc tagtagctgg gactgcaggc atgtgccacc  35640
atgcccaact aatttttgtt gttgttttct tttttcttc ttttcttttt tttttctttg  35700
gtagagacgg ggtttcacca tgttggccag gctggtcttg aactcctgac cttaagcaga  35760
cccaccttcc agctgggcgc ggtggctgac gcctgtaatc ccagcacttt gggaggccga  35820
ggcgggtgga tcacaaggtc aggagatcga gaccatcctg gctaacacgg tgaaacccca  35880
tttctactaa aaatacaaaa aattagtcag gtgtggtggt gggtgcctgt aatcccagct  35940
actcaggctg aggcaggaga atggcgtgaa cccgggaggt ggagcttgaa gtgagcgttg  36000
agatcgcgtc actgcactcc agcctgggcg acagagtgag actccgtctg aaaaaaaaaa  36060
aaagatccac tcggcctctc aaagtgctgg gattacaggc atgagccacc tgtacctggc  36120
ctcaaaatgg attaaaggtt taaatgtaaa acctgaaact gtataactat cagaagaaga  36180
cataagggaa aagctctgtg acattggtct gggcaatgaa tttttggatt tgacctcaaa  36240
agcactggca acaaaaacaa aaatggtcat atgggattat gtcaaacaaa aaagctctgc  36300
acagtaaagg aaactatcaa cagagtgaag agacaaccta tagaatgggt tgatatattt  36360
gcaaaccata tatctgatat ggagttaata tccaaaatat ataaggaact caattcggca  36420
agaaaacaaa tctaaaaaaa tgggcaaaga acctgataga catttatcaa aagaagacat  36480
acaaatggcc aacagttata tgaaaaaaat gcttagcatc gctaatcatc agagaaatgc  36540
```

-continued

```
aaattaaaac tacagtgtac ctcatacctg ttagaatggc tattataaaa aagataggcc  36600
aggtgcagtg gctcacacct gtaatccctg cactttggga ggccgaggtg ggtggatcac  36660
gaggtcagga ggtcgagacc atgctggcta acacggtgaa accccatctc tactaaaaat  36720
acaaaaaatt agccaggtgt ggtggcgggt gcctgtagtc ccagctactt gggaggctga  36780
ggcaggagaa tggcgtgaac ccgggaggca gagcttgcag taagccaaga ttgagccact  36840
gcactccagc ctgggtgaca gagcgagact ccgtctcaaa gaaaaaataa aaaaaaataa  36900
aaaaagataa caagtgttgg caaagatgtg gagaaaaggg agacctatac actgttggtg  36960
agactgtaac ttggtacagc cgttatggaa aacaacatgg aggttcctca aaaaattgaa  37020
aatagagcta ccatatgatc cagcaatccc actaccaggt atgtacccaa aggaattgaa  37080
atcagaatgt ggtagatata cctgcactca catgttcatt acagcactat tcacaatagc  37140
caagatatca acccaagcat ccattcacag atgaatggat aaaaagaaaa tgcggcatac  37200
atacacaatg gaatactatt tagcctttaa aaggaggaaa tcttgtcatt tgcaacatcg  37260
ttaataaacc tgtagaacat tattgtaaat gaaataagcc aggcatggaa agacaaatac  37320
ttgggatctt atttctatgt agaacctaaa aaagtcaaat tcatagaagc aagagtagaa  37380
tggtggttan nnnnnnnnnn nnnnnnnnnn nnnnnnnnnn nnnnnnnnnn nnnnnnnnnn  37440
nnnnnnnnnn nnnnnnnnnn nnnnnnnnnn nnnnnnnnnn nnnnnnnnnn nnnnnnnnnn  37500
nnnnnnnnnn nnnnnnnnnn nnnnnnnnnn nnnnnnnnnn nnnnnnnnnn nnnnnnnnnn  37560
nnnnnnnnnn nnnnnnnnnn nnnnnnnnnn nnnnnnnnnn nnnnnnnnnn nnatatttta  37620
aaacatgtta tatattcagt tttcatcagt ttaaaaaact taatttaaaa aaaaaaagtt  37680
ttgatgttga aaagtctgat ctaattttct tctcctatag gtaatttgga tacctatact  37740
ttgcctagat actcaaatat tttttcttta aagtgcaata attttaatat gttttgttgg  37800
tcatcatata gcagatattc tcagatatac catgtgttct gtcaatatat agattaaaaa  37860
aactttttaa aaataatgtt ttcttaaatt ttggttttta gtatttgctg tgttcccttt  37920
gattctcttc ttcaaagact cctatttttc attaaagact ttttttgcct gttaatattt  37980
ttcactttct tttgaattgt tttatttctt cttaaatttt aaaaacattt catatatata  38040
tatatatgta tttttttgag gcagagcctc actttgtctc ccaggctgga gtgcagtggt  38100
gtgatctcgg ctcattgcaa cctctgcctc ctgggttcaa gtgattctcc tgcgtcagcc  38160
tctcaagtag ctgcgagtac aggcatgtgc catcatgcct ggctaatatc ttctattttc  38220
aattagttta aattggaaag cttttaaatc tttgaaggca ttctatttca cttataattt  38280
cttttaagat tctcttgtat ttattaactc ttgtcttcct tctagtttag tttatttttg  38340
taatgatttt tccttccatt tctaaattcc tgagctctat caccttattt ctaatatgat  38400
ttatgtatca ttttctcagt gtcttttagc ttgttttaaa atagtaagtt acaattttaa  38460
tgttttgtgg gcatgtcttt ttttctctat aggaatgttc ttcttcttct ctgttttctt  38520
ttaacaactc tttatggtat ttgaccaaat actttttttgt cactcatttt tactgaaaaa  38580
cagttttctc aagcttttgg gaggaggaat agttcaagct gtctttatta atttcatagc  38640
tctccatctc ctgtttttttg gttttgttct ggtaaagcgt taaataatat ggtggcttgc  38700
tttctgagac ttcctgactc catagcctcc cctcgcttgt atcggggcct tctctttcct  38760
ttgtctctgt caccattgta attagcccaa ttctgattct cctcccagaa gtttctaatt  38820
gcgatgtcct gtcctggaaa ggagctttgg ctggttggtt tcaagttcat gtttcccatc  38880
```

-continued

```
tttctctggc ccctttgaga acctaccagt ggcccttata gtcacttttt ggtttgatga  38940
aacccttccc aatttcaact ggtgttctca aatagatctg ctctgatttt tagagtttgg  39000
tttatggctg ctgtggtgtt tcccattctc agttttcaga tgcgttgttg cttctttttc  39060
tttcaccaca ttaacattca ttccatgagg ggattgtggt tactgttggt tgtctccacg  39120
aacttgtatt ttggagtttg tgagctactt tgtcatctag ttttgttgtc catggtgttt  39180
tagttttgtt attggattac tttgcatgtt tttagggaat gatttggtga gatgaaaact  39240
attcagaata gttttttcta tttggatgat ctcatcaaat catcccctaa atctatacaa  39300
atcaggaaat ctattcaaat aggaaaaact attctgtgat tactcagatt ccctctcatt  39360
tccagtgcct agtcactctg agtgactagg gagtcattgc aggattttga gcaatggagt  39420
gacatgacct gactggtgtt ttaaaggctc tgtctggtga tagactgaga atagaccata  39480
gaaatgtaga ggaagaagta gggggaccta ttagaagaat gttgcagaaa taggctgggt  39540
ggatcacttg aggtcaggag tttgagacca gcctggccaa catggcgaaa ccctgtctct  39600
actaaaaata caaaaattag ctgggtgtgg tagtgggtgc ctgtaatccc agctactcag  39660
gaggctgagg ctggagaatt gcttgagccc atgaggtgga cgttgcagtg tgctgagatt  39720
gtgccactgc actccagcct gggcaacaag aatgtgactc catctcaaaa aaaaaaaaaa  39780
aaaaaaaaaa aaaaattgca gaaatccagg tgagagatgt ttgcttggac ttggggagca  39840
gcagtggagt taatgagaag tggccagatt tgcatatatt ttgaggtata gttgataaga  39900
tttcctgatg gatttgatgt gaagtatgag agaatgtagt tgaaaaataa ctctggtttt  39960
gtcctgagca actgtaagaa tggagttgct tttaactgag attagaaggc tgaggctgcc  40020
gtgcgggtaa ggtagacttt aggggtgaca taaagagctc agtttggact atgttgagct  40080
tgagatagtt attagacttc tgagtgaaga tactcttcgt gattctgcga gtcccatgac  40140
agcatgaggt aaaaaaagaa agacattggg ccgggcgcag tggctcacgc ctgtaatccc  40200
agcactttgg gaggtcgagg tgggcggatc acgaggtcag gagattgaga ccatcctagc  40260
taacacggtg aaaccccatt tctactaaat atacaaaaaa gtagctgggc ttggtggcgg  40320
gcgcctgtag tcccagctac tgggaggctg aggcaggaga atggcgtgaa cctgggaggc  40380
ggagcttgca gggagccgag atcgcaccac tgcactccag cccactgcac tccagcctgg  40440
gtggcagaac gagattccgt ctcaaaaaaa aaaaaagttt atcatagaaa attggaaaat  40500
atggataagt taggtaagaa aataaaaatc atgctgcatt gtaaacattc tgatatgatt  40560
ctaaacatac atataacatg catttagaac acatcgcttt tttctttcca acttttaggt  40620
tcagggagta catgcacagg tttgctaccg gtaaattgtc tgtcacgggg gtttggtgta  40680
cagattgttt catcacccag gtaataagca tagtactcta tgggtagttt ttcgatcctc  40740
accttcctcc caccctcgac ccttaagtag gcccaagcgt ctgttgttcc cctttgtatc  40800
tatgtgtgct cagtgcttag ctagcactta taagtgagaa catgcagtat ttggttttct  40860
gttcatgtat taattcgctt aggataatgg cctccaactc catccatgtt gctgcaaagg  40920
acactatttc attttttat agctgtgtag tattccatgg tgtatatcta ccacattttc  40980
atcatccagt ccactgttgt gggcatttag gttggttcca tgtcttagct attgtgaaca  41040
gtgttgcgat gaacatacag ttacatgtgt ctttatagta gaacgattta tattcctgtg  41100
ggtatatatc cagtaagggg gttactgggt ctaatggtag ttctgagttc tttgagaaat  41160
cttcgaactg ctgtccacag tggctaaact aatttacatt cccaccagca gatataagca  41220
tactcttttc tttgttttgt tttgttttaa aactaaagct tattctggcc aatttactct  41280
```

-continued

```
actattttct aataacagct catagatcag aaacggtctt tgttttaaac tttcctatcc  41340
atatgaaaca caatgatgtt ggggtaagag gggccttttc tctaaatgaa aatacaatac  41400
ttattctgta caattctaga gggcccagag atgtggaaat aatgtatttg taagaattat  41460
attaaacaat ctttatttga taaatagtac cttacaatcc taatgctatc tatcaagctt  41520
cagtaagagc aatttcagca tcaagtaatg aacagtagct aaactgacaa gagatcaatc  41580
aaaagggctt taaatggagc agcaccagct gatgtgctgc taaggctctg ggcattcagg  41640
actctcctat ggggaaaacg gaatcaaacc agcaggtgct ctggacctaa gccttcacat  41700
cgtgacctgc ctccctcctg ggggtgtggt ggcccacagt ccccctggca tttctcggcc  41760
cttgtgggct gcagacggaa atcctggcac caaaggacag cttgggaaag gctgaaactt  41820
gacctcacag tcaactggct tctgcctatt gtggtcattt tctttccaga gcacctagag  41880
cactcgcaca gtggacgtgg aagccaccca gcattcttgg gctgttttct catagaagag  41940
gaccttcctc taagcattgg aagcgtcttt ctccaattcc tgggccagat cttgggccat  42000
cttcttgtag gtcatgggtc tgacacacat ggttcaagtt ttcgtggcta ttgtgaatgg  42060
gattgtgttt ttgatttagc tctcagctcg gatattgttg gtgtatggaa atgctatttt  42120
tgtacaatga ttttgtatcc tgaaacttta ctgaagttgt ttatcagatc tagaagcttt  42180
tgggcagaga ctgtggggtt ttctaggtat aaagtcatat cgtctgcaaa tatggaagat  42240
agttgacttc cactcttcct ggatgccttt atttttctta ctactctatc taggacttcc  42300
agtactgtgt tgagtaggag tggtgagaga gggcatcctg gtcttattct ggttctcaat  42360
gggaatactt ccagtatggt atgcttccag cagcacatca actggtgctg ctccctttaa  42420
agcacttttg attgatctct tgttagttta gctattgttc attacttgat gctgaaattg  42480
ctcttattga agtttgatag atagcattag aattgtaagg tactatttat caaataaaga  42540
ttgtttaata taattcttac aaatacataa tttccacatc tgtgggccct ccagaacatt  42600
tcagcatgtt ctggatgttg gctgtgggtt tgtcatagat atcacttatt gttttgaggt  42660
atgttccttc gatgcctagc ttgttgagag tttttaacat gaagggatgc tgaattttat  42720
tgaaagcatt ttctgtgtct atcgagatga tcatgtagtt tttgtcttta gttctgttta  42780
tgtgatgaat cacatttatt ggtttgtgta tgttgaaccc accttgcatc ccagggataa  42840
agcctacttg attgtggtgg attagctttt gatgtgcttc tagtctctgt ttcctagtat  42900
ttttgttgag gatttttgca tctgtgttca tcagggatat tggcctgaag ttttcttttt  42960
ttgttgtatc tctgataggt tttggtgtca gaatgatgct gacctcatag aataagttgg  43020
caaggagtcc ctcttcctga atttttggga atagtttcag taggtttggt acaaggtctt  43080
ctttatacat ctgatagagt ttggttatga atccctcctg tctagggctt tttctggttg  43140
gtaggttttt tagtactaat tcaatttagg aactcattat tggtctgtag aacacatttt  43200
cacaaagttg aatttctatt gtatatacat tttaaaatct tctttcacaa gacatgacct  43260
gagcattttc taatagtgaa agtctttgaa aacatggttt ttaatggtat ttcattacat  43320
gttttactgt aataaaccta accacttgga ttatgtactc tttcactcat tcctttttgc  43380
atatctgttc catcccctat gctttaatat ggaggatttg gtttcttgta gtagttgctg  43440
ggtatcataa ttcagacctg tggtttggca gtcagcctgg ctgtagtgtt taactgagtc  43500
tcgtggaaga tccatgctta aaatgaatgt cgtggagaat tgtattcacc tcagtcattc  43560
aagactttgg catagacccc attccttgag gaggagttgc cgccactgtg actgccacag  43620
```

-continued

```
acggaaggaa gcctgggcag ttgggactgg ggagaacttg ctgagtcaca gatatcttgt  43680
ctcagtgtgc atgggccgtg tgtattgaaa tgtaccagtc tgtgaggcac tatgttttga  43740
ggtctcagta agctaaaggg gtgtagaatg gtatctagtt cataccgtag tatgctttag  43800
atctaagtgt tggttaattc tgtaaggact gaaggaatag gggagattta atgagctcct  43860
tgcagtctgc aggttattat cgagaaaaga aaattaggct ctcagttcca ggcccatttc  43920
cctctaatca ctgtgtcctt ttgaacaaaa gttggcaaac tttttctgta aagggccaga  43980
tatttttagc tttgcaggcc atatgatttc tgttgtaagc attgagctct tctgttatag  44040
agcaaaagca gccataggca gtacaggaac aaatggccat ggttatgttc tagtaaaact  44100
ttatttacat aacaggcagc aggccagatt ggagcaatag ttgtcaactc ctgctttgaa  44160
aatgttttgg aaactgtgtc tccgtctgtt agtggtcatt atcctcagtc tcttaggatc  44220
agagtttttc ttagattaca aaactggatc atacagacct gacttccagg tctgcgttct  44280
ctccactaca ctttgctgcc tcttagaaaa acataagcta aataactaga acccatggaa  44340
agagggaaaa gtgaagccca gagagctgat gcgggactaa gaggcaactc tgagagtttc  44400
aatgtggaat gtttgtgtgg ctccccaacc agaccgtgac ctccttgaag attgggactg  44460
catcgtatct tgttctcatt ttctatttta ttttaatgat ctatcctttg ggttgaacga  44520
atgtgtttct tgaacccgat aagtgcaaca ctgagtaaac acttgtttct tttctccctt  44580
ccatcctccc aacttagtag cttcaataca ttcttagctc tcctcacttg ctattctcta  44640
accataccac gtggctgggc acggtggctc atgcctgtag tcccagcact ttgggaagcc  44700
gaggtgggca gatcacctga ggtcaggagt tcaagaccag cctggccaat gtggcaaaac  44760
cccactaaaa atacaaaaat taactgggta tggtggtggc ctgtaatccc cagctactca  44820
ggaggctgag gcaggagaat cgcttgaacc caggaggcag aggttatagt gtgctgagat  44880
tgcgtcactg cactccagcc tgggtgacag agcaagagtc cgtctcaaaa aacaaaaaca  44940
aaaaaaaccc caggttatct ccatgaatgt gaatattgat gtggtccttc tgtcaggaag  45000
acatcacctg agaccacaca cagaaagcct atttttcctt aggatacagt cctacatcag  45060
ggttgacaaa gtttttttgt aagggttaga tagtaaatat tttagatttt gcaagccata  45120
tggtctcttc ctcagctact caactctgcc gttgtactac aagagcagcc atagacaatc  45180
tatacatgaa tgagtgtggc tgtgttccag taaactttac ttatggatat tgatactcag  45240
atttcacatg attttcatgt gtaatgaaat gtgattattt ttatttaaaa cattaaaaat  45300
gtaaaagcca ttttttgctt gcaggccaga caaaaacagg cagtgtgagt caatttaatt  45360
taatgtgtga ctcatagatg ctaacccttg ccttagctgc ttagtaactt gccctagtca  45420
tgtgttaccc catgaaaaga atggcctact tctgtcatat tgtctctaac ctctgtcatt  45480
tcatttatga tgctatgtat tatgtgtacc tttgtctctc ttgctggatt ctgagtatct  45540
tgagaggtag gccatggcct agtcagtcat ctttgtatcc ttaatatcaa acccacatag  45600
tgggtattta agaagtgact gttgaatttg aattttatgc ttgatatata taaaatgtca  45660
tttctgctga tcttaaagag aaacacttga ctgatatgca taggtttccc atgttcttcc  45720
ccttgagagg ccatagttaa ctgcatttgc tgctagcggc tcttgtaaac tcagtggtta  45780
tacagcaaag cctttgcaaa gtcttttatt ttagagctct ttttcagaca agaaatgatt  45840
atactttttc ttcaaatcat ttattcaatc ataatgataa atatggcttt cactattctg  45900
atgaagcaga gctaccatca gtgtgaaata ataatagccg ttgtttagtg agcatctact  45960
acattccagt caattcagat tttttctcta gatttttggt gaccttctga ttactattaa  46020
```

-continued

```
tttacatttt tttttattgt tctctacatg tcaaacaaaa caaagcaaca atatcaaaaa  46080
cccacatgct ttttcttcat actgtctata ttattgaatg acagacaaac atctgtcctt  46140
caagtcaaat attaattaat catagactcc tttctcttct tcttcacccc gccttatcta  46200
attggccact gtcttagctt tttttttttt ttttttttta aagatggagt cttaccctgt  46260
tgcctagtct ggagtgcagt ggtgtgatct cggttcaccg caacctccat ctcctgggtt  46320
caagcaattc tcctgcctca gcctcccaag tagctgggat tacagacatg caccaccaca  46380
cctggctaat tttgtatttt ttagtagaga tgggatttcg ccatgttggc caggatggtc  46440
tcgaactcct gacctcaaat aatccaccca ctttggtctc ccagtgtctt agcagtttta  46500
aaaattatct ttggaatttg tctcatctct atttctaatt catttaatct aattgaagcc  46560
ttaatcattt cttttcttcc aacatgttga gcatctgttc tgattttcct gaccccactt  46620
gcctcattct ccaattattc ttcccatagt tatcagcact gaatgctaat aataatactt  46680
tgttcatatc agttgttatt aaaactcttc acttattcct tattatcttc aaggtaagcc  46740
cagcttccca gtcatgacat acaagactct atgtgtgacc ccaatactta acacagatgt  46800
gtttcagaat tcagaatttt ttggatttta gaaaagtaat acggtttatg caatacatat  46860
ataacatcct ctgctcattc ctgaacactg atgggagtga atggcaggtg cttttaataa  46920
ttacgctgag gtaaattatg ctaggtgtaa actggacctg tcctgggcaa acgaggatgt  46980
tctttacaca gtttaagaat gtcaagcaaa gaacattagg gatgaagcaa tacagggaga  47040
atagatagag tgaagggagc agtgggttaa gtggagtcct ggagaaatat ttgaaaaggg  47100
agaaaggaat gtggctcctg aggtaggagg gaaacctgga gcaggtagcc ccacagaagc  47160
ccagggaaga ggcattgttt ttctattatt ttggaagcag atccccttta ggagactcct  47220
catcagataa tgattattca ctaagaggtt atattcttaa ttaaaagggc ctttaccttt  47280
tcttagaata ctatgtttga ataacttttt atgtattacg atataaaagt ctcttttaag  47340
catttctgtt ttatagtcat ttggccaaaa tctaattcag atccagctta aatccaaatg  47400
tcatttgatg ctacatttta tcctgaggtt gctagttatt tagtcaaata tagtgagtat  47460
aatcactaca ggcttagagt aaatttccat gtcaagaggt agaacacatt tattctgtaa  47520
tattgaatcc tgtaatattg aaaatcaaaa acagcccttt tttttcttct gtagaaaata  47580
agatttttaa ggaaggcagc aggaaaatag aacaagtgaa tattttacgt tcttagtggt  47640
ttatggttgg cagttttccc ccaacatttt gttacgaaaa gttaaaatgt acagaagaat  47700
tgaaagactt atacccacca gctagattgt gccattaaca tgttgctgta tttactttat  47760
cactgtccat ctctctgacc atctatttgt ccctctttcc atccatcagt ctgtcttttt  47820
tttggtaagc atttcaagta agttgactgg caatttttct aagcagctgt atctttattt  47880
tgttactgtt tttttcctgg atgttgtaat tacagtgtca agacatttaa taatgcacat  47940
gtttcagcta accctttccc caatttctag aaatctgaga ttgccaataa tccctgtcaa  48000
tcttaaatta ttttttaatt ctggtaaata gtgtcaaacc tgattagtgc cctctttctc  48060
aattgttttg taatccagac aactgttagt cattaaaaca taatttatag tggttttaaa  48120
gcatgatttt ctaaaaaatt ttaaataaat atttattcat attatgttgt tttcagagtg  48180
gagagatcta cagaccaagt aatcaagcca gtcaatgtag gagctctatc aaaatgggtt  48240
gggaagatac cgccagatgt tttacaagac atggcagtga ttgctcctat gcttgccaag  48300
cttggatatg acccatatgc caacccacct aactacggaa aacctgatcc caaaattatt  48360
```

-continued

```
gaaaacactc gaagggtaag tgagattttt taaagcaact gagaaaacta gattttgaat  48420
ttgggatctg aatacgtttt tttcttattt tatttcttgc tatttaatga tcagaaaaat  48480
atattttttt ttttttcatt tatttttatt ttattttatt ttattttttt tattatactc  48540
taagttttag ggtacatgtg cacattgtgc aggttagtta catatgtata catgtgccat  48600
gctggtgcgc tgcacccact aatgtgtcat ctagcattag gtatatctcc caatactatc  48660
cctcccccct cccccaaccc caccacagtc cccagagtgt gatattcccc ttcctgtgtc  48720
catgtgatct cattgttcaa ttcccaccta tgagtgagaa tatgcggtgt ttggtttttt  48780
gttcttgcaa tagtttactg agaatgatgg tttccagttt catccatgtc cctacaaagg  48840
atatgaactc atcatttttt atggctgcat agtattccat ggtgtatatg tgccacattt  48900
tcttaatcca gtctatcatt gttggacatt tgggttggtt ccaagtcttt gctattgtga  48960
atagtgccgc aataaacata cgtgtgcatg tgtctttata gcagcatgat ttatactcat  49020
ttgggtatat acccagtaat gggatggctg ggtcaaatgg tatttctagt tctagatccc  49080
tgaggaatcg ccacactgac ttccacaatg gttgaactag tttacagtcc caccaacagt  49140
gtaaaagtgt tcctatttct ccgcatcctc tccagcacct gttgtttcct gactttttaa  49200
tgattgccat tctacctggt gtgagatgat atctcatagt ggttttgatt tgcatttctc  49260
tgatggccag tgatgatgag catttcttca tggttttttg gctgcataaa tgtcttcttt  49320
tgagaagtgt ctgttcatgt ccttcgccca ctttttgatg gggttgtttg ttttttttctt  49380
gtaaatttgt ttgagttcat tgtagattct ggatattagc cctttgtcag atgagtagga  49440
tgcgaaaatt ttctcccatg ttgtaggttg cctgttcact ctgatggtag tttcttttgc  49500
tgtgcagaag ctctttagtt taattagatc ccatttgtca attttgtctt ttgttgccat  49560
tgcttttggt gttttggaca tgaagtcctt gcccacgcct atgtcctgaa tggtaatgcc  49620
taggttttct tctagggttt ttatggtttt aggtttaacg tttaaatctt taatccatct  49680
tgaattgatt tttgtataag gtgtaaggaa gggatccagt ttcagctttc tacatatggc  49740
tagccagttt tcccagcacc atttattaaa tagggaatcc tttccccatt gcttgttttt  49800
ctcaggtttg tcaaagatca gatagttgta gatatgcggc attatttctg agggctctgt  49860
tctgttccat tgatctatat ctctgttttg gtaccagtac catgctgttt tggttactgt  49920
agccttgtag tatagtttga agtcaggtag tgtgatgcct ccagctttgt tcttttggct  49980
taggattgac ttggcaatgc gggctctttt ttggttccat atgaacttta aagtagtttt  50040
ttccaattct gtgaagaaag tcattggtag cttgatgggg atggcattga atctgtaaat  50100
taccttgggc agtatggcca ttttcacgat attgattctt cctacccatg agcatggaat  50160
gttcttccat ttgtttgtgt cctcttttat ttccttgagc agtggtttgt agttctcctt  50220
gaagaggtcc ttcacatccc ttgtaagttg gattcctagg tattttattc tctttgaagc  50280
aattgtgaat gggagttcac ccatgatttg gctctctgtt tgtctgttgt tggtgtataa  50340
gaatgcttgt gatttttgta cattgatttt gtatcctgag actttgctga agttgcttat  50400
cagcttaagg agattttggg ctgagacgat ggggttttct agataaacaa tcatgtcgtc  50460
tgcaaacagg gacaatttga cttcctcttt tcctaattga ataccctttta tttccttctc  50520
ctgcctgatt gccctggcca gaacttccaa cactatgttg aataggagca gtgagagagg  50580
gcatccctgt cttgtgccag ttttcaaagg gaatgcttcc agtttttgcc cattcagtat  50640
gatattggct gtgggtttgt catagatagc tcttattatt ttgagatacg tcccatcaat  50700
acctaattta ttgagagttt ttagcatgaa gggttgttga attttgtcaa aggccttttc  50760
```

-continued tgcatctatt gagataatca tgtggttttt gtctttggct ctgtttatat gctggattac 50820
atttattgat ttgtgtatat tgaaccagcc ttgcatccca gggatgaagc ccacctgatc 50880
atggtggata agctttttga tgtgctgctg gattcagttt gccagtattt tattgaggat 50940
ttttgcatca atgttcatca aggatattgg tctaaaattc tctttttttgg ttgtgtctct 51000
gcctggcttt ggtatcagaa tgatgctggc ctcataaaat gagttaggga ggattccctc 51060
tttttctatt gattggaata gtttcagaag gaatggtacc agttcctcct tgtacctctg 51120
gtagaattcg gctgtgaatc catctggtcc tggactcttt ttggttggta aactattgat 51180
tattgccaca atttcagagc ctgttattgg tctattcaga gattcaactt cttcctggtt 51240
tagtcttggg agagtgtatg tgtcgaggaa tgtatccatt tcttctagat tttctagttt 51300
atttgcgtag aggtgtttgt agtattctct gatggtagtt tgtatttctg tgggatcggt 51360
ggtgatatcc cctttatcat tttttattgt gtctatttga ttcttctctc ttttttttctt 51420
tattagtctt gctagcggtc tatcaatttt gttgatcctt tcaaaaaacc agctcctgga 51480
ttcattgatt ttttgaaggg ttttttgtgt ctctatttcc ttcagttctg ctctgatttt 51540
agttatttct tgccttctgc tagcttttga atgtgtttgc tcttgctttt ctagttcttt 51600
taattgtgat gttagggtgt caattttgga tctttcctgc tttctcttgt aggcatttag 51660
tgctataaat ttccctctac acactgcttt gaatgcgtcc cagagattct ggtatgtggt 51720
gtctttgttc tcgttggttt caaagaacat ctttatttct gccttcattt cgttatgtac 51780
ccagtagtca ttcaggagca ggttgttcag tttccatgta gttgagcggc tttgagtgag 51840
attcttaatc ctgagttcta gtttgattgc actgtggtct gagagacagt ttgttataat 51900
ttctgttctt ttacatttgc tgaggagagc tttacttcca actatgtggt caattttgga 51960
ataggtgtgg tgtggtgctg aaaaaaatgt atattctgtt gatttggggt ggagagttct 52020
gtagatgtct attaggtctg cttggtgcag agctgagttc aattcctggg tatccttgtt 52080
gactttctgt ctcgttgatc tgtctaatat tgacagtggg gtgttaaagt cttccattat 52140
taatgtgtgg gagtctaagt ctctttgtag gtcactgagg acttgcttta tgaatctggg 52200
tgctcctgta ttgggtgcat aaatatttag gatagttagc tcctcttgtt gaattgatcc 52260
ctttaccatt atgtaatggc cttctttgtc tcttttgatc tttgttggtt taaagtctgt 52320
tttatcagag actaggattg caacccctgc cttttttttgt tttccatttg cttggtagat 52380
cttcctccat ccttttattt tgagcctatg tgtgtctctg cacgtgagat gggtttcctg 52440
aatacagcac actgatgggt cttgactctt tatccacctt gccagtctgt gtcttttaat 52500
tgcagaattt agtccattta tatttaaagt taatattgtt atgtgtgaat ttgatcctgt 52560
cattatgatg ttagctggtg attttgctca ttagttgatg cagtttcttc ctagtctcga 52620
tggtctttac attttggcat gattttgcag cggctggtac cggttgttcc tttccatgtt 52680
tagcgcttcc ttcaggagct cttttagggc aggcctggtg gtgacaaaat ctctcagcat 52740
ttgcttgtct ataaagtatt ttatttctcc ttcacttatg aagcttagtt tggctggata 52800
tgaaattctg ggttgaaaat tcttttcttt aagaatgttg aatattggcc cccactctct 52860
tctggcttgt agggtttctg ccgagagatc cgctgttagt ctgatgggct ttcctttgag 52920
ggtaacccga cctttctctc tggctgccct taacattttt tccttcattt caactttggt 52980
gaatctgaca attatgtgtc ttggagttgc tcttctcgag gagtatcttt gtggcgttct 53040
ctgtatttcc tgaatctgaa cgttggcctg ccttgctaga ttggggaagt tctcctggat 53100

-continued

```
aatatcctgc agagtgtttt ccaacttggt tccattctcc acatcacttt caggtacacc  53160
aatcagacgt agatttggtc ttttcacata gtcccatatt tcttggaggc tttgctcatt  53220
tctttttatt ctttttttctc taaacttccc ttctcgcttc atttcattca tttcatcttc  53280
cattgctgat accctttctt ccagttgatc gcatcggctc ctgaggcttc tgcattcttc  53340
acgtagttct cgagccttgg ttttcagctc catcagctcc tttaagcact tctctgtatt  53400
ggttattcta gttatacatt cttctaaatt tttttcaaag ttttcaactt ctttgccttt  53460
ggtttgaatg tcctcccgta gctcagagta atttgatcgt ctgaagcctt cttctctcag  53520
ctcgtcaaaa tcattctcca tccagctttg ttctgttgct ggtgaggaac tgcgttcctt  53580
tggaggagga gaggcgctct gcgttttaga gtttccagtt tttctgttct gtttttttccc  53640
catctttgtg gttttatcta cttttggtct ttgatgatgg tgatgtacag atgggttttc  53700
ggtgtagatg tcctttctgg ttgttagttt tccttctaac agacaggacc ctcagctgca  53760
ggtctgttgg aatacactgc cgtgtgaggt gtcagtgtgc ccctgctggg gggtgcctcc  53820
cagttaggct gctcgggggt caggggtcag ggacccactt gaggaggcag tctgcccgtt  53880
ctcagatctc cagctgcgtg ctgggagaac cactgctctc ttcaaagctg tcagacaggg  53940
acacttaagt ctgcagaggt tactgctgtc tttttgtttg tctgtgccct gcccccagag  54000
gtggagccta cagaggcagg caggcctcct tgagctgtgg tgggctccac ccagttcgag  54060
cttcccggct gctttgttta cctaagcaag cctgggcaat ggcgggcgcc cctccccccag  54120
cctcgctgcc gccttgcagt ttgatctcag actgctgtgc tagcaatcag cgagattccg  54180
tgggcgtagg accctctgag ccaggtgtgg gatatagtct cgtggtgcgc cgtttcttaa  54240
gccggtctga aaagcgcaat atttgggtgg gagtgacccg attttccagg tgcgtccgtc  54300
accccttttct ttgactcgga aagggaactc cctgacccct tgcgcttccc aggtgaggca  54360
atgcctcgcc ctgcttcggc tcgcgcacgg tgcgcacaca cactggcctg cgcccactgt  54420
ctggcactcc ctagtgagat gaacccggta cctcagatgg aaatgcagaa atcacccgtc  54480
ttctgcgtcg ctcacgctgg gagctgtaga ccggagctgt tcctattcgg ccatcttggc  54540
tcctcctccc ccagaaaaat attttgaatt agaaaaattt gggcctagtg gcctggcacg  54600
ctggctcatg cctgtaatcc cagcactttg ggaggtcgag gcgggtggat cacaaggtca  54660
ggagatcgag accatcctgg ctaacacggt gaaacccctt ctctactaaa tacacaaaaa  54720
attatccagg cgtggtggtg ggcgcctgta gtcccagcta cttgggaggc tgtggcagga  54780
gaatggcatg aacccgggag gcagagcttg cagtgagtag agatcacgcc actgcactcc  54840
agcctggatg acagagcgag actccatctc aaaaaaaaaa aagaaaaact tgggcccagc  54900
atagggctga cacctgtagt ttcagcactt tggaaggccg agatgcgagt gagcccagga  54960
tttcaagact agcctgggca acatagtgag acccccatct ctacaaagaa tataaaaatt  55020
atccaggcat ggtggcacat gactctagtc ccagctactt gggaggctga ggtgggagga  55080
ttgattgagc ctgagaggtc aaggctgcag tgagctgaga gtatgccact gtactgtagc  55140
ctgggtgaca gagcaagacc ccgtctcaaa ataagaaaaa agaatgaaga aaaattatat  55200
ttgtagaatg ctttcttatc agcagtcttc cactgcattt taaggataac tggctcgttg  55260
gggatagttc ttagggtatt ttgctcagtt tctaggaatg atactcactg ttgggagatt  55320
tattctcagc caattactgc agatctgcat aaacaccata attattagtg accttacttc  55380
tgatttcttt ctttctgtaa atctaatagc cactttactt ttaaaccttt gtttagatga  55440
ggcataattt ttggatacct aaaagctaaa cattggttac actagaaaaa ttattaaaca  55500
```

-continued

```
ctagccttct gattaagaga aagttgctat taaagtgaca ttacagtttt tattttaata  55560
agttatgctc acgtctttac aatatattat ttcagaaagt gctgaaaatt cagagctaga  55620
ttatatagcc taccagttga gtctatttca aatcagatct tatacattct tttctttatt  55680
gcagtaagat atatttaaca taaaatttac cactctgaca ctttttaaag tgcacaattc  55740
agtggcatta aatacattca cattgttgtg caactgtcac caccgtccat ctccagaaca  55800
ttttttgtct tcccaaactg aaattctgta cccatactct tcattgcctg gtccctgtca  55860
actgcagttt tttgtgtcac ttgtatatat tctttttttga aactacattt caaataagac  55920
aaccatgcta gcataagttc actgataggc tatttgattc caaggtgaaa attccttggc  55980
tttgtctgaa ttctcttgtt tatatcagtg tccttccctc cctacaacca tataaccgta  56040
tcatgttttt attctgtctt ttgataactt taattgacaa atttatgcca catttatttc  56100
atgagattaa tttctatgtg aattcctttc tcttaggtat tacttttatt tccccttttc  56160
aattcattat tagcagctat atgggaagag ctgccttctt gtaaaccatc acatatgagg  56220
gcaaattaaa aaaaacaata atcgctatcc tctttacact ttttatatat atataaatat  56280
ttccattata aaaatataag ctcattatat gaaacttaca aaattcaaag gataagagaa  56340
taaaaatcac ctgtaatgtt cccacctaga cacatacaca tattattctt ttttattttc  56400
ttatttattt acacatatta ttcttaatat tttgatgtat tttctctcct ctgcattatg  56460
ttaaacaaag gtaagattac gtatatcatc ttacctttat atacacagtt ttgtatccag  56520
tccttttaat attcacgagc attttcccat tgtgtgcatg ctttttaaac ataattttta  56580
tagttataaa ccttcataga agccacctta aattctttct gaagcacagt agtaaatgaa  56640
tgaataaatc aacaaacaaa atacatttcc ctggtagatg ttctacaatt gatttttacca  56700
ttttgttgtt taccgttttc tctttgacaa attgtgctgc agtgaacatc tttgcagata  56760
ctcaatttta ggattttttt tttaaggtag gatcaataaa aatagaacta aaccagggta  56820
aagtatctga gatttttaaa aggtgtttga tatctattga tactaaaaaa cctttgggct  56880
ggccacagtg gctcacgcct gtaatgccag cattttggga ggctgaggtg ggtggatcac  56940
ttgagctcag gagttcaaga ccagcctgga caacgtggca aaaccccatc tctacaaaaa  57000
atacaaaagt tagccaggtg tggtggcaca tgcctctggt ttcagctgct tgggaggctg  57060
aggtgagagg attgcttgag cccagaattt tgaggttaca gtgagctgag attgtgccac  57120
tgcactccag cctgggtgat ggagcgagat cctgtctcaa gaaaacaaaa acaaaaaaca  57180
aacaaacaaa aaacctttga actgccagca taattgaggt aatttatttt agatttttgt  57240
tggttttaat agatttcatt gattaatgta attgaacatt ttccagttat tagctatatg  57300
tatatattct tttatgaact aagtttttac tttatttatt tgagacagag tcttgctctg  57360
ttggcacaat cttggcttac tgcaacctgt gtctcctggg ttcaagtgat gattctcttg  57420
cctcaggtgg gattataggc acatgctacc acgcctggct aatttttttt aatttttttat  57480
ttttagtaaa gttagggttt cgttgtgttg gcctggctga tctcaaactc ctgacctcaa  57540
gtgatctacc tgccttggcc tcccaaagtg ctaggattac atgagccact ctttaaagtt  57600
ttatatgtat taaagttttg tgagctcttt gtaattggta attcatagct atctcctttg  57660
cacaatagtg aaagggtttt ttattaccaa gatacatgta caatgctatt ttgagggttc  57720
ttaggcagta gacattatag ttttcctaca tgcaaattgg cttggctaga ttatcctttg  57780
ctttcttgag tggtgggttg ggaagaatgc tatggtttga atccatgtga ctaaagaatc  57840
```

-continued

```
tatttcatac acacttgtgg tttttgaaag gatttcaaaa tacccactga aataaaaaaa  57900
cacccaccct ttcccccccc cccccccgtc tctgcctatc tttaaagtga cagataattt  57960
tgaggaagaa aagatgaagt gtgaactata gtggtgtttt tgggcctttt gtggtaatgc  58020
atacaaactg acagtcttgt cttgtgaggg taggtttcat aagacctttt tgcaaactaa  58080
atcctgtgta tcttcaaagc ttttttgcct gtaataagtc agatgctaat gtatccagca  58140
ctgatgatca tgaggttttt gtaaagcagt gcttgaaaag agattgttga ccgttagcta  58200
tgatatgaga tgggccccag agaaagaggt ggctggcgaa ggtgttttcc ttagttatgg  58260
ggtgagagtg ggagaaaaat aacattttga ctgagaatat aggatttata tctctaagcc  58320
taaaaatact gggttggttt tttttttttt tttttttttt tggtacaatt ctgggtagtc  58380
tgcaagtaat attgagtcag cacattttag ggacatatta cccaatattg aatggataat  58440
catgcttcat ggttactgtg actcacatag taaattggta atgaaacgtt aacatatttt  58500
ataccctgtc ccaccatagt ctctaatcct aaaattatag tatatttcag taaatggtgc  58560
tgtctaggtt acatcgtcag ccttcttgca tagattctta accttttaga cttaggaact  58620
tatttgagaa tttgatgaat cctgtggatc cccacctcag aaatacagac acatgaatac  58680
acagatttca ctcacaattt cagtggatac atagatatac cagaagtcca tcagattaag  58740
gactcctatt agccacaatt tcagtggatg catgtgtgcc agaagcctga cagattaagg  58800
actcctattt tatagtctcc ttgctcaagc tcatccactc atagggcttt cattacagcc  58860
tatttgctga ttatcataaa tctgtatttc ctagtgggtc tctttcctga gccctaggtt  58920
cattatttcc aactgtcttc tgtatgtgtc caccgaaatg ctctcaagga cctcaaattc  58980
aaagtccaaa attgaattta ttttctaaac ttgttccctg agaggcagaa gctaggtgga  59040
attgttcatt aaactgagca ggaatccacc ttgagagtgg ggatgatgct gtgctcatct  59100
atacttgcgg tacctatgag ccagagagca gatttgagga acagagtcct cagggcacat  59160
ggctcaaacc ccaaaacaat tcaagaacct ggttgctaaa gttagagagc tgaaaagcag  59220
atccaattta tgaatggaat atttagttgg aaacctgagt agatagtact gaggaagagc  59280
aagtgatcaa atggaaaagc atgtaccaag gtgcagaacc cacagtaaca gacaagaaga  59340
aacatgaaaa tgaagtcagc tgggggacag gggttagatt aaatccctaa accaaacaac  59400
aaaaagctgc agcagcagtt ggaattgata ttcttacatt aaaggtaaag cctggaatga  59460
atgcatactt gtgttttctg gttcctatac tcagcaaaaa ctgcttgttc ctgttttttt  59520
ctatctccat acatagcatg cttattcacc cagttaccca aattaggtct cctcacttaa  59580
aattcatgaa tgactccact gttactacag gatagagtct agacttctta gaatgacatt  59640
tacttttcta gtatttgggt attttctcat tatctttttg ttgttgattt ctaatgtgac  59700
cattatggtc agagaacact cattatggtt tgtttcagtc ctttgaaata tattgaatat  59760
tgttttatgg ccagtatatg gtcttatgtg atcagttgaa aaaatatgta ttctgtgatt  59820
gttgcagagt tctgtaaata tcagtgaggt caagaaattt tatagtgttg ttacagtcta  59880
aatcttattt gatttttttgg tctgctttat taatgttggg aaaattatga atttttcaaa  59940
ttttccttac atttctagca attttgtttc atgtatttag gatctatatt attgggaaca  60000
cacccattta gaccttcttg aagaagtaac tcttttgtaa ttatgaaata tttctcttta  60060
tctctgctgt taccctctga aagtctactt tatctgatat gaatatagcc caacagtgtt  60120
tttatgtata ctatatacat ggtatatttt cccgattctt ttacttttaa tctgtgtctt  60180
tatatagctg gctttgtttg ttaatccagt tttatagtct ctgcctttta aatggagagt  60240
```

-continued

```
taatccactt acatttaatg taattattca tctgattgga tttaaaacta ccatcttgct  60300
atttgttttt tatttggatc atctattttt gtttctttgt ttctcttttc ctgccttctt  60360
ttggattaat ctttttttggt attccatttt atatattatc tcctcttttt agctatacct  60420
cttcttttttg ttttgttttt gcttatagtg gttactgtaa gacatgggct gcacattttt  60480
tatattgtaa aaatccagat agtaggccgg gtgcagtggc tcacacctgt aatcccagca  60540
ctttgggagg ctgaggcagg tggatcacaa ggtcaggaga tcgagaccat cctggctaac  60600
atggtgaaac cccgtctct actaaaaata caaaaagaat tagctgggct tggttgtggg  60660
cacctgtagt cccagctact tgggaggctg aggcaggaga atggcatgaa cctgggaggt  60720
ggagcttgca gtgagctgtg atcactccac tgcactccag cctgggcaac agagcgagac  60780
accgtctcaa aaaaaaaaaa aatccagata gtaaatatat tatgctttgt gggccacagt  60840
tgggctcttt gttctttact tgaagatcca gattttcatc tggcatcatt tctctttagc  60900
ctgatgcact tcctttagca gttcttatag taaagacatg ttgactacta atgctcttag  60960
gttttttttt tttttttaa tttgaaaatg tgtttgtttt ttttttaatt tgagaatatt  61020
ttgctggaca tagagttcta ggctattggt cgttttgtat ttttttttaac tttcaacatt  61080
aaaaagatac tattttattg gcttcccatg tttttgatga aagtcagctg acattcttat  61140
gaatgtaatt ttttttcttt gactgctata agatttttcc ctatttttgg ttttcagcag  61200
tttgattata atataccaaa ttcgtagctc cgttctactg ccatctcctg tgtgggcctc  61260
agttttgatt agtttttatt agcctacctt tgaattcatt gatcccttct ttttctgtgt  61320
ccagtctgct gttaaaccca tctggtgact tcttcatttc agatcattta tttttcagtt  61380
ctagaatttc cctttctctg ctggaattct ttgctcttta cccattctgt tgatcttttc  61440
ctctaaatta tttaacatat tcataataac ttttaaagtc ttcatccacg gatctctccc  61500
tgttgacttt gtttctttat tatgggttat aggcacacct tggagagact gtgggtttgg  61560
ttccagacca ccaaaataaa gtgaatatcc caataaagca agtcacacat aatttggttt  61620
cccagtacat ataaaagtta tacactacat tgtagtctgt tcagtctgta gtagcattgt  61680
gtcaaaagaa aacacaatgc atatgcctta atttaaaata ctttattgct aaaaaaaaaa  61740
tgctagcaat catccaagcc ttcagcaagt cataatcatt ttgctggtgg agactcttac  61800
ctccatgttg atgactgcta gaccattcag ggtggtggtt gctaaagatt ggggtgacta  61860
tagcaatttg ttttgttatg taatattcta tatcctttgc tgtcttttca acaatattca  61920
cagcatcttc accaggagta gattccatct caagaaccac tttctctgct cattcttaag  61980
aagcaactca ttcattcaag ttcaatcata agattgtagc aattcaacca catcttcagg  62040
ctcacttcta gttatagttc ttttgctatt tctaccacat ctgcagttcc ttcctccact  62100
gaagtcttga acctctcaat gtcatccgtc tgattcttcc aaattcctgt taacattgaa  62160
attttgacct cctcccatga attacgaatg ttcttaatgg catctaaaat gatgaaccct  62220
ttccagaagg tttgcagttg actttgtgca aatccatcag aggagttggt atctatggca  62280
gctatagtct taagaaatgt atttcttaaa taataatctt gacagggcca ggtgcagtgt  62340
cttaaacctg taatcccagc actttgggag gccaaggtgg atggatcacc tgaggtcagg  62400
agttcaagac cagcctggcc aacatggcga aactccatct ctactaaaaa tacaaaaatt  62460
agctgggtgt ggtggcgcat gtgtgtaatc ccagccactc aagaggctga ggcaagagaa  62520
tcgcttgaac cggggaggga gaggttgcag tgagccaaga ttatgccact gcactccagc  62580
```

-continued

```
ctgggtgaca gagcgagact ccatctcaaa aaaaaaaaca aaaaacaaaa ccaacttgac  62640
agtagaaatt actccttgat ccgtggacta cagaatggat actgtgttag caagcatgaa  62700
aacagcattc atctccttgt atatctctat cagaactcat gggtgacaag gtgcattgtc  62760
aacgagcaat agtattttgt gagaaatctt ttttcctaag caataggtct caacagtggg  62820
ctgaaaattg catttttatg ttatggagat agcttctttc cttaatcttc ataaacaaac  62880
aacctctact agcctccaac ttttcctctc acagccttta taaaattgaa gagaattagg  62940
gccttgctct ggattaggct ttggcttaag ggaatgtcat ggctggcttt atctgtctag  63000
tccactaaaa cttttgccat gtctacagta agactctcac tttcttacca cttgtgtgtt  63060
cattggagta gcacttgaat ttacttcaag aacttttcct ttgtattcac aacttgacta  63120
tttgatgcaa gaggcctggc tttcagctta tcttggcttt caacatacct tcctcactaa  63180
gcttgattgt ttctagcttc tgacttaaag tgagagatat gcgactattc ctttcgtttg  63240
gacacttaga gcccattgtt ggattattaa tcggcctttt ttcaatatca atgtgtcaca  63300
ggaacagggg aggcccaagg gagagggaga gagatggggg aacaaacagc cagttggtgt  63360
agcagtcaga acatacacaa cattgattaa gttaattatg ttatatgggc ttaggatcgt  63420
ggcaccccaa aacaattaca tggtaacatc aaagatctct gatcgcacat caccgtaaca  63480
gatacaataa tgaagaaggt tcaaatattg caagaattac cacagtgtca taaagagaca  63540
tgaagggagt gcatgttgtt ggaaaaatgt caccaacaga cttgctcacc acaggattac  63600
cacacacctt caatttgtaa aaaacacaac atctgcaaag cacaatgaaa tgaggtatgc  63660
ctgtactcat ttgcttcttc acatgtctta gaagttttaa ctgcatactg gaccttttgt  63720
ataacagagg ggtagagaat gaactaggta atactttttg ttttattttt gttaaagaga  63780
gcagttcttt cctccagcag gtagctaagg tgatcactca aatttgacag tgaatcaagc  63840
tgagctgggg ctgagcagta gctttaattg atttcagttt gcctctggat tcaaatgaga  63900
ttaaggaaat ttgactttta gcccaacctt agctttctat atcatttaga cgagggggttc  63960
atttctttga ttttagcaag attgcagctg ggaggcagtt gggttgaaga ttaaattaat  64020
ttactttacc tctggattgc aactatagca gggccctgga acccaagcac cacacagcat  64080
tgggagatct ctttctgtct ctcactgtgc tcccaccagc acttactaag attctcttgt  64140
agtattacat gtaattgtca ggtcaagaga tttgttttta cacttgggac tctttcagat  64200
tctaattaat cataccagtc cacagtctca ctaaaagttt ggcttgtttc agcaaaatct  64260
ttccacctat gggagacctc cttttctgcc cacttgtacc cagacaggca attgattcaa  64320
ggtagctaga aacaggcttt tgtttctctg tgaagaactc atccttctcc agaaattggc  64380
tcagttagac ttcttggcat tcatttactg ctttttcatg gctttacaga aaagtatgaa  64440
gtttagttta tctggtgttt tcttgttttg atgagagcag tggtcttttg ggatcagctg  64500
cattcaaacc aggttggaac gctttagaat gatggcatta agattctttg ccttctgctt  64560
tcaaccttcc ttttcaacct catctctttt tattctttta accacaccac agtgcctccc  64620
tttcattccc acagcacatt gtatacctcc ataccttttgt tccttctgcc ttgattgtcc  64680
ttcttctcat cttacaactt tgtcctttga aactcaactc acatgacacc tcttctgtgc  64740
cacagatcct cctgctacaa tgtacctacc tttacttgtg tactttcaca ttatattgtg  64800
atgatttata ttatatgctg ctgcttttaa actaaggaca tgccagacat gccttcatct  64860
gaaaatgtta atatagttca aagtgttgct atagtctttg tttagttaaa gtaacaactt  64920
tctggtctga aaaaaaaaag actatgcatc ccttcaacag aataagatag ttttaaaagt  64980
```

-continued

```
aatgatatgg gagcatctct taagatatgg tcagtgttat gttttaccat ttgtatttag  65040
aaaaacagct gtgtgtgtat gtatgtatgt atgtatgtat gtatgtatgt atgtatgtat  65100
taatttattt tgaaacggag tctcattctg tcacccaggc tggagttcag tggtgcgatc  65160
tctgctcact gcaacccccg cctcctgggt tcaagcaatt ctcccacctc agcccctaga  65220
gtagctggtg ttacaggtgc atgccaccat gcctggctaa tttttatatt tttagtagtg  65280
acagggtttc accaagttgc ccaggctggt ctgaagctgc tgacctcagg cgatctgctc  65340
accttggcct ctcaaagtgc tgggattaca ggcgtgagtc actgcacctg gcttgtatat  65400
gtagtttttt aaaaaaataa ataagtaaag acttttcaag gacaaagata tcatttgcat  65460
tttgtagcct gagtgccagt aatacttgac aattacttga tgctcaataa aatgattctt  65520
attagcaaaa taaaccttac acgtagaaaa agaatatgcc aggaaccaag aaaagggata  65580
ttcagatatg aggctcttgg agttacggct cagctcacaa ggattctgcc gtaggtgaga  65640
aatgctccat tacccagagg caaagcccca gaggttgtgg cagcacttta tgactatgta  65700
tcagtctggg ctcagtcagg gaaacattga gccactgtta agtgttatag gagtgagggg  65760
tttaatatag taattaaggc ctatgcaaat atgggaggac tagagaagtg aaggtctgca  65820
cgttttttat tgtatactgg acacgttgtt tacaatagga gtagggaatg agctggatac  65880
agctacagtt ggaagaccag aggaataggc actgatgact gaaacctgca gctctagaga  65940
gggcagagaa gtgctaggaa actgcctctc gctgccaaag taggactcag tgtgggatcc  66000
caaggaaagg tctgtgaaga ctgccacggg gataaagtgg agctttagga gaggccagtg  66060
gagcgactgc atctgactgc cctgacctct taaaaataat ggcttctact tcatttccac  66120
cttctaaaac tcacagaagc ctctgaccca gaaccacaca gggaaaggaa ttctgggaga  66180
cttaattttc tgtcctagac aacagtggtg gtggtgccag ttgaccatcc agcataggcc  66240
attcctttgc cagcctggct tacatacaca cctacttaaa ccatatttaa ctgccagata  66300
aagctaaatg ctctgcttaa catgttgtaa ctatcgctta gcaaactgaa aacatgctaa  66360
gcactccctc aaagaggaga tgctgtattt catattgtgc tttgtacatt tctggctgat  66420
atgaatgtat tccactagct gagtcacatc ccctctttga tatcctaaaa cttacatata  66480
ctgagataca gagttagcca tttccttttt tttttttct tggcaaggtc ttgttctgtc  66540
acccaggctg cagtgcagtg gcgccatcat agctcactgc atccagaatc tcctgggccc  66600
aagcgatccg cctgccttag cttcttgact ataggtgtgc accaccacac ctagctaaat  66660
tttttttatt tttaactttt tgtagagaca agaggtatca ctgtgttgcc caggctgctc  66720
ttgaactcct ggcctcaagc aatcctgttg ccttagcctc tcaacgtgtt aggattatag  66780
gcatgaacca ccgtgcccag ccagagtcaa tacaccttat attagagagt attattagac  66840
agggaaaagt ggaaaaaaga attcgttaat atattcagta tatattcata tcaaagcaaa  66900
gaagaatatc tgccaaacta ttgtagttct cattttctgt acctttcatg tgatcatggc  66960
aggtatctgt catttctttc ttcctctagc cattccatgt tcctttggtc ctcagtagtc  67020
acctcagatg gtctttgttc tttgcctggt ggggtggcct aaaccttcat tctggggtgt  67080
atgtaccaat aaatggccat attgttttgc tctaatatcc cgttaacttt ccataataaa  67140
caagtgtaat agaaaatcct aggttccagg caatttcttt ccttcttcca ttgagtattt  67200
ttttcccatt gtgtatttta aacttggttc ttccttgata atcgggatca atcagcctag  67260
ctattatagt acctgcctta cttgtctttg gctaagtggc atgaggagca agaagtgctg  67320
```

-continued

```
agttaacagt ctcagctctc tgttcagtgg aaataatgtt gtgtctcccc caaagaagca  67380
cttctccctt gaggattaag acctgtaaac tgggagagcc cacagctgct gcgagttttc  67440
ttttggggaa ggattttgat aatatttagt gaatataggg ctatttcgat tttcttgttc  67500
ttgtatcaat tttgataaat tgtatttttt aaagtaattt ggccatttca cttaagttgt  67560
caaatttgtt ggcaggaagc tgcagtattt tcttagagtc cttctaatct ttgtcaaatt  67620
gatagtgata acttttctat tcctcatgtg atgacccctt gattccgcct ctgtccacac  67680
ctgttagtga ttccctccac ctgaatgtgg acaggacctg tgacttgctt ggaacgaata  67740
gaatacaaca aaggcgatgg gagatatgtg attgcatgat tatattatat aagattacag  67800
cactggactg gctggagtgt gcacgtctct ctctctctct ctctggacat aaagactgtt  67860
atcttgtata gactctgggt tcctttataa tactcttgtg aatgcattta cttttgtttt  67920
agcaggcaat caactcaggt aggctggatt atacattgtt ttgccttttg caggcagtga  67980
ttcaaatccc aattcagtta tcaaagcaaa gcctttgcta aactggtttg ggtttgtcct  68040
gtgcatgtgt gattcagagg ttaaggtgag acccgtgtag gtgcatacat aaaagtggag  68100
agctccttca cctgctgttt ctgctccagg agtttgctct gactccctgt ctttctttgg  68160
ctcctttccc tgcttgctct gaccagaaag aaaacaattc ctatcagagt tttagccacc  68220
tacgtgtgct gcttagtgac tgaagctgtc ccaccctcaa ggaaaaactt gatgagaaaa  68280
aaataaacaa acagaaaact caccctgtaa ggtcacttct ccaacttttt acttccctcc  68340
acaatctgcc tgcttttatt tactttccag atcctcatat agtttttttgt tttgttttgt  68400
tttgctgtgt tttgagatgg agtttcactc ttggtgccca ggctggagtg cagtggcaca  68460
atcttgtctc actgaaacct ccccctcccg ggttgaagcg actcttttgc ctcagcctcc  68520
tgagtagctt gggattacgg gcagccgcca ccatgcacgg ctaatttttg gtatttttag  68580
tagagacagg gtttcaccat gttggccagg ctggtcttga actcctgacc tcaggtgtcc  68640
cacccacttc agcctcccca cagtgctggg attacaggtg tgagccaccg cgcctggccc  68700
aaggtagtta ttttttaaaa gtttgctcaa actttatagt tgtaattaga gggaggaaca  68760
actttatggg atgtaggtgg cttaacctca ccataatgga accaaaactc cacttcattc  68820
acttttttttt tttagatgga gtctcgctct gtctgcagtg atgagatctc ggctcactgc  68880
aaggtccgcc tccccgggtt catgccattc tcctgcctca gcctcctgag tagctgggac  68940
tacaggcgtc tgccaccacg cccggctagt ttttttgtat ttttagtaga gacggggttt  69000
caccgtgtta gccaggatgg tctcgatctc ttgacttcgt gatccgcccg cctcggcctc  69060
ccaaagtgct gggattacag gtgtgagcca ctgcgcccgg cccacttcat tcactttaaa  69120
atgaagtact tgaccagaag cagtactgtt tagaatgcca ttatggtgaa taagatattt  69180
tgtaagggaa aggatgctgg tttttgacag aaatgttgtg ggcagagaag gaaatcttca  69240
ttgagtaaaa gcagtgtcct ttttagatgg aagcggtcca gtgtgatcat cctgctacag  69300
atggctgccc agaccccctg ggagcagcgc tttattgggg caccattgtt ggcctctcct  69360
gttggcaggt tggacactta gccatgattg ttgccaggtc agccttgaca ggtggaagcc  69420
tgtgtcactg agcacatgca tgaccttcat tcctgttgct ctcacagtag gatatgaact  69480
ttgttcatta gcgttctgag caagggaaac agtggctgat aaaataatga gtcattttgt  69540
ccacttggtt attgagagcc tcctctgctg agattataca ttggtcatca tttacatggg  69600
acacaaatac cctcacactt tgtcctgttt gagaatagtt tattgacata gctcttttct  69660
atatcttacc acaagtttcc caaccttatt ctaagtttct gaatttccag tcaaaccatc  69720
```

-continued

```
tgctgctgac cacaaatcag tgtggattcg tatttatagc catcactcct ttgacacaaa  69780
atgtgcagtc atgtacactg cttcgagtgt atgatgagca gcctaagcga cttgggcaac  69840
ttggtagcca gtggtaaagt gttcagtcct tactaaatcc tagtagcaag caagggctct  69900
ttctcaaaag ggagagtaat gatctccaga agttagcata gctttgctct aaaatcctag  69960
ggttctatac tgtgatttac ctctagggcc tgccatacct ccacacatca ctcatgaagt  70020
atcatcctgt atcttaagtt tttgttggcg atactaatct ctgcagttcc tctaggaatg  70080
cagtattact tttggtgtaa tattttggta gagagaggca gctctaatgt aacccctgag  70140
gtatggcttt agtatgctac ccatctctgt tagtcctagg gacaccatca ccaatcagcc  70200
accaccagag atctctacag ctcacaccat tctcttttcc tactctacct ctgcgtgtgc  70260
ttataaagta tagccatgtg cccattgttt ctgtcatgaa gcgtcaccag ttggctgctg  70320
tgactcagag atcttttcat ccttcccttg ggttcaggga atctatttct ctgacagcct  70380
ttcccattgt tatttctagc ctgcagcgaa caagcactaa agagcttttt agggatgttg  70440
ttgcccccttt caccaatgta tttctcaaag gcttggtaaa ggagtgagtt ctctagacat  70500
tcctgggatg tagttaggag atcagtgaac agatcagtca tacgtattaa atacacccca  70560
gtattcctta ttttctaacc ttttgaataa attttatttt gagactgagt tttgctcctg  70620
ttgcccaagc tggagtgcaa tggcactgtc tcagctcatt gcaacctctg ccttccgggt  70680
tcaagcactt ctcctgctca gtctcctcag tagctgggat tacaggtgcc cgacaccatg  70740
cccagctaat ttttgtattt ttagtagaga cagggtttca ccatgttggt caggctggtc  70800
ttggaactcc tgacctcagg tgatccaccc accttggcct cccaaagtgc tgggattaca  70860
ggcatgagcc actgcacctg gcttgaacaa cttttattta cagtatacca aggaggttct  70920
ggcatctaag cttcatttaa tgtaagccac tgatggatcc aggttttggc caaccaggtg  70980
aggaaattgt tagagttatt ccctgattac tcaagccaat atactgcatc caaaatatct  71040
ggttaatgta ctcatatatt gataaatttg accaagtcca acgttacatt ccttcttgtc  71100
tggtctaaca ttcttaggat tcattgctac acacttccta ggtttctgca agtacaaatg  71160
ggcaaaatct agcacaatga ccctagccct ctgagggtca cagcaggttg gttcaggagt  71220
aggaacctga cccaacacag gcaaataaag gtctttccct gggactgtga aatggtacca  71280
agggaagaaa ggtggtttct ctctggtagg gagggccact ggatataagg cacaggaact  71340
gttgctggaa gcgttagaca ctgctgactg cttgttcctt tttccctgtt agtaaagact  71400
attcctttaa aaaaccaaaa aaggtagata aaaatgccag atattcattt tcccatatac  71460
tcttgtgggt ggaatgacca cttgaccatt tttttgtagc cagtgataca taaggagatt  71520
ttttttaac agggaaaaaa agagcttaca aattttatgt gcacatgtgt gcatgggagt  71580
tatacaattc ttttaaaaaa aaaactcaaa tggctagatg attgacactt ttgtaccacc  71640
ctgagataca gaaagaatag gggcttggat catggccaaa caagttatgg tggcaaaaca  71700
ggttatggga ggaagagaag accacctttg cctggctagc aaaggtagtc ttgaactctc  71760
acaggcagca gccctcagaa agaatggata gtagccagtg ataaatgttt ctagcagacc  71820
tttaaaggtg ttagactctc agttaatcat tcttaggtct ggataaggag atgtttgcta  71880
gggattttct gggagagatt tagctttctg agaaaataaa gaattgtgtg aaaagagctt  71940
actctttcct tcctgctttt gaacattgct gtgaaagaac attatgctta gccctgctgc  72000
agccactttg tgatcctaag agaagttatc atcaataaca cactgaaggt gacagaagga  72060
```

-continued

```
agattagggc agaggcttcc cttgatttct gggcttagga ctgtccatcc acctcatgtc  72120
tggacttctt gttatgtgtt tgacatactt gtactcagtt attctattac cgtgtgttca  72180
ctgcaaatgg ggtcgtgttc ctcagtgtgt aagggaataa agccaaccca tcgagagaag  72240
cagagccaaa gaggtcaagg gagtgtctgg caggggttga ggtcctggtt ctggttgccc  72300
atgaagatca tttccagctc tgcccttgcc acagttccag gaaacatttc cctttttgac  72360
tgtattactt gaattgggtt tctgggctgt agtaggaata ttccaactaa taccatactg  72420
ggtaaatttg aagtatgata aattttaagc tacttctcac tttatttctt gtgcctaaat  72480
ttgaagagta tttatttatt tatttattta tttatttatt tatttattta tgagacaggg  72540
tctcgctctg ttgcccagag tgctctggaa tgcagtggca cgatcatagc ttactgcagc  72600
cttgacttct tgggctcagg tgatcctccc accttggcct cccaaagttc tgggattata  72660
ggcatatagg catgagccac tttgtctggc ctaaatttta gttaaagaaa ttcttatctc  72720
attctttcag aattttcata ggccttcaaa gcaacaacca tggagttaaa ttcatttcct  72780
caacttggca ggattttttt tttcccctat tgaagtattt tgtctttttt ttgtgtgtgt  72840
gtgacagggt ttcactcttc gctctgttgc ccaggctgga gtgcagtggc atgatgatag  72900
ctcactgtag ccttaaactc ccctgggctc aagccatcct cccacctcag ctccctgagt  72960
agctgagacc ataggcatgc accactatgc ccaactaatt attgtatttt ttgtagagac  73020
aagatgtcac catattaccc aggctggcct caaactcctg agctcaagtg attcacctgg  73080
cccggcctcc caaagtgctg ggattacagg agtgagccac tgtgcccagc cattttgttt  73140
tattttgaaa gaaggctgaa ttgattcctg caggcattct gtaaagaata tataaggaag  73200
ttcaaagtag cacattttac catctctcag aatacctcag tctttcttct gatgcatcac  73260
tttaaggctt cgattattaa acaagcaatt actaaacagt tgctttttgg aatactacct  73320
tctagtgctt caggagatgc aaagatctgg cttgtatcca ggaagaaaat acaggtaatt  73380
ggattggaga gagaagacat gccatagaag aaaatgaaat aataataaga tgggagaaga  73440
atttttactg tgttttaaag ggttaaaaac tgttggaaac ctaaaaattt gtccacagga  73500
cgaggctgaa agtctgagac taccccacag gaatagcctt gtcaaggcct gattgtgccc  73560
tttgactcat ccttcaaagt caaacctttc tcatcttctc tcccagcttt ggcactgtca  73620
ttccataagt gtatcccaat aatttgtgtt ttctgccaga aatccttttg gggctaatga  73680
gtttcatgca cttgtatttg ctgtgtaaag taggttttcc tatacttgta cttaccagat  73740
taaatgtcaa aggatccagc tctttgttgg ttttgtgtac aagcacaaat tgcacttgct  73800
catgccattc agaatttcgt acattttagt tgtcttttac aactgtaatc ccatctgaag  73860
gtctatggga aattcagttc cttaagaaat aggttcccct catccttctc tttctgcctt  73920
cattagtgag agtacttttt gagagcaaga gaacatttgc agtgaagagg tttagttgga  73980
tagctattta tacagttttc cttggaattt taaagaatga aataatttct ctttatgtca  74040
gcaaatgcct attctgaaca ttcagaatga ctgttctgaa cagtaatgtt taactcttaa  74100
aaaacatggt atttataaat gagaatataa taaatcagta ttagaagtca ttttttaccc  74160
catgctctaa ttcaggagaa aataggagat acttataggt taacttggtg tctgattacc  74220
agtgcctgat ataatttctc caattccctt tttaaaaatc tattaaaata tcgttaattt  74280
aaaaaatccc tttaaaatga agatatgaaa agctctatgc taaagaatag ggaaattttc  74340
cactaagtcg atcattgatt gtattgtggc ttttccttaa acccaaagat tacccaaaga  74400
ttactgtaga agtgacacta cgaaaaatca aattaatgat agggagagta tacattagat  74460
```

-continued

```
gctcttccag aatgtccagc aaaagaccag agatgaagat tgatagatga gagaaaatga  74520
tacctatgaa agaaaaaaat agagatttaa ctggtgacta atagatgtct gcaaaggagc  74580
caacagaagt ggaacaaaag catggatcaa atgtctcatt gtggaagact ttccagggtt  74640
gaaaatgacc tgaagaataa aagagctcac tgtattctaa agaacattat gaaaacgtgt  74700
ctgtacctag acatattttg ctggttttct tttgatttta aggatcctga aaaaaaaaaa  74760
aatcctgcat atatcaaggc acaaaaaaat gagctttcaa caaagaaaca aaaatgatgc  74820
tggtagccag gcgcggtggc tcatgcctgt aatcccagca ctttgggtgg ccaaggtggg  74880
cagatcacaa ggttaggagt ttgagaccag cctggccaac atggtgaaac cctgaatcta  74940
ctgaaaatac aaaaaattag ctgggtgtgg tggcatgtgc ctataatccc agctactcgg  75000
gaggctgagg caggagaatc atttgaactc gggaggcgga ggttgcagtg agccaagatc  75060
atgccataac tctccagctt gggtgacagg gcgagacttg atctcaaaaa aaataaaata  75120
ataaaataaa ataaacaaat tatgctggct acaaaatttt cttttgcaaa tactaaatgt  75180
tggaaaatga tggagcagtg ggcagtgatc cttagcttat gtggtctttg aactccctgc  75240
agtaatattt ggacctctat gtcttgatgc aagttgattt tcctgggaat agaatctata  75300
tcgttcctca tattttccag gatttcatga aacaaagagt taagaactac agtagtggag  75360
caatattcat ggtgcttttt ctttttcttt tgaaataatt aaaaacttac agaaaggctg  75420
taagaataat acagagaaat cctgtgtatt ctttcccaaa ttcatgtgtt tgtcttctct  75480
ctctttctct ctccttataa aatatttcaa tgttgttagt tatctcaaaa tggactttgt  75540
agttttttttt tcctccccta ccagtacagg tttcagtcta agatcacatc atatatatag  75600
ttttatattg ttttagtttt ctttatctgt aacagtttct cagatgctct ctgtcttcca  75660
tgatactgat atttttttga agaatgctgg caggttattt tacagtgttc ctcattctgg  75720
gtttgtctga tgtttcctct tgattattat tcgggttatg catatgaggc cacaatacta  75780
ggtaaattgt gtggtttcat tctcaaggta tccacatctg aaggcgtatg atgttcatct  75840
gtcacaccgt tgatgttaat ttcgatctca tggtaaatgt gttttttcgg tgtctccact  75900
ctatggttac ttttttatcc ctttcaatta aaaaacaatc agtggtcggg cactgtggct  75960
catgcctatg atcccaacac tttgggaggc agaggcagga ggatcgctta agcccaggaa  76020
ctcaagacca gcctgggcaa catagggaga ccccatctct actggactgg tggcatgtgc  76080
ctcttgtccc agctgcagga ggctgaggtg ggaggattgt ctgagcccag gatgtcaagc  76140
ctgcagtgag ctgagattgc accactgcac tccagcctga gtgacagagt gagaccctgt  76200
ctcaaaaaata aataaattaa ttaaaaataa aaacgatcaa tgtggaaaaa acttgaagac  76260
tgtgcaaata gccatatgtt gcttaacgat gggaatacat tgtgaaaaat gtgttattag  76320
gtgattctgt cattgtgcaa acaccatagg gtgtacttac ataaatttag atggtatagc  76380
ctgctacata gctaggctat atggtttagc ctattgttct taggctacaa aactgtacag  76440
cttgttactg tactgaatat tgtaggcagt tgtaacacta tgataagtat tatataaaca  76500
tgtctaaaca taggaagata cagtaaaaat acagaattat aatcttatgg gaccactgtc  76560
ataagtgtgg tttattactg accaaaatgt cattatgtgg cacatggctg tatcttgctt  76620
ttcatcaggc tttacactct agatgagcat ccattgatta ttcttaccca caccaatggt  76680
acagttatga tagttggaaa atgctgcttt tttccaactc cactactccc tccatttcat  76740
ggtattctaa tgaatgatca ttgtcacaaa attcaacacc taattgtatc tgttatgata  76800
```

-continued

```
atgaaaagaa acaaatgacc cattcaaaac agttcagttg aaaagagttt atcaaaggaa  76860
tgacttaaca cggtgtggcc acagtaaggg aatcaacaag gaatggtgaa gcacccagta  76920
actagcaaca gtgggaagcc attgccaccc ttagacctgc ggaggcaaag ggagggcaca  76980
tggttatcag gctcgtgaaa ctggaattca tagaggagga accacctaca ggtgctgtgt  77040
ctctagagaa aaacagccac tgtcagcaca gaggcaaggt tgagacaaag ctgggggaat  77100
cagctgagtt cttcctgctg ctgctctgac ctgttagtag tgctcacggt tgcccagtca  77160
taagccaaag gacaagaaag cctgggtgat gcaatctgga gagcttgacc tcctggggca  77220
cagaaggtgt tggggggttg tgggaatggt agtataacca gcacactagc taagatttta  77280
ttaatgtgac aagacaagaa aaagatctct gatgcgcaag aactgaatgg agagttcaga  77340
tcatgttctt agatgggaag attgaatagt ataaatatct tggttcttgc cacatgaatt  77400
tgtctactta attccaacag tctaatggaa ttacggaggg agtaggggtg atggtggggt  77460
aacattgtta aaatgattct aagttcaatc aggcaagaat aacaagaaaa aaaaattcgg  77520
gccaggtgcg gtagcacacg cctgtaatcc cagcactttg ggaggccaaa gcaggcagat  77580
cacctgaggt ctggagttcg agaccagcct gaccaacatg gagaaaccct gcctctacta  77640
aaaatacaaa attagccagg catggtagca catgcctgta atcccagcta ctcgggaggc  77700
tgaggcagga gaatcgcttg aactcaggat gcggaggttg cggtgagcca aattcatgcc  77760
attgcactcc agcctgggca acaagagtga aactccatct caaaaaaaaa aaaaaaattc  77820
tgatttcact gcgtaatttt aaaaaataata ttttaatttt gttttgaact aaatatttta  77880
aaattatttg tgttcataaa ttatttagaa ttgtttttaa gggttttcta agttacattt  77940
ttgttactcc tttctgactt aaatataata tagttaaaga atattatcta aatgatacta  78000
attctgtaaa atgttgttga agcttaatga tctaagacgg gtcagttttt gtgaatctta  78060
ctgtgtgtgt gttcctgaga aggatgtgta ttcactaatt aatgggtgct gggttttatt  78120
ggtaggccag aagtcaaact tgacagttat gtagccctta attcatgcta atgttttgta  78180
tcattggtct gtaaataact gaaagagctg tgttgaaatc ttccactttg tggatagatt  78240
tgttcatttc tctctaaagt tgtcaaattt tgctttattt tgaggctatt ttttgagagc  78300
ttacaaattt agattcatta gcattttcta gcaaattgaa cattttattg taacatacgg  78360
actatcacta aaaatgcttt ttgtcttaca gagtagaatt gctaaataaa atacaggatg  78420
ctcaattaaa tttgaatttc agataaatgt tgagtacttt tttagtataa gtatgttcta  78480
catattgcaa aaattattca tttttcacag gaacagaaaa ccagatacca cgtgttctca  78540
cttataaggg ggcactaaat gatgagaaca catggacaca tggcggagaa caagacactg  78600
gggtgtactg gagggtggag ggtggaggag ggagaggatc aggaaacata actaatgggt  78660
actaggctta atacctgggt gatgaaataa tctgtacagc aaacccccat gacatgagtt  78720
tacctataga acaaaactgt acatgttccc ctgaacttaa aataaaagtt aacaaaaaaa  78780
gtctggcatg gaaagacata aacatgcgtg gagctggttg tctctgatct tgcaccactt  78840
gtgataaagt tgtttgtagt atttaatgaa tgtgttcaaa aatctgtatc tttagttata  78900
tgtacttctt ggtcctaata ttactgattt gtgctaccta tacagttttg gtgggggtt  78960
tgcttatttg gggataaacc ttactactgg tttgtctctc ttattagtct tttcaagtaa  79020
tactttcttt ggctgtattc tgttgctcct tttctagctt gtttaattga acatttaatt  79080
aaatattcat cattcctttt gaaaaaattg ttgtttatct gacattcaaa tttaactagg  79140
catcctatgt tttgtttgtt tttgctaaat ttgggagcct atttaaaaac tattttgttt  79200
```

-continued

```
gatactaata tagctatccc caatattttt tggttataat ttccctagta tatcgttttt  79260
ataaatttca ttctttgagt ctttgtgttt taatgttttt tttttaatat cctatagtca  79320
gaattgttag tctaatctta cctatgttgt ttttctagga agtgtagggc ttttttattg  79380
ggattgcaga cctattgtcc cttttttaaa actatatttt caaatgcttt ttattttttcc 79440
cacttgtttt gtgcttttgt ggactgtttt ctttttgcat gattttaaaa aaattccatg  79500
ttctcttact attattttag acattacaca tatttattat tttgttaacc tttaaatatt  79560
actgtcaggc caggcacggt ggctcatgcc tgtaatccca tcactttggg aggccaaagc  79620
gggtggatca cctgaggtca ggtgttccag accagcctgg ccaacatggc gaaaccccgt  79680
ctctactaaa aatataaaaa ttagccaggc ggggtggcag gcgcctataa tcacagctac  79740
tgagaaggct gagtcaggag aatcgcttga acctggaggc agaggttaca gcgagccgag  79800
atcatgccat tgtactcgag cctcggcgac agagcaagac tctttctcaa aaataaataa  79860
ataaataaat atatattact gttcaaactc tacttgataa agttatttaa tatttttaaa  79920
tccccacaca aacatcctaa ctctgataac taccctttta atgcttatgc tattactgat  79980
gaatatttaa gttctttttt taacactata tgttagacat catcattact gttactttat  80040
atggacagta ttatgtttat gtatatgttt accatttccc atgctcacaa ttacttcttg  80100
catctaagat catctttctc agattggttt ccttttttttt cccccaagta cattcttcag 80160
aatttttttt ttttttaga cgaagtctca ctctgttgtc aggctggagt gcagtggcac  80220
gatctcagct cactgcaacc tccccctcct gggttcaagg gattctcctg cctcagcctc  80280
ccgagtagct cctactacag gtgcccgcca ccacgcctgg ccaatttttg catttttagt  80340
agagatgggg tttcaccatg ttgcccaggc tggtctcgat ctcctgacca tgtgactcgc  80400
cgccttggcc tctcaaagtg ctgggagtat aggcgtgagc caccacgccc agcctagaag  80460
ttttttggt aaaggtaaat tgatggtaga ctcagacttt gcatatttgg gaatattttt  80520
acttcactct aattcttgaa atgttgtttt gttgaataga ctaggtttat agtaatcttc  80580
catcagcact ttgaagatat tttaacattt tctgggccct agttttgcaa ttgagaagtt  80640
actatcagcg tagttgctat ttctttgtgg gtgactttac tctctgattt ttaaggtctt  80700
ctttatataa ctgtattttc caattttact acaatatagc taactgtggc ttttctcatt  80760
tatttgtttt gttttgtata tttatatgat ttcctgtatt ttatcagttc tataaaattc  80820
tcgaccattt ttctttgaat atttcttctt ctccgttctc tccattttgt cctttgaact  80880
ccagttattt gaatattaaa atgttgcatt ctgtcctcca gatagtttaa caactctttc  80940
atgttttctg ccttcttacc tctatctgct agataatttc tttagatcaa ttgtctgatt  81000
cactcattct ttcttcatct gtttcatttg ctctttaacg tgtccagtat attttaatta  81060
aaaatatata tgttgggtta tttttagcct gcctgctact ttaaaaaaat actcttttgt  81120
tccttttaaa acatcaaaag ttgatctgaa gtgtttcagc agttgaactc ctaggtcttc  81180
attgtcagcc tgctgtactt gttttcttca agaagataga tatctctaaa tgttgtcata  81240
tccttttttg ttattgaatc aaagtagctg aatttgatag aagttcagtg ttgcattgtc  81300
cagatacaca gttttgaggt ttgaaagctt gaataagtgc cagtggactt catgcaaatg  81360
ctttatatat ttttcaccta atatattttg aatttcaaca agtaacacat tctcttaaat  81420
actgacttga taggcaagtg agcatagcaa gcttcatctt ttagtgaaag tccattgatc  81480
ctgtttcgta attggatgaa gagtgtccaa actattgcca gtagctttct gttttcccat  81540
```

-continued

```
cattttttcaa cccagaaata tttatttttc tttccaggga ggcattagca gtaccctgga  81600
agctcccctc ctacccctcc aaattattcc ctcctcctct ttacttttct ccaaagataa  81660
tctctgtcct gaatcaaaaa tcgtccccgc ttcctggtag cacccgatct ggaagaaacc  81720
caaaatcacc taaccaaaac ctgaatcata taatagtctt ttctaatact cttttactga  81780
gacattccac aattcccaat tatatgtgtt attccttgct gaaatgaata atgaacccaa  81840
catgtgcaac tacagctatg ttcctggtaa cctttggctg ggaggattga caatattcat  81900
ttgtgtctgg tttctttctt tcttttttttc tttttctttt tttttttttt ttttttgaga  81960
cggagtcttg ctctgtcccc caggctggag tgcagtggca caatctcggc tcactgcaag  82020
ctccacctcc cgggttcact ccattctcct gcctcagcct cccgagttgc tgggactaca  82080
ggcgcccgcc accatgcctg gctaattttt tgtattttta gtagaggcgg ggtttcacca  82140
tgttagccag gatggtctcg atctcctgac cttgtgatct gcccgcctcg gcctcccaaa  82200
gtgctgggat tacaggcgtg agccaccgcg cccagcctgg tttctttctt tttaacattt  82260
tgtaagattc atgtttttgc atgtagtcat agtttttttt gtgtgtgtga tggaatttca  82320
ctcttgttgc ccaggctgga gtgcaatgga gtgatctcgt ctcaccacaa cctccgcctc  82380
ccaggttcaa gcgattctcc tgcctcagcc tcccgagtag ctggtattac agacatgtgc  82440
caccacgccc ggctaatttt gcatttttag tagagatggg gcttcaccat gttggtcagg  82500
ctggtctcaa actcctgacc tcaggtgatc tgcccgcctc agcctcccaa agtgctggga  82560
ttacagttgt gagccaccgt gcccggcctt gttcattttt gttatttaat attatgctat  82620
aattacataa ctatttggaa ctttttgact ctgttttaat gttgatacac agtatctttg  82680
tacatatcat ttggtgaaca tgaataatgc atttttgttg ggagtatgcc tgggagttat  82740
attgggagtt cccaagacca ctcatagtaa tcagaagtta tgattatgat tatagttgat  82800
tacagcaaaa ggatatgaag taaaagtcaa gaaagggaaa aggcacatgg gcaaagtctg  82860
gaaggaacca gctgctcact ttccaatgtg ccctctcagt ggagtcagac aggacatgtt  82920
tcatttcccc agcaacatgt gtgacaacac acacaaaatg tttccaatca aggaagctca  82980
cctgagcttt tgtgtccaga gtttttatta ggggtcagtc atgacatagg catttggtat  83040
tacctgcaca actgacttca gggtcaggct ccagatcccc agagaaaaag caggtgtcaa  83100
ccataaatca cattgttagc ataaactatc tggttaaacc agtacagcat ggcccaaggc  83160
ctcagacaca tgaaacattt cttatcagac ataagattct atgataggag gcagccaata  83220
gccagtcctg aaaacaggcc tgtcttggga atgtgcaacc aggcctgctg agttaataaa  83280
cttttccagc agagattgaa aaggatgggt caaaggatat ctgtaggtac aaatttgaga  83340
gatagtgcca aagagttttt caaagtgatt atacctgttt actctctaac cagcagatgt  83400
gtaagaactt cagttcttct actttgccaa taccttgtac agtttaatct tctaaaattg  83460
taattttctt cctcgtgtct attgatatct cattttggtt tacattttta tttccttagt  83520
aactgagact gagcaccttt tcatatgtca ttgaccagta gcctatgttg tgaagtgcca  83580
gttcaggttc tttgcctggt tttcttttga atcatttgct tttttctcat tgatttttag  83640
gaattattta catgttttga tatgtacact tcatgtgtgt ttcaaataac ttctcccatc  83700
tatctgcctt gccttttctc tctcttaagg ctgtcttttg aaaaatagaa gttaatttta  83760
atgtctaatt ttgtgatctt tttctttact gcttttggca taccatttaa taaatctttt  83820
ttccaattca agtccttgga tatatcctcc tatgttatct aatgaaaagt ttattgcttt  83880
acctttctct tttagatctg taacctgcct ggaattgatt tcttttcatt gtggtaagaa  83940
```

-continued

```
acacatgaca taaaatactc tcttaaagat ttacaactgt acatctcagt agtgttaaac  84000
atatttacag tgttgtaaaa cagattcaga aactttttat cttgaaaaac ggaaaacttt  84060
atactcatta aacaataact ctccattctt cttctcccca ctcccctcct tgctgctcct  84120
ggcagtccct attttacttt tgtctcgatt taagtacctc atgtggcatc aaatagtatt  84180
tgtctctttg tgactggctt gtttgagtta gcataatgtc ctcaagtttc atccatgtta  84240
caggatgtga caggacttcc tttttaaggc tgcatagtat ttcattgtat gtctgtacca  84300
cattttgttc atccattcat ctgttgatca atttgggttg cttccatttc ttggctattg  84360
tgaatagtgc tgcagtgaac atgatgtgca gatatctctt tgagttcttg ctttcagtta  84420
ttttgtgtat actcagaagt ggaattgctg aattatatgg gagttctatt ttttattttt  84480
tcaggaagct gccgtactgt tactccatag cagctgcact attttacatc ccttccagta  84540
gtgcacaaag gttccagttt tccacagctc accaacactt gttatttttt ttattttttt  84600
atttttttatt tttttaaata gtagccattc taatggatat gaatggtaac tcattatggt  84660
tttgatttgc atttctctga tgattagtga tgttgagcat cttttcatat gcttgttgtc  84720
tatttatgta tcatctttgg gaagaaatac tttgttcatt tttaattgga tttttttgatt  84780
ttttgctgtg aattgtagaa gttctttatg taattctgaa tattaacccc atagcagata  84840
catgacttgc aaaattgtgt ttctttagag ttgatttctt taactttatt ttgattcttt  84900
aattgggcca tctatccaga ccaggctggt ctcggactcc tgagctcagg caatcaaccc  84960
gtatcagcct tccaaagtgc tgggattaca ggcgtgagcc accctgcctg gccgctgtgg  85020
atttttaaat aaacgtcctt tatcatgtta aagaagcttt cttctgttct tagtttacta  85080
agtgttttgt tatgaagtga tgttgagttt tgcccagtgt tttttctgt gtgtattgag  85140
atgatgtgtt tttctttata ttttattatt atgtattaca ctggatgatt atcttacatt  85200
gaaccaccct agcattcctg agataaatcc aaattgggct gcatcgaaac taaaaacttt  85260
tgtattacaa atgttatgaa gaaagtgaaa agacaaccca cagatgctat ctagagattg  85320
gtatccagat tatataaaga attcttgcaa gtcaaataat aaaaatttac atcacccaat  85380
tagtagttta agtcagccag agttggttcc tcttgaatca cccaatttgt ggtgaattga  85440
aactataatc agatactact tcacacccac cgggatgctt ataataaaaa atacatggga  85500
aatagtacag tagttcctca aaaaattata gaattaccat ttgatccagc agttccactt  85560
ctgtgtatat atacaaaaga ggtcaaagca gggatacaga tatttgtgca ccagtgttca  85620
tagcagcact attcacaaca gtcagaaggt ggaaacaacc taaatgtcca tctacagatg  85680
aatgggtaaa caaaatgtgg taaagatgga tcaatagatc acaaaggaat attattcagc  85740
cttaaaaagg aatgaaattc tgatacatgc tacaataagg atgaaacttc aagacactgt  85800
gctgggtgaa ataagccaga cacaaaagga caaatgttgt ataatttgac ttatggggta  85860
catagaatag gtcaattcat agagatagaa agtagaatgg aggttatcag gggtggggta  85920
tgatttcatt cctgtaaagt tcagagttac tcttattgga ggaaaggata cattatgact  85980
agaaggaggg acaaggaagg ccactgggtc atcttctatt tctcaatctg tgtttactcc  86040
atagaatttg attgagctgt ttagctgtgg tttgcacatt ttcctttacg tataaacttt  86100
ttacatatat acttttatta aaatctactt aaaatgggaa aaaaaaagat atctagattt  86160
cagcttttaa atgctggtgc aatgatagcc attttcggct gggtgcagtg gctcacacct  86220
gtaatcccag cactttggga ggctgaggca gctggatcac ctgaggtcag gagttcaaga  86280
```

-continued

```
ccagcctggc taacatggtg aaactttgtc tctactaaaa attagccaaa cctggtggtg  86340
ggttcctgta atcccagcta ctcgggaggc tgaggaagga gaattgcttg aactcgggag  86400
gcagaggttt tgcagtgatc caagactgtg ccactgcact ccagcctggg tgacagagta  86460
agactctgtc tcaaaaaaaa aaaaaaaaaa aaaaaaaaaa aaacaagaca aaacactcat  86520
atctgaaatg tggtttacat agaatgttct tccaggcaaa aaaaacaaga ttaaaattac  86580
tggttttgaa aatgtattct gttctttctt atatcaaagt cttgatgttg gtggctagag  86640
agaacttctt aggttttcta cctgtattag tccgttttca tactgctata aagaactgcc  86700
caagacgggg taatttataa aggaaagagg tttaattgac tcatagttca gcatggctgg  86760
ggaggcctca ggaaacttaa aatcatagta gaaggtcaag aggaagcaag gcactttctt  86820
cacaagtcac aaaggagaag tgctaagtga aggatgaaga gccccatata aaaccatcac  86880
atctcgtgag aactcactca ctatcacgag gacagcatgg gggaacctct gccgtgattc  86940
agtgacttcc acctggtctc tcccttgaca cgtggggatt atggggatta taattcaaga  87000
ggagatttgg atggggacac aaagcctaac catatcacta ccatttttct tttctttttt  87060
tttcatgcct ggatttttc gttgttccct catgaacatt ttaaagtgta attaagcaaa  87120
agagaatact atacaatggt ttttaacaat ttttttaagt ttcccccctc cccccaagac  87180
agggtttccc aatgttgcct aggctggtct cgaactcctg gcctcaagtg attctcccac  87240
ctcaccctcc taagtagctg ggactacaga catgtgccac tgtgcccagc tgcctataca  87300
gtgtttttat tttattttat ttttttaaga tggagtcttg ctttatcacc caggctggag  87360
tgcagtggca ttatcttggc ttaccgcaac ctctgcctcc cggattcaaa tgattctcct  87420
gcctaagcct cccaagtagc tgggattaca ggcacccgcc tccatgcctg gctaattttt  87480
gtatttttag tagagacagg gtttcaccat gttggccagg ctggtctcga actcctgagc  87540
tcgtgatctg cccgccttgg cctcccaaat tgctggggtt acaggcgtga gccaccatgc  87600
ctggccttta atttttttaa aaagtaaaac ttctttaatt ttcttctcgc aagaattgaa  87660
tagaatgata gaatgaatgc cagtatttta taatgttgta tccagcaggt tgcaatcagg  87720
gaggctccaa cagagtcact ttttctgtct ttttatgttc aatctatgct gtaaattggt  87780
ttcagaaact tctgtgagtc tatcaactgt aaaaatggag atgactatga aaggatctta  87840
cgcttttatt cttctttgat ccacatgtct gtttgttcct ccatctagaa tataaagatg  87900
attaagactc tacctgtctc ctttaagtcc agtgaagaag atagatttac aattaatggt  87960
aattcagtat aactgccgta agaacagggc attcagaatg ccctgtgagc tcagagatgg  88020
cgctactgta ttctcatgtt taaaggataa gtaaaagttc cccagtttga gaaaagaggg  88080
gaaaaggact ccagtgaaag gaaattgatg aaattactgt tgactttact tgtatatatt  88140
aactgtcttt cagtgtctct gaaaacttga tttgggacta tttcctttga acagaaataa  88200
tagcattcct gcctgataaa tgtcctgtgg tcaaataata tgatttccta atcattctgc  88260
acactaaact tccccccacc aggaaatcaa tgccttaatg ctaaatttcc tctgtactac  88320
tttctgtaag agtaagaggt tcctatttca cagtcacgac acattcccaa ctcaattcac  88380
attccaatcc atcttgtcca acttcattga aagttgatac actgaaccat ttcctttact  88440
taaaagaaat agaattcttc ctaaattcta tctactgttg gaatagaaag aatatcatgc  88500
ttctagactg actaattttt tttcttcttg atataagtat tgacaacatt tattcatttg  88560
tttctaggca gcacaagact gttgaacttt cctagaactg agtctgagat ttgcaaagct  88620
gccaaaatat tttgaaacaa atgaaaatat gtaaacatga atgttatcag ctgttttaca  88680
```

-continued

```
gtatttgtgt tttagagata atgagcatct ggtggaccac aggagcccag ggggatttca  88740
aactccagat tcctttttgt gtaatcatat ctggctggag ttatttgttt tctctgcatg  88800
tgaaactatc aagtcataat tcttcaaagg ggaatgttta ttgcattatt taaaaataat  88860
aaattatatt actaaataaa taacagcagg ccaggcataa accaatgatg aaagtttgtc  88920
agaaactaag gcttctgatt aattctgtgc tctggactat aattggaagg aaggattata  88980
ttagagttta caatgagttt acagaaagaa aggagaggga taaattatat ttagttcaca  89040
gtaaatctga attcagaacc cctggttgta agactagtct tttaaccttt agagttaaaa  89100
aatgtatatg tacagctggg tgcagtggtt cacgcctgta atcctagcac tttgggaggc  89160
caaggtgggt ggatcgcttg aacccaggag tttgagacca ggatgggcaa aatggcaaaa  89220
ccctgactct ataaaaaata caaaaattag ctaggtgtgg tggcaggtgc ccatagtcct  89280
agctactcag gaggctgagg tgggaggatc ccttgagtct gggaggtcaa agctgcagtg  89340
agccgtgatt gtgctactgt actccagcct gggtgacaga gaaagaccct gtcttaaaaa  89400
aaaaaaaaag tgcgtgtgtg tgtgtgtgta tgtacgttga agaaaactat gagaaaaagc  89460
aaaaatgtag agtccataat gcataatgtt gtgttaagca catagtttag tcattggtac  89520
atatttctgg agatggtcta aagatctatt ttttaaaaac tgattttagt taaatcagag  89580
gttagcaaat cacagcctgc aggccaaatc tggcctatca tacattttgt ttgtctcttt  89640
gttgtgtttt tggtgttttt ttttctttct tttttttttc ctttcctttt tttttttttt  89700
tttttttttt ttggagacag agtcttgctc tgttacccag accaggctgg agtgcattgg  89760
tgcgatctca gctcactgca acctctgtct cccaggttca agcaattctc ctgcctcagc  89820
ctcctgagta gctgggatta taggtgtgca ccaccatgcc cagctaattt ttgtattttt  89880
agtagagatg ggttttacc atgttgccca ggctggtctc aaactcctga gctcaggcaa  89940
tcttctcgcc ccagcctccc aaagtgctgg gattacagac gtgagccacc gcgcctggcc  90000
ctatcataca ttttggtaaa taaagtttta ttagaacata ctatgctcaa tcatttatat  90060
gttttgtgtg gctgcatttg ccctgcagca gtagagctga gtagttggaa cagagactgt  90120
ggttcataca acctaaaata tttaccctgg cctttgttac agaataggtt gctaacctct  90180
gagtttctca gttttagccc attcacaaat gaaatagttt ttttttgttg ttttttttga  90240
gacagcctca ctctgtcgcc caggctggag tgcagtggca tgatcttggc tcactgcaac  90300
ctctgcctct tgggttcaag caattctctt gcctaaacct cctgagaagt tgggactata  90360
ggcacatgcc acaacgcctg gctaattttt gtatttttag tagagaccag gtttcgccat  90420
gttgaccagg ctggtcttga actcctggca tcaagtgatc tgcctgtctt ggcctcccaa  90480
agtgctggga tcccagcctc tctctctctc tttctcactc tctctctctc ccgctctctc  90540
tctctctctc tctctctctc tctctctata tatatatata tttttttttt tttttttttt  90600
ttttgagaca gggtctcatt ctgtcaccca ggctggagtg cagtggcata atcacagctc  90660
actgcagcct caaccccacg ggctcaagca attctcctgc ctcagcctcc caagtagctg  90720
ggattacagg tgcgcacaac cacgcccagc taatacttgt atttttttgt agagacgagg  90780
cttctccatg ttgtccaggc tgttctcgag ctcctggaac tcaagcaatc tgcctcaggc  90840
aggaatcctg aaattctggg attataggtg tgagccactt ctccctggcc cacaaatgac  90900
atattcctta taatctacta cagtgagctt tgcatggtta atatatttgt tgtgttgaaa  90960
ctatcttcct gatttttttcc aatttttttat agagaaacct ggaaagaata gtaccataaa  91020
```

-continued

```
tacctatata ccctaacaga gaattattgt taaaattttg ccatatttgc tttatcttct  91080
ctgtgcatat gtatactcac atggcttttt ttttattggt attagttgaa agttgcagat  91140
attatgcttc ctcagcgcat atccctaaga ataaaagcat tttcctcgac aactgattat  91200
gttaaaattt gaagacgtgt atgaggtttt tgtttgtgag ggctatatga ctggcgtttc  91260
tccagtatat gacactttgt tcatccctat gttcctcttt ataaactgca gaaattctaa  91320
atataatgca ttagttgtct attgcttgca agtagtagac tgaatgatgg ctccataaag  91380
atgtccactt ccattagata aagaaaatgt gtacatatac accatgaaat attgcacagc  91440
cataacaaag agcgaaatca tgttctttgc agcagtttgg atggcgcttg aggccattat  91500
cctaagtgaa ttaatgcaga aacagaaaac caagtacctc atgttctcac ttgtaagtga  91560
gaggtaaaca ctgggtacaa atggacataa agatggggac agtagacact gggaatacaa  91620
gagggcagaa gagggaagga aaaataaggg ttgaaaaact acctattggg tactgtgctc  91680
actacctggg tgacaggttc aatcatatcc caaacttcag catcacacac tataccccctg  91740
taacaaacct gcacatgtac cccctgaatc taaataaaag ttggaaaaac aaatcaaccc  91800
agatggccat ttcctaatcc ctggggtctg tgaatatgtt accttatctg gcaaaaggaa  91860
ctttacagat ggaattaagg aattttagat gaggagatta ccgatcatct ggtgggccta  91920
aagtaatcac cagggtcctc ataaaggaga ggcaagggag ttgaaggtag agaaggggct  91980
ctgaagatgg gaagcagaat aagtgtagga aatgtgagct tgccacactg ctagtgttga  92040
agatggtgag gctaagaatt ttcacatcca ctttcaaaac cattgtgtcc tggctccttt  92100
taaaccatct ttccctcaat ttctctgtcc tcttacatct tattgtaaac accaagaaga  92160
aacctggcag ttaactttgc ttggaaatct ttttagctag accatctaat tcattcggca  92220
cattttctac cttccacatc actgtaaaat tgggttgcta aactttccac aactacctaa  92280
cagagatccc ttgcctccag tttctactca gatgttcctc acattcctta aaactcacag  92340
tccacctcct aacaatctaa aatctaccaa ctatcaattc ctggcaattt aggctttacc  92400
gctcctctcc tgaaaggcct taaagtatta gaactgggcc ctattattag aacctatttc  92460
ccagttctaa tattcctccc acatttttgg tatgtgtgac aatggaactt tactcctgat  92520
accaaaatct gtatgattta tatatgaagc ataacaaatt attctaaaac gtattaatgg  92580
cttaaatcaa caaacgtgtt gtctcatagg ttctgtggtt caggaatcca ggcaaagcta  92640
cctagatgct tctagctcag gatctttcat gaagttgcag tcaagctgtc agctgggctg  92700
cagtcatcca aggctcagct gggagaggat ctgccttcaa gctctctcat gtgactgttg  92760
gcgggcctca ggttttcact ggctgttggc tggagatgcc agttatttgc cacatgagcc  92820
tctgtctacg gcagttgaca acatgcagct ggcctacctc agagcaagca accaagcaag  92880
agagcaagat agagtgctca agacaaaaga taacagactt tttgtaactt aatctcagaa  92940
gtaacatccc atcacttttg ccaaattctg gttgttagaa gccagtcact agatctgtcc  93000
cacacttgaa gagggttaaa caaggtcatg ttcttcataa gattaatcca agtacagaat  93060
tggcttaata acatttctga cgatttttcc tataacttgt aaaaccttgg ctatctgaaa  93120
cccttgggaa gtgaatcatc cttaaaagct aagtttctgg atagattttt accatgaagg  93180
gaccaaatct taataatttg gagtagaatc acttctgcat ttgatcacaa tatttcttgc  93240
cttttaaaat aaattactga tcattatttg aaattttatt tcatcaaaag aaaattagca  93300
attgtgtgtt ataaagagaa ggtgtctgtc ttctccttat gtagggtata gaactgttca  93360
tctctttact aaaaacttaa ggcttctgtc tgccttttat aatttctgtt tctttctttg  93420
```

-continued

```
tttcatttgt tacctcttag ttatcagtac ttgcccattg ccttcctgtt tactgtatct  93480
agtaagttgc tgcaaaagta attgtgattt ttgtattaaa acaaatggca ttagattctc  93540
ataggagcac gaacactttt gtgaactgtg catgtgaggc atctcggttg ttcttgcctt  93600
atgagactct aatgcctgat gatctttcac tgtctccgat cacccccaga tgagaccctc  93660
tagttgcagg aaaacaagct cagggcttct actgattctg caatatagtg agttgtgtaa  93720
taatttcact atatattatg atgtaataat aacagaaata aagtgcacag taaacgtaat  93780
gtgcttgaat catccggaaa ccatcccctc tgctggtcca tggaaagatt gtttttcaca  93840
aaaccggccc caaagttggg gactactgct atagagaatt ggatctgcgg tctacaagta  93900
atgttaatga catttatttt aagttgcact gagactttttg tttacatctt tttttttttt  93960
ttgagatgag agtctcgttt gtgttgctca ggctggagtg caaggcacaa tctcagctca  94020
ctgcaacgtc cgtctcctga gttcaagcga ttctcctgcc tcagcctccc gagtagctgg  94080
gattacaggt gcccgccacc aagcccagct aatttttttgt atttttaata gagatggggt  94140
ttcaccatac tggttggcca ggctggtctt gaactcctga cctcaggtga tccacccgcc  94200
tcggcctccc aaagtgctag gattacaggc atgagccaac atgcctggcc tgtttacatc  94260
ttaattatga attgttacta tagtcagccc tttgtatctg tggtttccac atccatagat  94320
tcaactaacc atggactgaa aatatgtggg ggggaaatga tgcttacatc tgtactgaac  94380
gtgacggact ttgtcattat ttcctaaaaa atacaggata actatttaca tagcatttgc  94440
attgtattag gtgttataag cagtctagag atgatttaaa gtatacagga ggatatgtgt  94500
atgttacgtg caaatactac accattttat ataaggcact tgagcacctg tggattttgt  94560
tattcacagg ggatcctgga aacaatcccc tgtggatacc aagagatgac tgtatagggg  94620
aggccgtggt gacagatgaa gtggcactgg gcttagtaag ggtaagaaag ctaagagtgg  94680
cctgaggaca gatgacaaac atgacatatt gctcacttta gccaatgctc agaatctctt  94740
aggtttttga aacttcacaa gcaatttagg caaactctcc tttcttctct atctctgtat  94800
tctatgtaat cccacagttg aaggctgttc ttatagtgga attaattata cctcactcca  94860
aaaacttgac cctgatttcc gtctacaaac ccaaagcagc aaatacaatt tacttttata  94920
tttgaattat tttctttgta atggtgtctg ttgacagcca aagcctcttg tatggaaaca  94980
taccaccact gccacaagta aaagctataa agcagtgtta aatactgtat atagagctca  95040
catttgtata tgcatttctt ttaggtctta tgtagtgtgt gtactgtgga agatcgagaa  95100
agtgcgttag gttgttagac aaaagaccca gaaggcctgc tagagatgcc acaggtggaa  95160
ctaagaaagc aatctctgtg tcactcaggc tttgagaaac ttccttcaga atcataaaac  95220
attagaactg ggaaggttaa aaaatcttta gtcttttttt cccagctcca gtctcttgtg  95280
aataattaac agtaaagtta aagattatgg gaattacgtg cctccttttt tcccttgcac  95340
aacatagaat ttgttttcta atagtagttt atttgttagc tttgcattcc cataagtgat  95400
ggtttccagc cttggcaaac ccttgcagcc tccagccaca agtcccctgg acctcagaga  95460
atgtatatac tgtatgtgca ccctaataac atgtttcctt aaaactagta ctactggatc  95520
ctctaacttt agtacatgtc tttcatgtcc aacttttcag aggccgccaa actagcaacc  95580
ctaaactcat ttgtcactat caaaacataa tatacgaata tggaaagcta atataaaaat  95640
ggtaagggac tgagccattt ggaaggtaac ttaatgtaag tgcctgaaaa acagggatac  95700
aaaaaagcaa agggacaaga agcaagccag ttcaccctga accctacaaa tgtttgggaa  95760
```

-continued

```
ttagaaacat caagtattac aaattagggg aaacggatga agtctgatac taaaaatagg  95820
gaggttgaca gtctgtgtag gaacagttag acttccagat ccttatctct ataccccacc  95880
tccccctctg cagaagagat agattccctt agggaggaag aaaactagag aaaataaaga  95940
cactaggggg agagtgtgat gtcagcaaga tagtggaata aaagatacct ggcatcactc  96000
ttcccacaaa aatgcaacta gaaattattc aggctgggcg cggtggctca ctcctgtaat  96060
cccagcatgt tgggaggccg aaacgtgtgg atcacttgag gtcaggagtt cgagaccagc  96120
ctggccaaca tggtgaaacg ccgtctctac taaaaataca agcattagct gggcatggtg  96180
gtgggtgcct gtaatcccag ctactcagga ggctgagaca ggagaattgc ttgaactcgg  96240
gagttggagg ttgcagtgag ccaagatcat gccactgcac tccagcctgg gtgaaagagc  96300
gagactcctc tcaaaaaaaa aaaaaaaagt attcaaagac aagaatatca acctgagttc  96360
accagaactt ggggaagaag tggagaaacc tcctgggcca acaaaatttt ttgtaaaata  96420
agtggtcatt tcagactgtg ccaccccttc cccccaagct ggcataacac cactcaggga  96480
gaattttcct agccctgcag tttccaaggt gagaggaagg aattggaggt gtgtattcag  96540
tctcctcact ggtctgggaa tcttcccagg gagcccactc ccgtcccatc agggagagcc  96600
aggagagctg aactatctgg ggtaaagtgg ggacaaagag cagggcactg attgtagcaa  96660
ctagtatatg gatcttgcag ctactctgta ctctaattag ccgagacacc ctattgacaa  96720
ggatggccag tgtcttagtg ccactggggt gtaatcagtg ggaaggcctg aatccctggt  96780
cggattttcc acaaaactta gtgctcacat ggaaccttcc cgtggcccag aaacagctat  96840
aagattggga ttaagctggg catggcagct catttctgta atcccatttt gggaggccaa  96900
gttgggtgga taatttgagc ccaggagttc aagaccagcc tgggcaacat agcaaaatcc  96960
cacttctacc acaaaaacaa aagttagctg catgtggtgg tacgtgcctg taatcccagc  97020
tacttcagag gctgaagcaa agagtcgctt gagcctggga gacagaggtt acagtgagcc  97080
aagatcgcac cactgaacgc cagcctgggc aacagagcaa aactgtgtct caaaaaaaaa  97140
aaaaagttgg gattaacttc cagtgtacac ttaagcactt aagactttca cagactggga  97200
aatgatgaca ggatagcaat atagttggag aacaatgttt acctttcggt ggtcactata  97260
agtcttcctg tctgtgaaac aatgtcaggg caagttagtt tagttttagt gcagtgtttt  97320
gaacggcagg gcaagttagt tctgttttag tgcaatgttt tgaatggcag ggcaagttag  97380
tttagtttta gtgcagtgtt tcagttctga tgctcactgt aagtcttccc cagaatggga  97440
agaaacaata ggccagtact taagctctca tactaagtaa aggcccgaaa tcaccaaaga  97500
acacctgcaa aacctagaag aaatggctgt gtcctcaaat gtgcaagcat caacataaac  97560
aagcaatgat tatgaaaact tagggaaata tgacaccacc aaaagaaacc aacaaagctc  97620
caccagtgga ctcagaagaa ttgaagatct atgaaatgtc agacagagaa ttcagaataa  97680
gcctctttaa aaagttcagt gaatctgcca ggcatggtgg cttacgcctg taatcccagc  97740
actttgggag gccgaggtgg gcagatcacg aggtcagggg atcgagacca tcctggctaa  97800
cacggtgaaa ccccatttct actaaaaata caaaaaataa gcagggcctg gtggtgggca  97860
cctgtagtcc cagctactcg ggaggctgag gcaggagaat ggtgtgaacc caggaggcgg  97920
agcttgcagt gagctgagat tgtgccactg cactccagcc tgggagacag agcaagactc  97980
cgcctcaaaa aaaaaaaaaa tgttcaggga atcacaagaa aatagagata gaaaattaaa  98040
tgaaatttag aaagcaatcc atgtatgtag tgagaaattt gacaaagaaa tagaaacaag  98100
aaaacaaata gaaatcctat ctataaacaa tacagtaact gaactggaat aactcattgg  98160
```

-continued

```
aaagctttag cagcagactt aatcaaataa aagaattggt gagcttcagg acagaacata  98220
tgaaattacc cattcagagg agcaagaata aaaaagggta aagaagacct acaagaattg  98280
tggaatacca tcaagcagac taacctctgc ataataggaa ttcctgaaga tgaggaagaa  98340
aagggtgtag aaagcatact taagcaaatc atggctgaaa aagtcccaaa tctagagaaa  98400
gatgacactg tctaggtaca ggaagctcag tgatcagcaa ttaaaatcaa cccaaagaag  98460
agatacctat ggcacataac aatctggtta acaaaaatca aagacaaaga aagattactc  98520
aaggcagcaa gagaaaagaa atgtgtccca ttcaacatac cccaatagag ctttcagcag  98580
atatcccagc agaaaccctg taggccagca aagagtggaa tggtatattt agagtgctga  98640
aggaaaagaa aaaaactgcc aagcaagaat actgtaccca gcaaagttac cctttataaa  98700
cacaaaggca agataaagat ttttccagac aaacaaaagt tgagggaatt catcaacacc  98760
agacctgtct tacaaaaaat gctaaaggga gctgttcagt cagaaagtga aggatgctaa  98820
tgggtaaaaa gaaagcatct aatggcatta aactcaccgg caaaagaaag aaaactcact  98880
ggtaaaagaa gacttctgaa aaattcagaa tattgtaata ctgcaaatgg gatgagtaaa  98940
ccacttatat tttaagtatg aagactaaaa gacaaatttt tttttttttt tttttttttt  99000
ttaagacaga gcctcgctct gtcactcaag ctggagagtg cagtggtgca atctcagctc  99060
actgcaacct gcacctcctg ggttgaagtg attctcatgc ctcagcctcc gagtaactgg  99120
gattacagat atgtgccaac acacctggct tatttttgta tttttagtag agacagtatt  99180
tcacaatgtt ggccaggctg gtctcgaact cctgacctca ggtgatccgc ccacctcggc  99240
ctcctgaagt gctgggatta caggcttgag ccaccatgtc cggccgacaa aactattaaa  99300
aacagtaact acaacggtta tttaggagac aggacaattg tttaagcaat aaaaagatta  99360
aatcaaaaca tcaaaaagtc aaaatggcaa tggcggtgtt aaagtataga gtttttgtta  99420
cttttctttg caaagttaag tgattatcag tttaaaataa cctattataa gatttttttg  99480
taagcctcac agtaaccata aagcaaaaac ctataataga tacactaaaa ataaatagca  99540
caaaatcaaa gcacgctgct agagaaaatc acttaccata gaggaagaca gtaagagagg  99600
aaaataggaa gaaagaatct acaaagcaac caaaaacaag gaacagtatg gcagtagtaa  99660
acccttacct gtcagtaata actttgaata taaatggatt aaattcttca attaagagtg  99720
gcagaatgga ttaaaaaaca agacccatcc atatgctggc tacaagaaac tcacttcatc  99780
tgtaaagata agcacagact gaaagtgaag gtatggaaaa agataattta tgcaaatgga  99840
aaccaaaaaa gagcaagaga gcctatagtt ttatcacata aaataaactt aaatcaagat  99900
ggttaaaaaa aagacaaggc cattatataa cgacaaaggg gtcagtacag caagaggata  99960
taacaatggt aaatatatat acacccaaca ccagagcacc caaatatata aagcaaatat 100020
taatagacct aaagagagag atagactgca atacagtaat actagggaac atccacactt 100080
tcaatgtgaa cagatcatcc agacagaaaa gaaacaaaga aacgtagaca ttaaactgta 100140
ctctggacca aatggaccta acagatattt acagaacatt ccatccaaca gttgcagaat 100200
acacattttt ctcaacagca catggaatat tctccaggat tgatcataca ttaggtcaca 100260
aaacaagttt taacaaattt ttaaaattga aattatattt atcttgtcac agtggaataa 100320
aactagaaat ctataatcag aggaacattg gaaacagtac aaattaatgg aaattaaaca 100380
acaaatggac caatgaagaa attttaaagt aaattttaaa atttcttgag acaaatgaaa 100440
atggaaacaa aataccaaaa cctatgggat acagcaaaag cggttctaag agggaagtgt 100500
```

-continued

```
atagcaataa acgtctatat caaaaaagta aaaagacttc aaataaccta acgatacacc 100560
tcaaggaact agaaaagcaa aaccaaacaa acccccaatt ttttgttctt tttttctccg 100620
tgaaaaaagg catctaaaaa acaaaccaat gttaatagaa agaaataata aaagagcaga 100680
agtaaatgaa accaagacta aaagaataca aagatcaatg aaatgaaaat gtttttttga 100740
ataggtaatc aaaattggca aacctttcag aagactaagt gttgggggt ggtgggtggg 100800
gggagaagaa gacccaaata agcaaaacca gaggtgaaaa atgggacatt gtaagtgata 100860
ccaccgatat acaaaaagat cattagagac tactatgaac aactatacac caaaaaattg 100920
caaagcctag aaggaatgtg taaattctct gacacataca acctaccaag attgaatcag 100980
gaagaaacaa aagacctcaa caaaccaata atgagtaatg agattgaagc catataaaaa 101040
aagtctctca accaagaaaa gcccaggacc tgttgcttca ctgctaaatt ctgccagaca 101100
tttaaagagc taataccaat cctactcaaa ctcctcaaaa caaaaatttt tttggaagag 101160
aagggattac ttcccaactc attctacaag ggcaacatta ccctgatacc aaaaccagac 101220
aggatgcaac aagaaaatga caggccaaca tccctgatga acacagatgc aaaaatcctc 101280
aacaaaatac taacaaacca agtgcaacaa tacattaaaa agatcatcct gggatacgaa 101340
gaggggaaga acagacttac ttgagggtgg ggggttggag gaaggagagg atcagaaaaa 101400
atacctattc ggtactatgc ttattacctg agtgatgaaa taatctgtac accaagcctc 101460
tgtgacacac agtttaccca cataacaaac cagcacatgt acccctcaac ctaaaaaaaa 101520
aaaaaaaaaa aatcatcatg ataaagtgga aatccgaggg atgcaaggat gattcagcat 101580
acccaaatca ataaacatag tacattacat taatacaatc aagaccaaaa accatatgat 101640
gatttcaata gatgctcaaa aagcattcag tagaattcag catcccttct tgataaaaat 101700
tctcaacaaa cggtatagaa ggaacatact tcggtgaggt gtagtggctc atgcctgtaa 101760
tcccagcaat ttgggaggct gaggtgagtg gatcccttga agtcaggagt ttgagaccag 101820
cctggcccac atggtgaaac cccatctcta ctaaaaatac aaagcctggg tgatagagcg 101880
agactttatc tcaaaaaaga aaaaaaaaag aaggaacata tctcaaacca tatatgacaa 101940
acccacagct aatgtcatgt tcaacagtga aaagctgaat aatgaataat ttttctctaa 102000
gattaggaac agacaaggat gcccactcta accacttctg ttcaacttag tacttgaagt 102060
cctagcccaa gcaattaggc aagagaaaga aataaagggt acccaaattg gaaaggaaga 102120
aaccacatta tctttatttg cagataacat gatcctgtat ttagaaaaac ctgaagactc 102180
ctccaaaaac tgctagaact gataaacaaa ttcacttaag tttcatgata caaaatcaac 102240
ataacaaaaa tctgtagcat ttctatacat caacagcaag caatctgaaa aagaaatcag 102300
aaaagcaatc ccatttacat agctacaaaa aaaataaaat acctaggcat gaacttaacc 102360
aaataagtga agaatctctg tgatgaaaac tgtaaaagac tgatgacaga aattgaagag 102420
gacatataga aaatgaaaag atacttcata ctcatggatt agaagaatta atattgttat 102480
ggagttcgag accagcctgg ccaacatagt gaaaccccat ctctactaaa aatagaaaaa 102540
ttagccaggc ctggttgtgg gtgcctataa tcccagctac tcaggaggct gaggcaggag 102600
aatcacttga acctgggagg cagagggtgc accaagccga gatcatgcca ctgcactcca 102660
gcctgggtga cagagtgaga ctccgtctca aaagtcagta ttacccaaag taatctacag 102720
agtcagtata atctctatca aaataccaat gacatttttc acagaaatag aaaaaaccta 102780
aaatttgtgt ggaatgacaa aagaccttga atacctaaag ctatcctgag cagaaagaac 102840
aaagttggag acatctcact gcctgacttt gaataccaca aagctatggt aaccaaaaca 102900
```

-continued

```
ccatggttct atatatatgt gcacacattt tatacacaca taggtatata aaacacctac 102960
aaatttttgt tttttgagac agagtctcgc tctgttgccc aggctggagt gcagtggcat 103020
gatcttggct cactgcaacc tccgcctcct gggttcaagc aattctctgc ctcagcctcc 103080
caagtagctg ggattgcagg cacccatcac aaatgcctgg ctaatgtttt tgtatttttg 103140
gtagagatgg ggtatcacca tcttggtcag gctggtcttg aactcctgac ctcatgatcc 103200
acctgcctcg gcctcccaaa gtgctgggat tccaggtgtg agccaccgca ctcagcctag 103260
acctacaaaa ttatacttgg agaatcctga caaaaaggct ggctgagaaa gcacacccat 103320
aattatactc aactctcata tagagaactc tatttaactt tgtagtgctt catagccaag 103380
acttgccaga aattggcaga acatctctaa cataagagag accaaaagaa agaaaaatgt 103440
acctcggaga taacaaaaac aatgtaataa gcaaaagaaa tcataaatga actgtaatta 103500
atattcttgt agaggtgagg tgaaggaaca agaataaatt gctattttct aaaacattca 103560
gaaagcttgg gaactaaaaa taggagagct gaaatttaaa atcagtgatt ggataaagtt 103620
gagaaaatat cttagtaaaa caaaaagaaa aaacaagaga tgacttagag agaaaagata 103680
agaaacttag aagcaaaatt caagttgtct gatgtttaac tgactggaat tccagaaaaa 103740
gagaatagag aaaacgaaca gcaggatgtt atcaaaatga caatataaga gtagatggac 103800
atgtatctgt ttccaatacc actgagtgag gaaaataagc cacagtacca tgaaactgta 103860
gaacaccaag gacaaagaga agctgcaaaa actgaaaaat caactcttca atcagaaaat 103920
tgaggcttca gggcaaacca ttctcccaaa aactggaggg aatggtgcat actgagaatc 103980
acagattacc tccagaaacc tcaccagatt ctcagggtaa agagaaaaat ctcctcaagc 104040
tttaggtagg gagaagggga aatcatcatc ttgaaataag ccgtagcact ccttagcaat 104100
ggtttgctct caaagtaaac tgtttaatca agcctaattg acatgtgctt taccagagcc 104160
taacagacct ggaggaagat gtgttagtcc atcttgcatt gctaaaaaag aatacctgag 104220
actggtaatt tataaagaag aggggtttat ttggctcaca tttctgcaga ctgtacaaga 104280
agcatggcac cagcatctat ctgcttagct tctggtgagg cctcaggaag ctttccctta 104340
tggtggaaca caaaggggaa caggcacagc acatggagag agagagagca agagagagag 104400
gggagggagg tgccagactc ttgaacaacc agatctcgca ccaggtcttg cgtgaactat 104460
agttatagag taagaactca ctcacaagtg cagggacaac atcaagccat tcatgaggga 104520
tctggcccca tgacccaaac acttcccact aggccccacc ttcaacactg ggaatcacat 104580
ttcagcatga gttggagggg aaaaataccc aaagtgtatc agaagggaaa cacccaactg 104640
cagccctctc tagccttcct gtcttaccta attggggaga agggaacctg agaagcactt 104700
gtgaaagtca cggcccaggc acacaggctc actaaaagac tgagaactaa ttatgtgatt 104760
ataagacact ccccccacca cacacacctc accaccacac caatcagtct cctgtgtaat 104820
gatagtggat tactgctaaa tgaactaatt ttcagaccct attctatttt aataaggagt 104880
ctttagggaa acgaagaaat gatagataca aaaacaagga tgtgattgta acaacgtggg 104940
tacagctgga ggccattatc ctaagtgaat taatgctgaa acaaaaaacc aaaaactaca 105000
tgttccgaac tcataagtgg gagctagaca ttgggtattc atggacataa agatgggaac 105060
agtagacact gggtactgca agagacagga gagagggagg ggagaaaggg ttgaaaagct 105120
gcctattggg tactatgctc acgacctggg tagcaggatc agttgtaccc cagacgtcag 105180
catcacacaa aatacccttg taacctgcac gtgtacccct gaatctaaaa taaaaattga 105240
```

-continued tttaaaaaag gacactaaag gaaatgtaac ctatacagct acacaaaaca gtaaacacaa 105300
cccaactctt agccagagaa acataaagcc tcaaacaaga ggacttttta ccgcagtttc 105360
ttctacccag tatatcatgt ctgctttcaa caaaaactta caagacatgc taaaaggcaa 105420
aaatcaaagt tgcatgaggc ataacaagaa tcagaaccat tgccagactc atttatggca 105480
gcgatttttg gaataatcag actggaaatt ttaaataagt atgattaata tactaaaggc 105540
tctaatggaa aaagtgaaca acatgcaaga aaggtgggta acataagcag acaatagaaa 105600
ctctaagaaa gaacccaaaa gaaatactag aaataagcaa tactataaca gaaatgaaga 105660
atgcccttgg acttattgat agagtggaaa ggacaataga taacctggga aagattcaat 105720
gagcttgaag atatgtcagt agaaagttcc aaaacttaaa ctgcaaagag aaaaaagaat 105780
aaatgacaga acatggcagg gcctggtggc tcacactgta tctccacact tcaggaggcc 105840
caggtgggaa gatcacttga gaccaagagt tgagggccag cctaggcaac agagagagat 105900
ctgttgactc cacaaaaaat aaaaaggaaa agaataggat atccaaaaac tgtgggacag 105960
ttacaaaatt atatatattt aagtccttgc tttggctgaa cctaacacta aaattggaac 106020
aataccaaga agattgcaca acatggccct gtgcaaggat gatatgtaag gtcatgaagc 106080
atagaaaaaa catttctaat tgtttttttt agatggagtc tcactctttc acctgagctg 106140
tagtgcagtg gcatgatctt ggctcactgc aacctctgct gcccagattc aagcgattct 106200
cctgcctcag cctccagagt agctgggatt acaggtgtct accactgcgc ctggctaatt 106260
tttgtaattt tagtggagat ggggtttcac catcttggcc aagctggtct tgaactcctg 106320
acctcgtgat ccacctgcct tggcctccca aagtgctggg attacaggtg tgaggcacct 106380
cacccagcca acatttctaa tttttttttt tttttttttt tagacatagt ctcactctgt 106440
cgcccaggct ggagtacagt ggggcaatct cggctcactg caagctccgc ctcctgggtt 106500
catgccattc ttctgcctca gcctccctag tagctgggac tacaggtgcc tgccaacaca 106560
tccagctaat tttttatact ttttagtaga gacggggttt caccatgtta gccgggatgg 106620
tctcgatctc ctgaccttgt gatccgcccg cctcggcctc ccaaagtgct gggattacag 106680
gcgtgagcca ccgcgcctgg ccaatttttt aaaaaattaa aaaaaatatg tgtatgtaaa 106740
attgtgtaca cacgatggga ataacaaagg aaaagagaga aaggaataga agaaccattt 106800
gaagtaataa tgactatttt caaaactaaa gacagatgcc aaaccacaaa tccagtttag 106860
aaagttaaga aaacaagcaa gataaatacc aaatgccagg tgcggtggct cacacctgta 106920
atcccagcat tttgggaggc cgaggtgggc agatcacttg aggtcaggag ttcaagacca 106980
gcctggccaa catggtgaaa ccctgtctct actaaaaata gaaaaattag gcctggtggc 107040
aggtgcctgt aatcccagct actcaagaga ctgaggcagg agaattgctt gaacctggga 107100
ggcagaggtt gcagtgagct gggcaccact gcactccagc ttgggcaaaa gagtgagact 107160
ccatctccaa aaaaaaaaaa aaaaaaaaaa gataaataca agaaagtctg tacccaggca 107220
cctaggcata tcataatcaa attgcagaaa atcaaagata acatcctgaa aaaacctaga 107280
ggaaaaaaaa cacctatgga gagtggagtg aaatatctct atatttatta tgtctttatt 107340
atgtttttaa ttatgttttt catttatttt tgtggttacc tggtaggtgt atatatttat 107400
ggggtacatg agatattttg atgcgggtat acaatatgta ataatcacat caggatgaat 107460
gaggtatctg tcacctcaag catttatcat tttcttgtat tacaaaccat ctagttatac 107520
tctagttgtt tttaaataaa tagttaatta ttgactgtag tcaccgtgtt gtgctatcaa 107580
atactagatt ttattccttc tatctaataa tatttttgta ccctataatt atcccctccc 107640

-continued ccacccacct acccactacc cttcccagcc tttggtaacc attgttctac tctctatttc 107700
catgagttca actgtcttaa tttttagctc ccacaaataa gtgagaacat gtaaagtttg 107760
tctttctata cctggcttat tttacttaac ataatgaccc ccacttccat ccatgttgtt 107820
gcagatgaca gggtcattct tttctatggc tgaatagtac atatatatat atatataata 107880
tttcctttat ccatttatct gttgatggac acttagattg atcccaaatc ttggctattg 107940
tgaatagtgc tgcagcaaac gtgagaatgc agatatctcc ttgatttact gatttccctt 108000
cttttgggta tattcctagt agtgggattg ctagatcata tggtagttcc atttttagtt 108060
ttttgaggaa cctccatact gttctccatg gtggttgtac taatttatat tcccaccaac 108120
agtgtaccag ggttcccttt tctccacatc ctcaccagca ttcgttattg cctgtctttt 108180
ggataaaagc cattttaact gggatgagat gatatctcat tgtagttttg atttgcatct 108240
ccctgatggt catgacgtaa tattgagtac cttttcatat acctgcttgc catttgtatg 108300
tctactttgt agtaatgtct attctgatct tttgcccatt ttttattgta ttattcgatt 108360
ttttattgac ttgtttgagc tctttattct ggttattagt ttcttgtcaa atggatagtt 108420
tgcaaatatt ttcttccatt tgggggattg tcacttccct ttgttgattg tatcctttgc 108480
tgcatagaag tttttacact tggcatgatc ccatttgtcc atttttgctt tgggtgcctg 108540
tctttgtggg gtattactca agaaatcttt gctcagtgca atgtcctgga gagttttcca 108600
aatgttttct tttagcagct tcatagtttg aggttttaga tttaagtatt taattcattt 108660
tgatttgatt tttgtatatg gcaagagata ggggtctagt ttctttcttt cttctttttt 108720
tcctttgctt tacttttttt tttttttttt tttttttttg agacagggtc tcactctgtc 108780
tcccaggctg gagtacagtg gtgtgatcac aactcattgc aacctccacc tcccaggttc 108840
aagtaattct aatgcctcag cctcctgagt agctgggatt tcaggtatat gccaccatgc 108900
ctggctaatt tttgtatttt gagtagagac ggggtttcac catgttgccc gggctggtct 108960
caaacttctg gcctcaagtg atccactggc cttgacttac taaagtgctg ggattatagg 109020
tgtgagccac catgtccagc aagtatctag tttcattcta ctacatatgg atatccagtt 109080
ttcccagcac catttattga agagactgtt ctttccccaa tgtatgttct tggcacattt 109140
gttggtaatg agttctctgt agatgtgtgg atatgtttct gggttatctg ttcttttcca 109200
tcaatctgtg tgtctatttt tatgccagta ccatgctgtt ttggttacta taactctgta 109260
gtataattcg aattcaggta atgttactcc accagtatta ttctttttgc tcaggatagc 109320
tttggttatt ctggatcttt tcatggttcc aggtaaactt tagaattgtt ttttctattt 109380
ctgagtagaa gaattttatt ttattcatag ctattgtaaa tgggattact ttcttgactt 109440
ctttttcaga ttgttcactg ttggcacata aaaatgctac tgatttttgt atgttggttt 109500
tgtcttcttc aactttctga atttattagt tctaatagtt tttttggtgg agtcttttgg 109560
tttttccaaa tataaggtta tattatctat aaacaaggat aatttgactt ctttctttct 109620
agtttggatg ccctttcttt ctattttctt attactgtaa gacttacaga atgaaatatt 109680
taaagtattg aaagaaaaac cccaccaacc tatggtaact ccatgtttcc agttggtagt 109740
tgcttaggca aaacaccttg gagtcattct tgattctcct tgtccctcac atcccacatc 109800
ctatctgtta ggatatcgag atgtaataag aaaaaaaaaa ttgtaatcct ccccttctta 109860
ccacctctat ttctatctcc ttggtccaag ccatcattat ctcttctctg gattattgct 109920
atagactcca tactacagtc taaacagagc aactagaatg attaaagtcc aatctagtac 109980

-continued

```
tactacagaa gcttcccatt tcactacctg tctatgaatt acttaatttc tctgtgtctc 110040
agttgcttca tctgttaaaa gagaataata cctcctcagg agattgtgtg attgatgagg 110100
aggcacttac ttaataccaa cctgatgcac agaaaatagt aaagtttagc gatttttttt 110160
attattttaa tttccaattt gcccttcaaa tcagaagctt agttttgtct tattcttcag 110220
tgcttgaggt gggagggttt gtagaaacat ttggcttctg aatacctagc tcattgctgt 110280
caagcagaat cctccatctt ttagtgcctg aaaatattca gatgtccaga aacattaacc 110340
aaaggaaatt ccatttctag ctctgctgtt tgtataggca atgtagtggg tcagttttct 110400
gcactgtgta gaaattgctt tgtcagtgga aaatgttatt ttcgtcggtt ttacagttcc 110460
taacttttga ggcatttgtt ccctggagga tactaaaaga aggaaatctt cagacagctg 110520
cccactgaat ttttgcgtga gcctttattt gatattttac ccagacccct tttggttttt 110580
tattacagta acatcgcata cctaggtttt ttttttcttc ttcatataag ccttacctat 110640
ctggaactgt cagtactagg aaggtactta tagtgttgaa tgttcccact catatttcct 110700
gttatgcctt atgcttttta taacaagcca aaaagaggaa gaaagatttc accatagatt 110760
tgctaaaggc aatgtgggat gcaatgagtg tggtttaatg gaagagccct ggggtgcggc 110820
ctctgagcct tgctctgcca ctgacacctg tatgactgcc tgggcttgag ttaaacgttc 110880
tgcataaatt ctagcagaag aggctagctc aaagaggaga ttcagtgtct gaatgtctga 110940
gagagtgtga aaataagaaa agttggctgg gcgccgtggc tcacacctgt aatgcagcac 111000
tttgggaggc cgaggcaggc ggatcacctg aggtcaggag ttcaagacca gcctgaccaa 111060
catggagaaa ccctgtctct attaaaaatt caaaaaagta gccaggcgtg gtggtgcatg 111120
cctgtaatcc cagctactca ggaagctgag gcaggagaag tgcttgaacc tgggaggcag 111180
aggttgtggt gagccaagat tgcgccattg cactccagcc tgggtgacag agcgaaactc 111240
cgtctcaaaa caacaacaac aacaacaaca aagtcaagtc acttgagacc tcaacccact 111300
gacaagagaa gagggactgg ggcagaccca acctgaactg gttctgtaaa gcagccacgg 111360
cacagaccag agtggactgt gggcctgagc agtgtatgcc cctggggcct ggaaagtagg 111420
ggctgggact tcatttcttg aatagaggga gaaggaaaga cacttgagaa tctggtaaaa 111480
acaaaaacaa caacaacaaa aaacccaaaa caaataaaac attctagtag cttcaggccc 111540
tccactgggc atggtgtctt cttgacccac agacaatagg caggcaaagt agatggaagc 111600
aagtgctaac atgatacaca gctcccaggg cttagacact tcccacctca gcaagctgga 111660
cccatccaag ctgtggtgtc agggtagaac aaatgattct ttttttcgag atggagtttc 111720
gctcttgttg cccagtctgg agtgcaatgc tgagatcagc tcactgcagc ctccgcctcc 111780
caggtttgag caattcacct gcctcagcct cctgagtagc tgggattaca ggcgcctgcc 111840
aacacgctca gctaattttt tgtattttaa gtagagatgg ggtttcacca tgttggccag 111900
gctggtctcg aactcctgac ctcaggtgat ctgcccgcct tcgcctccca aaatgctggg 111960
attacaggca tgagctaccg cgcccagccg aacaaatgat tcttatatgt agattcttta 112020
gggagcagct aagccagccc ccattgactg gggagatga tggtagcttt gagacactcc 112080
tagcagctgc agttttgtta tcctgcaccc tgttcacttt ccagggccat gcacctccac 112140
ggaaatacct tatctataag ccttgtgtct ctacttcagt ttaggtctcc tagactgtaa 112200
cggagaacaa aaaaaaaaaa tagaccaagt tttaggcatt gcaggaaaaa aaagtgtgtt 112260
cattctctga gcctccgaag taatgcagct atatttataa gtggatcagt aaaaggagaa 112320
acttctttag gtttttagac ctgggattca gcattgagat tttctgtgct ctgaaggact 112380
```

-continued atccagtaac tgtccttcca ataactttcc ttagtttctt gttacaatcg cgattccggt 112440
ggttatcaaa cttcttccta gtggattgct tttccactct tcattgacat tacttgttcc 112500
caagtttttt tttgctgttg caaagtgttg aaataaacat ctttgtactt aaatgatata 112560
tgtgtaacag taaattttta acattaaacc actgacttaa ttcatttatt gaattttgtt 112620
gtagtatatc acacatacag tataccaatc atttatcaat aactgatgtg ttcacaaaat 112680
gaacacatgc tcataatcac tactgatatc aagacagaaa attaccagca ccctggaagc 112740
ctctctcagc ttctctctct caatcactac cacctccttc ctacccaggg caaacagtat 112800
cctgatttct aagatcattg atttgtttta cctacttagt agctttaaat tttttaaatg 112860
aagatgtagt atattattct ttggaatctg gctccccacc tcctcatcat tatgttgaga 112920
ttcatctgtg ttgttgctaa tgtagcagag ttcatttttt tgttactgta tagtgtatca 112980
ttatatgcgt agatcacgtt ttttaattta ttctttctca ttgcactgtt ctgcaatgcc 113040
accttgccgt aaaccaggca tctgcatctg aggggctgtt tctggacctg tcattctgtt 113100
tcatcgatat atttatctat ccttgtgcca aaaccctact gtcttactta tggctatatc 113160
attaacttag ctaatgttta gagctatgta atgtagataa ttgtagctgt ataatagtaa 113220
tgtatcgata tctggtagaa taagttcttc tactttgtta ttcttttaaa actaccttga 113280
ctattcttgg ccctgtgtat ttccatataa cttttacaat caagttgaaa ttactccctc 113340
ccctccaaaa aaaaaaaaaa agcatgctag aattttgatt gggaattctt tgaggagaat 113400
ggctatcttt attatattaa atcttcctgt ccctgaaagt ggtatgtctg tttatgtggg 113460
tctttaattt ctctcaatag tgttttatag ttttctgtgt taaggtttta tatatctttt 113520
attgatttac tcttacatat tcagtgggct tttaaatgta ataaatggta tttatcacaa 113580
atttatcata aagattccta attattgcat gtattagaaa catttttata tattaaagca 113640
taggttttta attataagat tttatgagat ttacggttta tatcatttta agaatcactt 113700
aatattcaaa ttcaaatcac catgagaatt ctgggtaaat tgagaaaagt aaagttggat 113760
taaatccagg gttgtatcct tggagaattc aaaaggaacc aggaagagct tgttcctaaa 113820
ctgcgtgagt tctgtgttgg ttgcttgaga gagattgcct agggcttgct tcctctctca 113880
gctaaagtga ttgggatttg gcagtcaggg tgcttttgtt tttagggtac cctgagccct 113940
ctcctagcca gcccacattt gtgagcactc ggtaaacaca gagcaggagg gaattacagt 114000
gaatggggat ttccctcagt gctgcccact ggctgctctt gaactgacag gcttctttct 114060
cattctaaac tcaccagcag tggagcagta aacccggcca cggtcaggca tggcacatgt 114120
cctgcaatga tggggactgg acctgttgcc ttaaactcac gcctgctttg tttttccagg 114180
tctataaggg agaattccaa ctacctgact ttcttaaaga aaaaccacag gtactgtgtc 114240
tgctttttcc tcctgatgta tactagattg gctcttgcat tgaagtaata tttttaaaga 114300
gataatgaaa ttaaaaagac agaaacaaga aaaccaaaaa gaaaagaaga aaagggatag 114360
tgatatgtgc tggggaagaa agatcagcgt ctgggacttg ttgattttaa caataattta 114420
acacagtctt aatttcagag agctcagtgt ctcccaaaac cagggaaata ctttattgat 114480
aaccaaattc tgattgcttg aggtcctgca caagccgccc agtgggtaaa gctgctccag 114540
cgttccagtg cctaatttga aataaaaatg ttcagcgacc ctctctgttc ctactctgtg 114600
tactgtacat ccttgcccct ttgacttttc tcatttggag cccagatgac ttatatatac 114660
acatagtcac tggcccctgg gaaggacagt gagagtttga aggattaaag ccagcatggt 114720

-continued

```
ggctcatgcc tgtaatccca gcaatttgtg agaccgaggt tggcagatca cttgaagtcg 114780

ggagttcaag accagcatgg ccaacatggt gaaacctcat ctctactgaa aatataaaaa 114840

ttagccgagt attgcagaat ttgcctgtaa tcccagctac ttgggaggct gagggagaat 114900

cacatgaacc gggagttgga ggttgctgag ccaagattac accactgcac tacagcctgt 114960

gtgacagaac aagactgcct caaaaaaaga aaaaattagc taggcatggt ggcgaggcct 115020

ctggtcccag ctacttggga ggctgaggca ggaggatcgc ttgagcccat gaggtggagg 115080

ttgccatgag tttagattgt gccactgcac tccagcctgg gtgacagagt gagaccctgt 115140

ctcaaaaata aaaaaaatta agcagattca gagttttccc tgtaacgtct tctctcactg 115200

acttgcattc caatcctgtt tcctgggttg gaaagaaaca gggagtctca cggctgacat 115260

gcctagagga gcccggcatc ctgcctctgg gcatcactgt catgcccata tggaagtcag 115320

aaaaaatgga cactcatggc ctgagtgcag ccgacttccc tttccagcaa ggcgatgatg 115380

catgttgcct ccaggctgct gctgtcagtg attagcttgt caataggaag aggagactca 115440

gttttgaact cagtttctga aagcgttcca gatagaggtt ggtgaagcaa cagcacctca 115500

gagacttgtg tgaagtccag ttgcctgatg caagcctgga gtaaatgggc tgccctctct 115560

gagggaagcc atgtctcaca ccagagttga agcctcttcc ttcctgaccc ttttctgaaa 115620

acacttagcc gccagtaatt gatacatatg acttgagtgt ttcaaagtac tttcaaggca 115680

tattcttatt cacatatatt tactattcat ccattcattc acttattcac caattgttta 115740

cccagtgtct actatggtga ggaattagag taagtcctca ggagtcacgg gggaaagaaa 115800

gacctcaagg agctcctgat ttatccagaa gaatccgacc acctcgtgca gacaagggga 115860

cacagagctc tgggcccagg ctgggcatga tgtcccagaa acctgggcag attcatgaac 115920

agactgacac cggctgtgga aattggagcc agagaatatt ccaagaggct gtcttgaagg 115980

aatataaaat ccaaaagcgc ccaggtgcgg tggttcacgc ctgtaatccc agcactttgg 116040

gaggcccagg tgggtggatt gcctgaggtc aggagttcaa gatctgttta gccaacacag 116100

tgacaccccg tctctactaa aaatataaaa taattagcaa gacttggtgg tgtgcgcctg 116160

taatcccagc ctgggtgaca gagcgagagt ctgtctcaaa aaaaaaaaaa aaaaaaaaaa 116220

aaaattccaa aagccggttt gcataacaaa tctgaagaag tcaagaaaag gtatttgaga 116280

ctaaaactaa agggacactc ctgcttcaca acatacctaa aaatatttcc aaatggattg 116340

cacacctaaa tgtgaaaggc aaaataatga aagttgttag aggatataga agagccaggc 116400

atgaggctca cgcttgtaat cccagcactt tgggaggcag gcagattgct tgagtccagg 116460

cattcaaaac cagcctggga aacatagcca aacctcatct ctactaaaaa tacaaaaaat 116520

tagctgggtg tggtgcatgc ctgtagtccc agctacttgg gaggctgagg tgggaggatc 116580

acctgagccc ca                                                     116592
```

<210> SEQ ID NO 4
<211> LENGTH: 365
<212> TYPE: PRT
<213> ORGANISM: Human

<400> SEQUENCE: 4

```
Met Val Gly Lys Leu Lys Gln Asn Leu Leu Leu Ala Cys Leu Val Ile
 1               5                  10                  15

Ser Ser Val Thr Val Phe Tyr Leu Gly Gln His Ala Met Glu Cys His
            20                  25                  30

His Arg Ile Glu Glu Arg Ser Gln Pro Val Lys Leu Glu Ser Thr Arg
```

-continued

```
        35                  40                  45

Thr Thr Val Arg Thr Gly Leu Asp Leu Lys Ala Asn Lys Thr Phe Ala
    50                  55                  60

Tyr His Lys Asp Met Pro Leu Ile Phe Ile Gly Gly Val Pro Arg Ser
65                  70                  75                  80

Gly Thr Thr Leu Met Arg Ala Met Leu Asp Ala His Pro Asp Ile Arg
                85                  90                  95

Cys Gly Glu Glu Thr Arg Val Ile Pro Arg Ile Leu Ala Leu Lys Gln
            100                 105                 110

Met Trp Ser Arg Ser Ser Lys Glu Lys Ile Arg Leu Asp Glu Ala Gly
        115                 120                 125

Val Thr Asp Glu Val Leu Asp Ser Ala Met Gln Ala Phe Leu Leu Glu
    130                 135                 140

Ile Ile Val Lys His Gly Glu Pro Ala Pro Tyr Leu Cys Asn Lys Asp
145                 150                 155                 160

Pro Phe Ala Leu Lys Ser Leu Thr Tyr Leu Ser Arg Leu Phe Pro Asn
                165                 170                 175

Ala Lys Phe Leu Leu Met Val Arg Asp Gly Arg Ala Ser Val His Ser
            180                 185                 190

Met Ile Ser Arg Lys Val Thr Ile Ala Gly Phe Asp Leu Asn Ser Tyr
        195                 200                 205

Arg Asp Cys Leu Thr Lys Trp Asn Arg Ala Ile Glu Thr Met Tyr Asn
    210                 215                 220

Gln Cys Met Glu Val Gly Tyr Lys Lys Cys Met Leu Val His Tyr Glu
225                 230                 235                 240

Gln Leu Val Leu His Pro Glu Arg Trp Met Arg Thr Leu Leu Lys Phe
                245                 250                 255

Leu Gln Ile Pro Trp Asn His Ser Val Leu His His Glu Glu Met Ile
            260                 265                 270

Gly Lys Ala Gly Gly Val Ser Leu Ser Lys Val Glu Arg Ser Thr Asp
        275                 280                 285

Gln Val Ile Lys Pro Val Asn Val Gly Ala Leu Ser Lys Trp Val Gly
    290                 295                 300

Lys Ile Pro Pro Asp Val Leu Gln Asp Met Ala Val Ile Ala Pro Met
305                 310                 315                 320

Leu Ala Lys Leu Gly Tyr Asp Pro Tyr Ala Asn Pro Pro Asn Tyr Gly
                325                 330                 335

Lys Pro Asp Pro Lys Ile Ile Glu Asn Thr Arg Arg Val Tyr Lys Gly
            340                 345                 350

Glu Phe Gln Leu Pro Asp Phe Leu Lys Glu Lys Pro Gln
        355                 360                 365
```